United States Patent
Ceva et al.

(10) Patent No.: US 10,857,127 B2
(45) Date of Patent: Dec. 8, 2020

(54) VAGINAL DELIVERY SYSTEMS CONTAINING SELECTIVE ESTROGEN RECEPTOR MODULATOR (SERM) AND USES THEREOF

(71) Applicant: Azure Biotech, Inc., River Vale, NJ (US)

(72) Inventors: Valerie Ceva, New York, NY (US); Steven R. Goldstein, New York, NY (US); Susan L. Levinson, Morris Township, NJ (US); David D. Thompson, Gales Ferry, CT (US); Andreas Bernkop-Schnürch, Sankt Veit an der Glan (AT); Isabelle Nardin, Salzberg (AT)

(73) Assignee: Azure Biotech, Inc., River Vale, NJ (US)

( * ) Notice: Subject to any disclaimer, the term of this patent is extended or adjusted under 35 U.S.C. 154(b) by 0 days.

(21) Appl. No.: 15/600,693

(22) Filed: May 19, 2017

(65) Prior Publication Data

US 2017/0333394 A1  Nov. 23, 2017

Related U.S. Application Data

(60) Provisional application No. 62/339,802, filed on May 20, 2016.

(51) Int. Cl.
| | |
|---|---|
| A61K 31/40 | (2006.01) |
| A61K 9/107 | (2006.01) |
| A61K 9/00 | (2006.01) |
| A61K 47/10 | (2017.01) |
| A61K 47/14 | (2017.01) |
| A61K 47/24 | (2006.01) |
| A61K 47/26 | (2006.01) |
| A61K 47/44 | (2017.01) |

(52) U.S. Cl.
CPC ............ *A61K 31/40* (2013.01); *A61K 9/0019* (2013.01); *A61K 9/0034* (2013.01); *A61K 9/107* (2013.01); *A61K 9/1075* (2013.01); *A61K 47/10* (2013.01); *A61K 47/14* (2013.01); *A61K 47/24* (2013.01); *A61K 47/26* (2013.01); *A61K 47/44* (2013.01)

(58) Field of Classification Search
CPC ...................................................... A61K 31/40
See application file for complete search history.

(56) References Cited

U.S. PATENT DOCUMENTS

| | | |
|---|---|---|
| 2010/0021416 A1 | 1/2010 | Lichter et al. |
| 2010/0022656 A1 | 1/2010 | Buhl et al. |
| 2014/0350117 A1 | 11/2014 | Banov |
| 2016/0213639 A1 | 7/2016 | Suzuki et al. |

FOREIGN PATENT DOCUMENTS

| | | |
|---|---|---|
| CN | 1857242 A | 11/2006 |
| CN | 103830207 A | 6/2014 |
| WO | WO 2010/145010 A1 | 12/2010 |

OTHER PUBLICATIONS

Elnaggar, et al. Self-nanoemulsifying drug delivery systems of tamoxifen citrate: design and optimization. Int J Pharm. Oct. 1, 2009;380(1-2):133-41. Abstract.

Elsheikh, et al. Nanoemulsion liquid preconcentrates for raloxifene hydrochloride: optimization and in vivo appraisal. Int J Nanomedicine. 2012;7:3787-802.

*Primary Examiner* — Svetlana M Ivanova
(74) *Attorney, Agent, or Firm* — Wolf, Greenfield & Sacks, P.C.

(57) ABSTRACT

The present disclosure provides pharmaceutical compositions that include one or more selective estrogen receptor modulator(s) (SERM(s), e.g., Lasofoxifene) and four or more pharmaceutically acceptable excipients. The pharmaceutical compositions may be able to form nanodroplets (e.g., by self-nanoemulsifying) in vaginal fluid and to deliver the one or more SERM(s) to the vagina of a female subject. The pharmaceutical compositions may be useful in treating or preventing vulvovaginal atrophy, dyspareunia, sexual dysfunction, osteoporosis, or breast cancer in a female subject.

36 Claims, 17 Drawing Sheets

Water

| | Formulation number | 0h PDI | 0h SD | 2h PDI | 2h SD | 4h PDI | 4h SD |
|---|---|---|---|---|---|---|---|
| 2% | F1 | 0,037 | 0,011 | 0,052 | 0,022 | 0,060 | 0,006 |
| | F2 | 0,035 | 0,006 | 0,059 | 0,005 | 0,059 | 0,006 |
| | F3 | 0,039 | 0,003 | 0,044 | 0,008 | 0,055 | 0,007 |
| | F7 | 0,114 | 0,022 | 0,037 | 0,012 | 0,017 | 0,004 |
| | F8 | 0,058 | 0,029 | 0,025 | 0,011 | 0,040 | 0,012 |
| | F9 | 0,012 | 0,002 | 0,051 | 0,012 | 0,050 | 0,011 |
| 30% | F1 | 0,513 | 0,003 | 0,504 | 0,003 | 0,511 | 0,001 |
| | F2 | 0,461 | 0,005 | 0,456 | 0,009 | 0,454 | 0,012 |
| | F3 | 0,499 | 0,005 | 0,478 | 0,002 | 0,490 | 0,009 |
| | F7 | 0,444 | 0,010 | 0,433 | 0,006 | 0,438 | 0,006 |
| | F8 | 0,441 | 0,001 | 0,446 | 0,023 | 0,439 | 0,011 |
| | F9 | 0,432 | 0,004 | 0,426 | 0,006 | 0,431 | 0,008 |

Simulated Saliva

| | Formulation number | 0h PDI | 0h SD | 2h PDI | 2h SD | 4h PDI | 4h SD |
|---|---|---|---|---|---|---|---|
| 2% | F1 | 0,037 | 0,002 | 0,025 | 0,012 | 0,048 | 0,009 |
| | F2 | 0,043 | 0,008 | 0,036 | 0,004 | 0,039 | 0,008 |
| | F3 | 0,042 | 0,005 | 0,034 | 0,010 | 0,043 | 0,003 |
| | F7 | 0,050 | 0,014 | 0,037 | 0,021 | 0,030 | 0,012 |
| | F8 | 0,067 | 0,018 | 0,056 | 0,011 | 0,050 | 0,003 |
| | F9 | 0,038 | 0,016 | 0,029 | 0,006 | 0,029 | 0,006 |
| 30% | F1 | 0,499 | 0,011 | 0,505 | 0,006 | 0,492 | 0,002 |
| | F2 | 0,453 | 0,014 | 0,456 | 0,006 | 0,446 | 0,005 |
| | F3 | 0,490 | 0,004 | 0,490 | 0,004 | 0,494 | 0,002 |
| | F7 | 0,441 | 0,005 | 0,436 | 0,010 | 0,434 | 0,003 |
| | F8 | 0,434 | 0,011 | 0,428 | 0,009 | 0,428 | 0,009 |
| | F9 | 0,418 | 0,004 | 0,429 | 0,001 | 0,429 | 0,001 |

Simulated Tears

| | Formulation number | 0h PDI | 0h SD | 2h PDI | 2h SD | 4h PDI | 4h SD |
|---|---|---|---|---|---|---|---|
| 2% | F1 | 0,021 | 0,009 | 0,041 | 0,008 | 0,041 | 0,022 |
| | F2 | 0,049 | 0,017 | 0,055 | 0,008 | 0,055 | 0,011 |
| | F3 | 0,053 | 0,005 | 0,046 | 0,005 | 0,036 | 0,008 |
| | F7 | 0,103 | 0,031 | 0,032 | 0,011 | 0,057 | 0,021 |
| | F8 | 0,124 | 0,002 | 0,077 | 0,008 | 0,051 | 0,012 |
| | F9 | 0,084 | 0,011 | 0,075 | 0,015 | 0,051 | 0,017 |
| 30% | F1 | 0,507 | 0,007 | 0,512 | 0,008 | 0,503 | 0,000 |
| | F2 | 0,448 | 0,012 | 0,443 | 0,013 | 0,453 | 0,005 |
| | F3 | 0,495 | 0,017 | 0,495 | 0,008 | 0,483 | 0,001 |
| | F7 | 0,449 | 0,003 | 0,437 | 0,004 | 0,438 | 0,002 |
| | F8 | 0,448 | 0,011 | 0,466 | 0,006 | 0,444 | 0,005 |
| | F9 | 0,431 | 0,002 | 0,428 | 0,006 | 0,425 | 0,005 |

Simulated Vaginal Fluid

| | Formulation number | 0h PDI | 0h SD | 2h PDI | 2h SD | 4h PDI | 4h SD |
|---|---|---|---|---|---|---|---|
| 2% | F1 | 0,023 | 0,014 | 0,045 | 0,016 | 0,047 | 0,011 |
| | F2 | 0,051 | 0,009 | 0,045 | 0,018 | 0,033 | 0,014 |
| | F3 | 0,059 | 0,007 | 0,054 | 0,011 | 0,066 | 0,029 |
| | F7 | 0,065 | 0,016 | 0,060 | 0,002 | 0,054 | 0,011 |
| | F8 | 0,095 | 0,014 | 0,062 | 0,003 | 0,061 | 0,017 |
| | F9 | 0,079 | 0,008 | 0,071 | 0,010 | 0,050 | 0,026 |
| 30% | F1 | 0,507 | 0,009 | 0,531 | 0,005 | 0,531 | 0,005 |
| | F2 | 0,456 | 0,003 | 0,449 | 0,006 | 0,472 | 0,008 |
| | F3 | 0,507 | 0,008 | 0,510 | 0,005 | 0,514 | 0,009 |
| | F7 | 0,439 | 0,009 | 0,434 | 0,018 | 0,440 | 0,014 |
| | F8 | 0,424 | 0,006 | 0,423 | 0,003 | 0,422 | 0,005 |
| | F9 | 0,429 | 0,005 | 0,421 | 0,012 | 0,435 | 0,006 |

Figure 13

VAGINAL DELIVERY SYSTEMS CONTAINING SELECTIVE ESTROGEN RECEPTOR MODULATOR (SERM) AND USES THEREOF

RELATED APPLICATIONS

This application claims the benefit of the filing date under 35 U.S.C. § 119 of the U.S. Provisional Application Ser. No. U.S. 62/339,802, filed May 20, 2016, and entitled VAGINAL DELIVERY SYSTEMS CONTAINING SELECTIVE ESTROGEN RECEPTOR MODULATORS (SERMS) AND USES THEREOF, the entire contents of which is incorporated herein by reference.

BACKGROUND

Lasofoxifene, a third-generation selective estrogen receptor modulator (SERM), has been developed for the prevention and treatment of osteoporosis in postmenopausal woman [L. Gennari, D. Merlotti, G. Martini, R. Nuti, Lasofoxifene: a third-generation selective estrogen receptor modulator for the prevention and treatment of osteoporosis, Expert Opinion on Investigational Drugs, 15 (2006) 1091-1103]. It is a naphthalene derivate that differs structurally from the first- and second-generation SERMs such as Tamoxifen and Raloxifene. The active pharmaceutical ingredient (API) selectively binds to both estrogen receptor subtypes (estrogen receptor-alpha and -beta) with high affinity [L. Gennari, Lasofoxifene: a new type of selective estrogen receptor modulator for the treatment of osteoporosis, Drugs Today (Barc), 42 (2006) 355-367.]. Furthermore, Lasofoxifene shows efficacy in vaginal and vulvar atrophy in postmenopausal women [X. N. Wang, H. A. Simmons, C. T. Salatto, P. G. Cosgrove, D. D. Thompson, Lasofoxifene enhances vaginal mucus formation without causing cell hyperplasia and increases estrogen receptor beta and androgen receptor in rats, Menopause, 13 (2006) 609-620]. In contrast to Tamoxifen and Raloxifene, Lasofoxifene demonstrated a positive impact on vaginal tissue. Lasofoxifene decreases the vaginal pH in postmenopausal women and has a positive effect on the vaginal maturation index [O. Tan, K. Bradshaw, B. R. Carr, Management of vulvovaginal atrophy-related sexual dysfunction in postmenopausal women: an up-to-date review, Menopause, 19 (2012) 109-117].

Accordingly, a treatment of the vagina with Lasofoxifene would be of high therapeutic interest. So far, however, the development of systems for delivering Lasofoxifene directly to the vagina has not been achieved.

SUMMARY

Delivery of a SERM (e.g., Lasofoxifene (lasofoxifene)) to the vagina (e.g., a target tissue associated with a disease) of a female subject may be advantageous over systemic delivery of the SERM maybe because the delivery to the vagina may avoid systemic side effects (e.g., toxicity) that may be caused by systemic delivery. So far, however, no reported systems for delivering a SERM to the vagina have succeeded, maybe because of the cationic character of most SERMs leading to strong interactions with the anionic mucus exhibiting sialic and sulfonic acid substructures. Being ionically bound to the mucus, SERMs may spread insufficiently over the vaginal mucosa and cannot adequately reach (e.g., penetrate to) the underlying vaginal epithelium. The epithelial layer is a target for effective treatment but it is not desired to permeate of the vaginal mucosa to reach the lamina propria, or to minimize reaching the lamina propria. Furthermore, non-ionic SERMs may exhibit insufficient solubility in the vaginal fluid.

It was therefore an aim to develop a vaginal delivery system for SERMs (e.g., Lasofoxifene). In order to solve this problem, a novel self-nanoemulsifying drug delivery system (SNEDDS (SNEDDS formulation), such as the pharmaceutical compositions described herein) for SERMs (e.g., Lasofoxifene) was developed. The SNEDDS described herein are believed to be able to solve this problem (e.g., one or more aspects of this problem).

In one aspect, the present disclosure provides pharmaceutical compositions comprising:
(i) one or more SERM(s); and
(ii) four or more pharmaceutically acceptable excipients comprising:
(a) two or more (co)solvents, wherein:
the concentration of the first (co)solvent in the four or more pharmaceutically acceptable excipients is between 10% and 25% by weight, inclusive; and
the concentration of the second (co)solvent in the four or more pharmaceutically acceptable excipients is between 10% and 15% by weight, inclusive;
(b) one or more hydrophilic emulsifier(s), wherein the concentration of the first hydrophilic emulsifier in the four or more pharmaceutically acceptable excipients is between 15% and 35% by weight, inclusive; and
(c) one or more lipophilic emulsifier(s), wherein the concentration of the first lipophilic emulsifier in the four or more pharmaceutically acceptable excipients is between 25% and 40% by weight, inclusive;
provided that:
any two of: the one or more SERM(s) and the four or more pharmaceutically acceptable excipients are different from each other; and
the combined concentrations of the four or more pharmaceutically acceptable excipients are 100%.

The pharmaceutical compositions described herein may be able to deliver one or more SERM(s) directly (e.g., locally) to the vagina of a female subject in need thereof. The four or more pharmaceutically acceptable excipients may be compatible with the one or more SERM(s). The pharmaceutical compositions may be able to sufficiently spread the one or more SERM(s) over the vaginal mucosa. The pharmaceutical compositions may also be able to deliver the one or more SERM(s) to pass the vaginal mucosa over an extended period of time (e.g., 1, 2, 3, or 4 week(s), or 1, 2, 3, 4, 5, or 6 months, between the time of administration and the time when the concentration of the one or more SERM(s) in the vaginal mucosa is below the limit of quantification). Therefore, the pharmaceutical compositions may be able to directly deliver the one or more SERM(s) to a target tissue of the vagina in a controlled fashion (e.g., slow release). The pharmaceutical compositions may also be able to deliver the one or more SERM(s) to a target receptor (e.g., target receptor associated with a disease) before the one or more SERM(s) is/are deactivated.

In certain embodiments, the first SERM is lasofoxifene, bazedoxifene, raloxifene, arzoxifene, tamoxifen, or ormeloxifene, or a pharmaceutically acceptable salt, solvate, hydrate, polymorph, co-crystal, tautomer, stereoisomer, isotopically labeled derivative, or prodrug thereof.

In certain embodiments, the first (co)solvent is a polyalkylene glycol.

In certain embodiments, the second (co)solvent is a polyol.

In certain embodiments, the third (co)solvent is dimethyl sulfoxide.

In certain embodiments, the fourth (co)solvent is a polyol.

In certain embodiments, the first hydrophilic emulsifier is a non-ionic emulsifier, and the hydrophilic-lipophilic balance (HLB) value of the first hydrophilic emulsifier is between 12 and 14, inclusive.

In certain embodiments, the second hydrophilic emulsifier is a non-ionic emulsifier, and the HLB value of the second hydrophilic emulsifier is about 11 or between 13 and 15, inclusive.

In certain embodiments, the third hydrophilic emulsifier is a non-ionic emulsifier, and the HLB value of the third hydrophilic emulsifier is about 11.

In certain embodiments, the first lipophilic emulsifier is a non-ionic emulsifier, and the HLB value of the first lipophilic emulsifier is about 7.5.

The one or more SERM(s) in the pharmaceutical composition may be stable (e.g., chemically and/or physically stable) after being stored for a period of time (e.g., 1 month, 4 months, or 1 year). The four or more pharmaceutically acceptable excipients may be resistant to oxidation. In certain embodiments, the four or more pharmaceutically acceptable excipients further comprise: (e) one or more antioxidant(s), wherein the concentration of the first antioxidant in the four or more pharmaceutically acceptable excipients is not more than 5% by weight. In certain embodiments, the first antioxidant is butylated hydroxytoluene (BHT). In certain embodiments, the four or more pharmaceutically acceptable excipients further comprise: (f) one or more chelating agent(s), wherein the concentration of the first chelating agent in the four or more pharmaceutically acceptable excipients is not more than 5% by weight. In certain embodiments, the first chelating agent is ethylenediaminetetraacetic acid (EDTA), or a pharmaceutically acceptable salt thereof. In certain embodiments, the four or more pharmaceutically acceptable excipients are substantially free of tetraglycol and/or dimethyl sulfoxide. In certain embodiments, the pharmaceutical composition is substantially free of dioxygen.

In certain embodiments, the four or more pharmaceutically acceptable excipients consist of:

| Pharmaceutically acceptable excipient | Concentration in the four or more pharmaceutically acceptable excipients (% by weight) |
|---|---|
| polyethylene glycol 200 | about 10 |
| propylene glycol | about 10 |
| dimethyl sulfoxide | about 5 |
| KOLLIPHOR EL (macrogolglycerol ricinoleate) | about 28 |
| CAPMUL 907P (propylene glycol monoheptanoate) | about 28 |
| CAPTEX 300 EP/NF (glyceryl tricaprylate/tricaprate) | about 19. |

In certain embodiments, the four or more pharmaceutically acceptable excipients consist of:

| Pharmaceutically acceptable excipient | Concentration in the four or more pharmaceutically acceptable excipients (% by weight) |
|---|---|
| polyethylene glycol 200 | about 20 |
| propylene glycol | about 10 |
| dimethyl sulfoxide | about 2 |
| KOLLIPHOR EL (macrogolglycerol ricinoleate) | about 29 |
| CAPMUL 907P (propylene glycol monoheptanoate) | about 29 |
| CAPTEX 8000 (glyceryl tricaprylate) | about 10. |

In certain embodiments, the four or more pharmaceutically acceptable excipients consist of:

| Pharmaceutically acceptable excipient | Concentration in the four or more pharmaceutically acceptable excipients (% by weight) |
|---|---|
| polyethylene glycol 200 | about 20 |
| propylene glycol | about 10 |
| dimethyl sulfoxide | about 2 |
| KOLLIPHOR EL (macrogolglycerol ricinoleate) | about 19 |
| ACCONON MC8-2 (a mixture of monoesters, diesters, and triesters of glycerol, and monoesters and diesters of polyethylene glycols with a mean relative molecular weight between 200 and 400, inclusive) | about 10 |
| CAPMUL 907P (propylene glycol monoheptanoate) | about 29 |
| CAPTEX 8000 (glyceryl tricaprylate) | about 10. |

In certain embodiments, the four or more pharmaceutically acceptable excipients consist of:

| Pharmaceutically acceptable excipient | Concentration in the four or more pharmaceutically acceptable excipients (% by weight) |
|---|---|
| polyethylene glycol 200 | about 20 |
| propylene glycol | about 10 |
| dimethyl sulfoxide | about 5 |
| tetraglycol | about 9 |
| KOLLIPHOR EL | about 28 |
| CAPMUL 907P | about 28. |

In certain embodiments, the four or more pharmaceutically acceptable excipients consist of:

| Pharmaceutically acceptable excipient | Concentration in the four or more pharmaceutically acceptable excipients (% by weight) |
|---|---|
| polyethylene glycol 200 | about 15 |
| propylene glycol | about 10 |
| dimethyl sulfoxide | about 5 |
| tetraglycol | about 10 |
| KOLLIPHOR EL | about 25.5 |
| CAPMUL 907P | about 27 |
| CAPTEX 8000 | about 7.5. |

In certain embodiments, the four or more pharmaceutically acceptable excipients consist of:

| Pharmaceutically acceptable excipient | Concentration in the four or more pharmaceutically acceptable excipients (% by weight) |
| --- | --- |
| polyethylene glycol 200 | about 20 |
| propylene glycol | about 10 |
| dimethyl sulfoxide | about 5 |
| tetraglycol | about 10 |
| KOLLIPHOR EL | about 19 |
| TWEEN 85 (polyoxyethylenesorbitan trioleate) | about 7 |
| CAPMUL 907P | about 29. |

In certain embodiments, the four or more pharmaceutically acceptable excipients consist of:

| Pharmaceutically acceptable excipient | Concentration in the four or more pharmaceutically acceptable excipients (% by weight) |
| --- | --- |
| polyethylene glycol 200 | about 20 |
| propylene glycol | about 10 |
| dimethyl sulfoxide | about 5 |
| tetraglycol | about 9 |
| KOLLIPHOR EL | about 28 |
| CAPMUL PG-8 NF | about 28. |

In certain embodiments, the four or more pharmaceutically acceptable excipients consist of:

| Pharmaceutically acceptable excipient | Concentration in the four or more pharmaceutically acceptable excipients (% by weight) |
| --- | --- |
| polyethylene glycol 200 | about 20 |
| propylene glycol | about 10 |
| dimethyl sulfoxide | about 5 |
| tetraglycol | about 9 |
| KOLLIPHOR EL | about 28 |
| CAPRYOL 90 | about 28. |

In certain embodiments, the four or more pharmaceutically acceptable excipients consist of:

| Pharmaceutically acceptable excipient | Concentration in the four or more pharmaceutically acceptable excipients (% by weight) |
| --- | --- |
| polyethylene glycol 200 | about 21 |
| propylene glycol | about 10 |
| dimethyl sulfoxide | about 5 |
| tetraglycol | about 9 |
| KOLLIPHOR EL | about 27 |
| CAPMUL PG-8 NF | about 28 |
| butylated hydroxytoluene (BHT) | about 0.05. |

In certain embodiments, the four or more pharmaceutically acceptable excipients consist of:

| Pharmaceutically acceptable excipient | Concentration in the four or more pharmaceutically acceptable excipients (% by weight) |
| --- | --- |
| polyethylene glycol 200 | about 24 |
| propylene glycol | about 15 |
| dimethyl sulfoxide | about 5 |
| KOLLIPHOR EL | about 28 |
| CAPMUL PG-8 NF | about 28 |
| butylated hydroxytoluene (BHT) | about 0.05. |

In certain embodiments, the four or more pharmaceutically acceptable excipients consist of:

| Pharmaceutically acceptable excipient | Concentration in the four or more pharmaceutically acceptable excipients (% by weight) |
| --- | --- |
| polyethylene glycol 200 | about 19.99 |
| propylene glycol | about 9.995 |
| dimethyl sulfoxide | about 4.9975 |
| tetraglycol | about 8.9955 |
| KOLLIPHOR EL | about 27.986 |
| CAPMUL PG-8 NF | about 27.986 |
| butylated hydroxytoluene (BHT) | about 0.05. |

In certain embodiments, a pharmaceutical composition described herein is in the form of nanodroplets. In certain embodiments, the average size of the nanodroplets is between 10 nm and 100 nm, inclusive, as determined by dynamic light scattering (DLS). In certain embodiments, the polydispersity index (DPI) of the nanodroplets is between 0.1 and 0.7, inclusive.

In certain embodiments, a pharmaceutical composition described herein encapsulates the one or more SERM(s). In certain embodiments, a pharmaceutical composition described herein protects the one or more SERM(s) against mucus interactions (e.g., once the one or more SERM(s) getting in contact with water or bodily fluids).

In another aspect, the present disclosure provides methods of delivering one or more SERM(s) to a female subject in need thereof, the methods comprising contacting the vagina of the female subject with a pharmaceutical composition described herein.

In certain embodiments, the female subject is in need of treatment of vulvovaginal atrophy; and the amount of the pharmaceutical composition is therapeutically effective for treating vulvovaginal atrophy.

In certain embodiments, the female subject is in need of prevention of vulvovaginal atrophy; and the amount of the pharmaceutical composition is prophylactically effective for preventing vulvovaginal atrophy.

In certain embodiments, the female subject is in need of treatment of sexual dysfunction, osteoporosis, or breast cancer; and the amount of the pharmaceutical composition is therapeutically effective for treating sexual dysfunction, osteoporosis, or breast cancer, respectively.

In certain embodiments, the female subject is in need of prevention of sexual dysfunction, osteoporosis, or breast cancer; and the amount of the pharmaceutical composition is prophylactically effective for preventing sexual dysfunction, osteoporosis, or breast cancer, respectively.

In certain embodiments, a method described herein comprises contacting the vagina with the pharmaceutical composition more than once, wherein the frequency of contacting is once per week.

In another aspect, the present disclosure provides methods of preparing a pharmaceutical composition described herein comprising:
mixing the four or more pharmaceutically acceptable excipients to form a mixture of pharmaceutically acceptable excipients; and
mixing the one or more SERM(s) with the mixture of pharmaceutically acceptable excipients.

In another aspect, the present disclosure provides methods of preparing a pharmaceutical composition described herein comprising:
mixing the one or more SERM(s) with one or more of the (co)solvent(s) to form a mixture of the one or more SERM(s) and one or more of the (co)solvent(s); and
mixing the remaining pharmaceutically acceptable excipients with the mixture of SERM(s) and one or more of the (co)solvent(s).

In another aspect, the present disclosure provides kits comprising:
a pharmaceutical composition described herein; and
instructions for using the pharmaceutical composition.

In another aspect, the present disclosure provides uses of a pharmaceutical composition described herein in a method described herein.

The details of one or more embodiments of the present disclosure are set forth herein. Other features, objects, and advantages of the present disclosure will be apparent from the Detailed Description of Certain Embodiments, Examples, Figures (Drawings), and Claims.

BRIEF DESCRIPTION OF THE DRAWINGS

FIG. 10A shows the droplet size at 2% formulation in water. FIG. 10B shows the droplet size at 30% formulation in water. Before (white bars), cycle 1 (medium grey bars), cycle 2 (dark grey bars).

FIG. 13 shows the polydispersity index (PDI) and standard deviation (SD) of emulsion stability in water, simulated saliva, simulated tears, and simulated vaginal fluid for 2% formulation and 30% formulation at 0, 2, and 4 hours.

DETAILED DESCRIPTION OF CERTAIN EMBODIMENTS

Figure 1:
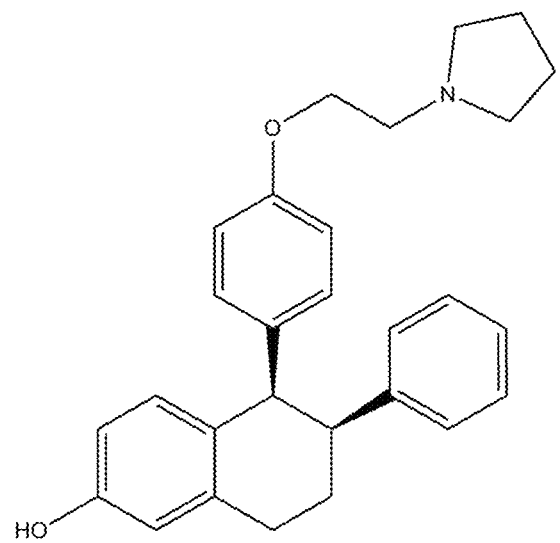
FIG. 1 shows the chemical structure of Lasofoxifene.

The present disclosure provides, in one aspect, pharmaceutical compositions comprising (i) one or more SERM(s); and (ii) four or more pharmaceutically acceptable excipients. In certain embodiments, the pharmaceutical compositions are SNEDDs. The pharmaceutical compositions may be useful for delivering the one or more SERM(s) to the vagina (e.g., a target tissue associated with the vaginal disease) of a female subject. In other aspects, the present disclosure provides methods of delivering one or more SERM(s) to a female subject in need thereof using the pharmaceutical compositions, methods of preparing the pharmaceutical compositions, and kits comprising the pharmaceutical compositions.

Pharmaceutical Compositions

In one aspect, the present disclosure provides pharmaceutical compositions comprising:
(i) one or more SERM(s); and
(ii) four or more pharmaceutically acceptable excipients comprising:
  (a) two or more (co)solvents, wherein:
    the concentration of the first (co)solvent in the four or more pharmaceutically acceptable excipients is between 10% and 25% by weight, inclusive; and
    the concentration of the second (co)solvent in the four or more pharmaceutically acceptable excipients is between 10% and 15% by weight, inclusive;
  (b) one or more hydrophilic emulsifier(s), wherein the concentration of the first hydrophilic emulsifier in the four or more pharmaceutically acceptable excipients is between 15% and 35% by weight, inclusive; and
  (c) one or more lipophilic emulsifier(s), wherein the concentration of the first lipophilic emulsifier in the four or more pharmaceutically acceptable excipients is between 25% and 40% by weight, inclusive;
provided that:
  any two of: the one or more SERM(s) and the four or more pharmaceutically acceptable excipients are different from each other; and
  the combined concentrations of the four or more pharmaceutically acceptable excipients are 100%.

The pharmaceutical compositions may be useful for delivering the one or more SERM(s) to the vagina (e.g., a target tissue associated with a disease) of a female subject in need thereof. The pharmaceutical compositions may also be useful for treating a disease in a female subject in need thereof. The pharmaceutical compositions may also be useful for preventing a disease in a female subject in need thereof. In certain embodiments, the disease is vulvovaginal atrophy, dyspareunia, sexual dysfunction, osteoporosis, or breast cancer.

The term "selective estrogen receptor modulator" or "SERM" refers to an agent (e.g., a small molecule (e.g., a molecule wherein the molecular weight of the molecule is not more than 2,000 g/mol), peptide, protein, or polynucleotide) that binds with high affinity to the estrogen receptor and has differential effects of estrogenic gene expression and biological responses. In certain embodiments, a SERM described herein is as defined in Wardell et al., *Steroids.* 2014, 90, 30-38. Examples of SERM include, but are not limited to, arzoxifene, bazedoxifene, droloxifene, ormeloxifene, ospemifene, raloxifene, lasofoxifene, TSE424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646, and pharmaceutically acceptable salts, solvates, hydrates, polymorphs, co-crystals, tautomers, stereoisomers, isotopically labeled derivatives, and prodrugs thereof (e.g., pharmaceutically acceptable salts thereof).

The term "(co)solvent" refers to a solvent or a co-solvent. The term "solvent" refers to a substance that is able to dissolve the one or more SERM(s) at 25° C. and 1 atmosphere to form a solution. The term "co-solvent" refers to a substance that is able to increase the ability of a solvent in dissolving the one or more SERM(s). In certain embodiments, the concentration of the one or more SERM(s) in the solution that consist of the one or more SERM(s) and the (co)solvent(s) is at least 1 ng/ml, at least 10 ng/ml, or at least 100 ng/ml. In certain embodiments, the concentration of the one or more SERM(s) in the solution that consist of the one or more SERM(s) and the (co)solvent(s) is at least 1 µg/ml. In certain embodiments, the concentration of the one or more SERM(s) in the solution that consist of the one or more SERM(s) and the (co)solvent(s) is at least 10 µg/ml. In certain embodiments, the concentration of the one or more SERM(s) in the solution that consist of the one or more SERM(s) and the (co)solvent(s) is at least 100 µg/ml. In certain embodiments, the concentration of the one or more SERM(s) in the solution that consist of the one or more SERM(s) and the (co)solvent(s) is at least 1 mg/ml. Examples of the (co)solvent include, but are not limited to TRANSCUTOL HP (highly purified diethylene glycol monoethyl ether EP/NF), TRANSCUTOL P (highly purified diethylene glycol monoethyl ether EP/NF), TRANSCUTOL V (highly purified diethylene glycol monoethyl ether EP/NF), TRANSCUTOL CG (ethoxydiglycol) polyethylene glycol, tetraglycol, triethylene glycol, pentaglycol, hexaglycol, dimethyl sulfoxide, and methylsulfonylmethane. Further examples of the (co)solvent include, but are not limited to, the organic solvents described herein.

The term "hydrophilic-lipophilic balance" or "HLB" refers to the degree to which an emulsifier is hydrophilic or lipophilic. In certain embodiments, the HLB is determined by Griffin's method, as shown below:

$$HLB = 20 \times M_h/M,$$

wherein $M_h$ is the molecular weight of the hydrophilic portion of the emulsifier, and M is the molecular weight of the emulsifier as a whole. In certain embodiments, the HLB is determined by a method described in Griffin et al., *Journal of the Society of Cosmetic Chemists,* 1949, 1(5): 311-326.

The term "hydrophilic emulsifier" refers to non-ionic emulsifiers exhibiting a HLB value greater than 10 and ionic emulsifiers that include monovalent cations. Examples of the hydrophilic emulsifier include, but are not limited to KOLLIPHOR P 188 (poly(ethylene glycol)-block-polypropylene glycol)-block-poly(ethylene glycol)), KOLLIPHOR HS 15 (polyethylene glycol (15)-hydroxystearate), KOLLIPHOR P407 (poly(ethylene glycol)-block-polypropylene glycol)-block-poly(ethylene glycol)), CREMOPHOR A 25 (macrogol (25)-cetostearyl ether), CREMOPHOR CO 410 (PEG-40 hydrogenated castor oil), isosorbide dimethyl ether (DMI), Poloxamer 124 (poly(ethylene glycol)-block-polypropylene glycol)-block-poly(ethylene glycol)), LABRASOL (caprylocaproyl macrogol-8 glycerides EP), TWEEN 20 (polyoxyethylene (20) sorbitan monolaurate), TWEEN 80 (polyoxyethylene (20) sorbitan monooleate), ACCONON CC-6 (polyoxyethylene 6 caprylic/capric glycerides), ACCONON C-44 (polyoxyethylene 32 lauric glycerides), ACCONON CO-7 (polyoxyethylene 7 coconut glycerides), ACCONON C-30 (polyoxyethylene 30 coconut glycerides), ACCONON C-80 (polyoxyethylene 80 coconut glycerides), ACCONON Sorb-20 (polyoxyethylene 20 sorbitol), ACCONON E (polyoxypropylene 15 stearyl ether), Accomid PK (palm kernelamide diethanolamide), sodium stearate, sodium oleate, potassium palmitate, and sodium laurate. Further examples of the hydrophilic emulsifier include, but are not limited to, cremophor EL.

The terms "emulsifier" and "surfactant" are used interchangeably.

The term "lipophilic emulsifier" refers to non-ionic emulsifiers exhibiting a HLB value not greater than 10 and ionic emulsifiers that include polyvalent cations. Examples of the lipophilic emulsifier include, but are not limited to CAP- MUL 908P (Cap 908P; or propylene glycol monocaprylate), CAPMUL MCM (Cap MCM; medium chain mono- and di-glycerides), CAPMUL MCM C8 (glyceryl monocaprylate), CAPMUL PG-8 (propylene glycol monocaprylate), CAPMUL 471 (glyceryl caprylate/caprate), CAPMUL 708G (glyceryl monocaprylate), CAPMUL 808G EP/NF (glyceryl monocaprylate), CAPMUL GDB EP/NF (glyceryl dibehenate), CAPMUL GMO-50 (glyceryl monooleate), CAPMUL GMO-50 EP/NF (glyceryl monooleate), CAPMUL GMS-50K (glyceryl monostearate), CAPMUL MCM C8 EP/NF (glyceryl monocaprylate), CAPMUL MCM C10 (glyceryl monocaprate), CAPMUL MCM NF (glyceryl caprylate/caprate), CAPMUL MCM EP (glyceryl caprylate/caprate), CAPMUL PG-2L (propylene glycol dilaurate), CAPMUL PG-2L EP/NF (propylene glycol dilaurate), CAPMUL PG-8 NF (propylene glycol monocaprylate), CAPMUL PG-8-70 NF (propylene glycol monocaprylate, NF Type 1 requirements), CAPMUL PG-12 (propylene glycol monolaurate), CAPMUL PG-12 EP/NF (propylene glycol monolaurate), CAPMUL S12L (sodium lauroyl lactylate), CAPMUL S18L (sodium stearoyl-2-lactylate), PECEOL (glycerol monooleate) (e.g., glycerol monooleates (type 40) EP or glyceryl monooleate (type 40) NF), LABRAFIL M1944CS (oleoyl macrogol-6 glycerides) (e.g., oleoyl macrogol-6 glycerides EP or oleoyl polyoxyl-6 glycerides NF), LABRAFIL 2125 CS (linoleoyl macrogol-6 glycerides) (e.g., linoleoyl polyoxyl-6 glycerides EP or linoleoyl polyoxyl-6 glycerides NF), LABRAFIL 2130 CS (lauroyl macrogol-6 glycerides) (e.g., lauroyl polyoxyl-6 glycerides EP or lauroyl polyoxyl-6 glycerides NF), BRIJ 30 (polyoxyethylene(4)lauryl ether, CAPRYOL PGMC (propylene glycol monocaprylate (type I) NF), CAPRYOL 90 (propylene glycol monocaprylate (type II) NF), calcium stearate, magnesium stearate, and calcium oleate.

The terms "treatment of a disease," "treat a disease," and "treating a disease" refer to reversing, alleviating, delaying the onset of, or inhibiting the progress of a disease. In some embodiments, treatment may be administered after one or more signs or symptoms of the disease have developed or have been observed. In other embodiments, treatment may be administered in the absence of signs or symptoms of the disease. For example, treatment may be administered to a susceptible female subject prior to the onset of symptoms (e.g., in light of a history of symptoms and/or in light of exposure to a pathogen). Treatment may also be continued after symptoms have resolved, for example, to delay or prevent recurrence.

The term "prevent a disease," "preventing a disease," or "prevention of a disease" refers to a prophylactic treatment of a female subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

The term "vulvovaginal atrophy", "VVA", "trophic vaginitis", "vaginal atrophy", or "urogenital atrophy" are used interchangeably and refer to an inflammation of the vagina and/or outer urinary tract of a female subject with symptoms such as thinning, shrinking, reduced flexibility, soreness, and/or itching, of the tissue(s) of the vagina and/or outer urinary tract; decreased lubrication in the vagina and/or the outer urinary tract; painful sexual intercourse; and/or bleeding after sexual intercourse. In certain embodiments, the cause of vulvovaginal atrophy is a decrease in the level of estrogen in the female subject. The decrease in the level of estrogen may occur naturally during perimenopause and/or post-menopause. The decrease in the level of estrogen may also occur due to breastfeeding and/or the use of medications intended to decrease estrogen to, for example, treat endometriosis.

The term "osteoporosis" or "osteoporotic" refers to a disease of a bone of a subject (e.g., female subject) where the density of the bone is 2.5 standard deviations below that of a young adult subject. In certain embodiments, the density of the bone is measured by dual-energy X-ray absorptiometry at the hip. An osteoporotic bone may have lost density and/or mass, and/or may contain abnormal tissue structure rendering a skeleton at risk for fractures. Therefore, the strength of an osteoporotic bone is lower than the strength of a healthy bone. A subject with osteoporosis may break a bone from a fall or, in serious cases, from sneezing and/or minor bumps. Symptoms of osteoporosis may also include loss of height of the subject, a stooped and/or hunched posture, reduced mobility, and/or pain. Osteoporosis may occur when the subject loses too much bone, makes too little bone, or both. Osteoporosis may occur in a subject (e.g., a post-menopausal woman) due to a decreased level of estrogen. Osteoporosis may also occur due to conditions such as alcoholism, smoking, insufficient exercise, anorexia, hyperthyroidism, surgical removal of the ovaries, and/or kidney disease. Osteoporosis may also occur due to treatments such as antiseizure medications, chemotherapy, proton pump inhibitors, selective serotonin reuptake inhibitors, and/or steroids.

The term "dyspareunia" refers to painful sexual intercourse. The pain may be on the external surface of the genitalia, and/or deeper in the pelvis upon deep pressure against the cervix. The pain may be felt in a portion or the whole of the vulva and/or vagina. The cause of dyspareunia may be anatomic or physiologic, including but not limited to estrogen deficiency, endometriosis, adenomyosis, lesions of the vagina, retroversion of the uterus, urinary tract infection, lack of lubrication, scar tissue, abnormal growths, presence of objects, bladder irritation, vulvodynia, conditions that affect the surface of the vulva, and/or muscular dysfunction. The cause of dyspareunia may also be psychosomatic, including but not limited to vaginismus, fear of pain and/or injury, feelings of guilt and/or shame, ignorance of sexual anatomy and/or physiology, and/or fear of pregnancy.

"Sexual dysfunction" in a female subject refers to a condition during any phase of the sexual response cycle that prevents the female subject from experiencing satisfaction from a sexual activity. A sexual response cycle may have four phases: excitement, plateau, orgasm, and resolution. Symptoms of sexual dysfunction include, but are not limited to, inhibited sexual desire, inability to become aroused, lack of orgasm, and/or painful intercourse. Sexual dysfunction may be caused by physical causes (e.g., diabetes, heart diseases, neurological disorders, hormonal imbalances, menopause, chronic diseases (e.g., kidney failure and/or liver failure), alcoholism, and/or drug abuse). Sexual dysfunction may also be caused by psychological causes (e.g., work-related stress, concerns about sexual performance, marital problems, relationship problems, depression, feelings of guilt, and/or the effects of a past sexual trauma). Hormones may play a role in regulating sexual function in the female subject. With the decrease in the levels of estrogen, the female subject may experience changes in sexual function as she ages. Poor vaginal lubrication and/or decreased genital sensation may be symptoms associated with decreased levels of estrogen. Moreover, decreased levels of testosterone may also contribute to a decline in sexual arousal, genital sensation, and/or orgasm.

In certain embodiments, the breast cancer is invasive breast cancer (e.g., invasive ductal carcinoma (IDC) or invasive lobular carcinoma (ILC)).

In certain embodiments, the target tissue is a tissue directly or indirectly underneath the vaginal mucosa. In certain embodiments, the target tissue is a tissue associated with a disease (e.g., vulvovaginal atrophy, dyspareunia, sexual dysfunction, osteoporosis, or breast cancer). In certain embodiments, a target receptor is an estrogen receptor.

Lasofoxifene adheres to the vaginal mucus layer and, in certain embodiments, does not penetrate to reach its target, the underlying tissue (e.g., epithelial tissue). A likely explanation for this phenomenon is ionic interactions, as on the one hand, the vaginal mucus has a negative net charge because of sialic acid and sulfonic acid substructures, and on the other hand Lasofoxifene is a cationic drug due to its tertiary amine substructure (FIG. 1). As experiments having been performed in a previous study by Thiomatrix showed that 78.7±3.8% of the drug was tightly bound to the mucus within 60 minutes, the vaginal drug delivery system had to ensure a protection against such unintended interactions. Consequently, the drug can only to a very limited extent spread over the vaginal mucosa and cannot penetrate the mucus gel layer in order to reach the underlying tissue and its target receptors. From the formulation point of view, encapsulation of the drug may avoid such unintended interactions. Such capsules need to spread on the mucosa and need to penetrate the mucus gel layer, however, they have to be in a size range<340 nm, as the pore size in fresh undiluted human cervicovaginal mucus was determined to be 340±70 nm [Lai S K, Wang Y Y, Hida K, Cone R, Hanes J., Nanoparticles reveal that human cervicovaginal mucus has an abundance of pores larger than viruses. Proc Natl Acad Sci USA. 2010 Jan. 12; 107(2):598-603]. In addition, such capsules need to exhibit a 'slippery' surface to move freely in the mucus gel layer. As only 0.5-0.75 mL of vaginal fluid is continually present in the vagina [A. Bernkop-Schnürch, M. Hornof, Intravaginal Drug Delivery Systems, Design, Challenges, and Solutions, American Journal of Drug Delivery, 1 (2013) 241-254], SNEDD formulations forming nanodroplets when diluted 1:2 with vaginal fluid may be desired. In certain embodiments, the nanodroplets exhibit a 'slippery' surface being capable of spreading, of penetrating the mucus gel layer, and/or of shielding the drug from interactions with the mucus by being incorporated in nanodroplets. In certain embodiments, the one or more lipophilic emulsifier(s) lead to a 'slippery' surface of the nanodroplets representing a zeta-potential of nearly zero. In certain embodiments, interactions and/or incompatibilities with the positively charged Lasofoxifene are prevented and/or excluded by using one or more lipophilic emulsifier(s) (e.g., lipophilic emulsifier(s) without any net charge).

A pharmaceutical composition described herein that comprises a SERM that is not lasofoxifene may also be useful for delivering the SERM to the vagina. Without being bound by any particular theory, a SERM that is not lasofoxifene may be delivered to the vagina by the pharmaceutical composition because of the structural similarity between lasofoxifene and the SERM that is not lasofoxifene.

In certain embodiments, the Tanimoto coefficient (see, e.g., Maggiora et al., *J. Med. Chem.*, 2014, 57, 3186-3204) of similarity between lasofoxifene and a SERM that is not lasofoxifene is between 0.5 and 1, between 0.6 and 1, between 0.7 and 1, between 0.8 and 1, or between 0.9 and 1, exclusive. In certain embodiments, a SERM (e.g., the active component of the SERM when the SERM includes multiple components (e.g., an ionic active component and a non-active counter-ion) that is not lasofoxifene includes a positive net charge under physiological conditions and includes a lipophilic moiety. In certain embodiments, a SERM (e.g., the active component of the SERM when the SERM includes multiple components (e.g., an ionic active component and a non-active counter-ion) that is not lasofoxifene includes an amine moiety (e.g., a tertiary or quaternary amine moiety) and a lipophilic moiety.

In certain embodiments, the pharmaceutical composition comprises only one SERM. In certain embodiments, the pharmaceutical composition comprises two or more SERM(s). In certain embodiments, the first SERM is lasofoxifene, bazedoxifene, raloxifene, arzoxifene, tamoxifen, or ormeloxifene, or a pharmaceutically acceptable salt, solvate, hydrate, polymorph, co-crystal, tautomer, stereoisomer, isotopically labeled derivative, or prodrug thereof. In certain embodiments, the first SERM is lasofoxifene, or a pharmaceutically acceptable salt, solvate, hydrate, polymorph, co-crystal, tautomer, stereoisomer, isotopically labeled derivative, or prodrug thereof. In certain embodiments, the first SERM is lasofoxifene, or a pharmaceutically acceptable salt thereof (e.g., lasofoxifene tartrate).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the SERMs described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of a SERM, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The SERMs described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a SERM that is associated with water. Typically, the number of the water molecules contained in a hydrate of a SERM is in a definite ratio to the number of the SERM molecules in the hydrate. Therefore, a hydrate of a SERM may be represented, for example, by the general formula $R \cdot x\, H_2O$, wherein R is the SERM, and x is a number greater than 0. A given SERM may form more than one type of hydrate, including, e.g., monohydrates (x is 1), lower hydrates (x is a number greater than 0 and smaller than 1, e.g., hemihydrates ($R \cdot 0.5\, H_2O$)), and polyhydrates (x is a number greater than 1, e.g., dihydrates ($R \cdot 2\, H_2O$) and hexahydrates ($R \cdot 6\, H_2O$)).

The term "tautomers" or "tautomeric" refers to two or more interconvertible SERMs resulting from at least one formal migration of a hydrogen atom and at least one change in valency (e.g., a single bond to a double bond or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that SERMs that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a SERM has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral SERM can exist as either individual enantiomer or as a mixture thereof. A mixture containing equal proportions of the enantiomers is called a "racemic mixture".

The term "polymorphs" refers to a crystalline form of a SERM (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a SERM can be prepared by crystallization under different conditions.

The term "prodrugs" refers to SERMs that have cleavable groups and become by solvolysis or under physiological conditions the SERMs described herein, which are pharmaceutically active in vivo. Such examples include, but are not limited to, choline ester derivatives and the like, N-alkylmorpholine esters and the like. Other derivatives of the SERMs described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the SERMs described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the SERMs described herein may be preferred.

In certain embodiments, the concentration of the first SERM in the pharmaceutical composition is between 0.1 µg/ml and 3,000 µg/ml, inclusive. In certain embodiments, the concentration of the first SERM in the pharmaceutical composition is between 0.1 µg/ml and 150 µg/ml, inclusive. In certain embodiments, the concentration of the first SERM in the pharmaceutical composition is between 150 µg/ml and 750 µg/ml, inclusive. In certain embodiments, the concentration of the first SERM in the pharmaceutical composition is between 1 µg/ml and 3,000 µg/ml, between 1 µg/ml and 1,000 µg/ml, between 10 µg/ml and 3,000 µg/ml, between 30 µg/ml and 3,000 µg/ml, between 150 µg/ml and 3,000 µg/ml, between 750 µg/ml and 3,000 µg/ml, between 0.1 µg/ml and 750 µg/ml, between 1 µg/ml and 750 µg/ml, between 10 µg/ml and 750 µg/ml, or between 30 µg/ml and 750 µg/ml, inclusive. In certain embodiments, the concentration of the first SERM in the pharmaceutical composition is between 0.1 µg/ml and 1 µg/ml, between 0.1 µg/ml and 10 µg/ml, between 1 µg/ml and 10 µg/ml, between 1 µg/ml and 150 µg/ml, or between 10 µg/ml and 150 µg/ml, inclusive. In certain embodiments, the concentration of the first SERM in the pharmaceutical composition is between 0.1 ng and 1 ng, between 0.1 ng and 10 ng, between 0.1 ng and 100 ng, between 1 ng/ml and 10 ng/ml, between 1 ng/ml and 100 ng/ml, between 1 ng/ml and 1 µg/ml, between 10 ng/ml and 100 ng/ml, or between 10 ng/ml and 1 µg/ml, inclusive. In certain embodiments, the concentration of the first SERM in the pharmaceutical composition is between 0.1 ng/ml and 100 ng/ml, inclusive. In certain embodiments, the concentration of the first SERM in the pharmaceutical composition is about 0.25 mg/ml, about 0.025 mg/ml, about 0.0025 mg/ml, or about 0.00025 mg/ml.

The pharmaceutical composition comprises four or more pharmaceutically acceptable excipients. In certain embodiments, the pharmaceutical composition comprises four or five pharmaceutically acceptable excipients. In certain embodiments, the pharmaceutical composition comprises six or seven pharmaceutically acceptable excipients. In certain embodiments, the pharmaceutical composition comprises eight, nine, or ten pharmaceutically acceptable excipients. In certain embodiments, the pharmaceutical composition comprises between eleven and twenty, inclusive, pharmaceutically acceptable excipients. In certain embodiments, the concentration of any pharmaceutically acceptable excipient in the four or more pharmaceutically acceptable excipients is at least 0.001%, at least 0.003%, at least 0.01%, at least 0.05%, at least 0.1%, at least 0.3%, or at least 1%, by weight. In certain embodiments, each two pharmaceutically acceptable excipients are different from each other. In certain embodiments, any pharmaceutically acceptable excipient is not a pharmaceutically acceptable salt, solvate, hydrate, polymorph, co-crystal, tautomer, stereoisomer, isotopically labeled derivative, or prodrug of any another pharmaceutically acceptable excipient.

In certain embodiments, the pharmaceutical composition comprises two (co)solvents. In certain embodiments, the first (co)solvent is a polyalkylene glycol. In certain embodiments, the polyalkylene glycol is a polyethylene glycol (PEG). In certain embodiments, the polyalkylene glycol is PEG 200. In certain embodiments, the polyalkylene glycol is PEG 300, PEG 400, PEG 500, PEG 600, PEG 700, PEG 800, PEG 900, or PEG 1000. In certain embodiments, the polyalkylene glycol is a methoxypolyethylene glycol (mPEG) (e.g., mPEG 350, mPEG 550, or mPEG 750). In certain embodiments, the polyalkylene glycol is a polypropylene glycol. In certain embodiments, the first (co)solvent is TRANSCUTOL HP (highly purified diethylene glycol monoethyl ether EP/NF). In certain embodiments, the first (co)solvent is TRANSCUTOL P (highly purified diethylene glycol monoethyl ether EP/NF), TRANSCUTOL V (highly purified diethylene glycol monoethyl ether EP/NF), or TRANSCUTOL CG (ethoxydiglycol).

In certain embodiments, the concentration of the first (co)solvent in the four or more pharmaceutically acceptable excipients is between 10% and 25% by weight, inclusive. the concentration of the first (co)solvent in the four or more pharmaceutically acceptable excipients is between 10% and 20%, between 10% and 15%, between 15% and 25%, between 15% and 20%, or between 20% and 25%, by weight, inclusive. In certain embodiments, the concentration of the first (co)solvent in the four or more pharmaceutically acceptable excipients is about 10% by weight. In certain embodiments, the concentration of the first (co)solvent in the four or more pharmaceutically acceptable excipients is about 20% by weight.

The term "about X," wherein X is a number or percentage, refers to "approximately X." In certain embodiments, "about X" refers to X±2%. In certain embodiments, "about X" refers to X±5%. In certain embodiments, "about X" refers to X±10%. In certain embodiments, "about X" refers to X±15%. In certain embodiments, "about X" refers to X±20%.

In certain embodiments, the second (co)solvent is a polyol. In certain embodiments, the second (co)solvent is a diol (e.g., a vicinal diol). In certain embodiments, the polyol is propylene glycol. In certain embodiments, the polyol is not ethylene glycol. In certain embodiments, the four or more pharmaceutically acceptable excipients are substantially free of ethylene glycol. In certain embodiments, the concentration of ethylene glycol in the four or more pharmaceutically acceptable excipients is not more than 1%, not more than 0.3%, not more than 0.1%, not more than 0.03%, not more than 0.01%, not more than 0.003%, or not more than 0.001%, by weight. In certain embodiments, the polyol is trimethylene glycol, 1,2-butylene glycol, 1,3-butanediol, 1,4-butanediol, 1,5-pentanediol, 1,2-hexylene glycol, 1,10-decanediol, 1,2-cyclohexanediol, 2-butene-1,4-diol, 3-cyclohexene-1,1-dimethanol, 4-methyl-3-cyclohexene-1,1-dimethanol, 3-methylene-1,5-pentanediol, diethylene glycol, (2-hydroxyethoxy)-1-propanol, 4-(2-hydroxyethoxy)-1-butanol, 5-(2-hydroxypropoxy)-1-pentanol, 1-(2-hydroxymethoxy)-2-hexanol, 1-(2-hydroxypropoxy)-2-octanol, 3-allyloxy-1,5-pentanediol, 2-[(allyloxy)methyl]-2-methyl-1,3-propanediol, [(4-pentenyloxy)-methyl]-1,3-propanediol, 2-methyl-2-[(10-undecenyloxy)-methyl]-1,3-propanediol, 3-(o-propenylphenoxy)-1,2-propanediol, thiodiglycol, or 2,2 [thiobis(ethyleneoxy)]-diethanol. In certain embodiments, the second (co)solvent is a triol, tetraol, pentaol, or hexaol. In certain embodiments, the second (co)solvent is glycerol.

In certain embodiments, the second (co)solvent in the four or more pharmaceutically acceptable excipients is between 10% and 15% by weight, inclusive. In certain embodiments, the second (co)solvent in the four or more pharmaceutically acceptable excipients is between 10% and 12% or between 12% and 15%, by weight, inclusive. In certain embodiments, the second (co)solvent in the four or more pharmaceutically acceptable excipients is about 10% by weight.

In certain embodiments, the two or more (co)solvents consist of two (co)solvents.

In certain embodiments, the two or more (co)solvents further comprise a third (co)solvent, wherein the concentration of the third (co)solvent in the four or more pharmaceutically acceptable excipients is not more than 10% by weight. In certain embodiments, the pharmaceutical composition comprises only three (co)solvents. In certain embodiments, the third (co)solvent is dimethyl sulfoxide (DMSO). In certain embodiments, the third (co)solvent is methylsulfonylmethane (MSM).

In certain embodiments, the concentration of the third (co)solvent in the four or more pharmaceutically acceptable excipients is not more than 10% by weight. In certain embodiments, the concentration of the third (co)solvent in the four or more pharmaceutically acceptable excipients is not more than 7%, not more than 5%, not more than 3%, not more than 2%, or not more than 1% by weight. In certain embodiments, the concentration of the third (co)solvent in the four or more pharmaceutically acceptable excipients is about 5% by weight. In certain embodiments, the concentration of the third (co)solvent in the four or more pharmaceutically acceptable excipients is about 2% by weight.

In certain embodiments, the two or more (co)solvents further comprise a fourth (co)solvent, wherein the concentration of the fourth (co)solvent in the four or more pharmaceutically acceptable excipients is not more than 10% by weight. In certain embodiments, the pharmaceutical composition comprises only four (co)solvents. In certain embodiments, the fourth (co)solvent is a polyol (e.g., a polyglycol). In certain embodiments, the fourth (co)solvent is tetraglycol (e.g., commercially available tetraglycol, such as Lot: BCBN1446V, Sigma-Aldrich, Vienna, Austria). In certain embodiments, the fourth (co)solvent is triethylene glycol, pentaglycol, or hexaglycol.

In certain embodiments, the concentration of the fourth (co)solvent in the four or more pharmaceutically acceptable excipients is not more than 10% by weight. In certain embodiments, concentration of the fourth (co)solvent in the four or more pharmaceutically acceptable excipients is not more than 7%, not more than 5%, not more than 3%, or not more than 1% by weight.

In certain embodiments, the four or more pharmaceutically acceptable excipients are substantially free of tetraglycol. In certain embodiments, the concentration of tetraglycol in the four or more pharmaceutically acceptable excipients is not more than 1%, not more than 0.3%, not more than 0.1%, not more than 0.03%, not more than 0.01%, not more than 0.003%, or not more than 0.001%, by weight.

In certain embodiments, the two or more (co)solvents further comprise a fifth (co)solvent, wherein the concentration of the fourth (co)solvent in the four or more pharmaceutically acceptable excipients is not more than 10% by weight. In certain embodiments, the two or more (co) solvents consist of five (co)solvents.

In certain embodiments, the first and second (co)solvents are polyethylene glycol 200 and propylene glycol, respectively. In certain embodiments, the first, second, and third (co)solvents are polyethylene glycol 200, propylene glycol, and DMSO, respectively. In certain embodiments, the first, second, third, and fourth (co)solvents are polyethylene glycol 200, propylene glycol, DMSO, and tetraglycol, respectively.

In certain embodiments, the concentrations of the first and second (co)solvents in the four or more pharmaceutically acceptable excipients are about 10% and about 10%, by weight, respectively. In certain embodiments, the concentrations of the first and second (co)solvents in the four or more pharmaceutically acceptable excipients are about 20% and about 10%, by weight, respectively. In certain embodiments, the concentrations of the first, second, and third (co)solvents in the four or more pharmaceutically acceptable excipients are about 10%, about 10%, and about 5%, by weight, respectively. In certain embodiments, the concentrations of the first, second, and third (co)solvents in the four or more pharmaceutically acceptable excipients are about 20%, about 10%, and about 2%, by weight, respectively.

In certain embodiments, the two or more (co)solvents further comprise water. In certain embodiments, the two or more (co)solvents are substantially free of water. In certain embodiments, the concentration of water in the two or more (co)solvents is not more than 1%, not more than 0.3%, not more than 0.1%, not more than 0.03%, not more than 0.01%, not more than 0.003%, or not more than 0.001%, by weight.

In certain embodiments, the hydrophilic emulsifier(s) are non-ionic emulsifier(s), and the HLB values of the hydrophilic emulsifier(s) are greater than 10. In certain embodiments, the hydrophilic emulsifier(s) are non-ionic emulsifier(s), and the HLB values of the hydrophilic emulsifier(s) are between 10 and 18, between 10 and 16, between 10 and 14, between 10 and 12, between 12 and 18, between 12 and 16, between 12 and 14, between 14 and 18, between 14 and 16, or between 16 and 18, inclusive. In certain embodiments, the hydrophilic emulsifier(s) are ionic emulsifier(s) that include monovalent cations.

In certain embodiments, the first hydrophilic emulsifier is a non-ionic emulsifier, and the HLB value of the first hydrophilic emulsifier is between 10 and 18, between 10 and 16, between 10 and 14, between 10 and 12, between 12 and 18, between 12 and 16, between 12.5 and 13.5, between 14 and 18, between 14 and 16, or between 16 and 18, inclusive. In certain embodiments, the first hydrophilic emulsifier is a non-ionic emulsifier, and the HLB value of the first hydrophilic emulsifier is between 12 and 14, inclusive. In certain embodiments, the first hydrophilic emulsifier is an ionic emulsifier that includes monovalent cation(s).

In certain embodiments, the first hydrophilic emulsifier is KOLLIPHOR EL (Cremophor EL; Crem EL; or macrogolglycerol ricinoleate). In certain embodiments, the first hydrophilic emulsifier is KOLLIPHOR RH 40 (macrogolglycerol hydroxystearate; Cremophor RH 40). In certain embodiments, the first hydrophilic emulsifier is KOLLIPHOR P 188 (poly(ethylene glycol)-block-poly(propylene glycol)-block-poly(ethylene glycol)), KOLLIPHOR HS 15 (polyethylene glycol (15)-hydroxystearate), or KOLLIPHOR P407 (poly(ethylene glycol)-block-polypropylene glycol)-block-poly(ethylene glycol)). In certain embodiments, the first hydrophilic emulsifier is CREMOPHOR A 25 (macrogol (25)-cetostearyl ether). In certain embodiments, the first hydrophilic emulsifier is CREMOPHOR CO 410 (PEG-40 hydrogenated castor oil). In certain embodiments, the first hydrophilic emulsifier is isosorbide dimethyl ether (DMI). In certain embodiments, the first hydrophilic emulsifier is Poloxamer 124 (poly(ethylene glycol)-block-poly(propylene glycol)-block-poly(ethylene glycol)). In certain embodiments, the first hydrophilic emulsifier is triacetin. In certain embodiments, the first hydrophilic emulsifier is LABRASOL (caprylocaproyl macrogol-8 glycerides EP or caprylocaproyl polyoxyl-8 glycerides NF).

In certain embodiments, the concentration of the first hydrophilic emulsifier in the four or more pharmaceutically acceptable excipients is between 15% and 35% by weight, inclusive. In certain embodiments, the concentration of the first hydrophilic emulsifier in the four or more pharmaceutically acceptable excipients is between 15% and 30%, between 15% and 25%, between 15% and 20%, between 20% and 35%, between 20% and 30%, between 20% and 25%, between 25% and 35%, between 25% and 30%, or between 30% and 35%, by weight, inclusive. In certain embodiments, the concentration of the first hydrophilic emulsifier in the four or more pharmaceutically acceptable excipients is about 28% or about 29%, by weight. In certain embodiments, the concentration of the first hydrophilic emulsifier in the four or more pharmaceutically acceptable excipients is about 19% by weight.

In certain embodiments, the one or more hydrophilic emulsifier(s) consist of one hydrophilic emulsifier.

In certain embodiments, the one or more hydrophilic emulsifier(s) further comprise a second hydrophilic emulsifier, wherein the concentration of the second hydrophilic emulsifier in the four or more pharmaceutically acceptable excipients is not more than 10% by weight. In certain embodiments, the one or more hydrophilic emulsifier(s) consist of two hydrophilic emulsifiers.

In certain embodiments, the second hydrophilic emulsifier is a non-ionic emulsifier, and the HLB value of the second hydrophilic emulsifier is between 10 and 18, between 10 and 16, between 10 and 14, between 10.5 and 11.5, between 12 and 18, between 12 and 16, between 12 and 14, between 12.5 and 14.5, between 14 and 18, between 14 and 16, or between 16 and 18, inclusive. In certain embodiments, the second hydrophilic emulsifier is a non-ionic emulsifier, and the HLB value of the second hydrophilic emulsifier is between 10 and 12, inclusive. In certain embodiments, the second hydrophilic emulsifier is a non-ionic emulsifier, and the HLB value of the second hydrophilic emulsifier is about 11. In certain embodiments, the second hydrophilic emulsifier is a non-ionic emulsifier, and the HLB value of the second hydrophilic emulsifier is between 13 and 15, inclusive. In certain embodiments, the second hydrophilic emulsifier is an ionic emulsifier that includes monovalent cation(s).

In certain embodiments, the second hydrophilic emulsifier is TWEEN 85 (polyoxyethylenesorbitan trioleate). In certain embodiments, the second hydrophilic emulsifier is ACCONON MC8-2 (a mixture of monoesters, diesters, and triesters of glycerol, and monoesters and diesters of polyethylene glycols with a mean relative molecular weight between 200 and 400, inclusive). In certain embodiments, the second hydrophilic emulsifier is TWEEN 20 (polyoxyethylene (20) sorbitan monolaurate) or TWEEN 80 (polyoxyethylene (20) sorbitan monooleate). In certain embodiments, the second hydrophilic emulsifier is ACCONON CC-6 (polyoxyethylene 6 caprylic/capric glycerides), ACCONON C-44 (polyoxyethylene 32 lauric glycerides), ACCONON CO-7 (polyoxyethylene 7 coconut glycerides), ACCONON C-30 (polyoxyethylene 30 coconut glycerides), ACCONON C-80 (polyoxyethylene 80 coconut glycerides), ACCONON Sorb-20 (polyoxyethylene 20 sorbitol), ACCONON E (polyoxypropylene 15 stearyl ether), or Accomid PK (palm kernelamide diethanolamide).

In certain embodiments, the concentration of the second hydrophilic emulsifier in the four or more pharmaceutically acceptable excipients is not more than 10% by weight. In certain embodiments, the concentration of the second hydrophilic emulsifier in the four or more pharmaceutically acceptable excipients is not more than 7%, not more than 5%, not more than 3%, or not more than 1%, by weight. In certain embodiments, the concentration of the second hydrophilic emulsifier in the four or more pharmaceutically acceptable excipients is between 5% and 10% or between 7% and 10%, by weight, inclusive.

In certain embodiments, the one or more hydrophilic emulsifier(s) further comprise a third hydrophilic emulsifier, wherein the concentration of the third hydrophilic emulsifier in the four or more pharmaceutically acceptable excipients is not more than 10% by weight. In certain embodiments, the one or more hydrophilic emulsifier(s) consist of three hydrophilic emulsifiers.

In certain embodiments, the third hydrophilic emulsifier is a non-ionic emulsifier, and the HLB value of the third hydrophilic emulsifier is between 10 and 18, between 10 and 16, or between 10 and 14, exclusive. In certain embodiments, the third hydrophilic emulsifier is a non-ionic emulsifier, and the HLB value of the third hydrophilic emulsifier is between 10.5 and 11.5, between 12 and 18, between 12 and 16, between 12 and 14, between 12.5 and 14.5, between 14 and 18, between 14 and 16, or between 16 and 18, inclusive. In certain embodiments, the third hydrophilic emulsifier is a non-ionic emulsifier, and the HLB value of the third hydrophilic emulsifier is between 10 and 12, exclusive. In certain embodiments, the third hydrophilic emulsifier is a non-ionic emulsifier, and the HLB value of the third hydrophilic emulsifier is about 11. In certain embodiments, the third hydrophilic emulsifier is a non-ionic emulsifier, and the HLB value of the third hydrophilic emulsifier is between 13 and 15, inclusive. In certain embodiments, the third hydrophilic emulsifier is an ionic emulsifier that includes monovalent cation(s).

In certain embodiments, the third hydrophilic emulsifier is TWEEN 85 (polyoxyethylenesorbitan trioleate). In certain embodiments, the third hydrophilic emulsifier is ACCONON MC8-2 (a mixture of monoesters, diesters, and triesters of glycerol, and monoesters and diesters of polyethylene glycols with a mean relative molecular weight between 200 and 400, inclusive). In certain embodiments, the third hydrophilic emulsifier is TWEEN 20 (polyoxyethylene (20) sorbitan monolaurate) or TWEEN 80 (polyoxyethylene (20) sorbitan monooleate). In certain embodiments, the third hydrophilic emulsifier is ACCONON CC-6 (polyoxyethylene 6 caprylic/capric glycerides), ACCONON C-44 (polyoxyethylene 32 lauric glycerides), ACCONON CO-7 (polyoxyethylene 7 coconut glycerides), ACCONON C-30 (polyoxyethylene 30 coconut glycerides), ACCONON C-80 (polyoxyethylene 80 coconut glycerides), ACCONON Sorb-20 (polyoxyethylene 20 sorbitol), ACCONON E (polyoxypropylene 15 stearyl ether), or Accomid PK (palm kernelamide diethanolamide).

In certain embodiments, the concentration of the third hydrophilic emulsifier in the four or more pharmaceutically acceptable excipients is not more than 10% by weight. In certain embodiments, the concentration of the third hydrophilic emulsifier in the four or more pharmaceutically acceptable excipients is not more than 7%, not more than 5%, or not more than 1%, by weight. In certain embodiments, the concentration of the third hydrophilic emulsifier in the four or more pharmaceutically acceptable excipients is not more than 3% by weight. In certain embodiments, the concentration of the third hydrophilic emulsifier in the four or more pharmaceutically acceptable excipients is between 5% and 10% or between 7% and 10%, by weight, inclusive.

In certain embodiments, the one or more hydrophilic emulsifier(s) further comprise a fourth hydrophilic emulsifier, wherein the concentration of the fourth hydrophilic emulsifier in the four or more pharmaceutically acceptable excipients is not more than 10% by weight. In certain embodiments, the one or more hydrophilic emulsifier(s) consist of four hydrophilic emulsifiers.

In certain embodiments, the first and second hydrophilic emulsifiers are KOLLIPHOR EL and ACCONON MC8-2, respectively. In certain embodiments, the first and second hydrophilic emulsifiers are KOLLIPHOR EL and TWEEN 85, respectively. In certain embodiments, the second and third hydrophilic emulsifiers are ACCONON MC8-2 and TWEEN 85, respectively. In certain embodiments, the first, second, and third hydrophilic emulsifiers are KOLLIPHOR EL, ACCONON MC8-2, and TWEEN 85, respectively.

In certain embodiments, the concentration of the first hydrophilic emulsifier in the four or more pharmaceutically acceptable excipients is between 20% and 35% by weight, inclusive; and the concentration of the second hydrophilic emulsifier in the four or more pharmaceutically acceptable excipients is not more than 5% by weight, inclusive. In certain embodiments, the concentration of the first hydrophilic emulsifier in the four or more pharmaceutically acceptable excipients is between 25% and 30% by weight, inclusive; and the concentration of the second hydrophilic emulsifier in the four or more pharmaceutically acceptable excipients is not more than 3% by weight, inclusive. In certain embodiments, the concentration of the first hydrophilic emulsifier in the four or more pharmaceutically acceptable excipients is between 15% and 25% by weight, inclusive; and the concentration of the second hydrophilic emulsifier in the four or more pharmaceutically acceptable excipients is between 5% and 10% by weight, inclusive. In certain embodiments, the concentration of the first hydrophilic emulsifier in the four or more pharmaceutically acceptable excipients is between 15% and 20% by weight, inclusive; and the concentration of the second hydrophilic emulsifier in the four or more pharmaceutically acceptable excipients is between 7% and 10% by weight, inclusive.

In certain embodiments, the lipophilic emulsifier(s) are non-ionic emulsifier(s), and the HLB values of the lipophilic emulsifier(s) are not greater than 10 as determined by Griffin's method. In certain embodiments, the lipophilic emulsifier(s) are non-ionic emulsifier(s), and the HLB values of the lipophilic emulsifier(s) are between 0.1 and 10, between 4 and 10, between 6 and 10, between 8 and 10, between 0.1 and 8, between 0.1 and 6, between 0.1 and 4, between 4 and 8, between 4 and 6, or between 6 and 8, inclusive. In certain embodiments, the lipophilic emulsifier(s) are non-ionic emulsifier(s), and the HLB values of the lipophilic emulsifier(s) are between 6.5 and 8.5, inclusive. In certain embodiments, the lipophilic emulsifier(s) are non-ionic emulsifier(s), and the HLB values of the lipophilic emulsifier(s) are between 7 and 8, inclusive. In certain embodiments, the lipophilic emulsifier(s) are non-ionic emulsifier(s), and the HLB values of the lipophilic emulsifier(s) are about 7.5. In certain embodiments, the lipophilic emulsifier(s) are ionic emulsifier(s) that include polyvalent cations.

In certain embodiments, the first lipophilic emulsifier is a non-ionic emulsifier, and the HLB value of the first lipophilic emulsifier is between 0.1 and 10, between 4 and 10, between 6 and 10, or between 8 and 10, exclusive. In certain embodiments, the first lipophilic emulsifier is a non-ionic emulsifier, and the HLB value of the first lipophilic emulsifier is between 0.1 and 8, between 0.1 and 6, between 0.1 and 4, between 4 and 8, between 4 and 6, or between 6 and 8, inclusive. In certain embodiments, the first lipophilic emulsifier is a non-ionic emulsifier, and the HLB value of the first lipophilic emulsifier is between 6.5 and 8.5, inclusive. In certain embodiments, the first lipophilic emulsifier is a non-ionic emulsifier, and the HLB value of the first lipophilic emulsifier is between 7 and 8, inclusive. In certain embodiments, the first lipophilic emulsifier is a non-ionic emulsifier, and the HLB value of the first lipophilic emulsifier is about 7.5. In certain embodiments, the first lipophilic emulsifier is an ionic emulsifier that includes polyvalent cation(s).

In certain embodiments, the first lipophilic emulsifier is CAPMUL 907P (Cap 907P; or propylene glycol monoheptanoate). In certain embodiments, the first lipophilic emulsifier is CAPMUL 908P (Cap 908P; or propylene glycol monocaprylate), CAPMUL MCM (Cap MCM; medium chain mono- and di-glycerides), CAPMUL MCM C8 (glyceryl monocaprylate), or CAPMUL PG-8 (propylene glycol monocaprylate). In certain embodiments, the first lipophilic emulsifier is CAPMUL 471 (glyceryl caprylate/caprate), CAPMUL 708G (glyceryl monocaprylate), CAPMUL 808G EP/NF (glyceryl monocaprylate), CAPMUL GDB EP/NF (glyceryl dibehenate), CAPMUL GMO-50 (glyceryl monooleate), CAPMUL GMO-50 EP/NF (glyceryl monooleate), CAPMUL GMS-50K (glyceryl monostearate), CAPMUL MCM C8 EP/NF (glyceryl monocaprylate), CAPMUL MCM C10 (glyceryl monocaprate), CAPMUL MCM NF (glyceryl caprylate/caprate), CAPMUL MCM EP (glyceryl caprylate/caprate), CAPMUL PG-2L (propylene glycol dilaurate), CAPMUL PG-2L EP/NF (propylene glycol dilaurate), CAPMUL PG-8 NF (propylene glycol monocaprylate), CAPMUL PG-8-70 NF (propylene glycol monocaprylate, NF Type 1 requirements), CAPMUL PG-12 (propylene glycol monolaurate), CAPMUL PG-12 EP/NF (propylene glycol monolaurate), CAPMUL S12L (sodium lauroyl lactylate), or CAPMUL S 18L (sodium stearoyl-2-lactylate). In certain embodiments, the first lipophilic emulsifier is PECEOL (glycerol monooleate) (e.g., glycerol monooleates (type 40) EP or glyceryl monooleate (type 40) NF). In certain embodiments, the first lipophilic emulsifier is LABRAFIL M1944CS (oleoyl macrogol-6 glycerides) (e.g., oleoyl macrogol-6 glycerides EP or oleoyl polyoxyl-6 glycerides NF). In certain embodiments, the first lipophilic emulsifier is LABRAFIL 2125 CS (linoleoyl macrogol-6 glycerides) (e.g., linoleoyl polyoxyl-6 glycerides EP or linoleoyl polyoxyl-6 glycerides NF) or LABRAFIL 2130 CS (lauroyl macrogol-6 glycerides) (e.g., lauroyl polyoxyl-6 glycerides EP or lauroyl polyoxyl-6 glycerides NF). In certain embodiments, the first lipophilic emulsifier is BRIJ 30 (polyoxyethylene(4)lauryl ether). In certain embodiments, the first lipophilic emulsifier is CAPRYOL PGMC (propylene glycol monocaprylate (type I) NF). In certain embodiments, the first lipophilic emulsifier is CAPRYOL 90 (propylene glycol monocaprylate (type II) NF).

In certain embodiments, the concentration of the first lipophilic emulsifier in the four or more pharmaceutically acceptable excipients is between 25% and 40% by weight, inclusive. In certain embodiments, the concentration of the first lipophilic emulsifier in the four or more pharmaceutically acceptable excipients is between 30% and 40%, between 30% and 35%, or between 35% and 40%, by weight, inclusive. In certain embodiments, the concentration of the first lipophilic emulsifier in the four or more pharmaceutically acceptable excipients is between 25% and 35% by weight. In certain embodiments, the concentration of the first lipophilic emulsifier in the four or more pharmaceutically acceptable excipients is between 25% and 30% by weight. In certain embodiments, the concentration of the first lipophilic emulsifier in the four or more pharmaceutically acceptable excipients is about 28% or about 29%, by weight.

In certain embodiments, the lipophilic emulsifier(s) consist of one lipophilic emulsifier.

In certain embodiments, the one or more lipophilic emulsifier(s) further comprise a second lipophilic emulsifier, wherein the concentration of the second lipophilic emulsifier in the four or more pharmaceutically acceptable excipients is not more than 10% by weight. In certain embodiments, the one or more lipophilic emulsifier(s) consist of two lipophilic emulsifiers.

In certain embodiments, the four or more pharmaceutically acceptable excipients do not comprise one or more organic solvent(s). In certain embodiments, the four or more pharmaceutically acceptable excipients are substantially free of organic solvent(s). In certain embodiments, the combined concentration of the organic solvent(s) in the four or more pharmaceutically acceptable excipients is not more than 1%, not more than 0.3%, not more than 0.1%, not more than 0.03%, not more than 0.01%, not more than 0.003%, or not more than 0.001%, by weight.

In certain embodiments, the four or more pharmaceutically acceptable excipients further comprise: (d) one or more organic solvent(s), wherein the concentration of the first organic solvent in the four or more pharmaceutically acceptable excipients is not more than 20% by weight.

The term "organic solvent" refers to a pharmaceutically acceptable organic solvent. Examples of the organic solvent include, but are not limited to the pharmaceutically acceptable organic solvents included in Grodowska et al., Acta Poloniae Pharmaceutica—Drug Research, Vol. 67 No. 1 pp. 3-12, 2010. In certain embodiments, the organic solvent is a pharmaceutically acceptable organic solvent that falls within the definition of ICH guidelines under class 2 or 3 solvents. Further examples of the organic solvent include, but are not limited to, tributyl citrate, tributyl acetyl citrate, triethyl citrate, triethyl acetyl citrate, ethyl oleate CAPTEX 170 (caprylic/capric acid ester of saturated fatty alcohol C12-18), CAPTEX 200 (propylene glycol dicaprylocaprate), CAPTEX 300 (glyceryl tricaprylate/tricaprate), CAPTEX 300 EP/NF (glyceryl tricaprylate/tricaprate), CAPTEX 300 Low C6 (glyceryl tricaprylate/tricaprate), CAPTEX 300 Low C6 EP/NF/JPE (glyceryl tricaprylate/tricaprate), CAPTEX 350 (glyceryl tricaprylate/caprate/laurate), CAPTEX 355 (glyceryl tricaprylate/tricaprate), CAPTEX 355 EP/NF/JPE (glycerol tricaprylate/caprate), CAPTEX 355 Low C6 (glycerol tricaprylate/caprate), CAPTEX 1000 (glyceryl tricaprate), CAPTEX GTO (triolein), CAPTEX NPGC (decanoic acid, mixed esters with neopentyl glycol and octanoic acid), CAPTEX SBE (C8-18 glycerides), CAPTEX 300 EP/NF/JPE, CAPTEX 300 Low C6 EP/NF/JPE, CAPTEX 355 EP/NF/JPE, CAPTEX 1000, LABRAFAC Lipophile WL 1349 (glyceryl tricaprylate/tricaprate), LABRAFAC CC (caprylic/capric triglyceride), DERMOFEEL MCT (tricaprylin), MIGLYOL 840, MIGLYOL 810 (a triglyceride of fractionated C8-10 coconut oil fatty acids), and MIGLYOL 812 (caprylic/capric triglyceride). Further examples of the organic solvent include, but are not limited to, alcohols, ketones, halogenated solvents, amides, ethers, sulfur containing sovlents, amines, nitriles, esters, aliphatic hydrocarbons, and aromatic hydrocarbons, each of which is pharmaceutically acceptable.

In certain embodiments, the four or more pharmaceutically acceptable excipients comprise only one organic solvent. In certain embodiments, the first organic solvent is tributyl citrate, tributyl acetyl citrate, triethyl citrate, triethyl acetyl citrate, or ethyl oleate. In certain embodiments, the first organic solvent is corn oil or cera liquida. In certain embodiments, the first organic solvent is a triglyceride. In certain embodiments, the first organic solvent is a triglyceride from a vegetable source (e.g., soybean oil, sunflower oil, palm oil, palm kernel oil, high erucic rapeseed oil, low erucic rapeseed oil, coconut oil, olive oil, sesame oil, peanut oil, or corn oil). In certain embodiments, the first organic solvent is a triglyceride from an animal source (e.g., fish oil, tallow, sardine oil, or dairy fat). In certain embodiments, the first organic solvent is a chemically (e.g., fully or partially hydrogenated), physically, and/or genetically modified triglyceride from a vegetable or animal source. In certain embodiments, the first organic solvent is a silicone (e.g., organo-silicone), paraffin, or wax (e.g., liquid wax (wax that is a liquid at 20° C. and 1 atmosphere)). In certain embodiments, the first organic solvent is a triglyceride that is a liquid at 20° C. and 1 atmosphere. In certain embodiments, the first organic solvent is a triglyceride that is a solid at 20° C. and 1 atmosphere. In certain embodiments, the first organic solvent is CAPTEX 300 EP/NF (glyceryl tricaprylate/tricaprate). In certain embodiments, the first organic solvent is CAPTEX 8000 (glyceryl tricaprylate). In certain embodiments, the first organic solvent is CAPTEX 355 EP/NF (glycerol tricaprylate/caprate) or CAPTEX 200P (propylene glycol dicaprylocaprate). In certain embodiments, the first organic solvent is CAPTEX 50 powder (powdered medium-chain triglycerides (MCTs), maltodextrin, food starch-modified, and silicon dioxide), CAPTEX 70 powder (powdered ingredient blend with MCTs), CAPTEX 100 (propylene glycol dicaprate), CAPTEX 170 EP (caprylic/capric acid ester of saturated fatty alcohol $C_{12-18}$), CAPTEX 170 (caprylic/capric acid ester of saturated fatty alcohol $C_{12-18}$), CAPTEX 200 (propylene glycol dicaprylocaprate), CAPTEX 300 (glyceryl tricaprylate/tricaprate), CAPTEX 300 EP/NF (glyceryl tricaprylate/tricaprate), CAPTEX 300 Low $C_6$ (glyceryl tricaprylate/tricaprate), CAPTEX 300 Low $C_6$ EP/NF/JPE (glyceryl tricaprylate/tricaprate), CAPTEX 350 (glyceryl tricaprylate/caprate/laurate), CAPTEX 355 (glyceryl tricaprylate/tricaprate), CAPTEX 355 EP/NF/JPE (glycerol tricaprylate/caprate), CAPTEX 355 Low $C_6$ (glycerol tricaprylate/caprate), CAPTEX 1000 (glyceryl tricaprate), CAPTEX BL-1 CAPTEX CA (powdered ingredient blend with MCTs), CAPTEX GTO (triolein), CAPTEX NPGC (decanoic acid, mixed esters with neopentyl glycol and octanoic acid), or CAPTEX SBE ($C_{8-18}$ glycerides). In certain embodiments, the first organic solvent is CAPTEX 300 EP/NF/JPE, CAPTEX 300 Low C6 EP/NF/JPE, CAPTEX 355 EP/NF/JPE, or CAPTEX 1000. In certain embodiments, the first organic solvent is LABRAFAC Lipophile WL 1349 (glyceryl tricaprylate/ tricaprate). In certain embodiments, the first organic solvent is LABRAFAC PG (propylene glycol dicaprylocaprate EP or propylene glycol dicaprylate/dicaprate NF) or LABRAFAC CC (caprylic/capric triglyceride). In certain embodiments, the first organic solvent is DERMOFEEL MCT (tricaprylin). In certain embodiments, the first organic solvent is MIGLYOL 840. In certain embodiments, the first organic solvent is MIGLYOL 810 (a triglyceride of fractionated $C_{8-10}$ coconut oil fatty acids) or MIGLYOL 812 (caprylic/capric triglyceride).

In certain embodiments, the concentration of the first organic solvent in the four or more pharmaceutically acceptable excipients is not more than 20% by weight. In certain embodiments, the concentration of the first organic solvent in the four or more pharmaceutically acceptable excipients is not more than 15%, not more than 10%, not more than 5%, not more than 3%, or not more than 1%, by weight. In certain embodiments, the concentration of the first organic solvent in the four or more pharmaceutically acceptable excipients is between 1% and 20%, between 1% and 15%, between 1% and 10%, between 1% and 5%, between 5% and 20%, between 5% and 10%, between 10% and 20%, or between 10% and 15%, by weight, inclusive. In certain embodiments, the concentration of the first organic solvent in the four or more pharmaceutically acceptable excipients is between 15% and 20% by weight, inclusive. In certain embodiments, the concentration of the first organic solvent in the four or more pharmaceutically acceptable excipients is about 19% by weight. In certain embodiments, the concentration of the first organic solvent in the four or more pharmaceutically acceptable excipients is between 5% and 15% by weight, inclusive. In certain embodiments, the concentration of the first organic solvent in the four or more pharmaceutically acceptable excipients is about 10% by weight.

In certain embodiments, the organic solvents further comprise a second organic solvent, wherein the concentration of the second organic solvent in the four or more pharmaceutically acceptable excipients is not more than 20% by weight. In certain embodiments, the organic solvents consist of two organic solvents. In certain embodiments, the second organic solvent is a triglyceride. In certain embodiments, the second organic solvent is a triglyceride from a vegetable source (e.g., soybean oil, sunflower oil, palm oil, palm kernel oil, high erucic rapeseed oil, low erucic rapeseed oil, coconut oil, olive oil, sesame oil, peanut oil, or corn oil). In certain embodiments, the second organic solvent is a triglyceride from an animal source (e.g., fish oil, tallow, sardine oil, or dairy fat). In certain embodiments, the second organic solvent is a chemically (e.g., fully or partially hydrogenated), physically, and/or genetically modified triglyceride from a vegetable or animal source. In certain embodiments, the second organic solvent is a silicone (e.g., organo-silicone), paraffin, or wax (e.g., liquid wax (wax that is a liquid at 20° C. and 1 atmosphere)). In certain embodiments, the second organic solvent is a triglyceride that is a liquid at 20° C. and 1 atmosphere. In certain embodiments, the second organic solvent is a triglyceride that is a solid at 20° C. and 1 atmosphere. In certain embodiments, the second organic solvent is CAPTEX 300 EP/NF (glyceryl tricaprylate/tricaprate). In certain embodiments, the second organic solvent is CAPTEX 8000 (glyceryl tricaprylate). In certain embodiments, the second organic solvent is CAPTEX 355 EP/NF (glycerol tricaprylate/caprate) or CAPTEX 200P (propylene glycol dicaprylocaprate). In certain embodiments, the second organic solvent is CAPTEX 50 powder (powdered medium-chain triglycerides (MCTs), maltodextrin, food starch-modified, and silicon dioxide), CAPTEX 70 powder (powdered ingredient blend with MCTs), CAPTEX 100 (propylene glycol dicaprate), CAPTEX 170 EP (caprylic/capric acid ester of saturated fatty alcohol $C_{12-18}$), CAPTEX 170 (caprylic/capric acid ester of saturated fatty alcohol $C_{12-18}$), CAPTEX 200 (propylene glycol dicaprylocaprate), CAPTEX 300 (glyceryl tricaprylate/tricaprate), CAPTEX 300 EP/NF (glyceryl tricaprylate/tricaprate), CAPTEX 300 Low $C_6$ (glyceryl tricaprylate/tricaprate), CAPTEX 300 Low $C_6$ EP/NF/JPE (glyceryl tricaprylate/tricaprate), CAPTEX 350 (glyceryl tricaprylate/caprate/laurate), CAPTEX 355 (glyceryl tricaprylate/tricaprate), CAPTEX 355 EP/NF/JPE (glycerol tricaprylate/caprate), CAPTEX 355 Low $C_6$ (glycerol tricaprylate/caprate), CAPTEX 1000 (glyceryl tricaprate), CAPTEX BL-1 CAPTEX CA (powdered ingredient blend with MCTs), CAPTEX GTO (triolein), CAPTEX NPGC (decanoic acid, mixed esters with neopentyl glycol and octanoic acid), or CAPTEX SBE ($C_{8-18}$ glycerides). In certain embodiments, the second organic solvent is CAPTEX 300 EP/NF/JPE, CAPTEX 300 Low C6 EP/NF/JPE, CAPTEX 355 EP/NF/JPE, or CAPTEX 1000. In certain embodiments, the second organic solvent is LABRAFAC Lipophile WL 1349 (glyceryl tricaprylate/tricaprate). In certain embodiments, the second organic solvent is LABRAFAC PG (propylene glycol dicaprylocaprate EP or propylene glycol dicaprylate/dicaprate NF) or LABRAFAC CC (caprylic/capric triglyceride). In certain embodiments, the second organic solvent is DERMOFEEL MCT (tricaprylin). In certain embodiments, the second organic solvent is MIGLYOL 840. In certain embodiments, the second organic solvent is MIGLYOL 810 (a triglyceride of fractionated $C_{8-10}$ coconut oil fatty acids) or MIGLYOL 812 (caprylic/capric triglyceride).

In certain embodiments, the concentration of the second organic solvent in the four or more pharmaceutically acceptable excipients is not more than 20% by weight. In certain embodiments, the concentration of the second organic solvent in the four or more pharmaceutically acceptable excipients is not more than 15%, not more than 10%, not more than 5%, not more than 3%, or not more than 1%, by weight. In certain embodiments, the concentration of the second organic solvent in the four or more pharmaceutically acceptable excipients is between 1% and 20%, between 1% and 15%, between 1% and 10%, between 1% and 5%, between 5% and 20%, between 5% and 10%, between 10% and 20%, or between 10% and 15%, by weight, inclusive. In certain embodiments, the concentration of the second organic solvent in the four or more pharmaceutically acceptable excipients is between 15% and 20% by weight, inclusive. In certain embodiments, the concentration of the second organic solvent in the four or more pharmaceutically acceptable excipients is about 19% by weight. In certain embodiments, the concentration of the second organic solvent in the four or more pharmaceutically acceptable excipients is between 5% and 15% by weight, inclusive. In certain embodiments, the concentration of the second organic solvent in the four or more pharmaceutically acceptable excipients is about 10% by weight.

In certain embodiments, the first organic solvent and the second organic solvent are CAPTEX 300 EP/NF and CAPTEX 8000, respectively.

In certain embodiments, the concentration of the first organic solvent in the four or more pharmaceutically acceptable excipients is between 15% to 20% by weight, inclusive; and the concentration of the second organic solvent in the four or more pharmaceutically acceptable excipients is not more than 5% by weight. In certain embodiments, the concentration of the first organic solvent in the four or more pharmaceutically acceptable excipients is about 19% by weight, inclusive; and the concentration of the second organic solvent in the four or more pharmaceutically acceptable excipients is not more than 3% by weight. In certain embodiments, the concentration of the first organic solvent in the four or more pharmaceutically acceptable excipients is between 5% to 15% by weight, inclusive; and the concentration of the second organic solvent in the four or more pharmaceutically acceptable excipients is not more than 5% by weight. In certain embodiments, the concentration of the first organic solvent in the four or more pharmaceutically acceptable excipients is about 10% by weight, inclusive; and the concentration of the second organic solvent in the four or more pharmaceutically acceptable excipients is not more than 3% by weight.

In certain embodiments, the organic solvents further comprise a third organic solvent, wherein the concentration of the third organic solvent in the four or more pharmaceutically acceptable excipients is not more than 10% by weight. In certain embodiments, the organic solvents consist of three organic solvents.

In certain embodiments, the four or more pharmaceutically acceptable excipients consist of:

| (1F). | |
|---|---|
| Pharmaceutically acceptable excipient | Concentration in the four or more pharmaceutically acceptable excipients (% by weight) |
| polyethylene glycol 200 | 10 to 25 |
| propylene glycol | 10 to 15 |
| dimethyl sulfoxide | 0 to 10 |
| KOLLIPHOR EL | 15 to 35 |
| CAPMUL 907P | 25 to 40 |
| CAPTEX 300 EP/NF | 0 to 20 |

The range "X1 to X2" or "X1-X2", wherein X1 is a number or percentage, X2 is a number or percentage, and X2 is greater than X1, refers to the range "between X1 and X2, inclusive."

In certain embodiments, the four or more pharmaceutically acceptable excipients consist of:

| (2F). | |
|---|---|
| Pharmaceutically acceptable excipient | Concentration in the four or more pharmaceutically acceptable excipients (% by weight) |
| polyethylene glycol 200 | 10 to 25 |
| propylene glycol | 10 to 15 |
| dimethyl sulfoxide | 0 to 10 |
| KOLLIPHOR EL | 15 to 35 |
| CAPMUL 907P | 25 to 40 |
| CAPTEX 8000 | 0 to 20 |

In certain embodiments, the four or more pharmaceutically acceptable excipients consist of:

(3F).

| Pharmaceutically acceptable excipient | Concentration in the four or more pharmaceutically acceptable excipients (% by weight) |
|---|---|
| polyethylene glycol 200 | 10 to 25 |
| propylene glycol | 10 to 15 |
| dimethyl sulfoxide | 0 to 10 |
| KOLLIPHOR EL | 15 to 35 |
| ACCONON MC8-2 | 0 to 10 |
| CAPMUL 907P | 25 to 40 |
| CAPTEX 8000 | 0 to 20 |

In certain embodiments, the four or more pharmaceutically acceptable excipients consist of:

(4F).

| Pharmaceutically acceptable excipient | Concentration in the four or more pharmaceutically acceptable excipients (% by weight) |
|---|---|
| polyethylene glycol 200 | 10 to 25 |
| propylene glycol | 10 to 15 |
| dimethyl sulfoxide | 0 to 10 |
| tetraglycol | 0 to 10 |
| KOLLIPHOR EL | 15 to 35 |
| CAPMUL 907P | 25 to 40 |

In certain embodiments, the four or more pharmaceutically acceptable excipients consist of:

(5F).

| Pharmaceutically acceptable excipient | Concentration in the four or more pharmaceutically acceptable excipients (% by weight) |
|---|---|
| polyethylene glycol 200 | 10 to 25 |
| propylene glycol | 10 to 15 |
| dimethyl sulfoxide | 0 to 10 |
| tetraglycol | 0 to 10 |
| KOLLIPHOR EL | 15 to 35 |
| CAPMUL 907P | 25 to 40 |
| CAPTEX 8000 | 0 to 20 |

In certain embodiments, the four or more pharmaceutically acceptable excipients consist of:

(6F).

| Pharmaceutically acceptable excipient | Concentration in the four or more pharmaceutically acceptable excipients (% by weight) |
|---|---|
| polyethylene glycol 200 | 10 to 25 |
| propylene glycol | 10 to 15 |
| dimethyl sulfoxide | 0 to 10 |
| tetraglycol | 0 to 10 |
| KOLLIPHOR EL | 15 to 35 |
| TWEEN 85 | 0 to 10 |
| CAPMUL 907P | 25 to 40 |

In certain embodiments, the four or more pharmaceutically acceptable excipients consist of:

(7F).

| Pharmaceutically acceptable excipient | Concentration in the four or more pharmaceutically acceptable excipients (% by weight) |
|---|---|
| polyethylene glycol 200 | 10 to 25 |
| propylene glycol | 10 to 15 |
| dimethyl sulfoxide | 0 to 10 |
| tetraglycol | 0 to 10 |
| KOLLIPHOR EL | 15 to 35 |
| CAPMUL PG-8 NF | 25 to 40 |

In certain embodiments, the four or more pharmaceutically acceptable excipients consist of:

(8F).

| Pharmaceutically acceptable excipient | Concentration in the four or more pharmaceutically acceptable excipients (% by weight) |
|---|---|
| polyethylene glycol 200 | 10 to 25 |
| propylene glycol | 10 to 15 |
| dimethyl sulfoxide | 0 to 10 |
| tetraglycol | 0 to 10 |
| KOLLIPHOR EL | 15 to 35 |
| CAPRYOL 90 | 25 to 40 |

In certain embodiments, the four or more pharmaceutically acceptable excipients consist of:

(1A).

| Pharmaceutically acceptable excipient | Concentration in the four or more pharmaceutically acceptable excipients (% by weight) |
|---|---|
| polyethylene glycol 200 | about 10 |
| propylene glycol | about 10 |
| dimethyl sulfoxide | about 5 |
| KOLLIPHOR EL | about 28 |
| CAPMUL 907P | about 28 |
| CAPTEX 300 EP/NF | about 19 |

In certain embodiments, the four or more pharmaceutically acceptable excipients consist of:

(1B).

| Pharmaceutically acceptable excipient | Concentration in the four or more pharmaceutically acceptable excipients (% by weight) |
|---|---|
| polyethylene glycol 200 | 10 ± 5% |
| propylene glycol | 10 ± 5% |
| dimethyl sulfoxide | 5 ± 5% |
| KOLLIPHOR EL | 28 ± 5% |
| CAPMUL 907P | 28 ± 5% |
| CAPTEX 300 EP/NF | 19 ± 5% |

The term "Y±Z %", when Y is a number, and Z is a number greater than 0, refers to a number between Y×(100−Z) % and Y×(100+Z) %, inclusive. For example, the concentration of polyethylene glycol 200 in the four or more pharmaceutically acceptable excipients (1B) is between (10×(100−5)%)% and (10×(100+5)%)%, that is, between 9.5% and 10.5%, by weight, inclusive.

In certain embodiments, the four or more pharmaceutically acceptable excipients consist of:

(1C).

| Pharmaceutically acceptable excipient | Concentration in the four or more pharmaceutically acceptable excipients (% by weight) |
|---|---|
| polyethylene glycol 200 | 10 ± 10% |
| propylene glycol | 10 ± 10% |
| dimethyl sulfoxide | 5 ± 10% |
| KOLLIPHOR EL | 28 ± 10% |
| CAPMUL 907P | 28 ± 10% |
| CAPTEX 300 EP/NF | 19 ± 10% |

In certain embodiments, the four or more pharmaceutically acceptable excipients consist of:

(1D).

| Pharmaceutically acceptable excipient | Concentration in the four or more pharmaceutically acceptable excipients (% by weight) |
|---|---|
| polyethylene glycol 200 | 10 ± 15% |
| propylene glycol | 10 ± 15% |
| dimethyl sulfoxide | 5 ± 15% |
| KOLLIPHOR EL | 28 ± 15% |
| CAPMUL 907P | 28 ± 15% |
| CAPTEX 300 EP/NF | 19 ± 15% |

In certain embodiments, the four or more pharmaceutically acceptable excipients consist of:

(1E).

| Pharmaceutically acceptable excipient | Concentration in the four or more pharmaceutically acceptable excipients (% by weight) |
|---|---|
| polyethylene glycol 200 | 10 ± 20% |
| propylene glycol | 10 ± 20% |
| dimethyl sulfoxide | 5 ± 20% |
| KOLLIPHOR EL | 28 ± 20% |
| CAPMUL 907P | 28 ± 20% |
| CAPTEX 300 EP/NF | 19 ± 20% |

In certain embodiments, the four or more pharmaceutically acceptable excipients consist of:

(2A).

| Pharmaceutically acceptable excipient | Concentration in the four or more pharmaceutically acceptable excipients (% by weight) |
|---|---|
| polyethylene glycol 200 | about 20 |
| propylene glycol | about 10 |
| dimethyl sulfoxide | about 2 |
| KOLLIPHOR EL | about 29 |
| CAPMUL 907P | about 29 |
| CAPTEX 8000 | about 10 |

In certain embodiments, the four or more pharmaceutically acceptable excipients consist of:

(2B).

| Pharmaceutically acceptable excipient | Concentration in the four or more pharmaceutically acceptable excipients (% by weight) |
|---|---|
| polyethylene glycol 200 | 20 ± 5% |
| propylene glycol | 10 ± 5% |
| dimethyl sulfoxide | 2 ± 5% |
| KOLLIPHOR EL | 29 ± 5% |
| CAPMUL 907P | 29 ± 5% |
| CAPTEX 8000 | 10 ± 5% |

In certain embodiments, the four or more pharmaceutically acceptable excipients consist of:

(2C).

| Pharmaceutically acceptable excipient | Concentration in the four or more pharmaceutically acceptable excipients (% by weight) |
|---|---|
| polyethylene glycol 200 | 20 ± 10% |
| propylene glycol | 10 ± 10% |
| dimethyl sulfoxide | 2 ± 10% |
| KOLLIPHOR EL | 29 ± 10% |
| CAPMUL 907P | 29 ± 10% |
| CAPTEX 8000 | 10 ± 10% |

In certain embodiments, the four or more pharmaceutically acceptable excipients consist of:

(2D).

| Pharmaceutically acceptable excipient | Concentration in the four or more pharmaceutically acceptable excipients (% by weight) |
|---|---|
| polyethylene glycol 200 | 20 ± 15% |
| propylene glycol | 10 ± 15% |
| dimethyl sulfoxide | 2 ± 15% |
| KOLLIPHOR EL | 29 ± 15% |
| CAPMUL 907P | 29 ± 15% |
| CAPTEX 8000 | 10 ± 15% |

In certain embodiments, the four or more pharmaceutically acceptable excipients consist of:

(2E).

| Pharmaceutically acceptable excipient | Concentration in the four or more pharmaceutically acceptable excipients (% by weight) |
|---|---|
| polyethylene glycol 200 | 20 ± 20% |
| propylene glycol | 10 ± 20% |
| dimethyl sulfoxide | 2 ± 20% |
| KOLLIPHOR EL | 29 ± 20% |
| CAPMUL 907P | 29 ± 20% |
| CAPTEX 8000 | 10 ± 20% |

In certain embodiments, the four or more pharmaceutically acceptable excipients consist of:

(3A).

| Pharmaceutically acceptable excipient | Concentration in the four or more pharmaceutically acceptable excipients (% by weight) |
|---|---|
| polyethylene glycol 200 | about 20 |
| propylene glycol | about 10 |
| dimethyl sulfoxide | about 2 |
| KOLLIPHOR EL | about 19 |
| ACCONON MC8-2 | about 10 |
| CAPMUL 907P | about 29 |
| CAPTEX 8000 | about 10 |

In certain embodiments, the four or more pharmaceutically acceptable excipients consist of:

(3B).

| Pharmaceutically acceptable excipient | Concentration in the four or more pharmaceutically acceptable excipients (% by weight) |
|---|---|
| polyethylene glycol 200 | 20 ± 5% |
| propylene glycol | 10 ± 5% |
| dimethyl sulfoxide | 2 ± 5% |
| KOLLIPHOR EL | 19 ± 5% |
| ACCONON MC8-2 | 10 ± 5% |
| CAPMUL 907P | 29 ± 5% |
| CAPTEX 8000 | 10 ± 5% |

In certain embodiments, the four or more pharmaceutically acceptable excipients consist of:

(3C).

| Pharmaceutically acceptable excipient | Concentration in the four or more pharmaceutically acceptable excipients (% by weight) |
|---|---|
| polyethylene glycol 200 | 20 ± 10% |
| propylene glycol | 10 ± 10% |
| dimethyl sulfoxide | 2 ± 10% |
| KOLLIPHOR EL | 19 ± 10% |
| ACCONON MC8-2 | 10 ± 10% |
| CAPMUL 907P | 29 ± 10% |
| CAPTEX 8000 | 10 ± 10% |

In certain embodiments, the four or more pharmaceutically acceptable excipients consist of:

(3D).

| Pharmaceutically acceptable excipient | Concentration in the four or more pharmaceutically acceptable excipients (% by weight) |
|---|---|
| polyethylene glycol 200 | 20 ± 15% |
| propylene glycol | 10 ± 15% |
| dimethyl sulfoxide | 2 ± 15% |
| KOLLIPHOR EL | 19 ± 15% |
| ACCONON MC8-2 | 10 ± 15% |
| CAPMUL 907P | 29 ± 15% |
| CAPTEX 8000 | 10 ± 15% |

In certain embodiments, the four or more pharmaceutically acceptable excipients consist of:

(3E).

| Pharmaceutically acceptable excipient | Concentration in the four or more pharmaceutically acceptable excipients (% by weight) |
|---|---|
| polyethylene glycol 200 | 20 ± 20% |
| propylene glycol | 10 ± 20% |
| dimethyl sulfoxide | 2 ± 20% |
| KOLLIPHOR EL | 19 ± 20% |
| ACCONON MC8-2 | 10 ± 20% |
| CAPMUL 907P | 29 ± 20% |
| CAPTEX 8000 | 10 ± 20% |

In certain embodiments, the four or more pharmaceutically acceptable excipients consist of:

(4A).

| Pharmaceutically acceptable excipient | Concentration in the four or more pharmaceutically acceptable excipients (% by weight) |
|---|---|
| polyethylene glycol 200 | about 20 |
| propylene glycol | about 10 |
| dimethyl sulfoxide | about 5 |
| tetraglycol | about 9 |
| KOLLIPHOR EL | about 28 |
| CAPMUL 907P | about 28 |

In certain embodiments, the four or more pharmaceutically acceptable excipients consist of:

(4B).

| Pharmaceutically acceptable excipient | Concentration in the four or more pharmaceutically acceptable excipients (% by weight) |
|---|---|
| polyethylene glycol 200 | 20 ± 5% |
| propylene glycol | 10 ± 5% |
| dimethyl sulfoxide | 5 ± 5% |
| tetraglycol | 9 ± 5% |
| KOLLIPHOR EL | 28 ± 5% |
| CAPMUL 907P | 28 ± 5% |

In certain embodiments, the four or more pharmaceutically acceptable excipients consist of:

(4C).

| Pharmaceutically acceptable excipient | Concentration in the four or more pharmaceutically acceptable excipients (% by weight) |
|---|---|
| polyethylene glycol 200 | 20 ± 10% |
| propylene glycol | 10 ± 10% |
| dimethyl sulfoxide | 5 ± 10% |
| tetraglycol | 9 ± 10% |
| KOLLIPHOR EL | 28 ± 10% |
| CAPMUL 907P | 28 ± 10% |

In certain embodiments, the four or more pharmaceutically acceptable excipients consist of:

| (4D). | |
|---|---|
| Pharmaceutically acceptable excipient | Concentration in the four or more pharmaceutically acceptable excipients (% by weight) |
| polyethylene glycol 200 | 20 ± 15% |
| propylene glycol | 10 ± 15% |
| dimethyl sulfoxide | 5 ± 15% |
| tetraglycol | 9 ± 15% |
| KOLLIPHOR EL | 28 ± 15% |
| CAPMUL 907P | 28 ± 15% |

In certain embodiments, the four or more pharmaceutically acceptable excipients consist of:

| (4E). | |
|---|---|
| Pharmaceutically acceptable excipient | Concentration in the four or more pharmaceutically acceptable excipients (% by weight) |
| polyethylene glycol 200 | 20 ± 20% |
| propylene glycol | 10 ± 20% |
| dimethyl sulfoxide | 5 ± 20% |
| tetraglycol | 9 ± 20% |
| KOLLIPHOR EL | 28 ± 20% |
| CAPMUL 907P | 28 ± 20% |

In certain embodiments, the four or more pharmaceutically acceptable excipients consist of:

| (5A). | |
|---|---|
| Pharmaceutically acceptable excipient | Concentration in the four or more pharmaceutically acceptable excipients (% by weight) |
| polyethylene glycol 200 | about 15 |
| propylene glycol | about 10 |
| dimethyl sulfoxide | about 5 |
| tetraglycol | about 10 |
| KOLLIPHOR EL | about 25.5 |
| CAPMUL 907P | about 27 |
| CAPTEX 8000 | about 7.5 |

In certain embodiments, the four or more pharmaceutically acceptable excipients consist of:

| (5B). | |
|---|---|
| Pharmaceutically acceptable excipient | Concentration in the four or more pharmaceutically acceptable excipients (% by weight) |
| polyethylene glycol 200 | 15 ± 5% |
| propylene glycol | 10 ± 5% |
| dimethyl sulfoxide | 5 ± 5% |
| tetraglycol | 10 ± 5% |
| KOLLIPHOR EL | 25.5 ± 5% |
| CAPMUL 907P | 27 ± 5% |
| CAPTEX 8000 | 7.5 ± 5% |

In certain embodiments, the four or more pharmaceutically acceptable excipients consist of:

| (5C). | |
|---|---|
| Pharmaceutically acceptable excipient | Concentration in the four or more pharmaceutically acceptable excipients (% by weight) |
| polyethylene glycol 200 | 15 ± 10% |
| propylene glycol | 10 ± 10% |
| dimethyl sulfoxide | 5 ± 10% |
| tetraglycol | 10 ± 10% |
| KOLLIPHOR EL | 25.5 ± 10% |
| CAPMUL 907P | 27 ± 10% |
| CAPTEX 8000 | 7.5 ± 10% |

In certain embodiments, the four or more pharmaceutically acceptable excipients consist of:

| (5D). | |
|---|---|
| Pharmaceutically acceptable excipient | Concentration in the four or more pharmaceutically acceptable excipients (% by weight) |
| polyethylene glycol 200 | 15 ± 15% |
| propylene glycol | 10 ± 15% |
| dimethyl sulfoxide | 5 ± 15% |
| tetraglycol | 10 ± 15% |
| KOLLIPHOR EL | 25.5 ± 15% |
| CAPMUL 907P | 27 ± 15% |
| CAPTEX 8000 | 7.5 ± 15% |

In certain embodiments, the four or more pharmaceutically acceptable excipients consist of:

| (5E). | |
|---|---|
| Pharmaceutically acceptable excipient | Concentration in the four or more pharmaceutically acceptable excipients (% by weight) |
| polyethylene glycol 200 | 15 ± 20% |
| propylene glycol | 10 ± 20% |
| dimethyl sulfoxide | 5 ± 20% |
| tetraglycol | 10 ± 20% |
| KOLLIPHOR EL | 25.5 ± 20% |
| CAPMUL 907P | 27 ± 20% |
| CAPTEX 8000 | 7.5 ± 20% |

In certain embodiments, the four or more pharmaceutically acceptable excipients consist of:

| (6A). | |
|---|---|
| Pharmaceutically acceptable excipient | Concentration in the four or more pharmaceutically acceptable excipients (% by weight) |
| polyethylene glycol 200 | about 20 |
| propylene glycol | about 10 |
| dimethyl sulfoxide | about 5 |
| tetraglycol | about 10 |
| KOLLIPHOR EL | about 19 |
| TWEEN 85 | about 7 |
| CAPMUL 907P | about 29 |

In certain embodiments, the four or more pharmaceutically acceptable excipients consist of:

| (6B). | |
|---|---|
| Pharmaceutically acceptable excipient | Concentration in the four or more pharmaceutically acceptable excipients (% by weight) |
| polyethylene glycol 200 | 20 ± 5% |
| propylene glycol | 10 ± 5% |
| dimethyl sulfoxide | 5 ± 5% |
| tetraglycol | 10 ± 5% |
| KOLLIPHOR EL | 19 ± 5% |
| TWEEN 85 | 7 ± 5% |
| CAPMUL 907P | 29 ± 5% |

In certain embodiments, the four or more pharmaceutically acceptable excipients consist of:

| (6C). | |
|---|---|
| Pharmaceutically acceptable excipient | Concentration in the four or more pharmaceutically acceptable excipients (% by weight) |
| polyethylene glycol 200 | 20 ± 10% |
| propylene glycol | 10 ± 10% |
| dimethyl sulfoxide | 5 ± 10% |
| tetraglycol | 10 ± 10% |
| KOLLIPHOR EL | 19 ± 10% |
| TWEEN 85 | 7 ± 10% |
| CAPMUL 907P | 29 ± 10% |

In certain embodiments, the four or more pharmaceutically acceptable excipients consist of:

| (6D). | |
|---|---|
| Pharmaceutically acceptable excipient | Concentration in the four or more pharmaceutically acceptable excipients (% by weight) |
| polyethylene glycol 200 | 20 ± 15% |
| propylene glycol | 10 ± 15% |
| dimethyl sulfoxide | 5 ± 15% |
| tetraglycol | 10 ± 15% |
| KOLLIPHOR EL | 19 ± 15% |
| TWEEN 85 | 7 ± 15% |
| CAPMUL 907P | 29 ± 15% |

In certain embodiments, the four or more pharmaceutically acceptable excipients consist of:

| (6E). | |
|---|---|
| Pharmaceutically acceptable excipient | Concentration in the four or more pharmaceutically acceptable excipients (% by weight) |
| polyethylene glycol 200 | 20 ± 20% |
| propylene glycol | 10 ± 20% |
| dimethyl sulfoxide | 5 ± 20% |
| tetraglycol | 10 ± 20% |
| KOLLIPHOR EL | 19 ± 20% |
| TWEEN 85 | 7 ± 20% |
| CAPMUL 907P | 29 ± 20% |

In certain embodiments, the four or more pharmaceutically acceptable excipients consist of:

| (7A). | |
|---|---|
| Pharmaceutically acceptable excipient | Concentration in the four or more pharmaceutically acceptable excipients (% by weight) |
| polyethylene glycol 200 | about 20 |
| propylene glycol | about 10 |
| dimethyl sulfoxide | about 5 |
| tetraglycol | about 9 |
| KOLLIPHOR EL | about 28 |
| CAPMUL PG-8 NF | about 28 |

In certain embodiments, the four or more pharmaceutically acceptable excipients consist of:

| (7B). | |
|---|---|
| Pharmaceutically acceptable excipient | Concentration in the four or more pharmaceutically acceptable excipients (% by weight) |
| polyethylene glycol 200 | 20 ± 5% |
| propylene glycol | 10 ± 5% |
| dimethyl sulfoxide | 5 ± 5% |
| tetraglycol | 9 ± 5% |
| KOLLIPHOR EL | 28 ± 5% |
| CAPMUL PG-8 NF | 28 ± 5% |

In certain embodiments, the four or more pharmaceutically acceptable excipients consist of:

| (7C). | |
|---|---|
| Pharmaceutically acceptable excipient | Concentration in the four or more pharmaceutically acceptable excipients (% by weight) |
| polyethylene glycol 200 | 20 ± 10% |
| propylene glycol | 10 ± 10% |
| dimethyl sulfoxide | 5 ± 10% |
| tetraglycol | 9 ± 10% |
| KOLLIPHOR EL | 28 ± 10% |
| CAPMUL PG-8 NF | 28 ± 10% |

In certain embodiments, the four or more pharmaceutically acceptable excipients consist of:

| (7D). | |
|---|---|
| Pharmaceutically acceptable excipient | Concentration in the four or more pharmaceutically acceptable excipients (% by weight) |
| polyethylene glycol 200 | 20 ± 15% |
| propylene glycol | 10 ± 15% |
| dimethyl sulfoxide | 5 ± 15% |
| tetraglycol | 9 ± 15% |
| KOLLIPHOR EL | 28 ± 15% |
| CAPMUL PG-8 NF | 28 ± 15% |

In certain embodiments, the four or more pharmaceutically acceptable excipients consist of:

| (7E). | |
|---|---|
| Pharmaceutically acceptable excipient | Concentration in the four or more pharmaceutically acceptable excipients (% by weight) |
| polyethylene glycol 200 | 20 ± 20% |
| propylene glycol | 10 ± 20% |
| dimethyl sulfoxide | 5 ± 20% |
| tetraglycol | 9 ± 20% |
| KOLLIPHOR EL | 28 ± 20% |
| CAPMUL PG-8 NF | 28 ± 20% |

In certain embodiments, the four or more pharmaceutically acceptable excipients consist of:

| (8A). | |
|---|---|
| Pharmaceutically acceptable excipient | Concentration in the four or more pharmaceutically acceptable excipients (% by weight) |
| polyethylene glycol 200 | about 20 |
| propylene glycol | about 10 |
| dimethyl sulfoxide | about 5 |
| tetraglycol | about 9 |
| KOLLIPHOR EL | about 28 |
| CAPRYOL 90 | about 28 |

In certain embodiments, the four or more pharmaceutically acceptable excipients consist of:

| (8B). | |
|---|---|
| Pharmaceutically acceptable excipient | Concentration in the four or more pharmaceutically acceptable excipients (% by weight) |
| polyethylene glycol 200 | 20 ± 5% |
| propylene glycol | 10 ± 5% |
| dimethyl sulfoxide | 5 ± 5% |
| tetraglycol | 9 ± 5% |
| KOLLIPHOR EL | 28 ± 5% |
| CAPRYOL 90 | 28 ± 5% |

In certain embodiments, the four or more pharmaceutically acceptable excipients consist of:

| (8C). | |
|---|---|
| Pharmaceutically acceptable excipient | Concentration in the four or more pharmaceutically acceptable excipients (% by weight) |
| polyethylene glycol 200 | 20 ± 10% |
| propylene glycol | 10 ± 10% |
| dimethyl sulfoxide | 5 ± 10% |
| tetraglycol | 9 ± 10% |
| KOLLIPHOR EL | 28 ± 10% |
| CAPRYOL 90 | 28 ± 10% |

In certain embodiments, the four or more pharmaceutically acceptable excipients consist of:

| (8D). | |
|---|---|
| Pharmaceutically acceptable excipient | Concentration in the four or more pharmaceutically acceptable excipients (% by weight) |
| polyethylene glycol 200 | 20 ± 15% |
| propylene glycol | 10 ± 15% |
| dimethyl sulfoxide | 5 ± 15% |
| tetraglycol | 9 ± 15% |
| KOLLIPHOR EL | 28 ± 15% |
| CAPRYOL 90 | 28 ± 15% |

In certain embodiments, the four or more pharmaceutically acceptable excipients consist of:

| (8E). | |
|---|---|
| Pharmaceutically acceptable excipient | Concentration in the four or more pharmaceutically acceptable excipients (% by weight) |
| polyethylene glycol 200 | 20 ± 20% |
| propylene glycol | 10 ± 20% |
| dimethyl sulfoxide | 5 ± 20% |
| tetraglycol | 9 ± 20% |
| KOLLIPHOR EL | 28 ± 20% |
| CAPRYOL 90 | 28 ± 20% |

In certain embodiments, the four or more pharmaceutically acceptable excipients consist of:

| (9A). | |
|---|---|
| Pharmaceutically acceptable excipient | Concentration in the four or more pharmaceutically acceptable excipients (% by weight) |
| polyethylene glycol 200 | about 21 |
| propylene glycol | about 10 |
| dimethyl sulfoxide | about 5 |
| tetraglycol | about 9 |
| KOLLIPHOR EL | about 27 |
| CAPMUL PG-8 NF | about 28 |
| butylated hydroxytoluene (BHT) | about 0.05 |

In certain embodiments, the four or more pharmaceutically acceptable excipients consist of:

| (9B). | |
|---|---|
| Pharmaceutically acceptable excipient | Concentration in the four or more pharmaceutically acceptable excipients (% by weight) |
| polyethylene glycol 200 | 21 ± 5% |
| propylene glycol | 10 ± 5% |
| dimethyl sulfoxide | 5 ± 5% |
| tetraglycol | 9 ± 5% |
| KOLLIPHOR EL | 27 ± 5% |
| CAPMUL PG-8 NF | 28 ± 5% |
| butylated hydroxytoluene (BHT) | 0.05 ± 5% |

In certain embodiments, the four or more pharmaceutically acceptable excipients consist of:

| (9C). | |
|---|---|
| Pharmaceutically acceptable excipient | Concentration in the four or more pharmaceutically acceptable excipients (% by weight) |
| polyethylene glycol 200 | 21 ± 10% |
| propylene glycol | 10 ± 10% |
| dimethyl sulfoxide | 5 ± 10% |
| tetraglycol | 9 ± 10% |
| KOLLIPHOR EL | 27 ± 10% |
| CAPMUL PG-8 NF | 28 ± 10% |
| butylated hydroxytoluene (BHT) | 0.05 ± 10% |

In certain embodiments, the four or more pharmaceutically acceptable excipients consist of:

| (9D). | |
|---|---|
| Pharmaceutically acceptable excipient | Concentration in the four or more pharmaceutically acceptable excipients (% by weight) |
| polyethylene glycol 200 | 21 ± 15% |
| propylene glycol | 10 ± 15% |
| dimethyl sulfoxide | 5 ± 15% |
| tetraglycol | 9 ± 15% |
| KOLLIPHOR EL | 27 ± 15% |
| CAPMUL PG-8 NF | 28 ± 15% |
| butylated hydroxytoluene (BHT) | 0.05 ± 15% |

In certain embodiments, the four or more pharmaceutically acceptable excipients consist of:

| (9E). | |
|---|---|
| Pharmaceutically acceptable excipient | Concentration in the four or more pharmaceutically acceptable excipients (% by weight) |
| polyethylene glycol 200 | 21 ± 20% |
| propylene glycol | 10 ± 20% |
| dimethyl sulfoxide | 5 ± 20% |
| tetraglycol | 9 ± 20% |
| KOLLIPHOR EL | 27 ± 20% |
| CAPMUL PG-8 NF | 28 ± 20% |
| butylated hydroxytoluene (BHT) | 0.05 ± 20% |

In certain embodiments, the four or more pharmaceutically acceptable excipients consist of:

| (10A). | |
|---|---|
| Pharmaceutically acceptable excipient | Concentration in the four or more pharmaceutically acceptable excipients (% by weight) |
| polyethylene glycol 200 | about 24 |
| propylene glycol | about 15 |
| dimethyl sulfoxide | about 5 |
| KOLLIPHOR EL | about 28 |
| CAPMUL PG-8 NF | about 28 |
| butylated hydroxytoluene (BHT) | about 0.05 |

In certain embodiments, the four or more pharmaceutically acceptable excipients consist of:

| (10B). | |
|---|---|
| Pharmaceutically acceptable excipient | Concentration in the four or more pharmaceutically acceptable excipients (% by weight) |
| polyethylene glycol 200 | 24 ± 5% |
| propylene glycol | 15 ± 5% |
| dimethyl sulfoxide | 5 ± 5% |
| KOLLIPHOR EL | 28 ± 5% |
| CAPMUL PG-8 NF | 28 ± 5% |
| butylated hydroxytoluene (BHT) | 0.05 ± 5% |

In certain embodiments, the four or more pharmaceutically acceptable excipients consist of:

| (10C). | |
|---|---|
| Pharmaceutically acceptable excipient | Concentration in the four or more pharmaceutically acceptable excipients (% by weight) |
| polyethylene glycol 200 | 24 ± 10% |
| propylene glycol | 15 ± 10% |
| dimethyl sulfoxide | 5 ± 10% |
| KOLLIPHOR EL | 28 ± 10% |
| CAPMUL PG-8 NF | 28 ± 10% |
| butylated hydroxytoluene (BHT) | 0.05 ± 10% |

In certain embodiments, the four or more pharmaceutically acceptable excipients consist of:

| (10D). | |
|---|---|
| Pharmaceutically acceptable excipient | Concentration in the four or more pharmaceutically acceptable excipients (% by weight) |
| polyethylene glycol 200 | 24 ± 15% |
| propylene glycol | 15 ± 15% |
| dimethyl sulfoxide | 5 ± 15% |
| KOLLIPHOR EL | 28 ± 15% |
| CAPMUL PG-8 NF | 28 ± 15% |
| butylated hydroxytoluene (BHT) | 0.05 ± 15% |

In certain embodiments, the four or more pharmaceutically acceptable excipients consist of:

| (10E). | |
|---|---|
| Pharmaceutically acceptable excipient | Concentration in the four or more pharmaceutically acceptable excipients (% by weight) |
| polyethylene glycol 200 | 24 ± 20% |
| propylene glycol | 15 ± 20% |
| dimethyl sulfoxide | 5 ± 20% |
| KOLLIPHOR EL | 28 ± 20% |
| CAPMUL PG-8 NF | 28 ± 20% |
| butylated hydroxytoluene (BHT) | 0.05 ± 20% |

In certain embodiments, the four or more pharmaceutically acceptable excipients consist of:

(11A).

| Pharmaceutically acceptable excipient | Concentration in the four or more pharmaceutically acceptable excipients (% by weight) |
|---|---|
| polyethylene glycol 200 | about 21 |
| propylene glycol | about 10 |
| dimethyl sulfoxide | about 5 |
| tetraglycol | about 9 |
| KOLLIPHOR EL | about 27 |
| CAPMUL PG-8 NF | about 28 |
| butylated hydroxyanisole (BHA) | about 0.05 |

In certain embodiments, the four or more pharmaceutically acceptable excipients consist of:

(12A).

| Pharmaceutically acceptable excipient | Concentration in the four or more pharmaceutically acceptable excipients (% by weight) |
|---|---|
| polyethylene glycol 200 | about 24 |
| propylene glycol | about 15 |
| dimethyl sulfoxide | about 5 |
| KOLLIPHOR EL | about 28 |
| CAPMUL PG-8 NF | about 28 |
| butylated hydroxyanisole (BHA) | about 0.05 |

In certain embodiments, the four or more pharmaceutically acceptable excipients consist of:

(13A).

| Pharmaceutically acceptable excipient | Concentration in the four or more pharmaceutically acceptable excipients (% by weight) |
|---|---|
| polyethylene glycol 200 | about 20 |
| propylene glycol | about 10 |
| dimethyl sulfoxide | about 5 |
| tetraglycol | about 9 |
| KOLLIPHOR EL | about 27 |
| CAPMUL PG-8 NF | about 27 |
| butylated hydroxytoluene (BHT) | about 2 |

In certain embodiments, the four or more pharmaceutically acceptable excipients consist of:

(14A).

| Pharmaceutically acceptable excipient | Concentration in the four or more pharmaceutically acceptable excipients (% by weight) |
|---|---|
| polyethylene glycol 200 | about 24 |
| propylene glycol | about 15 |
| dimethyl sulfoxide | about 5 |
| KOLLIPHOR EL | about 27 |
| CAPMUL PG-8 NF | about 27 |
| butylated hydroxytoluene (BHT) | about 2 |

In certain embodiments, the four or more pharmaceutically acceptable excipients consist of:

(15A).

| Pharmaceutically acceptable excipient | Concentration in the four or more pharmaceutically acceptable excipients (% by weight) |
|---|---|
| polyethylene glycol 200 | about 19.99 |
| propylene glycol | about 9.995 |
| dimethyl sulfoxide | about 4.9975 |
| tetraglycol | about 8.9955 |
| KOLLIPHOR EL | about 27.986 |
| CAPMUL PG-8 NF | about 27.986 |
| butylated hydroxytoluene (BHT) | about 0.05. |

In certain embodiments, the four or more pharmaceutically acceptable excipients consist of:

(15B).

| Pharmaceutically acceptable excipient | Concentration in the four or more pharmaceutically acceptable excipients (% by weight) |
|---|---|
| polyethylene glycol 200 | 19.99 ± 5% |
| propylene glycol | 9.995 ± 5% |
| dimethyl sulfoxide | 4.9975 ± 5% |
| tetraglycol | 8.9955 ± 5% |
| KOLLIPHOR EL | 27.986 ± 5% |
| CAPMUL PG-8 NF | 27.986 ± 5% |
| butylated hydroxytoluene (BHT) | 0.05 ± 5%. |

In certain embodiments, the four or more pharmaceutically acceptable excipients consist of:

(15C).

| Pharmaceutically acceptable excipient | Concentration in the four or more pharmaceutically acceptable excipients (% by weight) |
|---|---|
| polyethylene glycol 200 | 19.99 ± 10% |
| propylene glycol | 9.995 ± 10% |
| dimethyl sulfoxide | 4.9975 ± 10% |
| tetraglycol | 8.9955 ± 10% |
| KOLLIPHOR EL | 27.986 ± 10% |
| CAPMUL PG-8 NF | 27.986 ± 10% |
| butylated hydroxytoluene (BHT) | 0.05 ± 10%. |

In certain embodiments, the four or more pharmaceutically acceptable excipients consist of:

(15D).

| Pharmaceutically acceptable excipient | Concentration in the four or more pharmaceutically acceptable excipients (% by weight) |
|---|---|
| polyethylene glycol 200 | 19.99 ± 15% |
| propylene glycol | 9.995 ± 15% |
| dimethyl sulfoxide | 4.9975 ± 15% |
| tetraglycol | 8.9955 ± 15% |
| KOLLIPHOR EL | 27.986 ± 15% |
| CAPMUL PG-8 NF | 27.986 ± 15% |
| butylated hydroxytoluene (BHT) | 0.05 ± 15%. |

In certain embodiments, the four or more pharmaceutically acceptable excipients consist of:

(15E).

| Pharmaceutically acceptable excipient | Concentration in the four or more pharmaceutically acceptable excipients (% by weight) |
|---|---|
| polyethylene glycol 200 | 19.99 ± 20% |
| propylene glycol | 9.995 ± 20% |
| dimethyl sulfoxide | 4.9975 ± 20% |
| tetraglycol | 8.9955 ± 20% |
| KOLLIPHOR EL | 27.986 ± 20% |
| CAPMUL PG-8 NF | 27.986 ± 20% |
| butylated hydroxytoluene (BHT) | 0.05 ± 20%. |

In certain embodiments, the four or more pharmaceutically acceptable excipients consist of:

(16A).

| Pharmaceutically acceptable excipient | Concentration in the four or more pharmaceutically acceptable excipients (% by weight) |
|---|---|
| polyethylene glycol 200 | about 20.862 |
| propylene glycol | about 9.606 |
| dimethyl sulfoxide | about 5.099 |
| tetraglycol | about 9.096 |
| KOLLIPHOR EL | about 27.259 |
| CAPMUL PG-8 NF | about 28.028 |
| butylated hydroxytoluene (BHT) | about 0.05. |

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (1F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (1F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (1F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (2F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (2F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (2F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (3F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (3F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (3F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (4F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (4F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 μg/ml and 150 μg/ml, inclusive; and the four or more pharmaceutically acceptable excipients consist of (4F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (5F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 μg/ml and 750 μg/ml, inclusive; and the four or more pharmaceutically acceptable excipients consist of (5F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 μg/ml and 150 μg/ml, inclusive; and the four or more pharmaceutically acceptable excipients consist of (5F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (6F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 μg/ml and 750 μg/ml, inclusive; and the four or more pharmaceutically acceptable excipients consist of (6F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 μg/ml and 150 μg/ml, inclusive; and the four or more pharmaceutically acceptable excipients consist of (6F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (7F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 μg/ml and 750 μg/ml, inclusive; and the four or more pharmaceutically acceptable excipients consist of (7F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 μg/ml and 150 μg/ml, inclusive; and the four or more pharmaceutically acceptable excipients consist of (7F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (8F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 μg/ml and 750 μg/ml, inclusive; and the four or more pharmaceutically acceptable excipients consist of (8F). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 μg/ml and 150 μg/ml, inclusive; and the four or more pharmaceutically acceptable excipients consist of (8F).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (1A), (1B), (1C), (1D), or (1E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 μg/ml and 750 μg/ml, inclusive; and the four or more pharmaceutically acceptable excipients consist of (1A), (1B), (1C), (1D), or (1E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 μg/ml and 150 µg/ml, inclusive; and the four or more pharmaceutically acceptable excipients consist of (1A), (1B), (1C), (1D), or (1E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (2A), (2B), (2C), (2D), or (2E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (2A), (2B), (2C), (2D), or (2E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (2A), (2B), (2C), (2D), or (2E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (3A), (3B), (3C), (3D), or (3E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (3A), (3B), (3C), (3D), or (3E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (3A), (3B), (3C), (3D), or (3E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (4A), (4B), (4C), (4D), or (4E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (4A), (4B), (4C), (4D), or (4E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (4A), (4B), (4C), (4D), or (4E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (5A), (5B), (5C), (5D), or (5E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (5A), (5B), (5C), (5D), or (5E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (5A), (5B), (5C), (5D), or (5E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (6A), (6B), (6C), (6D), or (6E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (6A), (6B), (6C), (6D), or (6E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (6A), (6B), (6C), (6D), or (6E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (7A), (7B), (7C), (7D), or (7E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (7A), (7B), (7C), (7D), or (7E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (7A), (7B), (7C), (7D), or (7E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of (8A), (8B), (8C), (8D), or (8E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of (8A), (8B), (8C), (8D), or (8E). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of (8A), (8B), (8C), (8D), or (8E).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of any one of (9A) to (16A). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 150 µg/ml and 750 µg/ml, inclusive; and the four or more pharmaceutically acceptable excipients consist of any one of (9A) to (16A). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.1 µg/ml and 150 µg/ml, inclusive; and the four or more pharmaceutically acceptable excipients consist of any one of (9A) to (16A).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof; and the four or more pharmaceutically acceptable excipients consist of any one of (15A) to (15E) (e.g., (15A)).

In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the concentration of lasofoxifene, or the pharmaceutically acceptable salt, solvate, hydrate, polymorph, co-crystal, tautomer, stereoisomer, isotopically labeled derivative, or prodrug thereof, in the pharmaceutical composition is between 0.00025 mg/ml and 0.25 mg/ml, inclusive; and the four or more pharmaceutically acceptable excipients consist of any one of (1A) to (16A) (e.g., (15A)). In certain embodiments, the one or more SERM(s) consist of lasofoxifene, or a pharmaceutically acceptable salt, solvate, hydrate, polymorph, co-crystal, tautomer, stereoisomer, isotopically labeled derivative, or prodrug thereof, wherein the amount of lasofoxifene, or the pharmaceutically acceptable salt, solvate, hydrate, polymorph, co-crystal, tautomer, stereoisomer, isotopically labeled derivative, or prodrug thereof, is between 0.00025 mg and 0.25 mg, inclusive; and the four or more pharmaceutically acceptable excipients consist of any one of (1A) to (16A) (e.g., 15(A)).

In a pharmaceutical composition described herein, any two of: the one or more SERM(s) and the four or more pharmaceutically acceptable excipients are different from each other; and the combined concentrations of the four or more pharmaceutically acceptable excipients are 100%. For example, in any one of (1A) to (1F), (2A) to (2F), (3A) to (3F), (4A) to (4F), (5A) to (5F), (6A) to (6F), (7A) to (7F), and (8A) to (8F), the concentration of any one of the four or more pharmaceutically acceptable excipients is limited by the condition that the combined concentrations of the four or more pharmaceutically acceptable excipients are 100%. For example, in any one of (9A) to (16A), the concentration of any one of the four or more pharmaceutically acceptable excipients is limited by the condition that the combined concentrations of the four or more pharmaceutically acceptable excipients are 100%.

In certain embodiments, the pharmaceutical composition is in the form of an oil-in-water emulsion. In certain embodiments, the pharmaceutical composition is not in the form of a water-in-oil emulsion. In certain embodiments, the pharmaceutical composition is not in the form of a suspension. In certain embodiments, the pharmaceutical composition is in the form of nanodroplets. In certain embodiments, the pharmaceutical composition is in the form of nanodroplets upon contacting with vaginal fluid (e.g., upon contacting with about 2 parts (by volume) of vaginal fluid) and/or vaginal mucus. In certain embodiments, the pharmaceutical compositions self-nanoemulsify to form nanodroplets upon contacting with vaginal fluid (e.g., upon contacting with about 2 parts (by volume) of vaginal fluid) and/or vaginal mucus. A "nanodroplet" is a droplet, wherein the size of the droplet is less than 340 nm, as determined by DLS. In certain embodiments, the average size of the nanodroplets is between 1 nm and 300 nm, between 1 nm and 200 nm, between 1 nm and 50 nm, between 10 nm and 300 nm, between 10 nm and 200 nm, between 10 nm and 50 nm, between 30 nm and 300 nm, between 30 nm and 200 nm, between 30 nm and 100 nm, or between 30 nm and 50 nm, inclusive. In certain embodiments, the average size of the nanodroplets is between 1 nm and 100 nm, inclusive. In certain embodiments, the average size of the nanodroplets is between 10 nm and 100 nm, inclusive. In certain embodiments, the average size of the nanodroplets is between 10 nm and 50 nm, inclusive.

In certain embodiments, the DPI of the nanodroplets is between 0.1 and 1, between 0.1 and 0.5, between 0.1 and 0.3, between 0.2 and 1, between 0.2 and 0.7, between 0.2 and 0.4, between 0.4 and 1, or between 0.4 and 0.7, inclusive. In certain embodiments, the DPI of the nanodroplets is between 0.1 and 0.7, inclusive. In certain embodiments, the DPI of the nanodroplets is between 0.2 and 0.5, inclusive. In certain embodiments, the DPI of the nanodroplets is between 0.1 and 0.4, inclusive. In certain embodiments, the DPI of the nanodroplets is between 0.3 and 0.5, inclusive.

In certain embodiments, the average size of the nanodroplets is between 1 nm and 100 nm, inclusive, and the DPI of the nanodroplets is between 0.1 and 0.7, inclusive.

A "female" subject is a subject with a vagina. In certain embodiments, the female subject is a female human. In certain embodiments, the female subject is a female non-human animal. In certain embodiments, the female subject is a female mammal. In certain embodiments, the female subject is a female non-human mammal (e.g., dog, cat, cow, pig, horse, sheep, goat, rodent (e.g., mouse or rat), or non-human primate (e.g., monkey or chimpanzee), each of which is female. In certain embodiments, the female subject is a genetically engineered (e.g., transgenic) female subject. In certain embodiments, the female subject is a transgendered female subject (e.g., a subject with a vagina, the subject born without a vagina) (e.g., transgendered female human)).

A female subject in need thereof is a female subject in need of delivering a pharmaceutical composition described herein to the vagina of the female subject in need thereof. In certain embodiments, the female subject in need thereof is further in need of treatment of a disease (e.g., vulvovaginal atrophy, dyspareunia, sexual dysfunction, osteoporosis, or breast cancer). In certain embodiments, the female subject in need thereof is further in need of prevention of a disease (e.g., vulvovaginal atrophy, dyspareunia, sexual dysfunction, osteoporosis, or breast cancer). In certain embodiments, the female subject in need of delivering a pharmaceutical composition and further in need of prevention of a disease is a female subject who has (e.g., who has been diagnosed to have; or who has, based on family history) a higher than normal likelihood of developing a disease described herein. In certain embodiments, the female subject in need thereof is a woman (e.g., premenopausal woman or postmenopausal woman).

An "effective amount" of a pharmaceutical composition described herein refers to an amount of the one or more SERM(s) in the pharmaceutical composition sufficient to elicit the desired biological response. An effective amount may vary depending on such factors as the desired biological endpoint, the pharmacokinetics of the one or more SERM(s) or pharmaceutical composition, the disease being treated, the mode of administration, and the age and health of the female subject. In certain embodiments, an effective amount is a therapeutically effective amount. In certain embodiments, an effective amount is a prophylactic treatment. In certain embodiments, an effective amount is the amount of the one or more SERM(s) in a single dose. In certain embodiments, an effective amount is the combined amounts of one or more SERM(s) in multiple doses.

A "therapeutically effective amount" of a pharmaceutical composition described herein is an amount of the one or more SERM(s) in the pharmaceutical composition sufficient to provide a therapeutic benefit in the treatment of a disease or to reduce or eliminate one or more symptoms associated with the disease.

A "prophylactically effective amount" of a pharmaceutical composition described herein is an amount of the one or more SERM(s) in the pharmaceutical composition sufficient to prevent a disease or one or more symptoms associated with the disease, or prevent or delay the recurrence of the disease or one or more symptoms associated with the disease.

The terms "administering to a female subject" and "contacting the vagina of the female subject with" are used interchangeably.

The terms "administering" and "dosing" are used interchangeably.

The terms "administration", "dose", and "dosage" are used interchangeably.

An effective amount may be included in a single dose or multiple doses. In certain embodiments, when multiple doses are administered to a female subject, any two doses of the multiple doses include different or substantially the same amounts of the one or more SERM(s) in a pharmaceutical composition described herein. In certain embodiments, when multiple doses are administered to a female subject, the frequency of administering the multiple doses to the female subject is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the female subject is one dose per 1, 2, 3, 4, 5, or 6 days. In certain embodiments, the frequency of administering the multiple doses to the female subject is one dose per week (7 days). In certain embodiments, the frequency of administering the multiple doses to the female subject is one dose per 10 days, 2 weeks, 3 weeks, or 4 weeks. In certain embodiments, the frequency of administering the multiple doses to the female subject is one dose per month. In certain embodiments, the frequency of administering the multiple doses to the female subject is one dose per 2 months, 3 months, 4 months, 5 months, or 6 months. In certain embodiments, when multiple doses are administered to a female subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the female subject. In certain embodiments, the duration between the first dose and last dose of the multiple doses is three months, six months, or one year. In certain embodiments, the multiple doses consist of between 4 and 52 doses, inclusive. In certain embodiments, the multiple doses consist of between 2 and 12 doses, inclusive. In certain embodiments, the multiple doses consist of 1 dose, 2 doses, about 4 doses, about 8 doses, about 12 doses, about 18 doses, about 24 doses, about 36 doses, about 48 doses, about 78 doses, or about 104 doses. In certain embodiments, the duration between the first dose and last dose of the multiple doses is the lifetime of the female subject. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of the one or more SERM(s) described herein. In certain embodiments, a dose (e.g., a single dose, or any dose of multiple doses) described herein includes between 1 μg and 100 μg, inclusive, of the one or more SERM(s). In certain embodiments, a dose (e.g., a single dose, or any dose of multiple doses) described herein includes between 10 μg and 1 mg, inclusive, of the one or more SERM(s). In certain embodiments, a dose (e.g., a single dose, or any dose of multiple doses) described herein includes between 100 μg and 10 mg, inclusive, of the one or more SERM(s). In certain embodiments, a dose (e.g., a single dose, or any dose of multiple doses) described herein includes about 0.25 mg, about 0.025 mg, about 0.0025 mg, or about 0.00025 mg of the one or more SERM(s).

Dose ranges as described herein provide guidance for the administration of a pharmaceutical composition to an adult female subject. The amount to be administered to, for example, a female non-adult can be determined by a medical practitioner or person skilled in the art and can be lower or the same as that administered to a female adult. In certain embodiments, a dose described herein is a dose to an adult female human whose body weight is 70 kg.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the one or more SERM(s). The amount of the one or more SERM(s) is generally equal to the dosage of pharmaceutical composition which would be administered to a female subject and/or a convenient fraction of such a dosage, such as one-half or one-third of such a dosage.

In certain embodiments, the pharmaceutical composition further comprises additional pharmaceutically acceptable excipients, such as inert diluents, dispersing agents, granulating agents, additional emulsifiers, disintegrating agents, binding agents, preservatives, buffering agents, lubricating agents, and/or oils. In certain embodiments, the pharmaceutical composition further comprises cocoa butter, suppository wax, coloring agent, coating agent, or perfuming agent, or a combination thereof.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating agents and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary additional emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

The one or more SERM(s) may be unstable (e.g., chemically unstable, e.g., at least 0.001%, at least 0.01%, at least 0.1%, at least 1%, or at least 10%, degraded) after being stored (e.g., at room temperature) for a period of time (e.g., 7 days, 14 days, 1 month, 2 months, 3 months, 6 months, 12 months, 2 years, 3 years, or 5 years). The stability (e.g., chemical stability) of the one or more SERM(s) in the pharmaceutical composition may be determined with near infrared spectroscopy (NIR) and/or HPLC. The one or more SERM(s) may be oxidized by oxidant(s). For example, lasofoxifene may be oxidized as shown below:

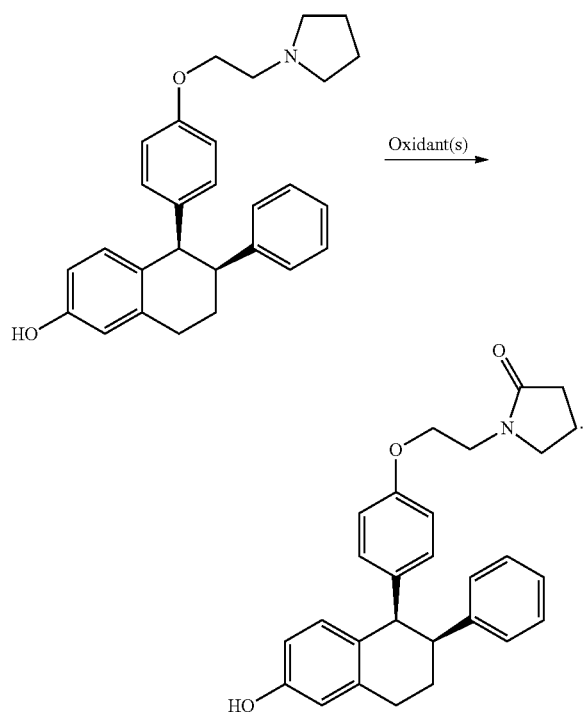

Lasofoxifene may also be oxidized as shown below:

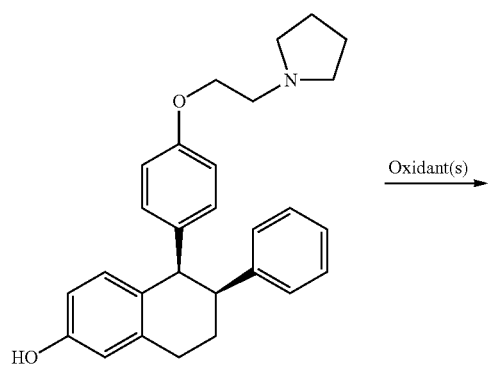

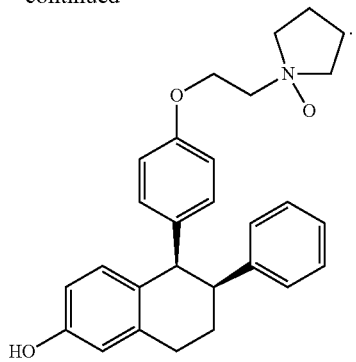

The oxidant(s) may include peroxide(s). Ether moieties of the four or more pharmaceutically acceptable excipients may react (e.g., with dioxygen ($O_2$)) to form peroxides:

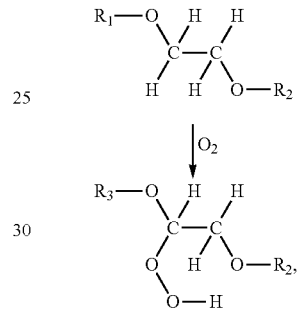

and the resuling peroxides may oxidize the one or more SERM(s) in the pharmaceutical composition. Shown in Table 1B is measured level of hydroperoxides in select pharmaceutically acceptable excipients (Wasylaschuk et al., *J. Pharm. Sci.*, 2007, 96(1):106-16).

TABLE 1B

Measured level of hydroperoxides in select pharmaceutically acceptable excipients.

| Excipient | # Lots Tested | Average HPO[a] (nmole/g) | High HPO Lot (nmole/g) | Low HPO Lot (nmole/g) |
|---|---|---|---|---|
| PVP | 5 | 7300 | 11000 | 3600 |
| PEG 400 | 4 | 2200 | 3300 | 1000 |
| PS80 | 8 | 1500 | 4600 | 180 |
| HPC | 21 | 300 | 890 | 50 |
| Poloxamer[b] | 7 | 30 | 50 | 10 |
| PEG solid[c] | 4 | 20 | 40 | <10 |
| MCG | 3 | <10 | <10 | <10 |
| Microcrystalline cellulose | 5 | <10 | 10 | <10 |
| Mannitol | 5 | <10 | <10 | <10 |
| Lactose | 5 | <10 | 10 | <10 |
| Sucrose | 5 | <10 | 20 | <10 |

The oxidant(s) may include a carboxlic acid.

Including one or more antioxidant(s) in the pharmaceutical composition may increase the stability (e.g., chemical stability) of the one or more SERM(s) in the pharmaceutical composition. Exemplary antioxidants include tocopherol, butylated hydroxyanisole (BHA), butylated hydroxytoluene (BHT), and cysteine. Additional exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. In certain embodiments, the four or more pharmaceutically acceptable excipients further comprise: (e) one or more antioxidant(s), wherein the concentration of the first antioxidant in the four or more pharmaceutically acceptable excipients is not more than 5% by weight. In certain embodiments, the first antioxidant is BHA, BHT, tocopherol, or cysteine. In certain embodiments, the first antioxidant is BHA (e.g., a mixture (e.g., a 1:1 (w:w) mixture) of 2-tert-Butyl-4-methoxyphenol and 3-tert-butyl-4-methoxyphenol). In certain embodiments, the first antioxidant is BHT (e.g., 2,6-di-tert-butyl-4-methylphenol). In certain embodiments, the concentration of the first antioxidant in the four or more pharmaceutically acceptable excipients is between 0.001% and 0.01%, between 0.001% and 0.1%, between 0.01% and 0.1%, between 0.01% and 1%, between 0.1% and 1%, or between 0.1% and 10%, inclusive, by weight. In certain embodiments, the concentration of the first antioxidant in the four or more pharmaceutically acceptable excipients is between 0.05% and 2%, inclusive, by weight. In certain embodiments, the concentration of the first antioxidant in the four or more pharmaceutically acceptable excipients is about 0.05% by weight. In certain embodiments, the concentration of the first antioxidant in the four or more pharmaceutically acceptable excipients is between 0.01% and 0.25%, or between 0.005% and 0.5%, inclusive, by weight. In certain embodiments, the four or more pharmaceutically acceptable excipients further comprise one antioxidant. In certain embodiments, the four or more pharmaceutically acceptable excipients further comprise two or three antioxidants.

In certain embodiments, the four or more pharmaceutically acceptable excipients are substantially free of DMSO. In certain embodiments, the concentration of DMSO in the four or more pharmaceutically acceptable excipients is not more than 1%, not more than 0.3%, not more than 0.1%, not more than 0.03%, not more than 0.01%, not more than 0.003%, or not more than 0.001%, by weight.

The oxidant(s) may include dioxygen. In certain embodiments, the pharmaceutical composition is substantially free of dioxygen. In certain embodiments, the concentration of dioxygen in the pharmaceutical composition is not more than 0.1%, not more than 0.03%, not more than 0.01%, not more than 0.003%, not more than 0.001%, not more than 0.0003%, or not more than 0.0001%, by weight.

The four or more pharmaceutically acceptable excipients may further include one or more chelating agent(s). The chelating agent may be able to increase the stability (e.g., chemical stability) of the one or more SERM(s) in the pharmaceutical composition. In certain embodiments, the chelating agent is able to reduce the oxidation of the one or more SERM(s) and/or one or more of the pharmaceutically acceptable excipients in the pharmaceutical composition. Exemplary chelating agents include ethylenediaminetetraacetic acid (EDTA) and salts (e.g., pharmaceutically acceptable salts thereof) and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. In certain embodiments, the four or more pharmaceutically acceptable excipients further comprise: (f) one or more chelating agent(s), wherein the concentration of the first chelating agent in the four or more pharmaceutically acceptable excipients is not more than 5% by weight. In certain embodiments, the first chelating agent is EDTA, or a pharmaceutically acceptable salt thereof. In certain embodiments, the concentration of the first chelating agent in the four or more pharmaceutically acceptable excipients is between 0.01% and 0.05%, between 0.01% and 0.1%, between 0.01% and 2%, between 0.01% and 5%, between 0.05% and 1%, between 0.05% and 2%, between 0.05% and 5%, between 1% and 2%, between 1% and 5%, or between 2% and 5%, inclusive, by weight. In certain embodiments, the four or more pharmaceutically acceptable excipients further comprise one chelating agent. In certain embodiments, the four or more pharmaceutically acceptable excipients further comprise two or three chelating agents.

In certain embodiments, the pharmaceutical composition further includes a combination of two or more of the embodiments described herein for reducing the oxidation of the one or more SERM(s) and/or one or more of the pharmaceutically acceptable excipients in the pharmaceutical composition. In certain embodiments, the four or more pharmaceutically acceptable excipients further comprise one or more antioxidant(s) (e.g., BHT) and are substantially free of tetraglycol.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof. In certain embodiments, the buffering agent is not water. In certain embodiments, the buffering agent is not ethyl alcohol.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In certain embodiments, the pharmaceutical composition is in the form of a suppository. A suppository may be prepared by mixing the pharmaceutical composition with suitable non-irritating pharmaceutically acceptable excipients such as cocoa butter, polyethylene glycol, a suppository wax, or a pharmaceutically acceptable excipient that is a solid at ambient temperature and 1 atmosphere but is a liquid at body temperature and 1 atmosphere, and therefore melt in the vagina and release the one or more SERM(s).

A pharmaceutical composition described herein can be administered in combination with one or more additional pharmaceutical agents (e.g., therapeutically and/or prophylactically active agents). The pharmaceutical compositions can be administered in combination with additional pharmaceutical agents that improve their activity (e.g., activity (e.g., potency and/or efficacy) in treating or preventing a disease in a female subject in need thereof, in preventing a disease in a female subject in need thereof, improve the delivery of the one or more SERM(s) to the vagina, improve bioavailability, improve safety, reduce drug resistance, reduce and/or modify metabolism, inhibit excretion, and/or modify distribution in a female subject. It will also be appreciated that the therapy employed may achieve a desired effect for the same disorder, and/or it may achieve different effects. In certain embodiments, a pharmaceutical composition described herein including the one or more SERM(s) described herein and one or more additional pharmaceutical agent(s) shows a synergistic effect.

The pharmaceutical composition can be administered concurrently with, prior to, or subsequent to one or more additional pharmaceutical agents, which may be useful as, e.g., combination therapies. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional pharmaceutical agent may be administered at a dose and/or on a time schedule determined for that pharmaceutical agent. The additional pharmaceutical agents may also be administered together with each other and/or with the pharmaceutical composition described herein in a single dose or administered separately in different doses. The particular combination to employ in a regimen will take into account compatibility of the pharmaceutical composition described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

The pharmaceutical composition may be suitable for intravaginal administration. In certain embodiments, pharmaceutical composition is suitable for intravaginal administration with an applicator. In certain embodiments, the applicator comprises a suppository (e.g., syringe or tube). In certain embodiments, the applicator comprises a spatula, rod, or ring. The applicator may be pressurized or unpressurized. In certain embodiments, the pharmaceutical composition is suitable for intravaginal administration without an applicator.

In certain embodiments, the pharmaceutical composition is in the form of a capsule. In certain embodiments, the pharmaceutical composition further comprises a capsule, wherein the capsule encapsulates the one or more SERM(s) and the four or more pharmaceutically acceptable excipients. In certain embodiments, the capsule is a single-piece gel capsule. In certain embodiments, the capsule is a two-piece gel capsule. In certain embodiments, the gel comprises gelatin. In certain embodiments, the gel comprises a plant polysaccharide, or a derivative thereof (e.g., carrageenan, starch derivative, or cellulose derivative).

In certain embodiments, one or more of:
the one or more SERM(s); and
the four or more pharmaceutically acceptable excipients are in the form of particles. In certain embodiments, the particles are nanoparticles. In certain embodiments, the particles are microparticles. In certain embodiments, the one or more SERM(s) and the four or more pharmaceutically acceptable excipients are in the form of particles. In certain embodiments, the particles encapsulate the one or more of:
the one or more SERM(s); and
the four or more pharmaceutically acceptable excipients. In certain embodiments, the particles encapsulate the one or more SERM(s) and the four or more pharmaceutically acceptable excipients. In certain embodiments, the pharmaceutical composition is in the form of a tablet or cream. In certain embodiments, the pharmaceutical composition is in the form of a suppository or ring.

Kits

In another aspect, the present disclosure provides kits (e.g., pharmaceutical packs). The kits provided may comprise one or more SERM(s) or a pharmaceutical composition described herein and a first container (e.g., a tube, vial, ampule, bottle, syringe, and/or dispenser package, or other suitable container). In certain embodiments, the first container comprises an applicator. In some embodiments, provided kits may optionally further include a second container comprising one or more of the pharmaceutical excipients described herein. In certain embodiments, the kit further includes an applicator. In some embodiments, (1) the one or more SERM(s) or pharmaceutical composition included in the first container and (2) the one or more of the pharmaceutical excipients included in the second container are combined to form one unit dosage form.

In certain embodiments, a kit described herein further includes instructions for using the one or more SERM(s) or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for delivering the one or more SERM(s) or pharmaceutical composition described herein to the vagina of a female subject in need thereof. In certain embodiments, the kits and instructions provide for treating a disease in a female subject in need thereof. In certain embodiments, the kits and instructions provide for preventing a disease in a female subject in need thereof.

Methods of Use

In another aspect, the present disclosure provides methods of delivering one or more SERM(s) to a female subject in need thereof, the methods comprising contacting the vagina of the female subject with a pharmaceutical composition described herein.

In certain embodiments, the female subject is in need of treatment of vulvovaginal atrophy; and the amount of the pharmaceutical composition is therapeutically effective for treating vulvovaginal atrophy.

In certain embodiments, the female subject is in need of prevention of vulvovaginal atrophy; and the amount of the pharmaceutical composition is prophylactically effective for preventing vulvovaginal atrophy.

In certain embodiments, the female subject is in need of treatment of sexual dysfunction; and the amount of the pharmaceutical composition is therapeutically effective for treating sexual dysfunction.

In certain embodiments, the female subject is in need of prevention of sexual dysfunction; and the amount of the pharmaceutical composition is prophylactically effective for preventing sexual dysfunction.

In certain embodiments, the female subject is in need of treatment of osteoporosis; and the amount of the pharmaceutical composition is therapeutically effective for treating osteoporosis.

In certain embodiments, the female subject is in need of prevention of osteoporosis; and the amount of the pharmaceutical composition is prophylactically effective for preventing osteoporosis.

In certain embodiments, the female subject is in need of treatment of breast cancer; and the amount of the pharmaceutical composition is therapeutically effective for treating breast cancer.

In certain embodiments, the female subject is in need of prevention (e.g., prophylactic treatment) of breast cancer; and the amount of the pharmaceutical composition is prophylactically effective for preventing (e.g., effective for prophylactically treating) breast cancer.

In certain embodiments, the step of contacting is as described herein for administering or dosing the pharmaceutical composition. In certain embodiments, the step of contacting comprises contacting the vaginal mucosa of the female subject with a pharmaceutical composition described herein.

In another aspect, the present disclosure provides uses of a pharmaceutical composition described herein in a method described herein.

Methods of Preparing the Pharmaceutical Compositions

In another aspect, the present disclosure provides methods of preparing a pharmaceutical composition described herein. In certain embodiments, the method of preparing the pharmaceutical composition is a method described herein.

In another aspect, the present disclosure provides methods of preparing a pharmaceutical composition described herein comprising:

(A) mixing the four or more pharmaceutically acceptable excipients to form a mixture of pharmaceutically acceptable excipients; and (B) mixing the one or more SERM(s) with the mixture of pharmaceutically acceptable excipients.

In another aspect, the present disclosure provides methods of preparing a pharmaceutical composition described herein comprising:

(A) mixing the one or more SERM(s) with one or more of the (co)solvent(s) to form a mixture of the one or more SERM(s) and one or more of the (co)solvent(s); and (B) mixing the remaining pharmaceutically acceptable excipients with the mixture of SERM(s) and one or more of the (co)solvent(s).

In certain embodiments, the four or more pharmaceutically acceptable excipients are mixted substantially at the same time to form the mixture of pharmaceutically acceptable excipients. In certain embodiments, two or three of the four or more pharmaceutically acceptable excipients are mixed at different times to form the mixture of pharmaceutically acceptable excipients. In certain embodiments, the step of mixing the four or more pharmaceutically acceptable excipients to form a mixture of pharmaceutically acceptable excipients comprises:

(a) mixing two or three of the four or more pharmaceutically acceptable excipients to form a first mixture of pharmaceutically acceptable excipients; and (b) mixing the remaining ones of the four or more pharmaceutically acceptable excipients with the first mixture of pharmaceutically acceptable excipients to form a mixture of pharmaceutically acceptable excipients.

In certain embodiments, the step of mixing the four or more pharmaceutically acceptable excipients to form a mixture of pharmaceutically acceptable excipients comprises:

(a) mixing a (co)solvent (e.g., tetraglycol) with an antioxidant (e.g., BHT, BHA, tocopherol, or cysteine (e.g., BHT)) to form a first mixture of pharmaceutically acceptable excipients; and (b) mixing the remaining ones of the four or more pharmaceutically acceptable excipients with the first mixture of pharmaceutically acceptable excipients to form a mixture of pharmaceutically acceptable excipients.

In certain embodiments, the step of mixing the four or more pharmaceutically acceptable excipients to form a mixture of pharmaceutically acceptable excipients comprises:

(i) mixing two or three of the four or more pharmaceutically acceptable excipients to form a first mixture of pharmaceutically acceptable excipients;

(ii) mixing the remaining ones of the four or more pharmaceutically acceptable excipients to form a second mixture of pharmaceutically acceptable excipients; and (iii) mixing the first mixture of pharmaceutically acceptable excipients with the second mixture of pharmaceutically acceptable excipients to form a mixture of pharmaceutically acceptable excipients.

In certain embodiments, the step of mixing the four or more pharmaceutically acceptable excipients to form a mixture of pharmaceutically acceptable excipients comprises:

(i) mixing a (co)solvent (e.g., tetraglycol) with an antioxidant (e.g., BHT, BHA, tocopherol, or cysteine (e.g., BHT)) to form a first mixture of pharmaceutically acceptable excipients;

(ii) mixing the remaining ones of the four or more pharmaceutically acceptable excipients to form a second mixture of pharmaceutically acceptable excipients; and (iii) mixing the first mixture of pharmaceutically acceptable excipients with the second mixture of pharmaceutically acceptable excipients to form a mixture of pharmaceutically acceptable excipients.

In certain embodiments, the difference between the time when step (A) is completed and the time when step (B) begins to be performed is about 1 hour, about 2 hours, about 6 hours, about 12 hours, about 2 days, about 4 days, about 7 days, about 14 days, or about 30 days. In certain embodiments, the difference between the time when step (A) is completed and the time when step (B) begins to be performed is about 1 day. In certain embodiments, the difference between the time when step (a) is completed and the time when step (b) begins to be performed is about 1 hour, about 2 hours, about 6 hours, about 12 hours, about 2 days, about 4 days, about 7 days, about 14 days, or about 30 days. In certain embodiments, the difference between the time when step (a) is completed and the time when step (b) begins to be performed is about 1 day. In certain embodiments, the difference between the time when step (i) is completed and the time when step (iii) begins to be performed is about 1 hour, about 2 hours, about 6 hours, about 12 hours, about 2 days, about 4 days, about 7 days, about 14 days, or about 30 days. In certain embodiments, the difference between the time when step (i) is completed and the time when step (iii) begins to be performed is about 1 day. In certain embodiments, the difference between the times described herein is referred to as "pre-incubation time".

EXAMPLES

In order that the present disclosure may be more fully understood, the following examples are set forth. The synthetic and biological examples described in this application are offered to illustrate the compounds (e.g., SERMs), pharmaceutical compositions, and methods provided herein and are not to be construed in any way as limiting their scope. A compound described herein may be tested two or more times under the same or different conditions for determining a property and, therefore, may show different values of the property.

Example 1. Lasofoxifene—Vaginal Mucus Interaction Studies

As Lasofoxifene is a cationic drug, the extent of interaction between the API and the negatively charged vaginal mucus was examined. Therefore, vaginal mucus was scraped off from freshly excised bovine vaginal mucosa. Briefly, a 0.01% (w/v) aqueous solution of Lasofoxifene was added to this mucus in a ratio of 1:4 (vaginal mucus:solution of Lasofoxifene). The reaction mixture was incubated over three hours at 37° C. At the beginning and every 60 minutes, aliquots (50 µl) were withdrawn. In order to remove mucus residues, samples were treated with ice cold acetonitrile in a ratio of 1:1. After centrifugation, the drug concentration was quantified via HPLC. For a control, the aqueous solution of the drug was diluted with water in the same volume as mucus.

Figure 2:
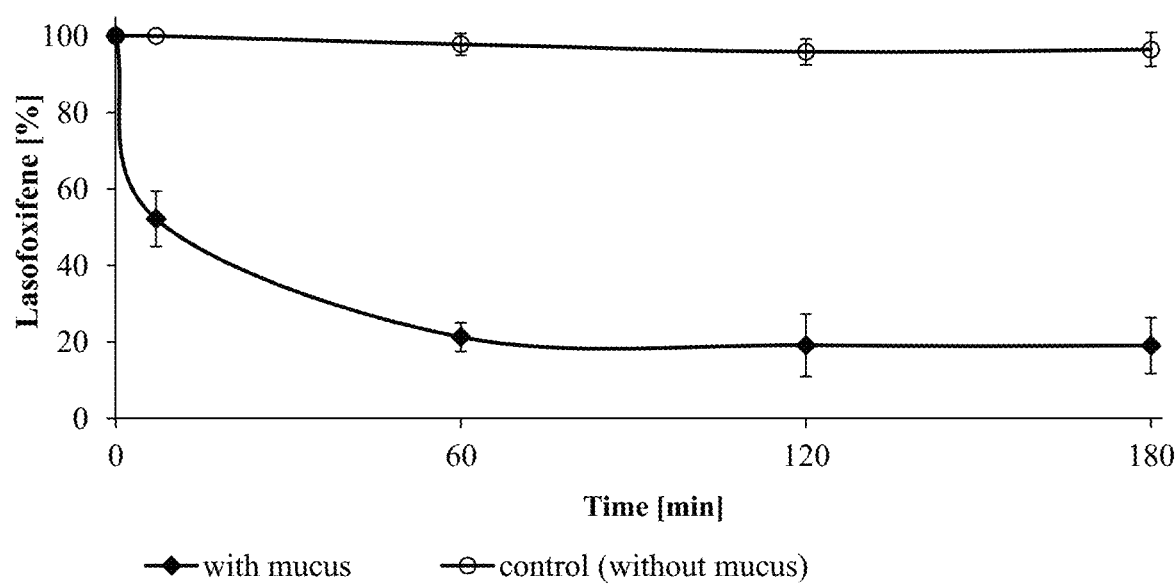
FIG. 2 shows drug mucus binding studies where Lasofoxifene was incubated with vaginal mucus for over three hours at 37° C. The indicated values are the means of at least three experiments±SD.

Results of this experiment, presented in FIG. 2, indicated an immediate interaction of the API with the mucus. As soon as the drug solution had been added to the vaginal mucus, the drug concentration decreased. After 60 minutes of incubation, approximately 80% of Lasofoxifene was tightly bound to the mucus.

Example 2. Preparation of Self-Nanoemulsifying Drug Delivery Systems (SNEDDSs)

Dissolution Studies in Organic Solvents and Surfactants

The solubility of Lasofoxifene was investigated by screening various organic solvents and surfactants in increasing concentrations. A list of possible solvents and surfactants is shown in Table 1. The results of preliminary composition of SNEDD formulations are shown in Table 2. The term "formulation" may refer to a pharmaceutical composition comprising four or more pharmaceutically acceptable excipients.

TABLE 1

List of possible solvents and surfactants

| Functionality | Comercial name | Chemical name | HLB |
| --- | --- | --- | --- |
| Water insoluble oils | Captex 300 | Glyceryl tricaprylate/tricaprate | <1 |
| | Dermofeel MCT | Tricaprylin | <1 |
| | Mygliol 840 | Propyleneglycol tricaprylate/tricaprate | <1 |
| Water insoluble surfactants (HLB < 12) | Peceol | Glycerol monooleate | 3 |
| | Capmul PG-12 | Propylene glycol monolaurate | 4.5 |
| | Capmul MCM EP | Caprylic/capric mono- & diglycerides | 5.5 |
| | Capmul 708G | Glyceryl monocaprylate | 6.5 |
| | Capmul PG-8 | Propylene glycol monocaprylate | 6.7 |
| | Capmul 907P | Propylene glycol monoheptanoate | 7.5 |
| | Labrafil M 1944 CS | Oleoyl macrogol-6 glycerides | 9 |
| Water soluble surfactants (HLB > 12) | Kolliphor EL | Macrogolglycerol ricinoleate | 13 |
| | Kolliphor RH 40 | Macrogolglycerol Hydroxystearate | 15 |
| Co-solvents | Transcutol HP | Diethylene glycol monoethyl ether | NA |
| | Polyethylene glycol 400 | Polyethylene glycol 400 | NA |
| | Propylene glycol | Propylene glycol | NA |

"Mygliol 840" denotes "MIGLYOL 840".

TABLE 1A

Exemplary source of select excipients

| Excipient brand name | Excipient generic name | Supplier |
| --- | --- | --- |
| CAPTEX 300 EP/NF/JPE | Glyceryl tricaprylate/tricaprate | Abitec |
| CAPTEX 300 Low $C_6$ EP/NF/JPE | Glyceryl tricaprylate/tricaprate | Abitec |
| CAPTEX 355 EP/NF/JPE | Glyceryl tricaprylate/tricaprate | Abitec |
| CAPTEX 1000 | Glyceryl tricaprate | Abitec |
| CAPMUL PG-8 NF | Propylene glycol monocaprylate | Abitec |
| LABRAFAC Lipophile WL 1349 | Glyceryl tricaprylate/tricaprate | Gattefosse |
| CAPRYOL 90 | propylene glycol monocaprylate (type II) NF | Gattefosse |
| CREMOPHOR EL | Polyoxyl 35 hydrogenated castor oil | BASF |
| CREMOPHOR EL | Polyoxyl 35 hydrogenated castor oil | Caesar & Loretz GmbH |
| CREMOPHOR EL | Polyoxyl 35 hydrogenated castor oil | Merck Millipore |

TABLE 2

Composition of SNEDD formulations tested in preliminary tests.

| Formulation number | Kolliphor EL | Capmul 907P | Capmul MCM | Capmul PG-8 | Capmul PG-12 | Transcutol | PEG 400 | Propylene glycol |
|---|---|---|---|---|---|---|---|---|
| F1 | 40 | 50 | | | | 10 | | |
| F2 | 40 | 50 | | | | | 10 | |
| F3 | 40 | 50 | | | | | | 10 |
| F4 | 40 | | 50 | | | 10 | | |
| F5 | 40 | | 50 | | | | 10 | |
| F6 | 40 | | 50 | | | | | 10 |
| F7 | 40 | | | 50 | | 10 | | |
| F8 | 40 | | | 50 | | | 10 | |
| F9 | 40 | | | 50 | | | | 10 |
| F10 | 40 | | | | 50 | 10 | | |
| F11 | 40 | | | | 50 | | 10 | |
| F12 | 40 | | | | 50 | | | 10 |

Results of the dissolution studies are shown in Table 3. Polyethylene glycol 200, Capmul MCM C8, as well as DMSO, seemed to be promising solvents for the API.

TABLE 3

Dissolution of Lasofoxifene in various organic solvents and surfactants in increasing concentrations

| | 1 mg/ml | 2 mg/ml | 3 mg/ml | 6 mg/ml |
|---|---|---|---|---|
| Cremophor A 25 | | not dissolved | x | x |
| Cremophor RH 40 | | not dissolved | x | x |
| Cremophor CO 410 | | not dissolved | x | x |
| Cremophor EL | dissolved* | partially dissolved | not dissolved | x |
| Isosorbide dimethyl ether (DMI) | dissolved* | partially dissolved | not dissolved | x |
| PEG 200 | dissolved | dissolved | dissolved* | partially dissolved |
| PEG 300 | | not dissolved | x | x |
| PEG 600 | | not dissolved | x | x |
| mPEG 350 | partially dissolved | not dissolved | not dissolved | x |
| mPEG 550 | partially dissolved | not dissolved | not dissolved | x |
| mPEG 750 | not dissolved | x | x | x |
| Triacetin (TAC) | | not dissolved | x | x |
| Tributyl citrate (TBC) | not dissolved | x | x | x |
| Tributyl acetyl citrate (TBAC) | not dissolved | x | x | x |
| Triethyl citrate (TEC) | not dissolved | x | x | x |
| Triethyl acetyl citrate (TEAC) | not dissolved | x | x | x |
| Tetraglycol (TG) | dissolved | dissolved | partially dissolved | not dissolved |
| Transcutol (TC) | dissolved | dissolved | dissolved | |
| Propylene glycol (PG) | dissolved | dissolved* | partially dissolved | not dissolved |
| Tween 20 | partially dissolved | not dissolved | not dissolved | x |
| Tween 80 | dissolved* | partially dissolved | not dissolved | x |
| Tween 85 | dissolved | dissolved | partially dissolved | not dissolved |
| Capmul MCM | partially dissolved | not dissolved | not dissolved | |
| Capmul MCM C8 | dissolved | dissolved | dissolved | partially dissolved |
| Capmul PG-8 | | not dissolved | x | x |
| Glycerol 99% | dissolved* | partially dissolved | not dissolved | x |
| Glycerol 85% | dissolved | partially dissolved | not dissolved | x |
| Labrafil M1944 CS | | not dissolved | x | x |
| Miglyol 840 | | not dissolved | x | x |
| Corn oil | not dissolved | x | x | x |
| Cera liquida | not dissolved | x | x | x |
| Ethyloleate | not dissolved | x | x | x |
| Brij 30 | dissolved* | partially dissolved | not dissolved | x |
| Poloxamer 124 | | not dissolved | x | x |
| Captex 355 EP/NF | | not dissolved | x | x |
| DMSO | dissolved | dissolved | dissolved | dissolved |

By screening various non-ionic solvents, polyethylene glycol 200 (PEG 200) and propylene glycol were identified as the most suitable solvents for Lasofoxifene, as they showed complete solubility at concentrations of 2 mg/ml in case of PEG 200 and 1 mg/ml in case of propylene glycol. In contrast, Lasofoxifene could not be dissolved in more lipophilic excipients, such as corn oil, Cera liquida, or tributyl citrate. However, the addition of PEG 200 is limited as the lipophilic mixture is not stable (e.g., not physically stable) at a concentration of more than 30% PEG 200. Therefore, in order to increase the solubility of Lasofoxifene in the developed SNEDDSs, dimethyl sulfoxide (DMSO) can be added in a concentration of up to 5%.

Based on the outcome of orientating solubility studies, identifying polyethylene glycol 200, capmul MCM C8, and DMSO to be promising solvents for the API, various SNEDDSs were prepared by assembling solvents and surfactants in different ratios. The resulting SNEDD formulations were verified regarding phase separation, formation of nanoemulsions after diluting with vaginal buffer, and solubility of Lasofoxifene.

Dissolution Studies in Polymeric Excipient/Solubilizer Combinations and Preparation of Various SNEDDSs Various SNEDDSs were prepared by assembling the most promising solvents and surfactants in different ratios. The resulting SNEDD formulations were verified regarding phase separation. Furthermore, formulations were diluted in a ratio of 1:2 with artificial vaginal fluid containing 2.6 mM MgSO4, 10.0 mM KCl, 40.0 mM glucose buffered with 50 mM acetate buffer pH 5.0 and visually examined after three hours concerning phase separation (↓).

In case of formulations 1-10, different ratios of PEG 200, Tween 85, Capmul MCM C8, tetraglycol as well as propylene glycol were investigated. Each of these SNEDDSs showed phase separation by dilution with artificial vaginal fluid. Therefore, formulations with additional solvents and surfactants were prepared. The results of formulations 11-15 are presented in Table 4.

TABLE 4

Dilution studies of various formulations; phase separation = ↓;

| Formulation No | PEG 200 % | Tween 85 % | Tween 20 % | Cap MCM C8 % | Crem EL % | TG % | TC % | TBC % | 1:2 |
|---|---|---|---|---|---|---|---|---|---|
| 11 | 10 | 10 | — | 30 | 30 | 20 | — | — | ↓ |
| 12 | 10 | 30 | — | 10 | 10 | 20 | — | 20 | — |
| 13 | — | 20 | — | 30 | 20 | 10 | — | 20 | ↓ |
| 14 | 20 | — | 20 | — | 15 | 30 | — | 15 | — |
| 15 | — | 20 | — | 30 | 20 | 20 | — | 10 | ↓ |

Further SNEDD formulations were developed by exchanging Cremophor EL with Cremophor RH 40 and tributyl citrate (TBC) by tributyl acetyl citrate (TBAC). The results of formulations 16-22 are listed in Table 5.

TABLE 5

Dilution studies of various formulations; phase separation = ↓;

| Formulation No | PEG 200 % | Tween 85 % | Labrasol % | Cap MCM C8 % | Crem RH 40 % | TC % | TBAC % | 1:2 |
|---|---|---|---|---|---|---|---|---|
| 16 | 20 | 15 | — | 10 | 10 | 30 | 15 | ↓ |
| 17 | 30 | 10 | 10 | — | 10 | 20 | 20 | ↓ |
| 18 | 20 | 20 | 10 | — | 10 | 20 | 20 | ↓ |
| 19 | 20 | 20 | 10 | — | 10 | 15 | 25 | — |
| 20 | 20 | 20 | 10 | — | 10 | 10 | 30 | — |
| 21 | 20 | 10 | — | 20 | — | 30 | 20 | ↓ |
| 22 | 15 | 15 | — | 20 | — | 20 | 30 | ↓ |

Additionally, formulations containing a high amount of Capmul 907P or Capmul 908P were prepared. The ratios of these SNEDDSs are shown in Table 6.

TABLE 6

Dilution studies of various formulations; phase separation = ↓;

| Formulation No | PEG 200 % | Cap 907P % | Cap 908P % | Crem EL % | Captex 8000 % | PG % | Acconon MC8-2 % | TG % | 1:2 |
|---|---|---|---|---|---|---|---|---|---|
| 23 | 20 | 40 | — | 30 | — | 10 | — | — | ↓ |
| 24 | 10 | 50 | — | 30 | — | 10 | — | — | ↓ |
| 25 | 10 | 40 | — | 40 | — | 10 | — | — | — |
| 26 | 10 | 40 | 10 | 30 | — | 10 | — | — | ↓ |
| 27 | 10 | — | 50 | 30 | — | 10 | — | — | ↓ |
| 28 | 10 | — | 40 | 40 | — | 10 | — | — | — |
| 29 | 20 | 50 | — | 30 | — | — | — | — | ↓ |
| 30 | 20 | 30 | 20 | 20 | — | 10 | — | — | ↓ |
| 31 | 10 | 40 | — | 30 | 10 | 10 | — | — | ↓ |
| 32 | 10 | 40 | — | 20 | 20 | 10 | — | — | — |
| 33 | 10 | 30 | — | 30 | 20 | 10 | — | — | — |
| 34 | 10 | 20 | — | 40 | — | — | 30 | — | — |
| 35 | 10 | 30 | — | 30 | — | — | 30 | — | ↓ |
| 36 | 20 | 30 | — | 40 | — | — | 10 | — | — |
| 37 | 20 | 40 | — | 30 | — | — | 10 | — | — |
| 38 | 10 | 30 | — | 30 | — | 10 | 20 | — | ↓ |
| 39 | 10 | 30 | — | 30 | — | — | 20 | 10 | ↓ |
| 40 | 10 | 40 | — | 30 | — | 10 | 10 | — | — |

Furthermore, different types of Captex, an organic solvent with a low HLB value of around 1, were used to prepare SNEDDSs. The resulting formulations are presented in Table 7.

TABLE 7

Dilution studies of various formulations; phase separation = ↓;

| Formulation No | PEG 200 % | Cap 907P % | Captex 200P % | Crem EL % | Captex 8000 % | PG % | Acconon MC8-2 % | Captex 300 EP/NF % | 1:2 |
|---|---|---|---|---|---|---|---|---|---|
| 41 | 10 | 40 | 20 | 20 | — | 10 | — | — | ↓ |
| 42 | 10 | 30 | 20 | 30 | — | 10 | — | — | — |
| 43 | 10 | 40 | — | 20 | — | 10 | — | 20 | ↓ |
| 1 | 10 | 30 | — | 30 | — | 10 | — | 20 | — |
| 45 | 20 | 40 | — | 20 | — | 10 | 10 | — | ↓ |
| 46 | 20 | 40 | — | 20 | 10 | 10 | — | — | ↓ |
| 47 | 20 | 30 | — | 20 | 20 | 10 | — | — | ↓ |
| 2 | 20 | 30 | — | 30 | 10 | 10 | — | — | — |
| 49 | 20 | 20 | — | 30 | 20 | 10 | — | — | — |
| 3 | 20 | 30 | — | 20 | 10 | 10 | 10 | — | — |
| 3 | <=20 | <=30 | — | <=30 | <=10 | 10 | | | |

In Tables 4 to 7 SNEDD formulations without any phase separation, after dilution and incubation at 37° C., are highlighted. For emulsions resulting in one phase, 750 µg/ml of Lasofoxifene was incorporated in the corresponding SNEDD formulations and visually investigated regarding dissolution. Due to insufficient solubility of the API in the SNEDD formulations, the addition of DMSO was necessary. In case of SNEDDSs containing 10% of PEG 200, DMSO in a concentration of 5% was added. ForSNEDDSs containing 20% of PEG 200, the addition of 2% of DMSO induced adequate solubility.

The highlighted SNEDDSs were prepared by first dissolving the API in PEG 200 and DMSO to maintain a final concentration of 750 µg/ml in an ultrasonic bath. Once the drug was completely dissolved, the remaining components of the SNEDD formulations were added.

After 48 hours, the resulting SNEDDSs were investigated regarding stability (e.g., physical stability) of the API. The 48-hours-old SNEDD formulations were centrifuged and examined visually for a precipitate. The developed SNEDDSs demonstrated sufficient stability (e.g., physical stability) and solubility for at least 48 hours.

Dissolution and Stability (e.g., Physical Stability) Studies of the Three Most Promising SNEDDSs The three most promising SNEDD formulations (formulation numbers 1, 2 and 3) demonstrated sufficient stability (e.g., physical stability) and solubility over a period of 48 hours; however, after 1, week a precipitate could be observed after centrifugation. The precipitation might be due to the two-step preparation method. In the first step, the API was dissolved into two components, resulting in a solvation shell. This solvation shell could have been destroyed if there were interfering components in the formulation. As a result, the drug was not stable in the formulation.

The composition of the most promising SNEDD formulations are shown in Table 8. The three SNEDDSs, listed in Table 8, were prepared as described above. Furthermore, the most feasible amount of Lasofoxifene which could be incorporated into the already prepared SNEDD formulations (1-3) was determined to be 150 µg/ml.

TABLE 8

Composition of the most promising SNEDDSs.

| formulation no | PEG 200 [%] | Cap 907P [%] | Crem EL [%] | PG [%] | Captex 8000 [%] | Captex 300 EP/NF [%] | Acconon MC8-2 [%] | DMSO [%] |
|---|---|---|---|---|---|---|---|---|
| 1 | 10 | 28 | 28 | 10 | — | 19 | — | 5 |
| 2 | 20 | 29 | 29 | 10 | 10 | — | — | 2 |
| 3 | 20 | 29 | 19 | 10 | 10 | — | 10 | 2 |

PEG 200—polyethylene glycol 200;

Cap 907P—Capmul 907P;

Crem EL—Cremophor EL;

PG—propylene glycol;

DMSO—dimethyl sulfoxide

When the API was dissolved in the lipophilic mixture in one step, a concentration of 150 µg/ml was achieved. After diluting the formulations containing Lasofoxifene with vaginal fluid, nanodroplets in a range of 30 to 90 nm were formed. All nanoemulsions were stable over 3 hours with the exception of formulation 1. Based on the increase in nanodroplet size, formulation 1 was identified to be comparatively unstable, resulting in a faster drug release.

Regarding the drug release profile, all other tested formulations demonstrated a sustained drug release over a time period of 24 hours.

Regarding stability of the SNEDDSs, the formulations prepared in two steps demonstrated a stability of at least 48 hours. By incorporating Lasofoxifene in one step, the stability of the SNEDD formulations could be increased up to at least three weeks.

Besides solvents, the addition of emulsifying agents is necessary for the spontaneous formation of nanoemulsions. Cremophor EL and Capmul 907P were chosen due to their positive impact on the solubility of Lasofoxifene. The combination of the three main components, PEG 200, Cremophor EL and Capmul 907P, resulted in the formation of nanoemulsions after contact with vaginal fluid, even after being diluted at a ratio of 1:2. Nevertheless, further excipients have to be added to the main components in order to maintain stable nanoemulsions without phase separations. Various SNEDDSs were developed showing differences in droplet size and drug release profile. In certain embodiments, the present disclosure includes the SNEDD formulations containing Captex 300 EP/NF, Captex 8000, Acconon MC8-2, Tween 85, Tetraglycol, and/or propylene glycol, as listed in Table 8.

All formulations were stable over 3 hours with the exception of formulations 1 and 6. Based on the increase as well as decrease in nanodroplet size both formulations were identified to be comparatively unstable, resulting in a faster drug release.

Development of Re-Formulations

Additionally, SNEDD formulations containing a higher feasible amount of drug were developed, as demonstrated in Table 9. Within these SNEDDSs, Lasofoxifene could be incorporated in one step at a concentration of 400 µg/ml in the case of formulations 4 and 5, and 500 µg/ml could be dissolved in formulation 6.

Furthermore, the interfering component of the formulations was explored by screening the various solvents, surfactants, and co-surfactants. Thereby, the three excipients Captex 8000, Captex 300 EP/NF, and Acconon MC8-2 could be defined as being inappropriate components. As a further step, these three excipients were replaced by different solvents and surfactants, such as tetraglycol, triacetin, and tween 85. These components were selected based on results of the orientating dissolution studies. The newly developed formulations were characterized regarding phase separation, emulsion formation, phase separation of the nanoemulsion, and the most feasible amount of incorporated API.

In formulations 4 and 5 a concentration of 400 µg/ml and in formulation 6 500 µg/ml, of the API was incorporated at once. All formulations formed an emulsion after dilution with artificial vaginal fluid buffered with acetate buffer pH 5.0 in ratio of 1:2. However, formulation 6 was determined to be a comparatively unstable (e.g., physically unstable) formulation.

Example 3: In Vitro Characterization of SNEDDSS

The drug loaded SNEDD formulations were diluted 1:2 with artificial vaginal fluid as described above and incubated for three hours at 37° C. while shaking (300 rpm) from time to time. The resulting emulsions were analyzed regarding droplet size distribution, and optionally zeta potential, utilizing a particle analyzer (Nicomp 380 ZLS Particle Size and Zeta Potential Analyzer). After three hours of incubation at 37° C., droplet size distribution and zeta potential were measured again to determine stability. The results are represented in Table 10 and Table 11.

TABLE 10

Droplet size and zeta potential of SNEDDSs 1, 2, and 3 after dilution at time point 0 and after 3 hours at 37° C. The indicated values are means of at least three experiments ± SD.

| formulation no. | 0 h | | 3 h | |
| --- | --- | --- | --- | --- |
| | droplet size [nm] | zeta potential [mV] | droplet size [nm] | zeta potential [mV] |
| 1 | 37.6 ± 1.2 | 0.3 ± 1.5 | 241.3 ± 127.3 | 2.2 ± 0.8 |
| 2 | 48.3 ± 0.9 | −2.6 ± 2.2 | 48.5 ± 0.8 | 0.5 ± 0.7 |
| 3 | 86.4 ± 4.4 | −1.8 ± 1.3 | 88.4 ± 3.9 | 1.0 ± 0.4 |

TABLE 9

Composition of the three re-formulations.

| formulation no. | PEG 200 [%] | Cap 907P [%] | Crem EL [%] | PG [%] | TG [%] | Tween 85 [%] | Captex 8000 [%] | DMSO [%] |
| --- | --- | --- | --- | --- | --- | --- | --- | --- |
| 4 | 20 | 28 | 28 | 10 | 9 | — | — | 5 |
| 5 | 15 | 27 | 25.5 | 10 | 10 | — | 7.5 | 5 |
| 6 | 20 | 29 | 19 | 10 | 10 | 7 | — | 5 |

PEG 200—polyethylene glycol 200;
Cap 907P—Capmul 907P;
Crem EL—Cremophor EL;
TG—tetraglycol;
PG—propylene glycol;
DMSO—dimethyl sulfoxide

TABLE 11

Droplet size of SNEDDSs 4, 5 and 6 after dilution at time point 0 and after 3 hours at 37° C. The indicated values are means of at least three experiments ± SD.

| formulation no. | 0 h droplet size [nm] | 3 h droplet size [nm] |
|---|---|---|
| 4 | 85.5 ± 2.4 | 86.8 ± 1.3 |
| 5 | 58.3 ± 0.3 | 59.0 ± 0.8 |
| 6 | 128.6 ± 6.8 | 107.8 ± 34.2 |

Each formulation showed nearly no change in droplet size and zeta potential after three hours of incubation at 37° C., expect formulations 1 and 6. Due to the increase in droplet size from 37.6±1.2 nm to 241.3±127.3 nm, formulation number 1 was identified as a comparatively unstable SNEDD formulation. Furthermore, formulation 6 seemed to be a less stable SNEDD formulation, based on its decrease in droplet size after an incubation period of 3 hours.

After dilution with artificial vaginal fluid at a ratio of 1:2, the resulting emulsions were analyzed regarding droplet size distribution and zeta potential. Results are shown in Table 12. The polydispersity index is a measure of the distribution of the droplet size. Formulations 14, 20, 33, 40 and 42 were measured only once due to a big droplet size or a wide range of droplet size distribution, as indicated by a high polydispersity index. Additionally, zeta potential was only determined for certain droplet size distributions.

TABLE 12

Droplet size, polydispersity index and zeta potential of SNEDDSs resulting in one phase after dilution 1:2 with artificial vaginal fluid.

| formulation no. | droplet size [nm] | polydispersity index | zeta potential [mV] |
|---|---|---|---|
| 12 | 93.0 ± 11.3 | 0.652 | not measured |
| 14 | 528.1 | 2.008 | not measured |
| 19 | 38.6 ± 2.1 | 0.353 | 1.9 ± 8.3 |
| 20 | 15.6 | 1.613 | not measured |
| 25 | 55.0 ± 0.3 | 0.525 | not measured |
| 28 | 2091.0 ± 1875.2 | 3.489 | not measured |
| 32 | 48.4 ± 12.5 | 0.265 | 2.7 ± 13.9 |
| 33 | 54.5 | 0.497 | not measured |
| 34 | 52.2 ± 7.6 | 0.441 | 0.4 ± 0.7 |
| 36 | 153.7 ± 4.3 | 0.694 | not measured |
| 37 | 164.6 ± 45.7 | 0.556 | −0.1 ± 0.7 |
| 40 | 185.0 | 0.475 | not measured |
| 42 | 466.6 | 0.281 | not measured |
| 1 | 37.6 ± 1.2 | 0.412 | 0.3 ± 1.5 |
| 2 | 48.3 ± 0.9 | 0.290 | −2.6 ± 2.2 |
| 49 | 169.4 ± 23.1 | 0.477 | not measured |
| 3 | 86.4 ± 4.4 | 0.443 | −1.8 ± 1.3 |

Furthermore, the droplet stability of the four most promising SNEDD formulations, which are highlighted in Table 12, was investigated after three hours at 37° C. The results are represented in Table 13.

TABLE 13

Droplet size and zeta potential of SNEDDSs 34, 1, 2, and 3 after dilution at time point 0 and after 3 hours at 37° C. The indicated values are means of at least three experiments ± SD.

| | 0 h | | 3 h | |
|---|---|---|---|---|
| formulation no. | droplet size [nm] | zeta potential [mV] | droplet size [nm] | zeta potential [mV] |
| 34 | 52.2 ± 7.6 | 0.4 ± 0.7 | 53.2 ± 3.6 | −0.3 ± 1.2 |
| 1 | 37.6 ± 1.2 | 0.3 ± 1.5 | 241.3 ± 127.3 | 2.2 ± 0.8 |
| 2 | 48.3 ± 0.9 | −2.6 ± 2.2 | 48.5 ± 0.8 | 0.5 ± 0.7 |
| 3 | 86.4 ± 4.4 | −1.8 ± 1.3 | 88.4 ± 3.9 | 1.0 ± 0.4 |

Figure 7:
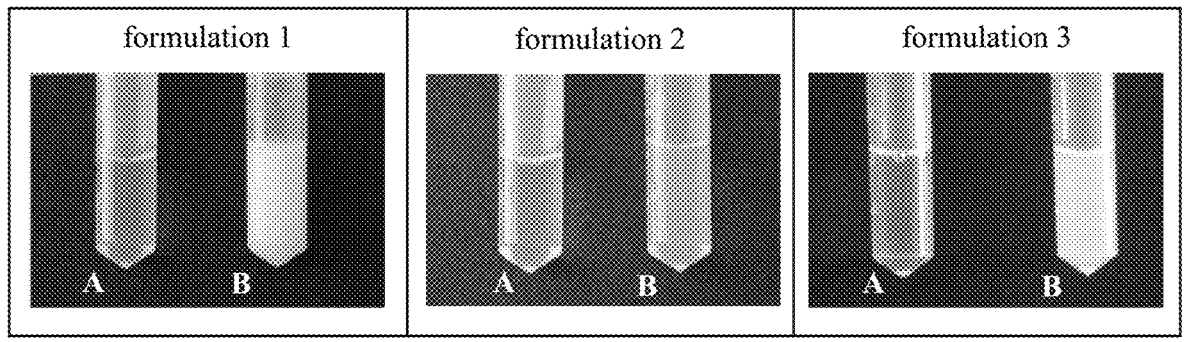
FIG. 7 shows the three most promising SNEDDSs: A: Prepared SNEDD formulation without dilution. B: Nanoemulsion: A SNEDDS after dilution 1:2 with artificial vaginal fluid and equilibration at 37° C.
Figure 8:
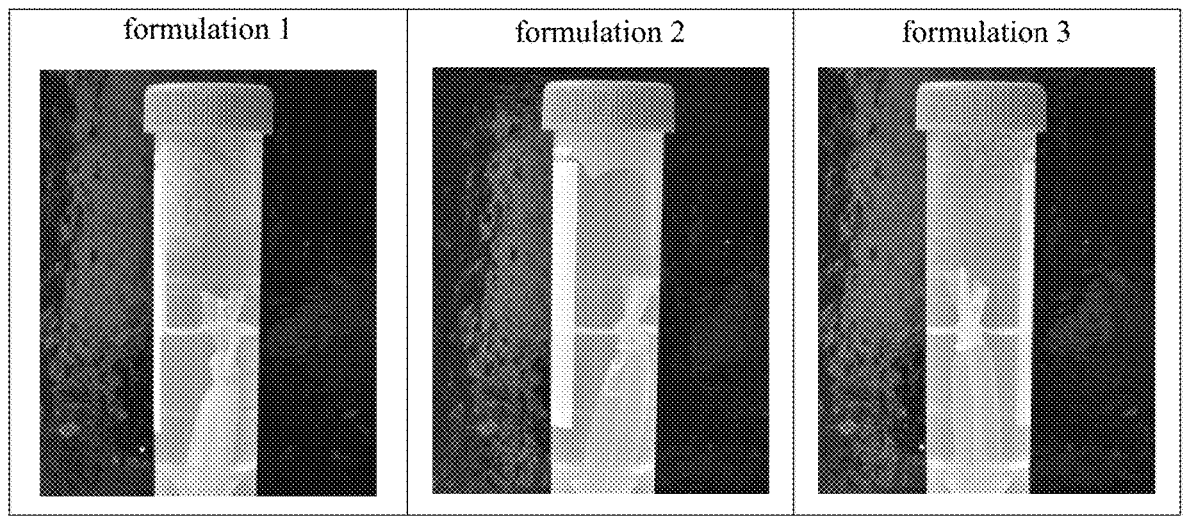
FIG. 8 shows the experimental setup of drug release studies.
Figure 9A:
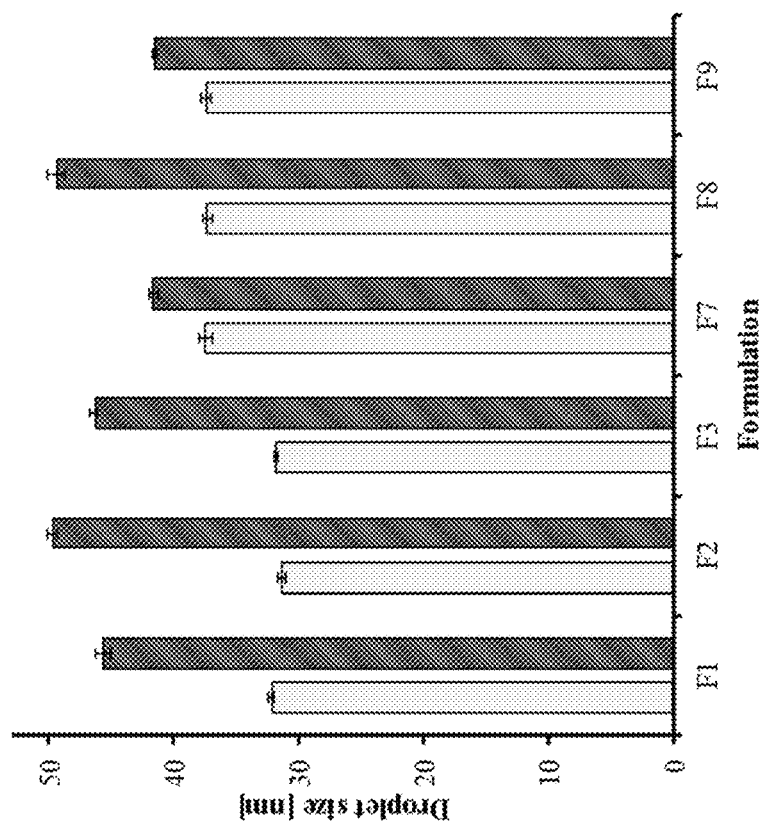
FIGS. 9A to 9D show the influence of medium (water (FIG. 9A), simulated saliva (FIG. 9B), simulated tears (FIG. 9C) and simulated vaginal fluid (FIG. 9D)) on SNEDDS droplet size at 2% formulation in medium (light grey bars) and 30% formulation in medium (dark grey shaded bars).
Figure 9B:
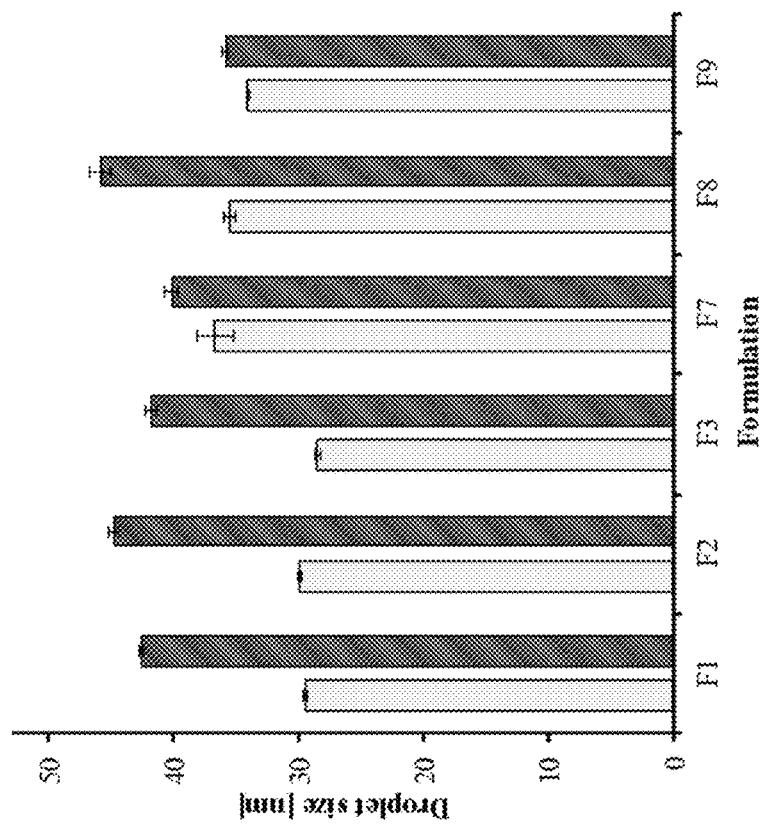
Figure 9C:
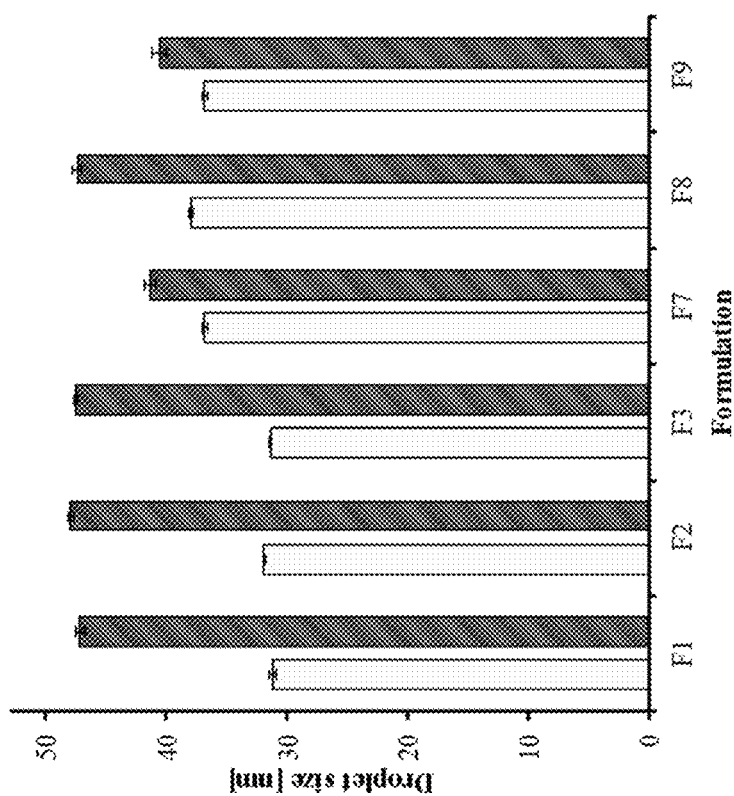
Figure 9D:
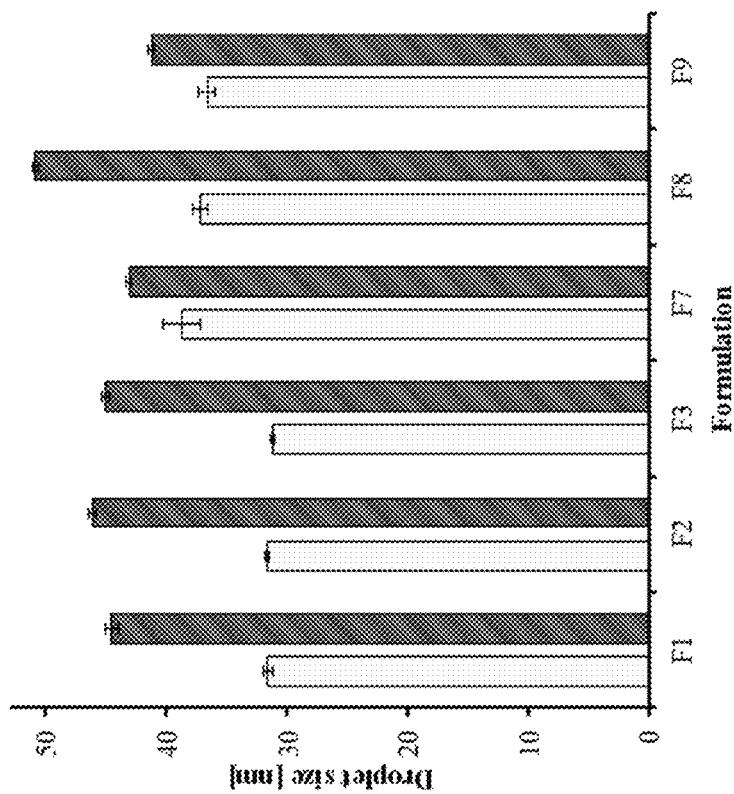

Each formulation showed nearly no change in droplet size and zeta potential after three hours at 37° C., expect formulation 1. Formulation 1 was identified as being a comparatively unstable SNEDD formulation, due to its increase in droplet size from 37.6±1.2 nm to 241.3±127.3 nm As demonstrated in FIG. 7, SNEDD formulations 1, 2 and 3 resulted in nanoemulsions after a 1:2 dilution with artificial vaginal fluid characterized by a milky or opalescent appearance. Based on the outcome of the droplet size and zeta potential measurement and the quality of formation of the nanoemulsion, these three SNEDD formulations were determined to be the three most promising SNEDDSs.

In Vitro Characterization of Re-Formulations

In order to get an impression about the emulsion type and the stability of the formed nanoemulsions, the droplet size was measured after dilution of the three re-formulations with artificial vaginal fluid at a ratio of 1:2. The results are shown in Table 14.

TABLE 14

Droplet size of the SNEDD re-formulations 4, 5, and 6 after dilution at time point 0 and after 3 hours at 37° C. The indicated values are means of at least three experiments ± SD.

| formulation no. | 0 h droplet size [nm] | 3 h droplet size [nm] |
|---|---|---|
| 4 | 85.5 ± 2.4 | 86.8 ± 1.3 |
| 5 | 58.3 ± 0.3 | 59.0 ± 0.8 |
| 6 | 128.6 ± 6.8 | 107.8 ± 34.2 |

Formulations 4 and 5 showed nearly no change in droplet size after three hours of incubation at 37° C. Formulation 6 was identified as being a comparatively unstable SNEDD formulation, due to its decrease in droplet size from 128.6±6.8 nm to 107.8±34.2 nm.

The Influence of Medium Quantity on SNEDDSs Droplet Size

The effects of four different media (water, simulated saliva, simulated tears, and simulated vaginal fluid) at two difference concentrations (2% and 30%) were tested for the SNEDD formulations' droplet size. The results are shown in FIGS. 9A to 9D. The polydispersity index (PDI) and standard deviation (SD) of the six formulations of SNEDDSs in the different media are shown in Table 15.

TABLE 15

PDI and SD of the six forumations in different media

| Formulation number | water | | | | simulated saliva | | | |
|---|---|---|---|---|---|---|---|---|
| | 2% | | 30% | | 2% | | 30% | |
| | PDI | SD | PDI | SD | PDI | SD | PDI | SD |
| F1 | 0.037 | 0.011 | 0.513 | 0.003 | 0.037 | 0.002 | 0.499 | 0.011 |
| F2 | 0.035 | 0.006 | 0.461 | 0.005 | 0.043 | 0.008 | 0.453 | 0.014 |
| F3 | 0.039 | 0.003 | 0.499 | 0.005 | 0.042 | 0.005 | 0.490 | 0.004 |
| F7 | 0.114 | 0.022 | 0.444 | 0.010 | 0.050 | 0.014 | 0.441 | 0.005 |
| F8 | 0.058 | 0.029 | 0.441 | 0.001 | 0.067 | 0.018 | 0.434 | 0.011 |
| F9 | 0.012 | 0.002 | 0.432 | 0.004 | 0.038 | 0.016 | 0.418 | 0.004 |

| Formulation number | simulated tears | | | | simulated vaginal fluid | | | |
|---|---|---|---|---|---|---|---|---|
| | 2% | | 30% | | 2% | | 30% | |
| | PDI | SD | PDI | SD | PDI | SD | PDI | SD |
| F1 | 0.021 | 0.009 | 0.507 | 0.007 | 0.023 | 0.014 | 0.507 | 0.009 |
| F2 | 0.049 | 0.017 | 0.448 | 0.012 | 0.051 | 0.009 | 0.456 | 0.003 |
| F3 | 0.053 | 0.005 | 0.495 | 0.017 | 0.059 | 0.007 | 0.507 | 0.008 |
| F7 | 0.103 | 0.031 | 0.449 | 0.003 | 0.065 | 0.016 | 0.439 | 0.009 |
| F8 | 0.124 | 0.002 | 0.448 | 0.011 | 0.095 | 0.014 | 0.424 | 0.006 |
| F9 | 0.084 | 0.011 | 0.431 | 0.002 | 0.079 | 0.008 | 0.429 | 0.005 |

The Influence of Medium on SNEDDSs Stability

The effect of four different media (water, simulated saliva, simulated tears, and simulated vaginal fluid) on SNEDDSs stability at 0, 2, and 4 hours was tested. The results are shown in FIGS. 12A to 12D. The polydispersity index (PDI) and standard deviation (SD) of the six formulations of SNEDDS in the different media at the three time points are shown in FIG. 13.

Example 4: Drug Release Studies of the Three Most Promising SNEDDSs

Furthermore, drug release studies were performed in artificial vaginal fluid at 7 time points utilizing HPLC analysis. The SNEDD formulations were diluted 1:2 with artificial vaginal fluid as described above. The resulting nanoemulsions were filled into dialysis tubes (cut off 14 kDa) which were placed into reagent tubes containing 20 ml of artificial vaginal fluid. Drug release studies were also performed with Lasofoxifene dissolved in artificial vaginal fluid containing 2% or 5% of DMSO serving as control. The drug release study took place at 37° C. while shaking. After 1, 2, 3, 4, 5, 6, and 24 hours, 200 µl samples were withdrawn from the outer phase and the volume was replaced with buffer equilibrated at 37° C. The amount of released drug was analyzed via HPLC.

Figure 3:
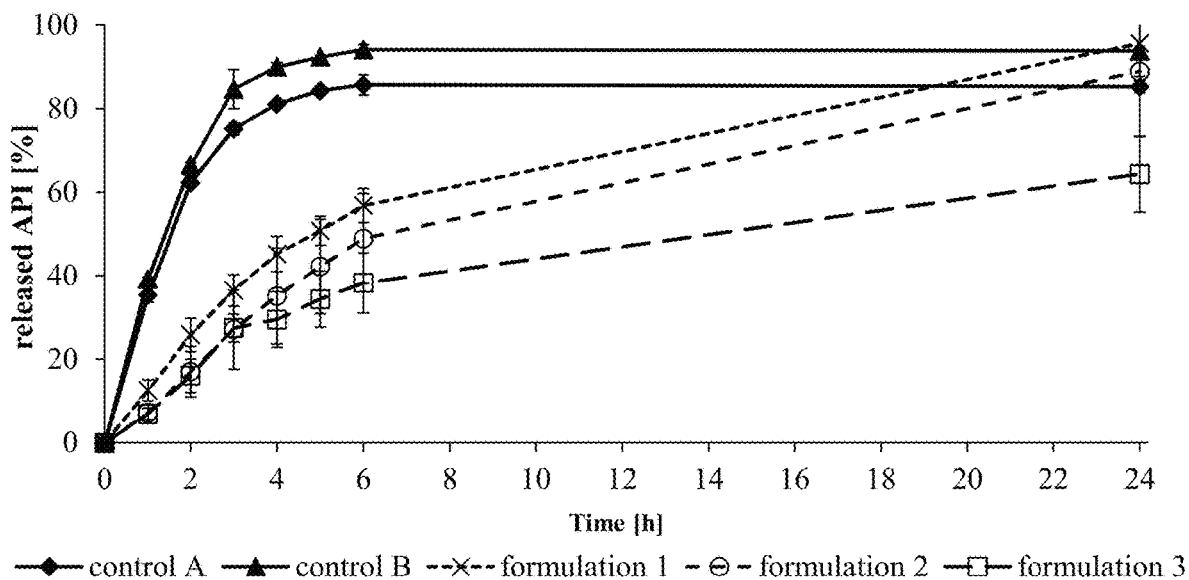
FIG. 3 shows the release of Lasofoxifene across a dialysis membrane. Control A: 2% DMSO. Control B: 5% DMSO. The indicated values are the means of at least three experiments±SD.

The drug release of Lasofoxifene across the dialysis membrane over 24 hours is demonstrated in FIG. 3. As expected, all three formulations indicated a slower and sustained drug release within 24 hours compared to controls A and B. Formulation 1 showed the fastest and most complete API release, followed by formulation 2.

Example 5: Evaluation of the Compatibility of SNEDDSs with Gelatin Capsules

The compatibility of the three most promising SNEDD formulations with gelatin capsules was investigated. Stability towards the capsule shell was confirmed for all three SNEDDSs.

The SNEDD formulations were filled into gelatin capsules and incubated for at least one week at room temperature. Afterwards, the gelatin capsules were investigated and stability towards the capsule shell was confirmed.

Example 6: Permeation Studies of SNEDDS on Freshly Excised Vaginal Mucosa

In order to investigate the influence of SNEDDSs on the permeation behavior of Lasofoxifene, permeation studies were performed with the SNEDD formulations on freshly excised bovine vaginal mucosa at pH 5.0. Therefore, Ussing type diffusion chambers with a surface area of 0.64 $cm^2$ were used and freshly obtained bovine vaginal mucosa was mounted in the chamber. Before permeation studies were started, the donor and acceptor compartments of the chamber were filled with 1.2 mL of artificial vaginal fluid as described above. Afterwards, the solution in the donor chamber was replaced by SNEDD formulations diluted 1:2 with artificial vaginal fluid. Permeation studies were performed over a 24 hour incubation period at 37° C. Additionally as control, the transport of Lasofoxifene dissolved in artificial vaginal fluid containing 2% or 5% of DMSO was investigated. At predetermined time points, aliquots (200 µl) were withdrawn from the acceptor chamber and the volume was replaced by the same medium equilibrated at 37° C. Samples were treated with ice-cold acetonitrile in a ratio of 1:1 to remove mucus residues. After centrifugation, the drug concentration was analyzed via HPLC. Cumulative corrections were made for the previously removed samples to determine the total amount permeated. Furthermore, after 24 hours of permeation studies, the available amount of drug in the donor chamber was quantified.

Figure 4:
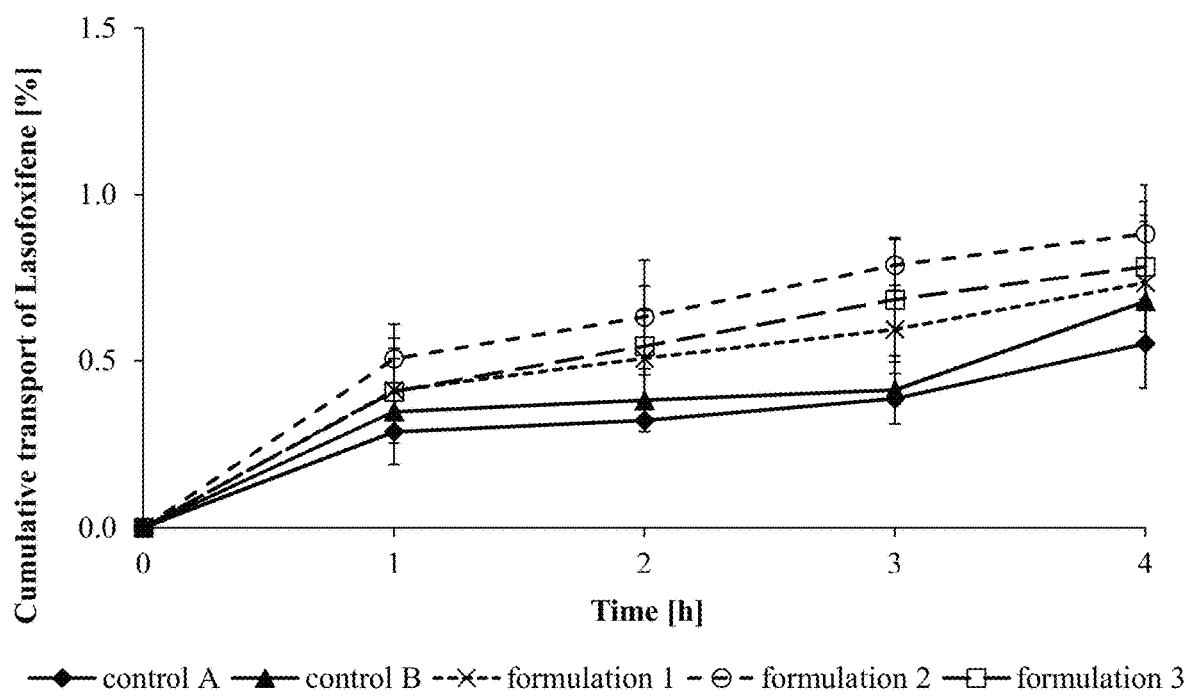
FIG. 4 shows permeation studies across freshly excised vaginal mucosa over 4 hours of incubation at 37° C. Control A: 2% DMSO. Control B: 5% DMSO. The indicated values are the means of at least three experiments±SD.
Figure 5:
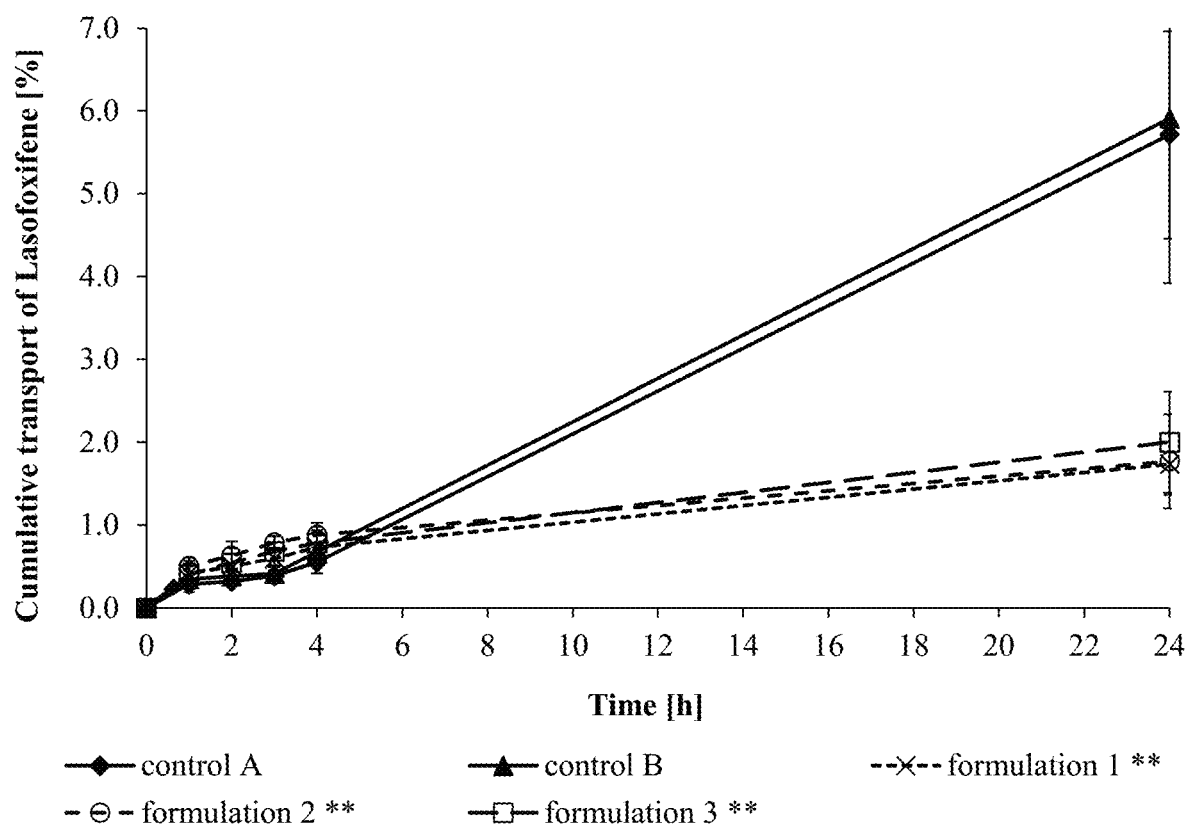
FIG. 5 shows permeation studies across freshly excised vaginal mucosa over 24 hours of incubation at 37° C. Control A: 2% DMSO. Control B: 5% DMSO. The indicated values are the means of at least three experiments±SD. (*$p<0.05$, $p<0.01$ and *$p<0.001$ compared to control A or B).

Results of these permeation studies are presented in FIG. 4 and FIG. 5. Within 4 hours of the permeation studies, no significant difference between control and formulations could be observed, whereas the permeation behavior changed significantly (p<0.01) over a time period of 24 hours. Consequently, all three formulations prevented the API from permeating across the tissue. After 24 hours the control solution showed a calculated $P_{app}$ value of $1.033*10^{-6}$ cm/s, whereas the formulations showed a calculated $P_{app}$ value in a range of $3.137*10^{-7}$ to $3.617*10^{-7}$ cm/s underlining the prevention of permeation across the tissue.

Figure 6:
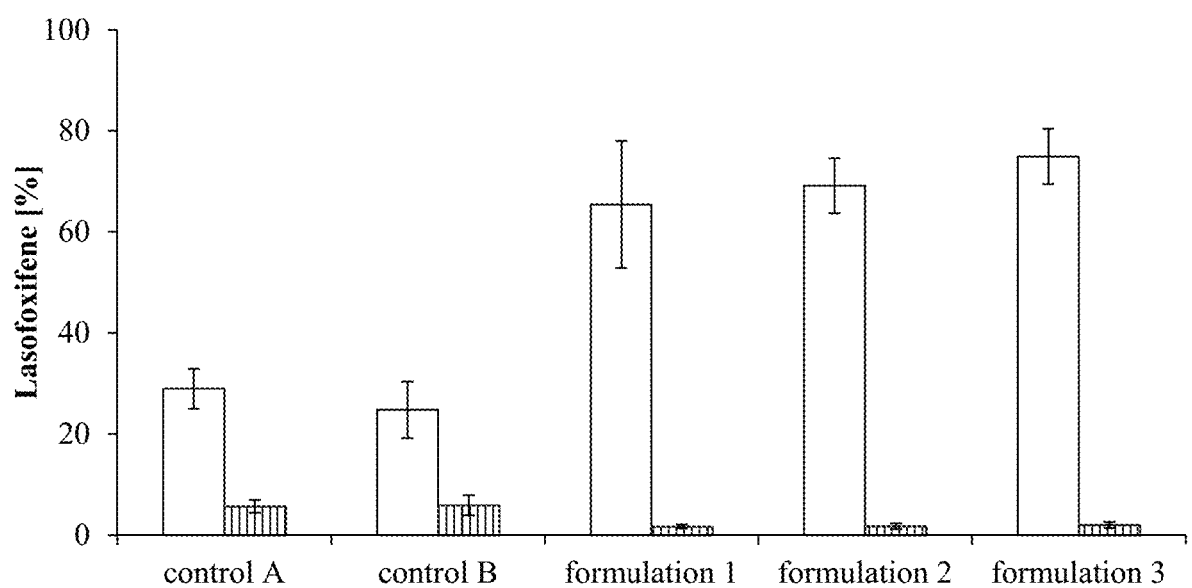
FIG. 6 shows the percent distribution of Lasofoxifene in solution of donor chamber (white bars) vs. acceptor chamber (striped bars) after 24 hours. The indicated values are the means of at least four experiments±SD (*$p<0.05$, $p<0.01$ and *$p<0.001$ compared to control A or B).

Furthermore, after 24 hours of permeation studies, the available amount of drug in the donor chamber was determined. FIG. 6 shows the distribution of Lasofoxifene in solution of the donor chamber vs. the acceptor chamber after 24 hours of incubation. This data indicated that the decrease of concentration in the donor compartment could be significantly (at least p<0.01) prohibited by incorporating the drug into SNEDDSs.

The calculated $P_{app}$ values are provided in Table 16.

TABLE 16

Calculated $P_{app}$ values of permeation studies across bovine vaginal mucsoa.

| | $P_{app}$ [cm/s] | |
|---|---|---|
| | within 4 h | within 24 h |
| control A | $5.988*10^{-7}$ | $1.033*10^{-6}$ |
| control B | $7.362*10^{-7}$ | $1.068*10^{-6}$ |
| formulation 1 | $7.967*10^{-7}$ | $3.137*10^{-7}$ |
| formulation 2 | $9.574*10^{-7}$ | $3.199*10^{-7}$ |
| formulation 3 | $8.508*10^{-7}$ | $3.617*10^{-7}$ |

Example 7: Dissolution and Incorporation Studies in State-of-the-Art O/W Creams

Additionally, Lasofoxifene was incorporated in three different state-of-the-art o/w creams, as listed in Table 17. For comparison reasons and as back-up formulations Lasofoxifene was incorporated in the three state-of-the-art o/w creams: Excipial Hydrocreme, Nonionic Hydrophilic Cream DAB and Nonionic Hydrophilic Cream SR DAC. Each o/w cream was prepared with the two different concentrations of 166 µg/g and 500 µg/g of API. Thereby, o/w creams with two different concentrations were prepared. On the one hand Lasofoxifene was added to the state-of-the-art creams in a concentration of 500 µg/g. On the other hand the API was incorporated in a concentration of 166 µg/g resulting in an applied amount of 500 µg of Lasofoxifene by administering 3 g of the o/w cream.

TABLE 17

Different state-of-the-art o/w creams

| o/w cream | components |
|---|---|
| Excipial Hydrocreme | isopropyl myristate, cetearyl alcohol, glyceryl stearate, pentylene glycol, polysorbate 20, paraffin, water |
| Nonionic Hydrophilic Cream DAB | polysorbate 60, cetylstearylalcohol, glycerol, white soft paraffin, water |
| Nonionic Hydrophilic Cream SR DAC | nonionic emulsifying alcohol, 2-ethylhexyl lauromyristate, glycerol, potassium sorbate, citric acid, water |

All o/w creams were prepared homogeneously and were free from palpable or observable particles.

In order to evaluate the stability of the drug loaded creams with artificial vaginal fluid, they were incubated with vaginal buffer for three hours at 37° C. Within three hours, all prepared o/w creams demonstrated no change in consistence indicating sufficient compatibility with artificial vaginal fluid.

Furthermore, the stability of the o/w creams containing Lasofoxifene was investigated under accelerated conditions (40° C./75% RH). After one month, the state-of-the-art creams did not break nor did they show any other alteration. Therefore, a sufficient stability at 40° C. and 75% over at least one month could be observed.

Example 8: Stability Studies: Freeze-Thaw Cycles

Additionally, freeze-thaw cycles were performed with all the SNEDD formulations (1, 2, 3, 4, 5, and 6) in order to evaluate their stability under stressed conditions. Therefore, SNEDDSs containing the highest feasible amount of Lasofoxifene were prepared. The freeze-thaw cycles were conducted five times by changing the temperature every 4 to 14 hours in the order as demonstrated in Table 18. After every freeze-thaw cycle, the formulations were centrifuged and visually examined for a precipitate. Furthermore, the SNEDDSs were diluted with artificial vaginal fluid previously equilibrated at 37° C. in a ratio of 1:2 to evaluate the formation of nanoemulsions.

TABLE 18

Order of freeze-thaw cycles. The temperature was changed every 4 to 14 hours.

| Storage place | Temperature [° C.] |
|---|---|
| Climatic chamber | 25 |
| Incubator | 40 |
| Refrigerator | 5 |
| Freezer | −20 |

Figure 10B:
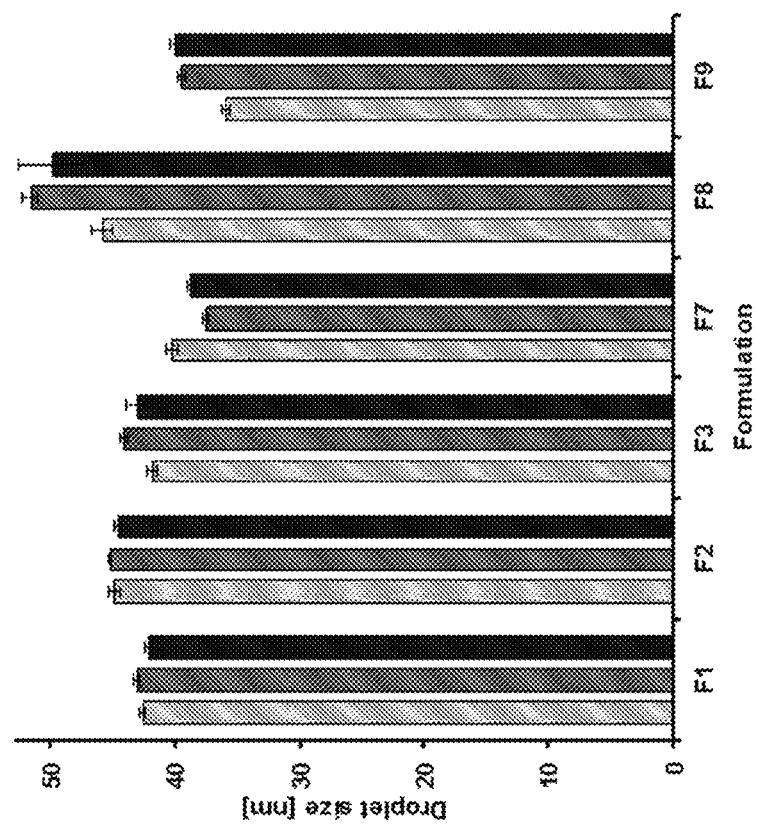
FIGS. 10A to 10B show the droplet size after freezing and heating cycles.
Figure 10A:
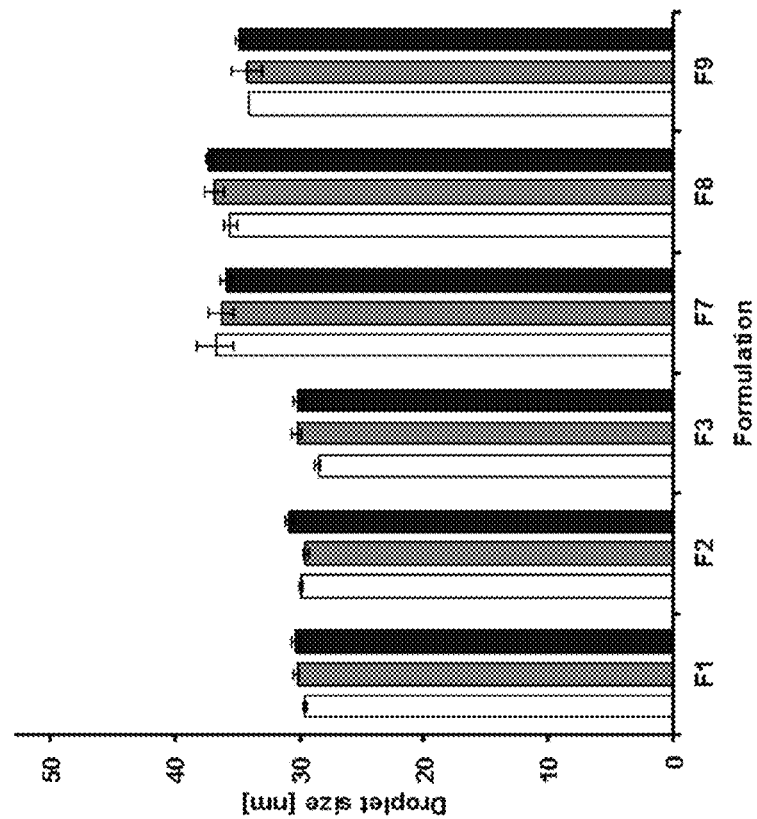
Figure 11:
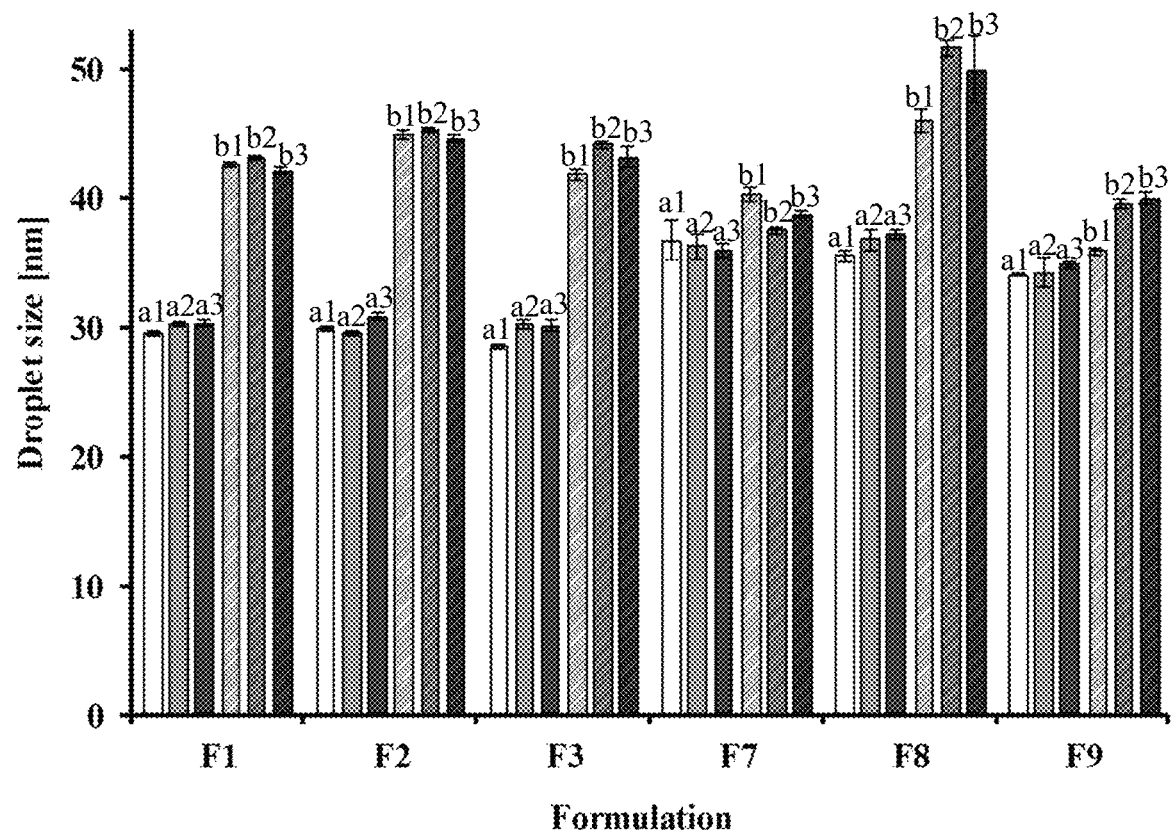
FIG. 11 shows the droplet size at 2% formulation in water ("a") and at 30% formulation in water ("b") with freezing and heating cycles. Before ("1"), cycle 1 ("2"), cycle 2 ("3").
Figure 12B:
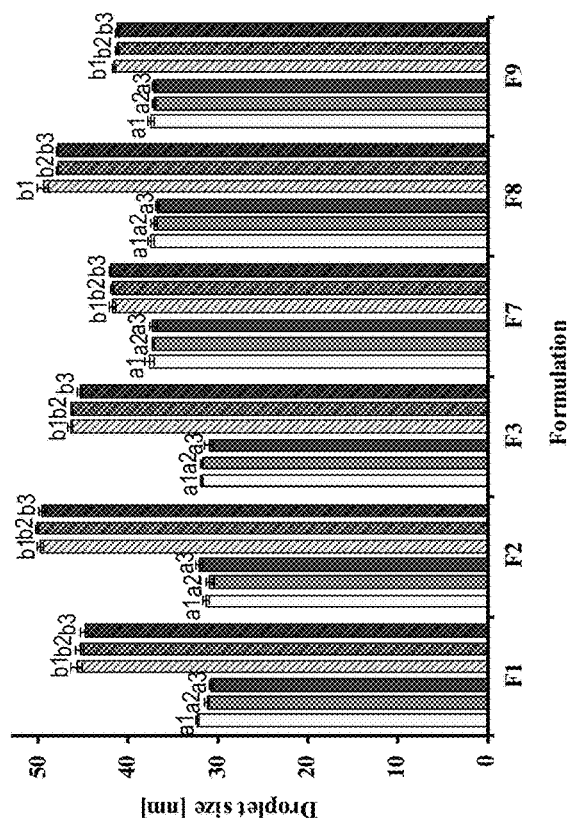
FIGS. 12A to 12D show the emulsion stability in water (FIG. 12A), simulated saliva (FIG. 12B), simulated tears (FIG. 12C), and simulated vaginal fluid (FIG. 12D). 2% formulation in medium ("a"); 30% formulation in medium ("b"). Time 0 h ("1"), time 2 h ("2"), time 4 h ("3").
Figure 12A:
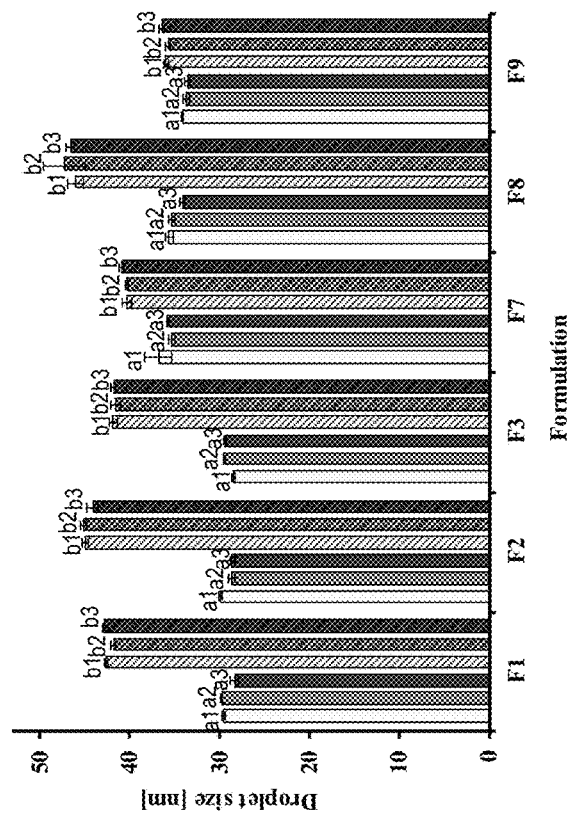
Figure 12D:
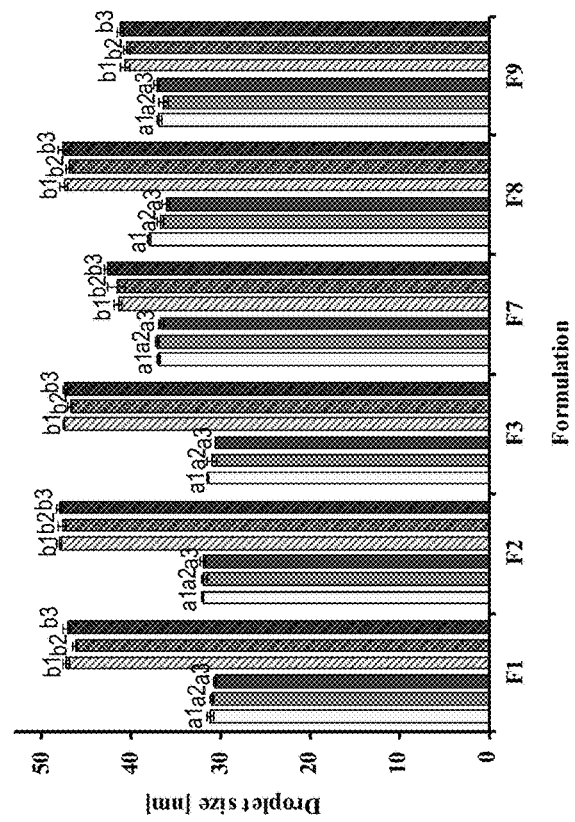
Figure 12C:
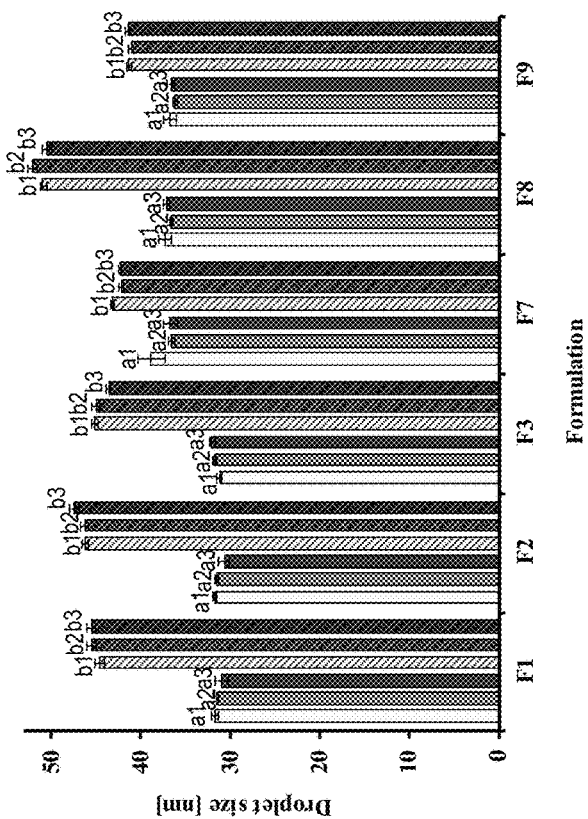
Figure 14:
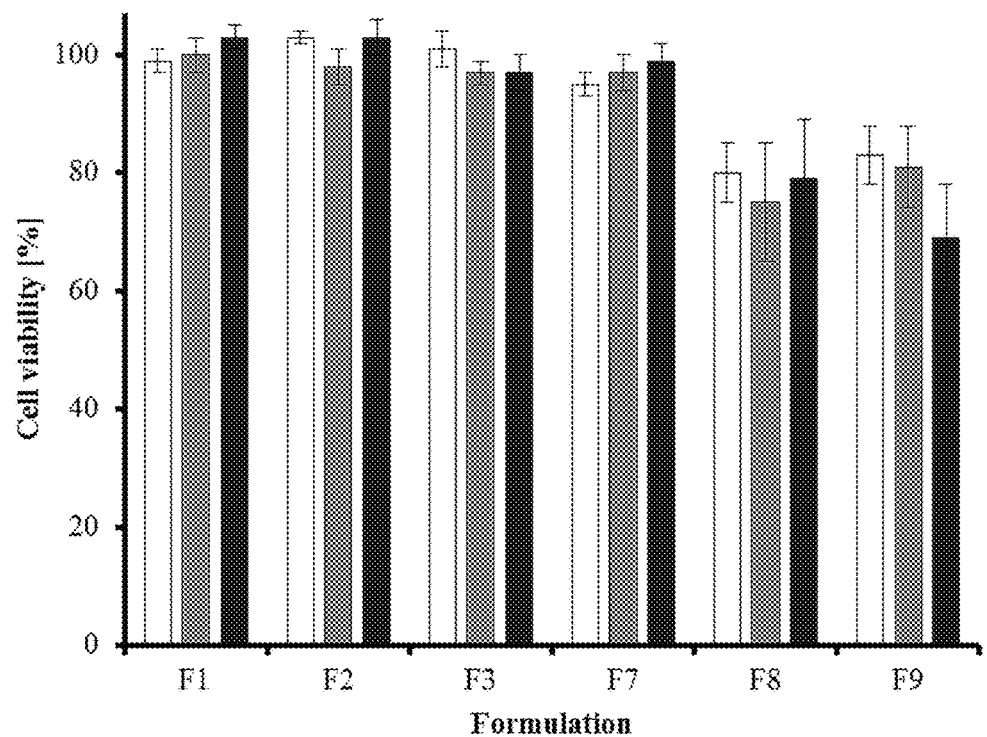
FIG. 14 shows the cell viability of Caco-2 cells after 1 hour (white bars), 2 hours (medium grey bars) and 4 hours (dark grey bars) of incubation.

The formulations were subjected to two freezing/heating cycles. Each cycle consisted of 24 hours of freezing at −22° C. in the freezer and 24 hours of heating at 65° C. in a water bath. After each cycle the droplet size and PDI were determined. The results are shown in FIGS. 10A to 10B and 11. The polydispersity index and standard deviation of the six formulations after 0, 2, and 4 hours are given in Table 19.

TABLE 19

PDI and SD of the six formulations

| | Formulation number | 0 h PDI | 0 h SD | 2 h PDI | 2 h SD | 4 h PDI | 4 h SD |
|---|---|---|---|---|---|---|---|
| 2% | F1 | 0.044 | 0.014 | 0.064 | 0.024 | 0.052 | 0.015 |
| | F2 | 0.039 | 0.004 | 0.065 | 0.023 | 0.064 | 0.017 |
| | F3 | 0.064 | 0.044 | 0.064 | 0.014 | 0.038 | 0.015 |
| | F7 | 0.114 | 0.022 | 0.251 | 0.081 | 0.079 | 0.017 |
| | F8 | 0.058 | 0.029 | 0.138 | 0.028 | 0.101 | 0.012 |
| | F9 | 0.008 | 0.009 | 0.203 | 0.080 | 0.041 | 0.011 |
| 30% | F1 | 0.498 | 0.011 | 0.486 | 0.004 | 0.486 | 0.006 |
| | F2 | 0.458 | 0.007 | 0.450 | 0.007 | 0.459 | 0.008 |
| | F3 | 0.468 | 0.008 | 0.477 | 0.010 | 0.471 | 0.014 |
| | F7 | 0.444 | 0.010 | 0.437 | 0.013 | 0.444 | 0.008 |
| | F8 | 0.439 | 0.011 | 0.553 | 0.108 | 0.475 | 0.064 |
| | F9 | 0.435 | 0.002 | 0.423 | 0.009 | 0.433 | 0.006 |

All formulations did not show any precipitation after centrifugation. Additionally, the freeze-thaw cycles did not lead to any alteration in the formation of nanoemulsions. Therefore, it was concluded that all formulations demonstrate a sufficient stability under stressed conditions.

Additional Materials and Methods

HPLC Quantification Method

For the quantification of Lasofoxifene, an appropriate HPLC method was developed by ThioMatrix. An HPLC System (Merck) with a LaChrome Elite® for Hitachi™ with a DAD-Detector (Merck) and HPLC Software (Merck) with a mobile phase of 0.1% TFA: ACN (30:70 v/v) pH=3.0 was used for the HPLC. The settings for the Lasofoxifene analysis were as follows: Macherey-Nagel NUCLEOSIL® C18, 5 µm, 4×125 mm columns, 0.6 ml/min flow rate, the Auto sampler was set to 10° C., the column oven was set to 40° C., the detection was set to 230 nm, the injection volume was 20 µl, the retention time was 2.8 min, and the runtime was 6 min.

Dissolution Studies in Organic Solvents and Surfactants

First, 1 mg of Lasofoxifene was weighed into Eppendorf vessels and 500 µl of organic solvents and surfactants as listed in Table 20 were added. In cases of insufficient dissolution of the API, samples were treated with ultrasound for 30 min and, if necessary, heated to 50° C. while shaking (300 rpm). Afterwards, samples were examined visually regarding drug dissolution. In case of entire dissolution, the experiment was repeated with increasing drug concentrations until maximum dissolution was achieved. In addition, further organic solvents and surfactants were tested.

TABLE 20

Organic solvents/surfactants used to dissolve Lasofoxifene

| Organic solvents/surfactants | Additional information |
|---|---|
| Cremophor A 25 | Macrogol (25)-cetostearyl ether |
| Cremophor RH 40 | Macrogolglycerol hydroxystearate |
| Cremophor CO 410 | |
| isosorbide dimethyl ether | |
| PEG 200 | Polyethylene glycol |
| PEG 300 | |
| PEG 600 | |
| mPEG 350 | Methoxypolyethylene glycol |
| mPEG 550 | |
| mPEG 750 | |
| Triacetin (TAC) | |
| tributyl citrate (TBC) | |
| tributyl acetyl citrate (TBAC) | |
| triethyl citrate (TEC) | |
| triethyl acetyl citrate (TEAC) | |
| Tetraglycol (TG) | |
| Transcutol (TC) | Diethylene glycol monoethyl ether |
| Tween 20 | Polyethylene glycol sorbitan monolaurate |
| Tween 80 | Polyethylene glycol sorbitan monostearate |

In Vitro Characterization of SNEDDSs

As only 0.5-0.75 ml of vaginal fluid is continually present in the vagina [4], the prepared SNEDD formulations were diluted 1:2 with artificial vaginal fluid containing 2.6 mM $MgSO_4$, 10.0 mM KCl, 40.0 mM glucose buffered with 50 mM acetate buffer pH 5.0 and incubated for three hours at 37° C. while shaking (300 rpm) from time to time. The resulting emulsions were examined visually regarding phase separation. With emulsions resulting in one phase, 750 µg/ml of Lasofoxifene was incorporated in the corresponding SNEDD formulations and visually investigated concerning dissolution. The resulting SNEDDSs containing the API were equilibrated at ambient temperature and incubated for at least 48 hours. After centrifugation, the SNEDD formulations were again examined visually regarding drug dissolution.

Statistical Data Analysis

Amounts were calculated utilizing a calibration curve of Lasofoxifene. $P_{app}$ (apparent permeability coefficients) for Lasofoxifene were calculated using the following equation:

$$P_{app} = Q/A*c*t$$

Where $P_{app}$ is the apparent permeability coefficient (cm/s), Q is the total amount permeated throughout the incubation time (µg), A is the diffusion area of the Ussing chamber ($cm^2$), c is the initial concentration of the test compound in the donor compartment ($µg/cm^3$) and t is the total time of the experiment(s).

All studies and tests were carried out in quadruplicate at least unless otherwise noted. Statistical data analyses were performed using the Student t-test with $p<0.05$ as the minimal level of significance.

Example 9: Effect of Compound on Vaginal Epithelium of Ovariectomized Young Rats—Dosing Frequency Studies A total of 96 young, about 6-8 weeks old, female Sprague Dawley rats were used in this pilot study. The rats were randomized by body weight into six (6) per group and sixteen (16) groups. Ninety (N=90) of the animals were ovariectomized (OVX), and six (N=6) of the animals have a sham OVX surgery. One group of six (6) animals were terminated along with the sham-operated group at Day-14 post-OVX surgery. Three groups of eighteen (18) animals were respectively terminated along with the vehicle group at Day-14, Day-17 or Day-21 post-OVX surgery. The dosing regimens, starting on Day 14 post OVX, by inserting a capsule containing the desired Lasofoxifene formulations (e.g., Test Articles F-1-L, F-1-H, F-2-L, F-2-H) into vaginal tract under brief general anesthesia.

Experimental Procedures

Test Article

The following test articles were employed:

| Test Article group number | Test Article number | The one or more SERM(s) | The concentration of the one or more SERM(s) in the Test Article | The four or more pharmaceutically acceptable excipients |
|---|---|---|---|---|
| F-1 or AZU-201 | F-1-L | Lasofoxifene | 1 µg/mL (low dose) | 4 |
| | F-1-H | Lasofoxifene | 10 µg/mL (high dose) | 4 |
| F-2 or AZU-202 | F-2-L | Lasofoxifene | 1 µg/mL (low dose) | 5 |
| | F-2-H | Lasofoxifene | 10 µg/mL (high dose) | 5 |

Animals

A total of 106 SD female rats were ordered from a qualified local vendor, 96 rats were placed on study and 10 rats serve as spares. These rats, about 6 weeks old, were housed at PharmaLegacy for about 1 week to reach the desired age for the experiment.

The procedures that were applied on animals in this protocol have been approved by PharmaLegacy Laboratories IACUC. See Table 21 below for more details.

TABLE 21

Animals

| | |
|---|---|
| Animal species and strain: | Sprague Dawley rats |
| History of treatment: | Naive |
| Sex, age and weight: | Female, 6-8 weeks old |
| Breeder/supplier: | SLAC |
| Test Facility: | PharmaLegacy Laboratories Vivarium |
| Adaptation: | 1 week |
| Room: | Conventional Room |
| Room temperature: | 19-26° C. |
| Room relative humidity: | 40-70% |
| Light cycle: | Fluorescent light for 12-hour light (08:00-20:00) and 12-hour dark |
| Animal hosting: | 2 rats/cage by treatment group |
| Food: | Free access to food (irradiated, Shanghai SLAC Laboratory Animal Co. Ltd., China) |
| Water: | Free access to water (municipal tap water filtered by water purification system) |

Receipt, Health Evaluation and Acclimatization

Upon receipt the animals were unpacked and placed in cages. A health inspection was performed on each animal to include evaluation of the coat, extremities and orifices. Each animal was also examined for any abnormal signs in posture or movement.

Environment

The animals were housed in the PharmaLegacy Laboratories vivarium in clear polycarbonate plastic cages (400 mm×240 mm×200 mm); 2 animals per cage. The bedding material was autoclaved corn-cob bedding (Shanghai MaoSheng Biologic Science & Technology Development Co., Ltd., China) that was changed twice a week. The room number in which the animals were housed throughout the study period were detailed in the study records. The room in which the animals were housed was an area within the facility that has filtered air ventilation at the rate of 10-20 air changes per hour. The temperature was maintained at (19-26° C.) (66-79° F.) with a relative humidity of 40-70%. Temperature and humidity were continuously monitored and recorded. Illumination was fluorescent light for 12-hour light (08:00-20:00) and 12-hour dark.

Food and Water

Animals have ad libitum access to rodent food (irradiated, Shanghai SLAC Laboratory Animal Co. Ltd., China). The manufacturer has supplied a certificate of analysis for each batch of diet received by PharmaLegacy Laboratories. The Certificates of analysis was retained in the PharmaLegacy Laboratories archives.

Water from PharmaLegacy Laboratories in house production was available to animals ad libitum throughout the study period. Water, from the municipal water supply, was filtered and sterilized by water purification system. Water analyses were performed twice per year and included analyses of heavy metals, nitrates, dissolved minerals, total plate count and coliforms. Certificates of analysis were retained in the PharmaLegacy Laboratories archives.

It was not anticipated that the level of known contaminants in the feed and water would interfere with the purpose or conduct of this study.

Cage and Animal Identification

A unique number was assigned to each animal. Prior to the allocation of animals to treatment groups, cages were labeled with cards identifying study number, species/strain, sex, cage number and animal number. After allocation to treatment groups the cages were labeled with cards which were color coded, and identify treatment groups as well as the information outlined above. Group allocation was documented in the randomization records. Cages were stratified within the racks to reduce the effect of any environmental influences on the study.

Surgery

The animals were anesthetized with 1.5-3.0% Isoflurane to effect with a 0.8-1.5 liter flow rate of oxygen during the surgery. When the animals were anesthetized, atropine (0.05 mg/kg, s.c.), gentamicin (20 mg/kg, i.m.) and buprenorphine (0.05 mg/kg, i.m.) were administered for preventing salivate, anti-infection and pain relief, respectively. Bilateral ovariectomy was performed from a low abdominal approach. The skin was surgically cleaned, shaved and incised at the low abdominal midline. The abdominal muscles were incised to enter the abdominal cavity. The freely movable peri-ovarian fat containing the right ovary and uterine horn were grasped with forceps and exteriorized. The uterine horn was occluded with a double knot suture several mm caudal to the Fallopian tube. After crushing the ovarian blood vessels with a hemostat, the ligated portion of uterine horn and peri-ovarian fat with the enclosed ovary were cut with a dissecting scissors and removed. The remaining tissue were released from the hemostat and muscle. The incision was closed with single suture. The entire procedure was repeated on left side. The low abdominal midline skin incision was closed with three or four wound clips.

Post-Surgery Management

Animals received pain medication, including but not limited to Buprenorphine Hydrochloride (0.05 mg/kg) and Gentamicin (20 mg/kg, i.m.) after surgery. All animals were monitored until they regained consciousness. Animals were monitored on a daily basis, in addition to general health. All animals continue to receive pain medication if pain symptoms persist; and, along with clinical conditions were documented in the Study Records.

Allocation to Groups and Treatment

Rats were assigned to treatment groups by randomization in BioBook system (IDBS) based on the body weights. Grouping according to the below table 1. Each rat was dosed with ready to use solution, 100 into vaginal tract with a syringe. Table 22 shows the allocation of the rats to groups and subsequent treatment.

TABLE 22

Allocation to Groups and Treatment

| Group | Group Name | Label Name | Dose | N | Dosing | Terminate |
|---|---|---|---|---|---|---|
| G1 | Vehicle | AZU-201 -formulation buffer | 0.6 mL | 6 | Day 0 | Day 0 |
| G2 | Vehicle | AZU-201 -formulation buffer | 0.6 mL | 6 | Day 0 | Day 3 |
| G3 | Vehicle | AZU-201 -formulation buffer | 0.6 mL | 6 | Day 0 | Day 7 |
| G4 | Sham | N/A | N/A | 6 | N/A | Day 0 |
| G5 | F-1 | AZU-201 - 1 µg/mL | Low(0.3 µg/kg 0.6 mL) | 6 | Day 0 | Day 3 |
| G6 | F-1 | AZU-201 - 10 µg/mL | High(3.0 µg/kg 0.6 mL) | 6 | Day 0 | Day 3 |
| G7 | F-2 | AZU-202 - 1 µg/mL | Low(0.3 µg/kg 0.6 mL) | 6 | Day 0 | Day 3 |
| G8 | F-2 | AZU-202 - 10 µg/mL | High(3.0 µg/kg 0.6 mL) | 6 | Day 0 | Day 3 |
| G9 | F-1 | AZU-201 - 1 µg/mL | Low(0.3 µg/kg 0.6 mL) | 6 | Day 0 | Day 7 |
| G10 | F-1 | AZU-201 - 10 µg/mL | High(3.0 µg/kg 0.6 mL) | 6 | Day 0 | Day 7 |
| G11 | F-2 | AZU-202 - 1 µg/mL | Low(0.3 µg/kg 0.6 mL) | 6 | Day 0 | Day 7 |
| G12 | F-2 | AZU-202 - 10 µg/mL | High(3.0 µg/kg 0.6 mL) | 6 | Day 0 | Day 7 |
| G13 | F-1 | AZU-201 - 1 µg/mL | Low(0.3 µg/kg 1.2 mL) | 6 | Day 0, Day 4 | Day 7 |
| G14 | F-1 | AZU-201 - 10 µg/mL | High(3.0 µg/kg 1.2 mL) | 6 | Day 0, Day 4 | Day 7 |
| G15 | F-2 | AZU-202 - 1 µg/mL | Low(0.3 µg/kg 1.2 mL) | 6 | Day 0, Day 4 | Day 7 |
| G16 | F-2 | AZU-202 - 10 µg/mL | High(3.0 µg/kg 1.2 mL) | 6 | Day 0, Day 4 | Day 7 |

Annotation:

Groups 1 (N=6): Day-0 vehicle; dose once at 100 µL on Day-0 at 14-day post OVX, and terminate at Day-14 post OVX.

Groups 2 (N=6): Day-3 vehicle; dose once at 100 µL on Day-0 at 14-day post OVX, and terminate at Day-17 post OVX.

Groups 3 (N=6): Day-7 vehicle; dose once at 100 µL on Day-0 at 14-day post OVX, and terminate at Day-21 post OVX.

Groups 4 (N=6): Day-0 sham: terminate at Day-14 post sham-operation.

Groups 5 (N=6): F-1-L; dose once at 0.3 µg/kg (100 µL) on Day-0 at 14-day post OVX, and terminated at Day-3 after dosing.

Groups 6 (N=6): F-1-H; dose once at 3.0 µg/kg (100 µL) on Day-0 at 14-day post OVX, and terminated at Day-3 after dosing.

Groups 7 (N=6): F-2-L; dose once at 0.3 µg/kg (100 µL) on Day-0 at 14-day post OVX, and terminated at Day-3 after dosing.

Groups 8 (N=6): F-2-H; dose once at 3.0 µg/kg (100 µL) on Day-0 at 14-day post OVX, and terminated at Day-3 after dosing.

Groups 9 (N=6): F-1-L; dose once at 0.3 µg/kg (100 µL) on Day-0 at 14-day post OVX, and terminated at Day-7 after dosing.

Groups 10 (N=6): F-1-H; dose once at 3.0 µg/kg (100 µL) on Day-0 at 14-day post OVX, and terminated at Day-7 after dosing.

Groups 11 (N=6): F-2-L; dose once at 0.3 µg/kg (100 µL) on Day-0 at 14-day post OVX, and terminated at Day-7 after dosing.

Groups 12 (N=6): F-2-H; dose once at 3.0 µg/kg (100 µL) on Day-0 at 14-day post OVX, and terminated at Day-7 after dosing.

Groups 13 (N=6): F-1-L; dose twice at respectively 0.3 µg/kg (100 µL) on Day-0 and Day-4 at 14-day and 18-day post OVX, and terminated at Day-7 after dosing.

Groups 14 (N=6): F-1-H; dose twice at respectively 3.0 µg/kg (100 µL) on Day-0 and Day-4 at 14-day and 18-day post OVX, and terminated at Day-7 after dosing.

Groups 15 (N=6): F-2-L; dose twice at respectively 0.3 µg/kg (100 µL) on Day-0 and Day-4 at 14-day and 18-day post OVX, and terminated at Day-7 after dosing.

Groups 16 (N=6): F-2-H; dose twice at respectively 3.0 µg/kg (100 µL) on Day-0 and Day-4 at 14-day and 18-day post OVX, and terminated at Day-7 after dosing.

Body Weight

Animals were weighed upon arrival and at least once weekly for the duration of treatment for health evaluation and calculation of doses.

Clinical Observations

Animals were observed daily for signs of ill health and general reaction to surgery and treatments. All exceptions to normal healthy appearance and behavior were recorded and detailed in standard PharmaLegacy Laboratories clinical observations forms.

Necropsy

All animals were humanely sacrificed by $CO_2$ and the vaginal and uterine wet-weight were collected from each, and about 0.5 mL blood were collected for analysis of serum cholesterol level. Each uterus and vagina was weighed separately and was placed in 10% NBF for at least 48 hours before being sent to Histology Laboratory for tissue processing. The paraffin blocks of these tissues were sectioned, about 4-8 µm in thickness, and one section were stained with H & E for general microscopic evaluation, and one section were stained with PAS for assessment of mucification of the epithelium.

Semi-Quantitative Assessment and Histomorphometry

The PAS stained sections were used to evaluate the amount of mucification by visual approximation on a 0-4 scale, with the 4 stands for the highest amount.

The H & E stained sections were used to measure the height of the vaginal epithelium at minimum of ten (10) sites per slide. Photomicrographs of the slides were included in the appendix or burned on a DVD disc to accompany the final report.

Statistics

Data were analyzed using GraphPad Prism software (GraphPad Software, Inc., La Jolla, Calif., USA) and are expressed as the mean±SD. Groups differences were analyzed using one-way analysis of variance and if a significant difference was detected, followed by the Tukey's multiple comparisons test. $P<0.05$ was considered significantly different. * on behalf of $P<0.05$, ** on behalf of $P<0.01$.

Results

Wet Weight

Figure 15:
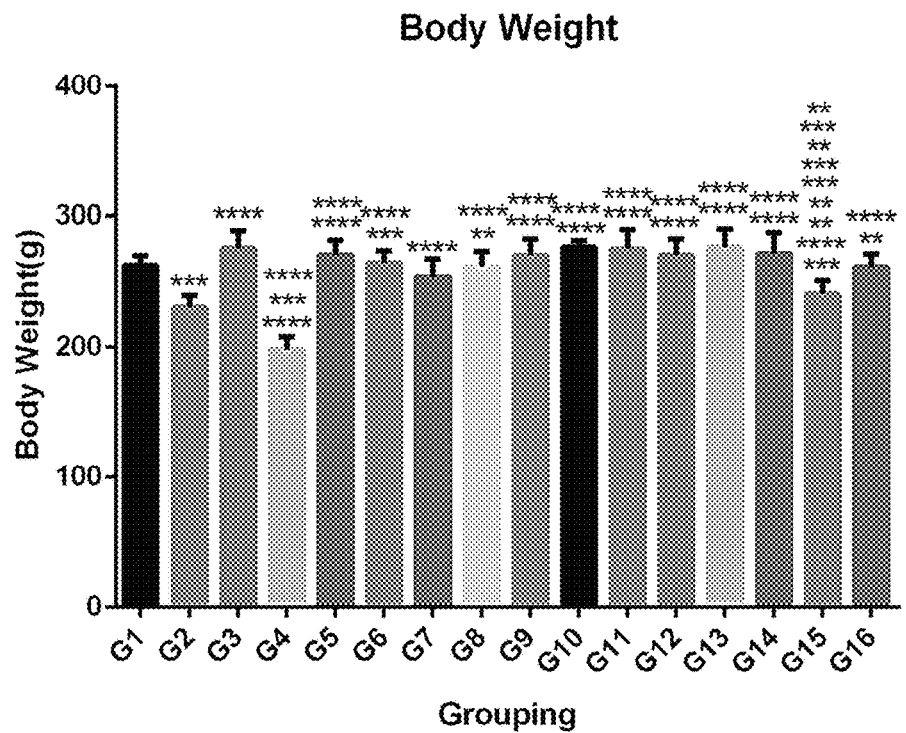
FIG. 15 shows grouping versus body weight in grams.

All groups that received ovariectomy surgery had elevated body weights, in contrast to that of the Sham group (Group 4). Treatments with F-1 and F-2 under low (F-1-L, Group 5) and high (F-1-H, Group 6; F-2-H, Group 8) had higher weight gains than that of the vehicle group (Group 2) terminated at Day-3 after dosing. There was no significant difference observed between groups terminated at Day-7 after dosing, except F-2-L with twice dosing (Group 15), to the vehicle group (Group 3). FIG. 15 and Table 23 correspond to body weight data for the groups. Table 29 shows raw wet weight data.

Vagina Wet Weights

Figure 16:
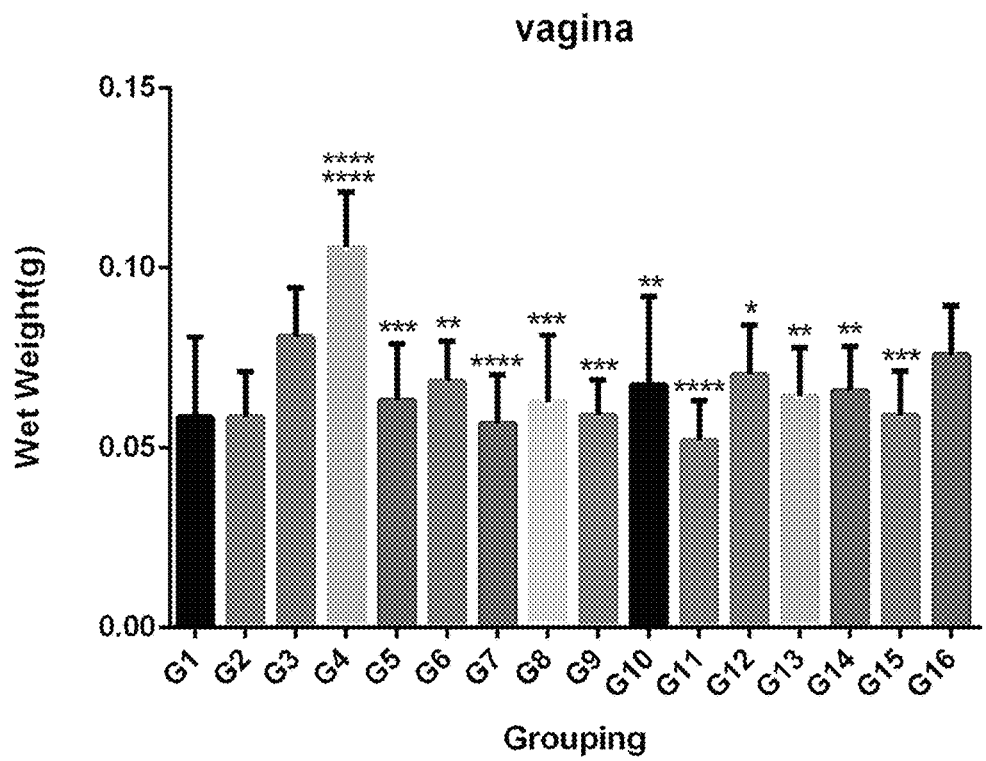
FIG. 16 shows grouping versus vaginal tissue wet weight in grams.

Wet weights of vaginal tissues collected at necropsy from the ovariectomized rats were significantly lighter than that of the Sham (Group 4), as expected. There was no significant difference among the treatment groups, i.e., F-1 or F-2 or low or high dose or single or multiple dosing regimen, on the same termination day of Day-3 and Day-7. FIG. 16 and Table 24 correspond to vagina wet weight data for the groups.

Uterine Wet Weights

Figure 17:
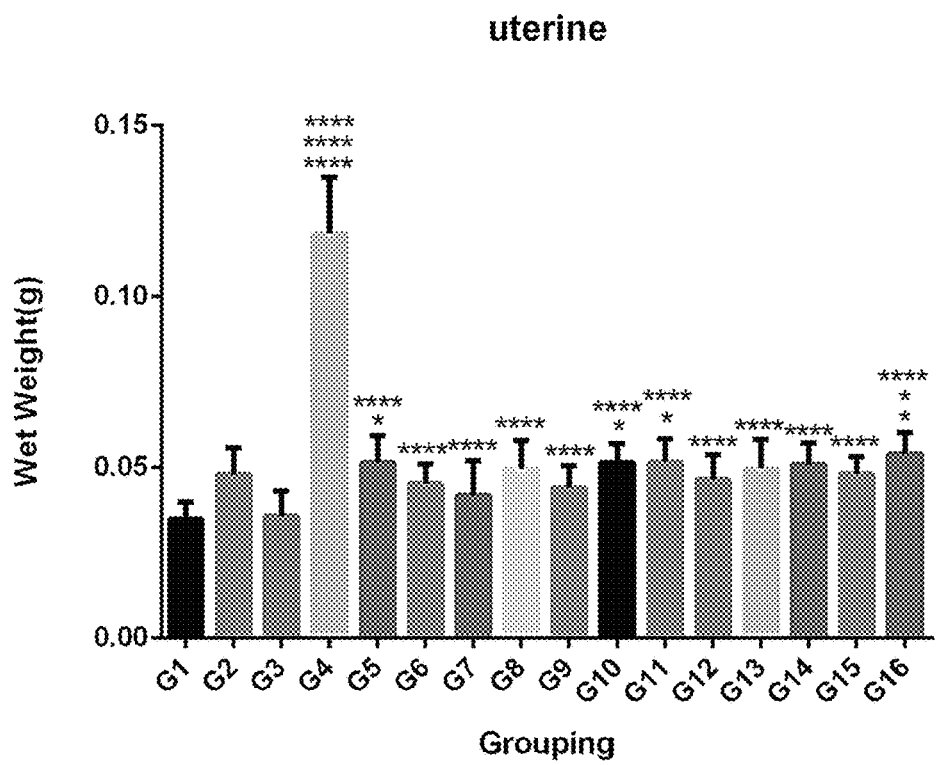
FIG. 17 shows grouping versus uterine tissue wet weight in grams.

The wet weights of uterine tissues measured at necropsy showed that all ovariectomized rats had lower values. No significant difference was found among the groups that were terminated on Day-3. Group 16 (F-2-H, twice dosing) had significantly higher weights than that of the vehicle group (Group 3) terminated at Day-7 after dosing. FIG. 17 and Table 25 correspond to uterine wet weight data for the groups.

Blood Cholesterol Level

Figure 18:
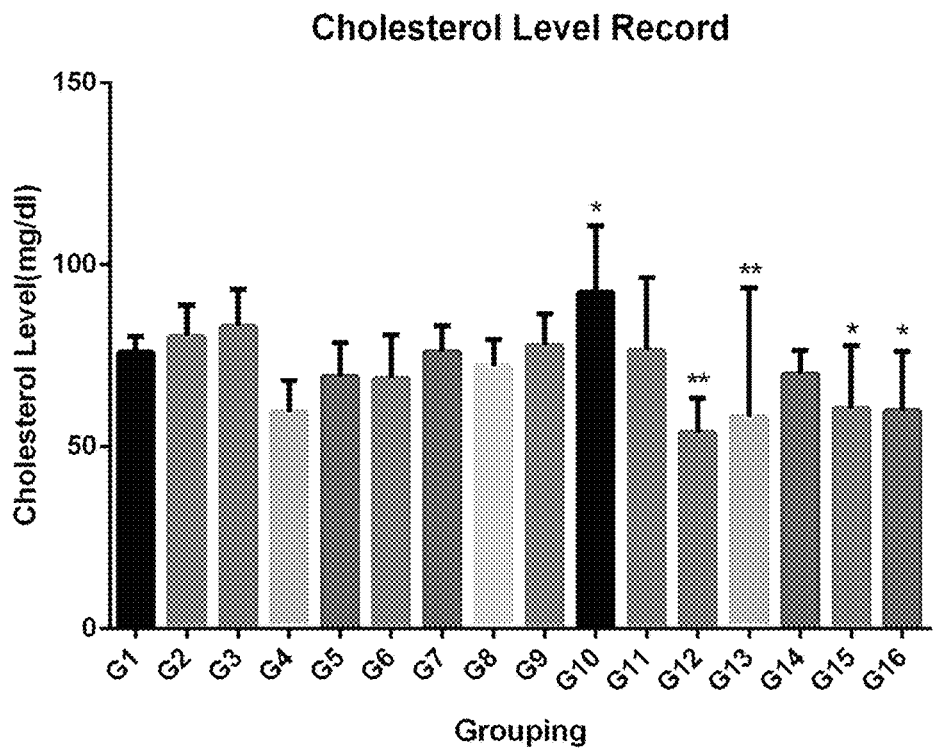
FIG. 18 shows grouping versus blood cholesterol level in milligrams per deciliter.

Cholesterol level among the groups were not significantly different, except that of the Group 10 (F-1-H, Day-7 termination after dosing), to Group 4 (Sham), Group 12 (F-2-H, Day-7 termination after dosing), Group 15 & Group 16 (F-2-L & F-2-H, twice dosing, Day-7 termination after dosing). FIG. 18 and Table 26 correspond to blood cholesterol level data for the groups. Table 31 shows raw blood cholesterol level data.

Mucification of Vaginal Epithelium

Figure 19:
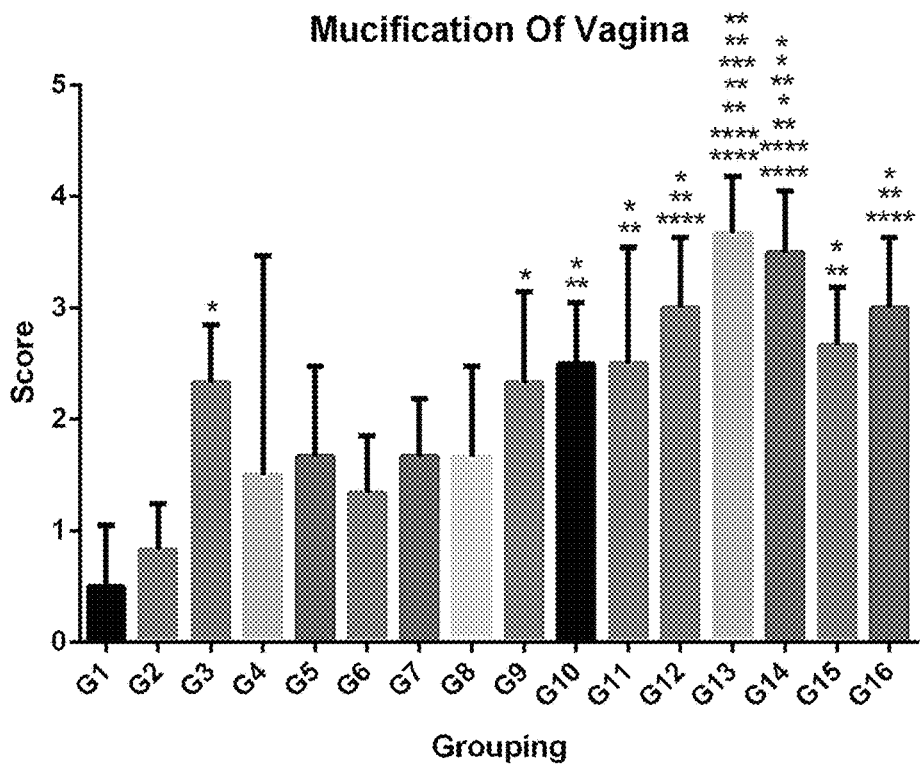
FIG. 19 shows grouping versus mucification of vaginal epithelium demonstrated by Periodic acid-Schiff (PAS) histology staining.

Mucfication demonstrated by PAS staining showed little staining in the uterus. In the vaginal epithelium, Group 13 and Group 14 showed greater mucification scores compared to the Sham group (Group 4). However, under same condition of either Day-3 or Day-7 termination the ovariectomized rats treated with test articles in various regiments were not significantly different from the others. FIG. 19 and Table 27 correspond to the mucification of vaginal epithelium. Table 32 shows raw mucification of vaginal epithelium data.

Thickness of the Vaginal Epithelium

Figure 20:
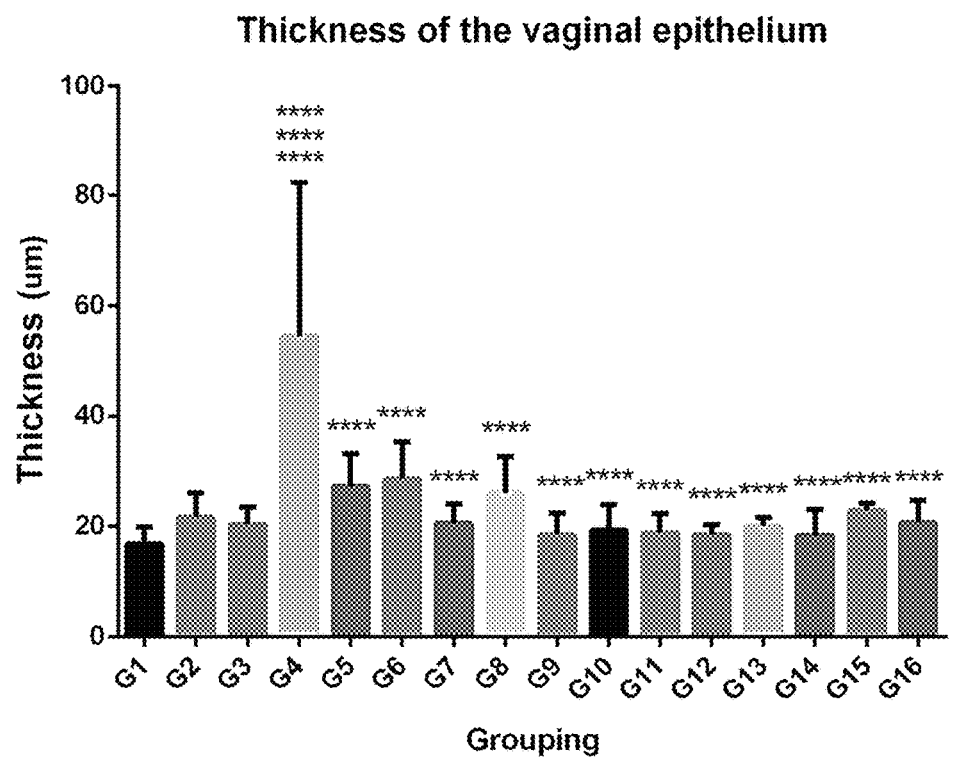
FIG. 20 shows grouping versus vaginal epithelium thickness in micrometers.

The thickness of the vaginal epithelium as measure by morphometric methods was not significantly different among the groups. FIG. 20 and Table 28 correspond to vaginal epithelium thickness data for the groups.

Discussion

Wet Weight

For body weight, all ovariectomized rats gained weights, as compared to that of Group 4 (Sham, Day 0 termination). Group 2 (Day 3 termination Vehicle) seemed to react to dosing manipulation and did not gain as much as all other groups. For body weight on Day 3 termination, Group 5 (F-1-L, dosing once, Day 3 termination), Group 6 (F-1-H, dosing once, Day 3 termination), and Group 8 (F-2-H, dosing once, Day 3 termination) gained more weights than Group 2 (Vehicle). Thereafter, all groups had similar gains on body weights.

For uterine weight, all ovariectomized rats had less wet weights, as compared to that of Group 4 (Sham, Day 0 termination). Group 5 (F-1-L, dosing once, Day 3 termination), G10 (F-1-H, dosing once, Day 7 termination), and Group 16 (F-2-H, Day 0 and Day 4 dosing twice, Day 7 termination) had heavier uterine weights than that of Group 1 (Vehicle, Day 0). Group 16 (F-2-H, Day 0 and Day 4 dosing twice, Day 7 termination) had heavier uterine than that of Group 3 (Vehicle, Day 0 termination).

For vagina weight, all ovariectomized rats had less wet weights, as compared to that of Group 4 (Sham, Day 0 termination), except Group 16 (F-2-H, Day 0 and Day 4 dosing twice, Day 7 termination).

Blood Cholesterol Level

No significant effects observed on serum cholesterol level, as compared to the Sham. The high serum cholesterol values seen in Group 10 were due to 2 outlier values obtained in two of the animals in the group. F-2 given at high dose and Day 7 termination (Group 12), F-1 and F-2 both low and high doses with twice dosing and D7 termination (Groups 13-16) had lower averaged serum cholesterol level to those vehicle ones (Groups 1-3), visually observed from the bar chart.

Mucification of Vaginal Epithelium

The data seemed to indicate that F-1-L (Group 13) and F-1-H (Group 14) when given twice at Day 0 and Day 4 have significant large number of epithelial cells showing PAS positive stain (mucification) than that of given once (Group 5 & Group 6) and the Sham (Group 4). The mean values of scores on mucification from those F-1 and F-2 treated groups and terminated at Day 7 (Groups 9 through 16) were higher than the vehicle of Day-7 termination, but did not show statistical significance.

Thickness of the Vaginal Epithelium

The thickness of the vaginal epithelium in the ovariectomized rats were significantly lower than that of the Sham (Group 4). Under same condition of either Day-3 or Day-7 termination the ovariectomized rats treated with test articles in various regiments were not significantly different from the others.

Overall the effects of test articles were shown most obviously in Group 13 (F-1-L, twice dosing and termination at Day-7 after dosing) and Group 14 (F-1-H, twice dosing and termination at Day-7 after dosing).

TABLE 23

| | | Wet Body Weight Grouping | | | |
|---|---|---|---|---|---|
| Tukey's multiple comparisons test | Mean Diff. | 95% CI of diff. | Significant? | Summary | Adjusted P Value |
| G1 vs. G2 | 32.50 | 8.572 to 56.43 | Yes | *** | 0.0007 |
| G1 vs. G3 | −13.00 | −36.93 to 10.93 | No | ns | 0.8579 |
| G1 vs. G4 | 65.00 | 41.07 to 88.93 | Yes | **** | <0.0001 |
| G1 vs. G5 | −8.000 | −31.93 to 15.93 | No | ns | 0.9981 |
| G1 vs. G6 | −1.833 | −25.76 to 22.09 | No | ns | >0.9999 |
| G1 vs. G7 | 9.333 | −14.59 to 33.26 | No | ns | 0.9906 |
| G1 vs. G8 | 0.8333 | −23.09 to 24.76 | No | ns | >0.9999 |
| G1 vs. G9 | −7.500 | −31.43 to 16.43 | No | ns | 0.9991 |
| G1 vs. G10 | −13.83 | −37.76 to 10.09 | No | ns | 0.7925 |
| G1 vs. G11 | −12.83 | −36.76 to 11.09 | No | ns | 0.8694 |
| G1 vs. G12 | −8.000 | −31.93 to 15.93 | No | ns | 0.9981 |
| G1 vs. G13 | −14.00 | −37.93 to 9.928 | No | ns | 0.7779 |
| G1 vs. G14 | −9.000 | −32.93 to 14.93 | No | ns | 0.9935 |
| G1 vs. G15 | 22.00 | −1.928 to 45.93 | No | ns | 0.1066 |
| G1 vs. G16 | 1.333 | −22.59 to 25.26 | No | ns | >0.9999 |
| G2 vs. G3 | −45.50 | −69.43 to −21.57 | Yes | **** | <0.0001 |
| G2 vs. G4 | 32.50 | 8.572 to 56.43 | Yes | *** | 0.0007 |
| G2 vs. G5 | −40.50 | −64.43 to −16.57 | Yes | **\*\*\*\* | <0.0001** |
| G2 vs. G6 | −34.33 | −58.26 to −10.41 | Yes | **\*\*\* | 0.0003** |
| G2 vs. G7 | −23.17 | −47.09 to 0.7609 | No | ns | 0.0681 |
| G2 vs. G8 | −31.67 | −55.59 to −7.739 | Yes | **\*\* | 0.0012** |
| G2 vs. G9 | −40.00 | −63.93 to −16.07 | Yes | **** | <0.0001 |
| G2 vs. G10 | −46.33 | −70.26 to −22.41 | Yes | **** | <0.0001 |
| G2 vs. G11 | −45.33 | −69.26 to −21.41 | Yes | **** | <0.0001 |
| G2 vs. G12 | −40.50 | −64.43 to −16.57 | Yes | **** | <0.0001 |
| G2 vs. G13 | −46.50 | −70.43 to −22.57 | Yes | **** | <0.0001 |
| G2 vs. G14 | −41.50 | −65.43 to −17.57 | Yes | **** | <0.0001 |
| G2 vs. G15 | −10.50 | −34.43 to 13.43 | No | ns | 0.9721 |
| G2 vs. G16 | −31.17 | −55.09 to −7.239 | Yes | ** | 0.0015 |
| G3 vs. G4 | 78.00 | 54.07 to 101.9 | Yes | **** | <0.0001 |
| G3 vs. G5 | 5.000 | −18.93 to 28.93 | No | ns | >0.9999 |
| G3 vs. G6 | 11.17 | −12.76 to 35.09 | No | ns | 0.9531 |
| G3 vs. G7 | 22.33 | −1.594 to 46.26 | No | ns | 0.0941 |
| G3 vs. G8 | 13.83 | −10.09 to 37.76 | No | ns | 0.7925 |
| G3 vs. G9 | 5.500 | −18.43 to 29.43 | No | ns | >0.9999 |
| G3 vs. G10 | −0.8333 | −24.76 to 23.09 | No | ns | >0.9999 |

TABLE 23-continued

Wet Body Weight Grouping

| Tukey's multiple comparisons test | Mean Diff. | 95% CI of diff. | Significant? | Summary | Adjusted P Value |
|---|---|---|---|---|---|
| G3 vs. G11 | 0.1667 | −23.76 to 24.09 | No | ns | >0.9999 |
| G3 vs. G12 | 5.000 | −18.93 to 28.93 | No | ns | >0.9999 |
| G3 vs. G13 | −1.000 | −24.93 to 22.93 | No | ns | >0.9999 |
| G3 vs. G14 | 4.000 | −19.93 to 27.93 | No | ns | >0.9999 |
| G3 vs. G15 | 35.00 | 11.07 to 58.93 | Yes | ***** | 0.0002** |
| G3 vs. G16 | 14.33 | −9.594 to 38.26 | No | ns | 0.7475 |
| G4 vs. G5 | −73.00 | −96.93 to −49.07 | Yes | **** | <0.0001 |
| G4 vs. G6 | −66.83 | −90.76 to −42.91 | Yes | **** | <0.0001 |
| G4 vs. G7 | −55.67 | −79.59 to −31.74 | Yes | **** | <0.0001 |
| G4 vs. G8 | −64.17 | −88.09 to −40.24 | Yes | **** | <0.0001 |
| G4 vs. G9 | −72.50 | −96.43 to −48.57 | Yes | **** | <0.0001 |
| G4 vs. G10 | −78.83 | −102.8 to −54.91 | Yes | **** | <0.0001 |
| G4 vs. G11 | −77.83 | −101.8 to −53.91 | Yes | **** | <0.0001 |
| G4 vs. G12 | −73.00 | −96.93 to −49.07 | Yes | **** | <0.0001 |
| G4 vs. G13 | −79.00 | −102.9 to −55.07 | Yes | **** | <0.0001 |
| G4 vs. G14 | −74.00 | −97.93 to −50.07 | Yes | **** | <0.0001 |
| G4 vs. G15 | −43.00 | −66.93 to −19.07 | Yes | **** | <0.0001 |
| G4 vs. G16 | −63.67 | −87.59 to −39.74 | Yes | **** | <0.0001 |
| G5 vs. G6 | 6.167 | −17.76 to 30.09 | No | ns | >0.9999 |
| G5 vs. G7 | 17.33 | −6.594 to 41.26 | No | ns | 0.4388 |
| G5 vs. G8 | 8.833 | −15.09 to 32.76 | No | ns | 0.9946 |
| G5 vs. G9 | 0.5000 | −23.43 to 24.43 | No | ns | >0.9999 |
| G5 vs. G10 | −5.833 | −29.76 to 18.09 | No | ns | >0.9999 |
| G5 vs. G11 | −4.833 | −28.76 to 19.09 | No | ns | >0.9999 |
| G5 vs. G12 | 0.0 | −23.93 to 23.93 | No | ns | >0.9999 |
| G5 vs. G13 | −6.000 | −29.93 to 17.93 | No | ns | >0.9999 |
| G5 vs. G14 | −1.000 | −24.93 to 22.93 | No | ns | >0.9999 |
| G5 vs. G15 | 30.00 | 6.072 to 53.93 | Yes | ** | 0.0028 |
| G5 vs. G16 | 9.333 | −14.59 to 33.26 | No | ns | 0.9906 |
| G6 vs. G7 | 11.17 | −12.76 to 35.09 | No | ns | 0.9531 |
| G6 vs. G8 | 2.667 | −21.26 to 26.59 | No | ns | >0.9999 |
| G6 vs. G9 | −5.667 | −29.59 to 18.26 | No | ns | >0.9999 |
| G6 vs. G10 | −12.00 | −35.93 to 11.93 | No | ns | 0.9182 |
| G6 vs. G11 | −11.00 | −34.93 to 12.93 | No | ns | 0.9585 |
| G6 vs. G12 | −6.167 | −30.09 to 17.76 | No | ns | >0.9999 |
| G6 vs. G13 | −12.17 | −36.09 to 11.76 | No | ns | 0.9096 |
| G6 vs. G14 | −7.167 | −31.09 to 16.76 | No | ns | 0.9995 |
| G6 vs. G15 | 23.83 | −0.09421 to 47.76 | No | ns | 0.0520 |
| G6 vs. G16 | 3.167 | −20.76 to 27.09 | No | ns | >0.9999 |
| G7 vs. G8 | −8.500 | −32.43 to 15.43 | No | ns | 0.9964 |
| G7 vs. G9 | −16.83 | −40.76 to 7.094 | No | ns | 0.4901 |
| G7 vs. G10 | −23.17 | −47.09 to 0.7609 | No | ns | 0.0681 |
| G7 vs. G11 | −22.17 | −46.09 to 1.761 | No | ns | 0.1002 |
| G7 vs. G12 | −17.33 | −41.26 to 6.594 | No | ns | 0.4388 |
| G7 vs. G13 | −23.33 | −47.26 to 0.5942 | No | ns | 0.0637 |
| G7 vs. G14 | −18.33 | −42.26 to 5.594 | No | ns | 0.3429 |
| G7 vs. G15 | 12.67 | −11.26 to 36.59 | No | ns | 0.8803 |
| G7 vs. G16 | −8.000 | −31.93 to 15.93 | No | ns | 0.9981 |
| G8 vs. G9 | −8.333 | −32.26 to 15.59 | No | ns | 0.9971 |
| G8 vs. G10 | −14.67 | −38.59 to 9.261 | No | ns | 0.7156 |
| G8 vs. G11 | −13.67 | −37.59 to 10.26 | No | ns | 0.8066 |
| G8 vs. G12 | −8.833 | −32.76 to 15.09 | No | ns | 0.9946 |
| G8 vs. G13 | −14.83 | −38.76 to 9.094 | No | ns | 0.6991 |
| G8 vs. G14 | −9.833 | −33.76 to 14.09 | No | ns | 0.9846 |
| G8 vs. G15 | 21.17 | −2.761 to 45.09 | No | ns | 0.1438 |
| G8 vs. G16 | 0.5000 | −23.43 to 24.43 | No | ns | >0.9999 |
| G9 vs. G10 | −6.333 | −30.26 to 17.59 | No | ns | 0.9999 |
| G9 vs. G11 | −5.333 | −29.26 to 18.59 | No | ns | >0.9999 |
| G9 vs. G12 | −0.5000 | −24.43 to 23.43 | No | ns | >0.9999 |
| G9 vs. G13 | −6.500 | −30.43 to 17.43 | No | ns | 0.9998 |
| G9 vs. G14 | −1.500 | −25.43 to 22.43 | No | ns | >0.9999 |
| G9 vs. G15 | 29.50 | 5.572 to 53.43 | Yes | ** | 0.0037 |
| G9 vs. G16 | 8.833 | −15.09 to 32.76 | No | ns | 0.9946 |
| G10 vs. G11 | 1.000 | −22.93 to 24.93 | No | ns | >0.9999 |
| G10 vs. G12 | 5.833 | −18.09 to 29.76 | No | ns | >0.9999 |
| G10 vs. G13 | −0.1667 | −24.09 to 23.76 | No | ns | >0.9999 |
| G10 vs. G14 | 4.833 | −19.09 to 28.76 | No | ns | >0.9999 |
| G10 vs. G15 | 35.83 | 11.91 to 59.76 | Yes | *** | 0.0001 |
| G10 vs. G16 | 15.17 | −8.761 to 39.09 | No | ns | 0.6654 |
| G11 vs. G12 | 4.833 | −19.09 to 28.76 | No | ns | >0.9999 |
| G11 vs. G13 | −1.167 | −25.09 to 22.76 | No | ns | >0.9999 |
| G11 vs. G14 | 3.833 | −20.09 to 27.76 | No | ns | >0.9999 |
| G11 vs. G15 | 34.83 | 10.91 to 58.76 | Yes | *** | 0.0002 |
| G11 vs. G16 | 14.17 | −9.761 to 38.09 | No | ns | 0.7629 |
| G12 vs. G13 | −6.000 | −29.93 to 17.93 | No | ns | >0.9999 |

TABLE 23-continued

Wet Body Weight Grouping

| Tukey's multiple comparisons test | Mean Diff. | 95% CI of diff. | Significant? | Summary | Adjusted P Value |
|---|---|---|---|---|---|
| G12 vs. G14 | −1.000 | −24.93 to 22.93 | No | ns | >0.9999 |
| G12 vs. G15 | 30.00 | 6.072 to 53.93 | Yes | ** | 0.0028 |
| G12 vs. G16 | 9.333 | −14.59 to 33.26 | No | ns | 0.9906 |
| G13 vs. G14 | 5.000 | −18.93 to 28.93 | No | ns | >0.9999 |
| G13 vs. G15 | 36.00 | 12.07 to 59.93 | Yes | *** | 0.0001 |
| G13 vs. G16 | 15.33 | −8.594 to 39.26 | No | ns | 0.6482 |
| G14 vs. G15 | 31.00 | 7.072 to 54.93 | Yes | ** | 0.0017 |
| G14 vs. G16 | 10.33 | −13.59 to 34.26 | No | ns | 0.9757 |
| G15 vs. G16 | −20.67 | −44.59 to 3.261 | No | ns | 0.1705 |

TABLE 24

Vagina Wet Weights

| Tukey's multiple comparisons test | Mean Diff. | 95% CI of diff. | Significant? | Summary | Adjusted P Value |
|---|---|---|---|---|---|
| G1 vs. G2 | −6.667e−005 | −0.03107 to 0.03094 | No | ns | >0.9999 |
| G1 vs. G3 | −0.02243 | −0.05344 to 0.008572 | No | ns | 0.4409 |
| G1 vs. G4 | −0.0470 | −0.07801 to −0.01599 | Yes | **** | <0.0001 |
| G1 vs. G5 | −0.004583 | −0.03559 to 0.02642 | No | ns | >0.9999 |
| G1 vs. G6 | −0.009967 | −0.04097 to 0.02104 | No | ns | 0.9988 |
| G1 vs. G7 | 0.001850 | −0.02916 to 0.03286 | No | ns | >0.9999 |
| G1 vs. G8 | −0.004083 | −0.03509 to 0.02692 | No | ns | >0.9999 |
| G1 vs. G9 | −0.0004500 | −0.03146 to 0.03056 | No | ns | >0.9999 |
| G1 vs. G10 | −0.008933 | −0.03994 to 0.02207 | No | ns | 0.9997 |
| G1 vs. G11 | 0.006683 | −0.02432 to 0.03769 | No | ns | >0.9999 |
| G1 vs. G12 | −0.01178 | −0.04279 to 0.01922 | No | ns | 0.9928 |
| G1 vs. G13 | −0.005783 | −0.03679 to 0.02522 | No | ns | >0.9999 |
| G1 vs. G14 | −0.007267 | −0.03827 to 0.02374 | No | ns | >0.9999 |
| G1 vs. G15 | −0.0003833 | −0.03139 to 0.03062 | No | ns | >0.9999 |
| G1 vs. G16 | −0.01728 | −0.04829 to 0.01372 | No | ns | 0.8329 |
| G2 vs. G3 | −0.02237 | −0.05337 to 0.008639 | No | ns | 0.4461 |
| G2 vs. G4 | −0.04693 | −0.07794 to −0.01593 | Yes | **** | <0.0001 |
| G2 vs. G5 | −0.004517 | −0.03552 to 0.02649 | No | ns | >0.9999 |
| G2 vs. G6 | −0.009900 | −0.04091 to 0.02111 | No | ns | 0.9989 |
| G2 vs. G7 | 0.001917 | −0.02909 to 0.03292 | No | ns | >0.9999 |
| G2 vs. G8 | −0.004017 | −0.03502 to 0.02699 | No | ns | >0.9999 |
| G2 vs. G9 | −0.0003833 | −0.03139 to 0.03062 | No | ns | >0.9999 |
| G2 vs. G10 | −0.008867 | −0.03987 to 0.02214 | No | ns | 0.9997 |
| G2 vs. G11 | 0.006750 | −0.02426 to 0.03776 | No | ns | >0.9999 |
| G2 vs. G12 | −0.01172 | −0.04272 to 0.01929 | No | ns | 0.9932 |
| G2 vs. G13 | −0.005717 | −0.03672 to 0.02529 | No | ns | >0.9999 |
| G2 vs. G14 | −0.007200 | −0.03821 to 0.02381 | No | ns | >0.9999 |
| G2 vs. G15 | −0.0003167 | −0.03132 to 0.03069 | No | ns | >0.9999 |
| G2 vs. G16 | −0.01722 | −0.04822 to 0.01379 | No | ns | 0.8369 |
| G3 vs. G4 | −0.02457 | −0.05557 to 0.006439 | No | ns | 0.2890 |
| G3 vs. G5 | 0.01785 | −0.01316 to 0.04886 | No | ns | 0.7975 |
| G3 vs. G6 | 0.01247 | −0.01854 to 0.04347 | No | ns | 0.9874 |
| G3 vs. G7 | 0.02428 | −0.006722 to 0.05529 | No | ns | 0.3073 |
| G3 vs. G8 | 0.01835 | −0.01266 to 0.04936 | No | ns | 0.7634 |
| G3 vs. G9 | 0.02198 | −0.009022 to 0.05299 | No | ns | 0.4764 |
| G3 vs. G10 | 0.0135 | −0.01751 to 0.04451 | No | ns | 0.9739 |
| G3 vs. G11 | 0.02912 | −0.001889 to 0.06012 | No | ns | 0.0894 |
| G3 vs. G12 | 0.01065 | −0.02036 to 0.04166 | No | ns | 0.9975 |
| G3 vs. G13 | 0.01665 | −0.01436 to 0.04766 | No | ns | 0.8683 |
| G3 vs. G14 | 0.01517 | −0.01584 to 0.04617 | No | ns | 0.9321 |
| G3 vs. G15 | 0.02205 | −0.008956 to 0.05306 | No | ns | 0.4711 |
| G3 vs. G16 | 0.005150 | −0.02586 to 0.03616 | No | ns | >0.9999 |
| G4 vs. G5 | 0.04242 | 0.01141 to 0.07342 | Yes | *** | 0.0007 |
| G4 vs. G6 | 0.03703 | 0.006028 to 0.06804 | Yes | ** | 0.0059 |
| G4 vs. G7 | 0.04885 | 0.01784 to 0.07986 | Yes | **** | <0.0001 |
| G4 vs. G8 | 0.04292 | 0.01191 to 0.07392 | Yes | *** | 0.0005 |
| G4 vs. G9 | 0.04655 | 0.01554 to 0.07756 | Yes | *** | 0.0001 |
| G4 vs. G10 | 0.03807 | 0.007061 to 0.06907 | Yes | ** | 0.0039 |
| G4 vs. G11 | 0.05368 | 0.02268 to 0.08469 | Yes | **** | <0.0001 |
| G4 vs. G12 | 0.03522 | 0.004211 to 0.06622 | Yes | * | 0.0117 |
| G4 vs. G13 | 0.04122 | 0.01021 to 0.07222 | Yes | ** | 0.0011 |
| G4 vs. G14 | 0.03973 | 0.008728 to 0.07074 | Yes | ** | 0.0020 |
| G4 vs. G15 | 0.04662 | 0.01561 to 0.07762 | Yes | *** | 0.0001 |
| G4 vs. G16 | 0.02972 | −0.001289 to 0.06072 | No | ns | 0.0747 |
| G5 vs. G6 | −0.005383 | −0.03639 to 0.02562 | No | ns | >0.9999 |

TABLE 24-continued

| | Vagina Wet Weights | | | | |
|---|---|---|---|---|---|
| Tukey's multiple comparisons test | Mean Diff. | 95% CI of diff. | Significant? | Summary | Adjusted P Value |
| G5 vs. G7 | 0.006433 | −0.02457 to 0.03744 | No | ns | >0.9999 |
| G5 vs. G8 | 0.0005000 | −0.03051 to 0.03151 | No | ns | >0.9999 |
| G5 vs. G9 | 0.004133 | −0.02687 to 0.03514 | No | ns | >0.9999 |
| G5 vs. G10 | −0.00435 | −0.03536 to 0.02666 | No | ns | >0.9999 |
| G5 vs. G11 | 0.01127 | −0.01974 to 0.04227 | No | ns | 0.9954 |
| G5 vs. G12 | −0.0072 | −0.03821 to 0.02381 | No | ns | >0.9999 |
| G5 vs. G13 | −0.0012 | −0.03221 to 0.02981 | No | ns | >0.9999 |
| G5 vs. G14 | −0.002683 | −0.03369 to 0.02832 | No | ns | >0.9999 |
| G5 vs. G15 | 0.004200 | −0.02681 to 0.03521 | No | ns | >0.9999 |
| G5 vs. G16 | −0.0127 | −0.04371 to 0.01831 | No | ns | 0.9850 |
| G6 vs. G7 | 0.01182 | −0.01919 to 0.04282 | No | ns | 0.9925 |
| G6 vs. G8 | 0.005883 | −0.02512 to 0.03689 | No | ns | >0.9999 |
| G6 vs. G9 | 0.009517 | −0.02149 to 0.04052 | No | ns | 0.9993 |
| G6 vs. G10 | 0.001033 | −0.02997 to 0.03204 | No | ns | >0.9999 |
| G6 vs. G11 | 0.01665 | −0.01436 to 0.04766 | No | ns | 0.8683 |
| G6 vs. G12 | −0.001817 | −0.03282 to 0.02919 | No | ns | >0.9999 |
| G6 vs. G13 | 0.004183 | −0.02682 to 0.03519 | No | ns | >0.9999 |
| G6 vs. G14 | 0.002700 | −0.02831 to 0.03371 | No | ns | >0.9999 |
| G6 vs. G15 | 0.009583 | −0.02142 to 0.04059 | No | ns | 0.9992 |
| G6 vs. G16 | −0.007317 | −0.03832 to 0.02369 | No | ns | >0.9999 |
| G7 vs. G8 | −0.005933 | −0.03694 to 0.02507 | No | ns | >0.9999 |
| G7 vs. G9 | −0.002300 | −0.03331 to 0.02871 | No | ns | >0.9999 |
| G7 vs. G10 | −0.01078 | −0.04179 to 0.02022 | No | ns | 0.9971 |
| G7 vs. G11 | 0.004833 | −0.02617 to 0.03584 | No | ns | >0.9999 |
| G7 vs. G12 | −0.01363 | −0.04464 to 0.01737 | No | ns | 0.9716 |
| G7 vs. G13 | −0.007633 | −0.03864 to 0.02337 | No | ns | >0.9999 |
| G7 vs. G14 | −0.009117 | −0.04012 to 0.02189 | No | ns | 0.9996 |
| G7 vs. G15 | −0.002233 | −0.03324 to 0.02877 | No | ns | >0.9999 |
| G7 vs. G16 | −0.01913 | −0.05014 to 0.01187 | No | ns | 0.7058 |
| G8 vs. G9 | 0.003633 | −0.02737 to 0.03464 | No | ns | >0.9999 |
| G8 vs. G10 | −0.00485 | −0.03586 to 0.02616 | No | ns | >0.9999 |
| G8 vs. G11 | 0.01077 | −0.02024 to 0.04177 | No | ns | 0.9972 |
| G8 vs. G12 | −0.0077 | −0.03871 to 0.02331 | No | ns | >0.9999 |
| G8 vs. G13 | −0.0017 | −0.03271 to 0.02931 | No | ns | >0.9999 |
| G8 vs. G14 | −0.003183 | −0.03419 to 0.02782 | No | ns | >0.9999 |
| G8 vs. G15 | 0.0037 | −0.02731 to 0.03471 | No | ns | >0.9999 |
| G8 vs. G16 | −0.0132 | −0.04421 to 0.01781 | No | ns | 0.9786 |
| G9 vs. G10 | −0.008483 | −0.03949 to 0.02252 | No | ns | 0.9998 |
| G9 vs. G11 | 0.007133 | −0.02387 to 0.03814 | No | ns | >0.9999 |
| G9 vs. G12 | −0.01133 | −0.04234 to 0.01967 | No | ns | 0.9951 |
| G9 vs. G13 | −0.005333 | −0.03634 to 0.02567 | No | ns | >0.9999 |
| G9 vs. G14 | −0.006817 | −0.03782 to 0.02419 | No | ns | >0.9999 |
| G9 vs. G15 | 6.667e−005 | −0.03094 to 0.03107 | No | ns | >0.9999 |
| G9 vs. G16 | −0.01683 | −0.04784 to 0.01417 | No | ns | 0.8586 |
| G10 vs. G11 | 0.01562 | −0.01539 to 0.04662 | No | ns | 0.9156 |
| G10 vs. G12 | −0.002850 | −0.03386 to 0.02816 | No | ns | >0.9999 |
| G10 vs. G13 | 0.00315 | −0.02786 to 0.03416 | No | ns | >0.9999 |
| G10 vs. G14 | 0.001667 | −0.02934 to 0.03267 | No | ns | >0.9999 |
| G10 vs. G15 | 0.00855 | −0.02246 to 0.03956 | No | ns | 0.9998 |
| G10 vs. G16 | −0.00835 | −0.03936 to 0.02266 | No | ns | 0.9998 |
| G11 vs. G12 | −0.01847 | −0.04947 to 0.01254 | No | ns | 0.7552 |
| G11 vs. G13 | −0.01247 | −0.04347 to 0.01854 | No | ns | 0.9874 |
| G11 vs. G14 | −0.01395 | −0.04496 to 0.01706 | No | ns | 0.9654 |
| G11 vs. G15 | −0.007067 | −0.03807 to 0.02394 | No | ns | >0.9999 |
| G11 vs. G16 | −0.02397 | −0.05497 to 0.007039 | No | ns | 0.3284 |
| G12 vs. G13 | 0.006000 | −0.02501 to 0.03701 | No | ns | >0.9999 |
| G12 vs. G14 | 0.004517 | −0.02649 to 0.03552 | No | ns | >0.9999 |
| G12 vs. G15 | 0.0114 | −0.01961 to 0.04241 | No | ns | 0.9948 |
| G12 vs. G16 | −0.005500 | −0.03651 to 0.02551 | No | ns | >0.9999 |
| G13 vs. G14 | −0.001483 | −0.03249 to 0.02952 | No | ns | >0.9999 |
| G13 vs. G15 | 0.005400 | −0.02561 to 0.03641 | No | ns | >0.9999 |
| G13 vs. G16 | −0.0115 | −0.04251 to 0.01951 | No | ns | 0.9943 |
| G14 vs. G15 | 0.006883 | −0.02412 to 0.03789 | No | ns | >0.9999 |
| G14 vs. G16 | −0.01002 | −0.04102 to 0.02099 | No | ns | 0.9987 |
| G15 vs. G16 | −0.0169 | −0.04791 to 0.01411 | No | ns | 0.8549 |

TABLE 25

| Tukey's multiple comparisons test | Mean Diff. | 95% CI of diff. | Significant? | Summary | Adjusted P Value |
|---|---|---|---|---|---|
| | | Uterine Wet Weights | | | |
| G1 vs. G2 | −0.01315 | −0.02957 to 0.003273 | No | ns | 0.2729 |
| G1 vs. G3 | −0.0007333 | −0.01716 to 0.01569 | No | ns | >0.9999 |
| G1 vs. G4 | −0.08353 | −0.09996 to −0.06711 | Yes | **** | <0.0001 |
| G1 vs. G5 | −0.01667 | −0.03309 to −0.0002437 | Yes | * | 0.0431 |
| G1 vs. G6 | −0.01047 | −0.02689 to 0.005956 | No | ns | 0.6569 |
| G1 vs. G7 | −0.006867 | −0.02329 to 0.009556 | No | ns | 0.9819 |
| G1 vs. G8 | −0.0147 | −0.03112 to 0.001723 | No | ns | 0.1317 |
| G1 vs. G9 | −0.009217 | −0.02564 to 0.007206 | No | ns | 0.8259 |
| G1 vs. G10 | −0.01663 | −0.03306 to −0.0002104 | Yes | * | 0.0440 |
| G1 vs. G11 | −0.01687 | −0.03329 to −0.0004437 | Yes | * | 0.0381 |
| G1 vs. G12 | −0.01172 | −0.02814 to 0.004706 | No | ns | 0.4655 |
| G1 vs. G13 | −0.01482 | −0.03124 to 0.001606 | No | ns | 0.1239 |
| G1 vs. G14 | −0.01602 | −0.03244 to 0.0004063 | No | ns | 0.0637 |
| G1 vs. G15 | −0.0133 | −0.02972 to 0.003123 | No | ns | 0.2560 |
| G1 vs. G16 | −0.0192 | −0.03562 to −0.002777 | Yes | ** | 0.0079 |
| G2 vs. G3 | 0.01242 | −0.004006 to 0.02884 | No | ns | 0.3651 |
| G2 vs. G4 | −0.07038 | −0.08681 to −0.05396 | Yes | **** | <0.0001 |
| G2 vs. G5 | −0.003517 | −0.01994 to 0.01291 | No | ns | >0.9999 |
| G2 vs. G6 | 0.002683 | −0.01374 to 0.01911 | No | ns | >0.9999 |
| G2 vs. G7 | 0.006283 | −0.01014 to 0.02271 | No | ns | 0.9923 |
| G2 vs. G8 | −0.00155 | −0.01797 to 0.01487 | No | ns | >0.9999 |
| G2 vs. G9 | 0.003933 | −0.01249 to 0.02036 | No | ns | >0.9999 |
| G2 vs. G10 | −0.003483 | −0.01991 to 0.01294 | No | ns | >0.9999 |
| G2 vs. G11 | −0.003717 | −0.02014 to 0.01271 | No | ns | >0.9999 |
| G2 vs. G12 | 0.001433 | −0.01499 to 0.01786 | No | ns | >0.9999 |
| G2 vs. G13 | −0.001667 | −0.01809 to 0.01476 | No | ns | >0.9999 |
| G2 vs. G14 | −0.002867 | −0.01929 to 0.01356 | No | ns | >0.9999 |
| G2 vs. G15 | −0.0001500 | −0.01657 to 0.01627 | No | ns | >0.9999 |
| G2 vs. G16 | −0.00605 | −0.02247 to 0.01037 | No | ns | 0.9947 |
| G3 vs. G4 | −0.0828 | −0.09922 to −0.06638 | Yes | **** | <0.0001 |
| G3 vs. G5 | −0.01593 | −0.03236 to 0.0004896 | No | ns | 0.0669 |
| G3 vs. G6 | −0.009733 | −0.02616 to 0.006690 | No | ns | 0.7616 |
| G3 vs. G7 | −0.006133 | −0.02256 to 0.01029 | No | ns | 0.9939 |
| G3 vs. G8 | −0.01397 | −0.03039 to 0.002456 | No | ns | 0.1893 |
| G3 vs. G9 | −0.008483 | −0.02491 to 0.007940 | No | ns | 0.8989 |
| G3 vs. G10 | −0.0159 | −0.03232 to 0.0005229 | No | ns | 0.0682 |
| G3 vs. G11 | −0.01613 | −0.03256 to 0.0002896 | No | ns | 0.0595 |
| G3 vs. G12 | −0.01098 | −0.02741 to 0.005440 | No | ns | 0.5778 |
| G3 vs. G13 | −0.01408 | −0.03051 to 0.002340 | No | ns | 0.1791 |
| G3 vs. G14 | −0.01528 | −0.03171 to 0.001140 | No | ns | 0.0965 |
| G3 vs. G15 | −0.01257 | −0.02899 to 0.003856 | No | ns | 0.3451 |
| G3 vs. G16 | −0.01847 | −0.03489 to −0.002044 | Yes | *** | 0.0133** |
| G4 vs. G5 | 0.06687 | 0.05044 to 0.08329 | Yes | **** | <0.0001 |
| G4 vs. G6 | 0.07307 | 0.05664 to 0.08949 | Yes | **** | <0.0001 |
| G4 vs. G7 | 0.07667 | 0.06024 to 0.09309 | Yes | **** | <0.0001 |
| G4 vs. G8 | 0.06883 | 0.05241 to 0.08526 | Yes | **** | <0.0001 |
| G4 vs. G9 | 0.07432 | 0.05789 to 0.09074 | Yes | **** | <0.0001 |
| G4 vs. G10 | 0.0669 | 0.05048 to 0.08332 | Yes | **** | <0.0001 |
| G4 vs. G11 | 0.06667 | 0.05024 to 0.08309 | Yes | **** | <0.0001 |
| G4 vs. G12 | 0.07182 | 0.05539 to 0.08824 | Yes | **** | <0.0001 |
| G4 vs. G13 | 0.06872 | 0.05229 to 0.08514 | Yes | **** | <0.0001 |
| G4 vs. G14 | 0.06752 | 0.05109 to 0.08394 | Yes | **** | <0.0001 |
| G4 vs. G15 | 0.07023 | 0.05381 to 0.08666 | Yes | **** | <0.0001 |
| G4 vs. G16 | 0.06433 | 0.04791 to 0.08076 | Yes | **** | <0.0001 |
| G5 vs. G6 | 0.006200 | −0.01022 to 0.02262 | No | ns | 0.9932 |
| G5 vs. G7 | 0.009800 | −0.006623 to 0.02622 | No | ns | 0.7526 |
| G5 vs. G8 | 0.001967 | −0.01446 to 0.01839 | No | ns | >0.9999 |
| G5 vs. G9 | 0.007450 | −0.008973 to 0.02387 | No | ns | 0.9629 |
| G5 vs. G10 | 3.333e-005 | −0.01639 to 0.01646 | No | ns | >0.9999 |
| G5 vs. G11 | −0.0002000 | −0.01662 to 0.01622 | No | ns | >0.9999 |
| G5 vs. G12 | 0.004950 | −0.01147 to 0.02137 | No | ns | 0.9994 |
| G5 vs. G13 | 0.001850 | −0.01457 to 0.01827 | No | ns | >0.9999 |
| G5 vs. G14 | 0.0006500 | −0.01577 to 0.01707 | No | ns | >0.9999 |
| G5 vs. G15 | 0.003367 | −0.01306 to 0.01979 | No | ns | >0.9999 |
| G5 vs. G16 | −0.002533 | −0.01896 to 0.01389 | No | ns | >0.9999 |
| G6 vs. G7 | 0.003600 | −0.01282 to 0.02002 | No | ns | >0.9999 |
| G6 vs. G8 | −0.004233 | −0.02066 to 0.01219 | No | ns | >0.9999 |
| G6 vs. G9 | 0.00125 | −0.01517 to 0.01767 | No | ns | >0.9999 |
| G6 vs. G10 | −0.006167 | −0.02259 to 0.01026 | No | ns | 0.9936 |
| G6 vs. G11 | −0.0064 | −0.02282 to 0.01002 | No | ns | 0.9907 |
| G6 vs. G12 | −0.001250 | −0.01767 to 0.01517 | No | ns | >0.9999 |
| G6 vs. G13 | −0.004350 | −0.02077 to 0.01207 | No | ns | 0.9999 |
| G6 vs. G14 | −0.005550 | −0.02197 to 0.01087 | No | ns | 0.9979 |
| G6 vs. G15 | −0.002833 | −0.01926 to 0.01359 | No | ns | >0.9999 |
| G6 vs. G16 | −0.008733 | −0.02516 to 0.007690 | No | ns | 0.8766 |

TABLE 25-continued

Uterine Wet Weights

| Tukey's multiple comparisons test | Mean Diff. | 95% CI of diff. | Significant? | Summary | Adjusted P Value |
|---|---|---|---|---|---|
| G7 vs. G8 | −0.007833 | −0.02426 to 0.008590 | No | ns | 0.9442 |
| G7 vs. G9 | −0.002350 | −0.01877 to 0.01407 | No | ns | >0.9999 |
| G7 vs. G10 | −0.009767 | −0.02619 to 0.006656 | No | ns | 0.7571 |
| G7 vs. G11 | −0.0100 | −0.02642 to 0.006423 | No | ns | 0.7250 |
| G7 vs. G12 | −0.00485 | −0.02127 to 0.01157 | No | ns | 0.9995 |
| G7 vs. G13 | −0.00795 | −0.02437 to 0.008473 | No | ns | 0.9374 |
| G7 vs. G14 | −0.00915 | −0.02557 to 0.007273 | No | ns | 0.8334 |
| G7 vs. G15 | −0.006433 | −0.02286 to 0.009990 | No | ns | 0.9902 |
| G7 vs. G16 | −0.01233 | −0.02876 to 0.004090 | No | ns | 0.3765 |
| G8 vs. G9 | 0.005483 | −0.01094 to 0.02191 | No | ns | 0.9981 |
| G8 vs. G10 | −0.001933 | −0.01836 to 0.01449 | No | ns | >0.9999 |
| G8 vs. G11 | −0.002167 | −0.01859 to 0.01426 | No | ns | >0.9999 |
| G8 vs. G12 | 0.002983 | −0.01344 to 0.01941 | No | ns | >0.9999 |
| G8 vs. G13 | −0.0001167 | −0.01654 to 0.01631 | No | ns | >0.9999 |
| G8 vs. G14 | −0.001317 | −0.01774 to 0.01511 | No | ns | >0.9999 |
| G8 vs. G15 | 0.0014 | −0.01502 to 0.01782 | No | ns | >0.9999 |
| G8 vs. G16 | −0.0045 | −0.02092 to 0.01192 | No | ns | 0.9998 |
| G9 vs. G10 | −0.007417 | −0.02384 to 0.009006 | No | ns | 0.9643 |
| G9 vs. G11 | −0.00765 | −0.02407 to 0.008773 | No | ns | 0.9538 |
| G9 vs. G12 | −0.002500 | −0.01892 to 0.01392 | No | ns | >0.9999 |
| G9 vs. G13 | −0.005600 | −0.02202 to 0.01082 | No | ns | 0.9977 |
| G9 vs. G14 | −0.0068 | −0.02322 to 0.009623 | No | ns | 0.9834 |
| G9 vs. G15 | −0.004083 | −0.02051 to 0.01234 | No | ns | >0.9999 |
| G9 vs. G16 | −0.009983 | −0.02641 to 0.006440 | No | ns | 0.7274 |
| G10 vs. G11 | −0.0002333 | −0.01666 to 0.01619 | No | ns | >0.9999 |
| G10 vs. G12 | 0.004917 | −0.01151 to 0.02134 | No | ns | 0.9995 |
| G10 vs. G13 | 0.001817 | −0.01461 to 0.01824 | No | ns | >0.9999 |
| G10 vs. G14 | 0.0006167 | −0.01581 to 0.01704 | No | ns | >0.9999 |
| G10 vs. G15 | 0.003333 | −0.01309 to 0.01976 | No | ns | >0.9999 |
| G10 vs. G16 | −0.002567 | −0.01899 to 0.01386 | No | ns | >0.9999 |
| G11 vs. G12 | 0.00515 | −0.01127 to 0.02157 | No | ns | 0.9991 |
| G11 vs. G13 | 0.00205 | −0.01437 to 0.01847 | No | ns | >0.9999 |
| G11 vs. G14 | 0.0008500 | −0.01557 to 0.01727 | No | ns | >0.9999 |
| G11 vs. G15 | 0.003567 | −0.01286 to 0.01999 | No | ns | >0.9999 |
| G11 vs. G16 | −0.002333 | −0.01876 to 0.01409 | No | ns | >0.9999 |
| G12 vs. G13 | −0.0031 | −0.01952 to 0.01332 | No | ns | >0.9999 |
| G12 vs. G14 | −0.0043 | −0.02072 to 0.01212 | No | ns | 0.9999 |
| G12 vs. G15 | −0.001583 | −0.01801 to 0.01484 | No | ns | >0.9999 |
| G12 vs. G16 | −0.007483 | −0.02391 to 0.008940 | No | ns | 0.9615 |
| G13 vs. G14 | −0.0012 | −0.01762 to 0.01522 | No | ns | >0.9999 |
| G13 vs. G15 | 0.001517 | −0.01491 to 0.01794 | No | ns | >0.9999 |
| G13 vs. G16 | −0.004383 | −0.02081 to 0.01204 | No | ns | 0.9999 |
| G14 vs. G15 | 0.002717 | −0.01371 to 0.01914 | No | ns | >0.9999 |
| G14 vs. G16 | −0.003183 | −0.01961 to 0.01324 | No | ns | >0.9999 |
| G15 vs. G16 | −0.005900 | −0.02232 to 0.01052 | No | ns | 0.9959 |

TABLE 26

Blood Cholesterol Level

| Tukey's multiple comparisons test | Mean Diff. | 95% CI of diff. | Significant? | Summary | Adjusted P Value |
|---|---|---|---|---|---|
| G1 vs. G2 | −4.333 | −33.92 to 25.25 | No | ns | >0.9999 |
| G1 vs. G3 | −7.133 | −36.72 to 22.45 | No | ns | >0.9999 |
| G1 vs. G4 | 16.58 | −13.00 to 46.17 | No | ns | 0.8271 |
| G1 vs. G5 | 6.750 | −22.83 to 36.33 | No | ns | >0.9999 |
| G1 vs. G6 | 7.200 | −22.38 to 36.78 | No | ns | >0.9999 |
| G1 vs. G7 | −0.1000 | −29.68 to 29.48 | No | ns | >0.9999 |
| G1 vs. G8 | 3.800 | −25.78 to 33.38 | No | ns | >0.9999 |
| G1 vs. G9 | −1.917 | −31.50 to 27.67 | No | ns | >0.9999 |
| G1 vs. G10 | −16.32 | −45.90 to 13.27 | No | ns | 0.8436 |
| G1 vs. G11 | −0.5500 | −30.13 to 29.03 | No | ns | >0.9999 |
| G1 vs. G12 | 22.15 | −7.434 to 51.73 | No | ns | 0.3817 |
| G1 vs. G13 | 17.90 | −11.68 to 47.48 | No | ns | 0.7339 |
| G1 vs. G14 | 6.033 | −23.55 to 35.62 | No | ns | >0.9999 |
| G1 vs. G15 | 15.60 | −13.98 to 45.18 | No | ns | 0.8834 |
| G1 vs. G16 | 16.22 | −13.37 to 45.80 | No | ns | 0.8496 |
| G2 vs. G3 | −2.800 | −32.38 to 26.78 | No | ns | >0.9999 |
| G2 vs. G4 | 20.92 | −8.667 to 50.50 | No | ns | 0.4813 |
| G2 vs. G5 | 11.08 | −18.50 to 40.67 | No | ns | 0.9937 |
| G2 vs. G6 | 11.53 | −18.05 to 41.12 | No | ns | 0.9907 |
| G2 vs. G7 | 4.233 | −25.35 to 33.82 | No | ns | >0.9999 |
| G2 vs. G8 | 8.133 | −21.45 to 37.72 | No | ns | 0.9998 |
| G2 vs. G9 | 2.417 | −27.17 to 32.00 | No | ns | >0.9999 |
| G2 vs. G10 | −11.98 | −41.57 to 17.60 | No | ns | 0.9865 |
| G2 vs. G11 | 3.783 | −25.80 to 33.37 | No | ns | >0.9999 |
| G2 vs. G12 | 26.48 | −3.100 to 56.07 | No | ns | 0.1316 |
| G2 vs. G13 | 22.23 | −7.350 to 51.82 | No | ns | 0.3753 |
| G2 vs. G14 | 10.37 | −19.22 to 39.95 | No | ns | 0.9969 |
| G2 vs. G15 | 19.93 | −9.650 to 49.52 | No | ns | 0.5651 |
| G2 vs. G16 | 20.55 | −9.034 to 50.13 | No | ns | 0.5123 |
| G3 vs. G4 | 23.72 | −5.867 to 53.30 | No | ns | 0.2711 |
| G3 vs. G5 | 13.88 | −15.70 to 43.47 | No | ns | 0.9510 |
| G3 vs. G6 | 14.33 | −15.25 to 43.92 | No | ns | 0.9369 |
| G3 vs. G7 | 7.033 | −22.55 to 36.62 | No | ns | >0.9999 |
| G3 vs. G8 | 10.93 | −18.65 to 40.52 | No | ns | 0.9945 |

TABLE 26-continued

Blood Cholesterol Level

| Tukey's multiple comparisons test | Mean Diff. | 95% CI of diff. | Significant? | Summary | Adjusted P Value |
|---|---|---|---|---|---|
| G3 vs. G9 | 5.217 | −24.37 to 34.80 | No | ns | >0.9999 |
| G3 vs. G10 | −9.183 | −38.77 to 20.40 | No | ns | 0.9992 |
| G3 vs. G11 | 6.583 | −23.00 to 36.17 | No | ns | >0.9999 |
| G3 vs. G12 | 29.28 | −0.3005 to 58.87 | No | ns | 0.0553 |
| G3 vs. G13 | 25.03 | −4.550 to 54.62 | No | ns | 0.1957 |
| G3 vs. G14 | 13.17 | −16.42 to 42.75 | No | ns | 0.9684 |
| G3 vs. G15 | 22.73 | −6.850 to 52.32 | No | ns | 0.3381 |
| G3 vs. G16 | 23.35 | −6.234 to 52.93 | No | ns | 0.2950 |
| G4 vs. G5 | −9.833 | −39.42 to 19.75 | No | ns | 0.9982 |
| G4 vs. G6 | −9.383 | −38.97 to 20.20 | No | ns | 0.9990 |
| G4 vs. G7 | −16.68 | −46.27 to 12.90 | No | ns | 0.8207 |
| G4 vs. G8 | −12.78 | −42.37 to 16.80 | No | ns | 0.9756 |
| G4 vs. G9 | −18.50 | −48.08 to 11.08 | No | ns | 0.6861 |
| G4 vs. G10 | −32.90 | −62.48 to −3.316 | Yes | * | 0.0153 |
| G4 vs. G11 | −17.13 | −46.72 to 12.45 | No | ns | 0.7904 |
| G4 vs. G12 | 5.567 | −24.02 to 35.15 | No | ns | >0.9999 |
| G4 vs. G13 | 1.317 | −28.27 to 30.90 | No | ns | >0.9999 |
| G4 vs. G14 | −10.55 | −40.13 to 19.03 | No | ns | 0.9962 |
| G4 vs. G15 | −0.9833 | −30.57 to 28.60 | No | ns | >0.9999 |
| G4 vs. G16 | −0.3667 | −29.95 to 29.22 | No | ns | >0.9999 |
| G5 vs. G6 | 0.4500 | −29.13 to 30.03 | No | ns | >0.9999 |
| G5 vs. G7 | −6.850 | −36.43 to 22.73 | No | ns | >0.9999 |
| G5 vs. G8 | −2.950 | −32.53 to 26.63 | No | ns | >0.9999 |
| G5 vs. G9 | −8.667 | −38.25 to 20.92 | No | ns | 0.9996 |
| G5 vs. G10 | −23.07 | −52.65 to 6.517 | No | ns | 0.3144 |
| G5 vs. G11 | −7.300 | −36.88 to 22.28 | No | ns | >0.9999 |
| G5 vs. G12 | 15.40 | −14.18 to 44.98 | No | ns | 0.8933 |
| G5 vs. G13 | 11.15 | −18.43 to 40.73 | No | ns | 0.9933 |
| G5 vs. G14 | −0.7167 | −30.30 to 28.87 | No | ns | >0.9999 |
| G5 vs. G15 | 8.850 | −20.73 to 38.43 | No | ns | 0.9995 |
| G5 vs. G16 | 9.467 | −20.12 to 39.05 | No | ns | 0.9988 |
| G6 vs. G7 | −7.300 | −36.88 to 22.28 | No | ns | >0.9999 |
| G6 vs. G8 | −3.400 | −32.98 to 26.18 | No | ns | >0.9999 |
| G6 vs. G9 | −9.117 | −38.70 to 20.47 | No | ns | 0.9992 |
| G6 vs. G10 | −23.52 | −53.10 to 6.067 | No | ns | 0.2840 |
| G6 vs. G11 | −7.750 | −37.33 to 21.83 | No | ns | 0.9999 |
| G6 vs. G12 | 14.95 | −14.63 to 44.53 | No | ns | 0.9135 |
| G6 vs. G13 | 10.70 | −18.88 to 40.28 | No | ns | 0.9956 |
| G6 vs. G14 | −1.167 | −30.75 to 28.42 | No | ns | >0.9999 |
| G6 vs. G15 | 8.400 | −21.18 to 37.98 | No | ns | 0.9997 |
| G6 vs. G16 | 9.017 | −20.57 to 38.60 | No | ns | 0.9993 |
| G7 vs. G8 | 3.900 | −25.68 to 33.48 | No | ns | >0.9999 |
| G7 vs. G9 | −1.817 | −31.40 to 27.77 | No | ns | >0.9999 |
| G7 vs. G10 | −16.22 | −45.80 to 13.37 | No | ns | 0.8496 |
| G7 vs. G11 | −0.4500 | −30.03 to 29.13 | No | ns | >0.9999 |
| G7 vs. G12 | 22.25 | −7.334 to 51.83 | No | ns | 0.3740 |
| G7 vs. G13 | 18.00 | −11.58 to 47.58 | No | ns | 0.7261 |
| G7 vs. G14 | 6.133 | −23.45 to 35.72 | No | ns | >0.9999 |
| G7 vs. G15 | 15.70 | −13.88 to 45.28 | No | ns | 0.8783 |
| G7 vs. G16 | 16.32 | −13.27 to 45.90 | No | ns | 0.8436 |
| G8 vs. G9 | −5.717 | −35.30 to 23.87 | No | ns | >0.9999 |
| G8 vs. G10 | −20.12 | −49.70 to 9.467 | No | ns | 0.5494 |
| G8 vs. G11 | −4.350 | −33.93 to 25.23 | No | ns | >0.9999 |
| G8 vs. G12 | 18.35 | −11.23 to 47.93 | No | ns | 0.6983 |
| G8 vs. G13 | 14.10 | −15.48 to 43.68 | No | ns | 0.9445 |
| G8 vs. G14 | 2.233 | −27.35 to 31.82 | No | ns | >0.9999 |
| G8 vs. G15 | 11.80 | −17.78 to 41.38 | No | ns | 0.9884 |
| G8 vs. G16 | 12.42 | −17.17 to 42.00 | No | ns | 0.9812 |
| G9 vs. G10 | −14.40 | −43.98 to 15.18 | No | ns | 0.9346 |
| G9 vs. G11 | 1.367 | −28.22 to 30.95 | No | ns | >0.9999 |
| G9 vs. G12 | 24.07 | −5.517 to 53.65 | No | ns | 0.2494 |
| G9 vs. G13 | 19.82 | −9.767 to 49.40 | No | ns | 0.5751 |
| G9 vs. G14 | 7.950 | −21.63 to 37.53 | No | ns | 0.9999 |
| G9 vs. G15 | 17.52 | −12.07 to 47.10 | No | ns | 0.7628 |
| G9 vs. G16 | 18.13 | −11.45 to 47.72 | No | ns | 0.7156 |
| G10 vs. G11 | 15.77 | −13.82 to 45.35 | No | ns | 0.8747 |
| G10 vs. G12 | 38.47 | 8.883 to 68.05 | Yes | ** | 0.0016 |
| G10 vs. G13 | 34.22 | 4.633 to 63.80 | Yes | ** | 0.0092 |
| G10 vs. G14 | 22.35 | −7.234 to 51.93 | No | ns | 0.3664 |
| G10 vs. G15 | 31.92 | 2.333 to 61.50 | Yes | * | 0.0220 |
| G10 vs. G16 | 32.53 | 2.950 to 62.12 | Yes | * | 0.0175 |
| G11 vs. G12 | 22.70 | −6.884 to 52.28 | No | ns | 0.3405 |
| G11 vs. G13 | 18.45 | −11.13 to 48.03 | No | ns | 0.6902 |
| G11 vs. G14 | 6.583 | −23.00 to 36.17 | No | ns | >0.9999 |
| G11 vs. G15 | 16.15 | −13.43 to 45.73 | No | ns | 0.8535 |
| G11 vs. G16 | 16.77 | −12.82 to 46.35 | No | ns | 0.8153 |
| G12 vs. G13 | −4.250 | −33.83 to 25.33 | No | ns | >0.9999 |
| G12 vs. G14 | −16.12 | −45.70 to 13.47 | No | ns | 0.8554 |
| G12 vs. G15 | −6.550 | −36.13 to 23.03 | No | ns | >0.9999 |
| G12 vs. G16 | −5.933 | −35.52 to 23.65 | No | ns | >0.9999 |
| G13 vs. G14 | −11.87 | −41.45 to 17.72 | No | ns | 0.9877 |
| G13 vs. G15 | −2.300 | −31.88 to 27.28 | No | ns | >0.9999 |
| G13 vs. G16 | −1.683 | −31.27 to 27.90 | No | ns | >0.9999 |
| G14 vs. G15 | 9.567 | −20.02 to 39.15 | No | ns | 0.9987 |
| G14 vs. G16 | 10.18 | −19.40 to 39.77 | No | ns | 0.9974 |
| G15 vs. G16 | 0.6167 | −28.97 to 30.20 | No | ns | >0.9999 |

TABLE 27

Mucification of vaginal epithelium

| Tukey's multiple comparisons test | Mean Diff. | 95% CI of diff. | Significant? | Summary | Adjusted P Value |
|---|---|---|---|---|---|
| G1 vs. G2 | −0.3333 | −1.964 to 1.297 | No | ns | >0.9999 |
| G1 vs. G3 | −1.833 | −3.464 to −0.2027 | Yes | * | 0.0133 |
| G1 vs. G4 | −1.000 | −2.631 to 0.6307 | No | ns | 0.7149 |
| G1 vs. G5 | −1.167 | −2.797 to 0.4640 | No | ns | 0.4605 |
| G1 vs. G6 | −0.8333 | −2.464 to 0.7973 | No | ns | 0.9063 |
| G1 vs. G7 | −1.167 | −2.797 to 0.4640 | No | ns | 0.4605 |
| G1 vs. G8 | −1.167 | −2.797 to 0.4640 | No | ns | 0.4605 |
| G1 vs. G9 | −1.833 | −3.464 to −0.2027 | Yes | * | 0.0133 |
| G1 vs. G10 | −2.000 | −3.631 to −0.3693 | Yes | ** | 0.0040 |
| G1 vs. G11 | −2.000 | −3.631 to −0.3693 | Yes | ** | 0.0040 |
| G1 vs. G12 | −2.500 | −4.131 to −0.8693 | Yes | **** | <0.0001 |
| G1 vs. G13 | −3.167 | −4.797 to −1.536 | Yes | **** | <0.0001 |
| G1 vs. G14 | −3.000 | −4.631 to −1.369 | Yes | **** | <0.0001 |
| G1 vs. G15 | −2.167 | −3.797 to −0.5360 | Yes | ** | 0.0011 |
| G1 vs. G16 | −2.500 | −4.131 to −0.8693 | Yes | **** | <0.0001 |
| G2 vs. G3 | −1.500 | −3.131 to 0.1307 | No | ns | 0.1062 |
| G2 vs. G4 | −0.6667 | −2.297 to 0.9640 | No | ns | 0.9853 |
| G2 vs. G5 | −0.8333 | −2.464 to 0.7973 | No | ns | 0.9063 |
| G2 vs. G6 | −0.5000 | −2.131 to 1.131 | No | ns | 0.9993 |
| G2 vs. G7 | −0.8333 | −2.464 to 0.7973 | No | ns | 0.9063 |
| G2 vs. G8 | −0.8333 | −2.464 to 0.7973 | No | ns | 0.9063 |
| G2 vs. G9 | −1.500 | −3.131 to 0.1307 | No | ns | 0.1062 |
| G2 vs. G10 | −1.667 | −3.297 to −0.03601 | Yes | * | 0.0400 |
| G2 vs. G11 | −1.667 | −3.297 to −0.03601 | Yes | * | 0.0400 |
| G2 vs. G12 | −2.167 | −3.797 to −0.5360 | Yes | ** | 0.0011 |
| G2 vs. G13 | −2.833 | −4.464 to −1.203 | Yes | **** | <0.0001 |
| G2 vs. G14 | −2.667 | −4.297 to −1.036 | Yes | **** | <0.0001 |
| G2 vs. G15 | −1.833 | −3.464 to −0.2027 | Yes | * | 0.0133 |
| G2 vs. G16 | −2.167 | −3.797 to −0.5360 | Yes | ** | 0.0011 |
| G3 vs. G4 | 0.8333 | −0.7973 to 2.464 | No | ns | 0.9063 |
| G3 vs. G5 | 0.6667 | −0.9640 to 2.297 | No | ns | 0.9853 |
| G3 vs. G6 | 1.000 | −0.6307 to 2.631 | No | ns | 0.7149 |
| G3 vs. G7 | 0.6667 | −0.9640 to 2.297 | No | ns | 0.9853 |
| G3 vs. G8 | 0.6667 | −0.9640 to 2.297 | No | ns | 0.9853 |
| G3 vs. G9 | 0.0 | −1.631 to 1.631 | No | ns | >0.9999 |
| G3 vs. G10 | −0.1667 | −1.797 to 1.464 | No | ns | >0.9999 |
| G3 vs. G11 | −0.1667 | −1.797 to 1.464 | No | ns | >0.9999 |
| G3 vs. G12 | −0.6667 | −2.297 to 0.9640 | No | ns | 0.9853 |
| G3 vs. G13 | −1.333 | −2.964 to 0.2973 | No | ns | 0.2421 |
| G3 vs. G14 | −1.167 | −2.797 to 0.4640 | No | ns | 0.4605 |
| G3 vs. G15 | −0.3333 | −1.964 to 1.297 | No | ns | >0.9999 |
| G3 vs. G16 | −0.6667 | −2.297 to 0.9640 | No | ns | 0.9853 |
| G4 vs. G5 | −0.1667 | −1.797 to 1.464 | No | ns | >0.9999 |
| G4 vs. G6 | 0.1667 | −1.464 to 1.797 | No | ns | >0.9999 |
| G4 vs. G7 | −0.1667 | −1.797 to 1.464 | No | ns | >0.9999 |
| G4 vs. G8 | −0.1667 | −1.797 to 1.464 | No | ns | >0.9999 |
| G4 vs. G9 | −0.8333 | −2.464 to 0.7973 | No | ns | 0.9063 |

TABLE 27-continued

Mucification of vaginal epithelium

| Tukey's multiple comparisons test | Mean Diff. | 95% CI of diff. | Significant? | Summary | Adjusted P Value |
|---|---|---|---|---|---|
| G4 vs. G10 | −1.000 | −2.631 to 0.6307 | No | ns | 0.7149 |
| G4 vs. G11 | −1.000 | −2.631 to 0.6307 | No | ns | 0.7149 |
| G4 vs. G12 | −1.500 | −3.131 to 0.1307 | No | ns | 0.1062 |
| G4 vs. G13 | −2.167 | −3.797 to −0.5360 | Yes | ** | 0.0011 |
| G4 vs. G14 | −2.000 | −3.631 to −0.3693 | Yes | ** | 0.0040 |
| G4 vs. G15 | −1.167 | −2.797 to 0.4640 | No | ns | 0.4605 |
| G4 vs. G16 | −1.500 | −3.131 to 0.1307 | No | ns | 0.1062 |
| G5 vs. G6 | 0.3333 | −1.297 to 1.964 | No | ns | >0.9999 |
| G5 vs. G7 | 0.0 | −1.631 to 1.631 | No | ns | >0.9999 |
| G5 vs. G8 | 0.0 | −1.631 to 1.631 | No | ns | >0.9999 |
| G5 vs. G9 | −0.6667 | −2.297 to 0.9640 | No | ns | 0.9853 |
| G5 vs. G10 | −0.8333 | −2.464 to 0.7973 | No | ns | 0.9063 |
| G5 vs. G11 | −0.8333 | −2.464 to 0.7973 | No | ns | 0.9063 |
| G5 vs. G12 | −1.333 | −2.964 to 0.2973 | No | ns | 0.2421 |
| G5 vs. G13 | −2.000 | −3.631 to −0.3693 | Yes | ** | 0.0040 |
| G5 vs. G14 | −1.833 | −3.464 to −0.2027 | Yes | * | 0.0133 |
| G5 vs. G15 | −1.000 | −2.631 to 0.6307 | No | ns | 0.7149 |
| G5 vs. G16 | −1.333 | −2.964 to 0.2973 | No | ns | 0.2421 |
| G6 vs. G7 | −0.3333 | −1.964 to 1.297 | No | ns | >0.9999 |
| G6 vs. G8 | −0.3333 | −1.964 to 1.297 | No | ns | >0.9999 |
| G6 vs. G9 | −1.000 | −2.631 to 0.6307 | No | ns | 0.7149 |
| G6 vs. G10 | −1.167 | −2.797 to 0.4640 | No | ns | 0.4605 |
| G6 vs. G11 | −1.167 | −2.797 to 0.4640 | No | ns | 0.4605 |
| G6 vs. G12 | −1.667 | −3.297 to −0.03601 | Yes | * | 0.0400 |
| G6 vs. G13 | −2.333 | −3.964 to −0.7027 | Yes | *** | 0.0003 |
| G6 vs. G14 | −2.167 | −3.797 to −0.5360 | Yes | ** | 0.0011 |
| G6 vs. G15 | −1.333 | −2.964 to 0.2973 | No | ns | 0.2421 |
| G6 vs. G16 | −1.667 | −3.297 to −0.03601 | Yes | * | 0.0400 |
| G7 vs. G8 | 0.0 | −1.631 to 1.631 | No | ns | >0.9999 |
| G7 vs. G9 | −0.6667 | −2.297 to 0.9640 | No | ns | 0.9853 |
| G7 vs. G10 | −0.8333 | −2.464 to 0.7973 | No | ns | 0.9063 |
| G7 vs. G11 | −0.8333 | −2.464 to 0.7973 | No | ns | 0.9063 |
| G7 vs. G12 | −1.333 | −2.964 to 0.2973 | No | ns | 0.2421 |
| G7 vs. G13 | −2.000 | −3.631 to −0.3693 | Yes | ** | 0.0040 |
| G7 vs. G14 | −1.833 | −3.464 to −0.2027 | Yes | * | 0.0133 |
| G7 vs. G15 | −1.000 | −2.631 to 0.6307 | No | ns | 0.7149 |
| G7 vs. G16 | −1.333 | −2.964 to 0.2973 | No | ns | 0.2421 |
| G8 vs. G9 | −0.6667 | −2.297 to 0.9640 | No | ns | 0.9853 |
| G8 vs. G10 | −0.8333 | −2.464 to 0.7973 | No | ns | 0.9063 |
| G8 vs. G11 | −0.8333 | −2.464 to 0.7973 | No | ns | 0.9063 |
| G8 vs. G12 | −1.333 | −2.964 to 0.2973 | No | ns | 0.2421 |
| G8 vs. G13 | −2.000 | −3.631 to −0.3693 | Yes | ** | 0.0040 |
| G8 vs. G14 | −1.833 | −3.464 to −0.2027 | Yes | * | 0.0133 |
| G8 vs. G15 | −1.000 | −2.631 to 0.6307 | No | ns | 0.7149 |
| G8 vs. G16 | −1.333 | −2.964 to 0.2973 | No | ns | 0.2421 |
| G9 vs. G10 | −0.1667 | −1.797 to 1.464 | No | ns | >0.9999 |
| G9 vs. G11 | −0.1667 | −1.797 to 1.464 | No | ns | >0.9999 |
| G9 vs. G12 | −0.6667 | −2.297 to 0.9640 | No | ns | 0.9853 |
| G9 vs. G13 | −1.333 | −2.964 to 0.2973 | No | ns | 0.2421 |
| G9 vs. G14 | −1.167 | −2.797 to 0.4640 | No | ns | 0.4605 |
| G9 vs. G15 | −0.3333 | −1.964 to 1.297 | No | ns | >0.9999 |
| G9 vs. G16 | −0.6667 | −2.297 to 0.9640 | No | ns | 0.9853 |
| G10 vs. G11 | 0.0 | −1.631 to 1.631 | No | ns | >0.9999 |
| G10 vs. G12 | −0.5000 | −2.131 to 1.131 | No | ns | 0.9993 |
| G10 vs. G13 | −1.167 | −2.797 to 0.4640 | No | ns | 0.4605 |
| G10 vs. G14 | −1.000 | −2.631 to 0.6307 | No | ns | 0.7149 |
| G10 vs. G15 | −0.1667 | −1.797 to 1.464 | No | ns | >0.9999 |
| G10 vs. G16 | −0.5000 | −2.131 to 1.131 | No | ns | 0.9993 |
| G11 vs. G12 | −0.5000 | −2.131 to 1.131 | No | ns | 0.9993 |
| G11 vs. G13 | −1.167 | −2.797 to 0.4640 | No | ns | 0.4605 |
| G11 vs. G14 | −1.000 | −2.631 to 0.6307 | No | ns | 0.7149 |
| G11 vs. G15 | −0.1667 | −1.797 to 1.464 | No | ns | >0.9999 |
| G11 vs. G16 | −0.5000 | −2.131 to 1.131 | No | ns | 0.9993 |
| G12 vs. G13 | −0.6667 | −2.297 to 0.9640 | No | ns | 0.9853 |
| G12 vs. G14 | −0.5000 | −2.131 to 1.131 | No | ns | 0.9993 |
| G12 vs. G15 | 0.3333 | −1.297 to 1.964 | No | ns | >0.9999 |
| G12 vs. G16 | 0.0 | −1.631 to 1.631 | No | ns | >0.9999 |
| G13 vs. G14 | 0.1667 | −1.464 to 1.797 | No | ns | >0.9999 |
| G13 vs. G15 | 1.000 | −0.6307 to 2.631 | No | ns | 0.7149 |
| G13 vs. G16 | 0.6667 | −0.9640 to 2.297 | No | ns | 0.9853 |
| G14 vs. G15 | 0.8333 | −0.7973 to 2.464 | No | ns | 0.9063 |
| G14 vs. G16 | 0.5000 | −1.131 to 2.131 | No | ns | 0.9993 |
| G15 vs. G16 | −0.3333 | −1.964 to 1.297 | No | ns | >0.9999 |

TABLE 28

Thickness of the Vaginal Epithelium

| Tukey's multiple comparisons test | Mean Diff. | 95% CI of diff. | Significant? | Summary | Adjusted P Value |
|---|---|---|---|---|---|
| G1 vs. G2 | −4.833 | −21.37 to 11.71 | No | ns | 0.9996 |
| G1 vs. G3 | −3.500 | −20.04 to 13.04 | No | ns | >0.9999 |
| G1 vs. G4 | −37.67 | −54.21 to −21.13 | Yes | **** | >0.0001 |
| G1 vs. G5 | −10.33 | −26.87 to 6.207 | No | ns | 0.6876 |
| G1 vs. G6 | −11.83 | −28.37 to 4.707 | No | ns | 0.4606 |
| G1 vs. G7 | −3.667 | −20.21 to 12.87 | No | ns | >0.9999 |
| G1 vs. G8 | −9.167 | −25.71 to 7.374 | No | ns | 0.8388 |
| G1 vs. G9 | −1.667 | −18.21 to 14.87 | No | ns | >0.9999 |
| G1 vs. G10 | −2.500 | −19.04 to 14.04 | No | ns | >0.9999 |
| G1 vs. G11 | −2.000 | −18.54 to 14.54 | No | ns | >0.9999 |
| G1 vs. G12 | −1.667 | −18.21 to 14.87 | No | ns | >0.9999 |
| G1 vs. G13 | −3.167 | −19.71 to 13.37 | No | ns | >0.9999 |
| G1 vs. G14 | −1.500 | −18.04 to 15.04 | No | ns | >0.9999 |
| G1 vs. G15 | −6.000 | −22.54 to 10.54 | No | ns | 0.9955 |
| G1 vs. G16 | −3.833 | −20.37 to 12.71 | No | ns | >0.9999 |
| G2 vs. G3 | 1.333 | −15.21 to 17.87 | No | ns | >0.9999 |
| G2 vs. G4 | −32.83 | −49.37 to −16.29 | Yes | **** | <0.0001 |
| G2 vs. G5 | −5.500 | −22.04 to 11.04 | No | ns | 0.9982 |
| G2 vs. G6 | −7.000 | −23.54 to 9.540 | No | ns | 0.9798 |
| G2 vs. G7 | 1.167 | −15.37 to 17.71 | No | ns | >0.9999 |
| G2 vs. G8 | −4.333 | −20.87 to 12.21 | No | ns | 0.9999 |
| G2 vs. G9 | 3.167 | −13.37 to 19.71 | No | ns | >0.9999 |
| G2 vs. G10 | 2.333 | −14.21 to 18.87 | No | ns | >0.9999 |
| G2 vs. G11 | 2.833 | −13.71 to 19.37 | No | ns | >0.9999 |
| G2 vs. G12 | 3.167 | −13.37 to 19.71 | No | ns | >0.9999 |
| G2 vs. G13 | 1.667 | −14.87 to 18.21 | No | ns | >0.9999 |
| G2 vs. G14 | 3.333 | −13.21 to 19.87 | No | ns | >0.9999 |
| G2 vs. G15 | −1.167 | −17.71 to 15.37 | No | ns | >0.9999 |
| G2 vs. G16 | 1.000 | −15.54 to 17.54 | No | ns | >0.9999 |
| G3 vs. G4 | −34.17 | −50.71 to −17.63 | Yes | **** | <0.0001 |
| G3 vs. G5 | −6.833 | −23.37 to 9.707 | No | ns | 0.9838 |
| G3 vs. G6 | −8.333 | −24.87 to 8.207 | No | ns | 0.9154 |
| G3 vs. G7 | −0.1667 | −16.71 to 16.37 | No | ns | >0.9999 |
| G3 vs. G8 | −5.667 | −22.21 to 10.87 | No | ns | 0.9975 |
| G3 vs. G9 | 1.833 | −14.71 to 18.37 | No | ns | >0.9999 |
| G3 vs. G10 | 1.000 | −15.54 to 17.54 | No | ns | >0.9999 |
| G3 vs. G11 | 1.500 | −15.04 to 18.04 | No | ns | >0.9999 |
| G3 vs. G12 | 1.833 | −14.71 to 18.37 | No | ns | >0.9999 |
| G3 vs. G13 | 0.3333 | −16.21 to 16.87 | No | ns | >0.9999 |
| G3 vs. G14 | 2.000 | −14.54 to 18.54 | No | ns | >0.9999 |
| G3 vs. G15 | −2.500 | −19.04 to 14.04 | No | ns | >0.9999 |
| G3 vs. G16 | −0.3333 | −16.87 to 16.21 | No | ns | >0.9999 |
| G4 vs. G5 | 27.33 | 10.79 to 43.87 | Yes | **** | <0.0001 |
| G4 vs. G6 | 25.83 | 9.293 to 42.37 | Yes | **** | <0.0001 |
| G4 vs. G7 | 34.00 | 17.46 to 50.54 | Yes | **** | <0.0001 |
| G4 vs. G8 | 28.50 | 11.96 to 45.04 | Yes | **** | <0.0001 |
| G4 vs. G9 | 36.00 | 19.46 to 52.54 | Yes | **** | <0.0001 |
| G4 vs. G10 | 35.17 | 18.63 to 51.71 | Yes | **** | <0.0001 |
| G4 vs. G11 | 35.67 | 19.13 to 52.21 | Yes | **** | <0.0001 |
| G4 vs. G12 | 36.00 | 19.46 to 52.54 | Yes | **** | <0.0001 |
| G4 vs. G13 | 34.50 | 17.96 to 51.04 | Yes | **** | <0.0001 |
| G4 vs. G14 | 36.17 | 19.63 to 52.71 | Yes | **** | <0.0001 |
| G4 vs. G15 | 31.67 | 15.13 to 48.21 | Yes | **** | <0.0001 |
| G4 vs. G16 | 33.83 | 17.29 to 50.37 | Yes | **** | <0.0001 |
| G5 vs. G6 | −1.500 | −18.04 to 15.04 | No | ns | >0.9999 |
| G5 vs. G7 | 6.667 | −9.874 to 23.21 | No | ns | 0.9871 |
| G5 vs. G8 | 1.167 | −15.37 to 17.71 | No | ns | >0.9999 |
| G5 vs. G9 | 8.667 | −7.874 to 25.21 | No | ns | 0.8884 |

TABLE 28-continued

Thickness of the Vaginal Epithelium

| Tukey's multiple comparisons test | Mean Diff. | 95% CI of diff. | Significant? | Summary | Adjusted P Value |
|---|---|---|---|---|---|
| G5 vs. G10 | 7.833 | −8.707 to 24.37 | No | ns | 0.9472 |
| G5 vs. G11 | 8.333 | −8.207 to 24.87 | No | ns | 0.9154 |
| G5 vs. G12 | 8.667 | −7.874 to 25.21 | No | ns | 0.8884 |
| G5 vs. G13 | 7.167 | −9.374 to 23.71 | No | ns | 0.9750 |
| G5 vs. G14 | 8.833 | −7.707 to 25.37 | No | ns | 0.8730 |
| G5 vs. G15 | 4.333 | −12.21 to 20.87 | No | ns | 0.9999 |
| G5 vs. G16 | 6.500 | −10.04 to 23.04 | No | ns | 0.9899 |
| G6 vs. G7 | 8.167 | −8.374 to 24.71 | No | ns | 0.9272 |
| G6 vs. G8 | 2.667 | −13.87 to 19.21 | No | ns | >0.9999 |
| G6 vs. G9 | 10.17 | −6.374 to 26.71 | No | ns | 0.7116 |
| G6 vs. G10 | 9.333 | −7.207 to 25.87 | No | ns | 0.8200 |
| G6 vs. G11 | 9.833 | −6.707 to 26.37 | No | ns | 0.7576 |
| G6 vs. G12 | 10.17 | −6.374 to 26.71 | No | ns | 0.7116 |
| G6 vs. G13 | 8.667 | −7.874 to 25.21 | No | ns | 0.8884 |
| G6 vs. G14 | 10.33 | −6.207 to 26.87 | No | ns | 0.6876 |
| G6 vs. G15 | 5.833 | −10.71 to 22.37 | No | ns | 0.9966 |
| G6 vs. G16 | 8.000 | −8.540 to 24.54 | No | ns | 0.9378 |
| G7 vs. G8 | −5.500 | −22.04 to 11.04 | No | ns | 0.9982 |
| G7 vs. G9 | 2.000 | −14.54 to 18.54 | No | ns | >0.9999 |
| G7 vs. G10 | 1.167 | −15.37 to 17.71 | No | ns | >0.9999 |
| G7 vs. G11 | 1.667 | −14.87 to 18.21 | No | ns | >0.9999 |
| G7 vs. G12 | 2.000 | −14.54 to 18.54 | No | ns | >0.9999 |
| G7 vs. G13 | 0.5000 | −16.04 to 17.04 | No | ns | >0.9999 |
| G7 vs. G14 | 2.167 | −14.37 to 18.71 | No | ns | >0.9999 |
| G7 vs. G15 | −2.333 | −18.87 to 14.21 | No | ns | >0.9999 |
| G7 vs. G16 | −0.1667 | −16.71 to 16.37 | No | ns | >0.9999 |
| G8 vs. G9 | 7.500 | −9.040 to 24.04 | No | ns | 0.9630 |
| G8 vs. G10 | 6.667 | −9.874 to 23.21 | No | ns | 0.9871 |
| G8 vs. G11 | 7.167 | −9.374 to 23.71 | No | ns | 0.9750 |
| G8 vs. G12 | 7.500 | −9.040 to 24.04 | No | ns | 0.9630 |
| G8 vs. G13 | 6.000 | −10.54 to 22.54 | No | ns | 0.9955 |
| G8 vs. G14 | 7.667 | −8.874 to 24.21 | No | ns | 0.9556 |
| G8 vs. G15 | 3.167 | −13.37 to 19.71 | No | ns | >0.9999 |
| G8 vs. G16 | 5.333 | −11.21 to 21.87 | No | ns | 0.9987 |
| G9 vs. G10 | −0.8333 | −17.37 to 15.71 | No | ns | >0.9999 |
| G9 vs. G11 | −0.3333 | −16.87 to 16.21 | No | ns | >0.9999 |
| G9 vs. G12 | 0.0 | −16.54 to 16.54 | No | ns | >0.9999 |
| G9 vs. G13 | −1.500 | −18.04 to 15.04 | No | ns | >0.9999 |
| G9 vs. G14 | 0.1667 | −16.37 to 16.71 | No | ns | >0.9999 |
| G9 vs. G15 | −4.333 | −20.87 to 12.21 | No | ns | 0.9999 |
| G9 vs. G16 | −2.167 | −18.71 to 14.37 | No | ns | >0.9999 |
| G10 vs. G11 | 0.5000 | −16.04 to 17.04 | No | ns | >0.9999 |
| G10 vs. G12 | 0.8333 | −15.71 to 17.37 | No | ns | >0.9999 |
| G10 vs. G13 | −0.6667 | −17.21 to 15.87 | No | ns | >0.9999 |
| G10 vs. G14 | 1.000 | −15.54 to 17.54 | No | ns | >0.9999 |
| G10 vs. G15 | −3.500 | −20.04 to 13.04 | No | ns | >0.9999 |
| G10 vs. G16 | −1.333 | −17.87 to 15.21 | No | ns | >0.9999 |
| G11 vs. G12 | 0.3333 | −16.21 to 16.87 | No | ns | >0.9999 |
| G11 vs. G13 | −1.167 | −17.71 to 15.37 | No | ns | >0.9999 |
| G11 vs. G14 | 0.5000 | −16.04 to 17.04 | No | ns | >0.9999 |
| G11 vs. G15 | −4.000 | −20.54 to 12.54 | No | ns | >0.9999 |
| G11 vs. G16 | −1.833 | −18.37 to 14.71 | No | ns | >0.9999 |
| G12 vs. G13 | −1.500 | −18.04 to 15.04 | No | ns | >0.9999 |
| G12 vs. G14 | 0.1667 | −16.37 to 16.71 | No | ns | >0.9999 |
| G12 vs. G15 | −4.333 | −20.87 to 12.21 | No | ns | 0.9999 |
| G12 vs. G16 | −2.167 | −18.71 to 14.37 | No | ns | >0.9999 |
| G13 vs. G14 | 1.667 | −14.87 to 18.21 | No | ns | >0.9999 |
| G13 vs. G15 | −2.833 | −19.37 to 13.71 | No | ns | >0.9999 |
| G13 vs. G16 | −0.6667 | −17.21 to 15.87 | No | ns | >0.9999 |
| G14 vs. G15 | −4.500 | −21.04 to 12.04 | No | ns | 0.9998 |
| G14 vs. G16 | −2.333 | −18.87 to 14.21 | No | ns | >0.9999 |
| G15 vs. G16 | 2.167 | −14.37 to 18.71 | No | ns | >0.9999 |

TABLE 29

Wet Weight

| Animal # | Animal ID | Group | | Body Weight(g) | Wet Weight(g) uterine | Wet Weight(g) vagina |
|---|---|---|---|---|---|---|
| 1 | 4657 | G1 | G1 | 271 | 0.0368 | 0.0476 |
| 2 | 4741 | | G1 | 268 | 0.0379 | 0.0458 |
| 3 | 4652 | | G1 | 264 | 0.0416 | 0.1036 |
| 4 | 4683 | | G1 | 264 | 0.0301 | 0.0566 |
| 5 | 4731 | | G1 | 250 | 0.033 | 0.0509 |
| 6 | 4703 | | G1 | 258 | 0.0289 | 0.047 |
| 7 | 4682 | G2 | G2 | 242 | 0.0389 | 0.0658 |
| 8 | 4688 | | G2 | 240 | 0.0471 | 0.0583 |
| 9 | 4722 | | G2 | 230 | 0.0619 | 0.0403 |
| 10 | 4680 | | G2 | 227 | 0.05 | 0.0564 |
| 11 | 4738 | | G2 | 222 | 0.0438 | 0.0534 |
| 12 | 4736 | | G2 | 219 | 0.0455 | 0.0777 |
| 13 | 4713 | G3 | G3 | 291 | 0.0285 | 0.0603 |
| 14 | 4725 | | G3 | 291 | 0.0404 | 0.0791 |
| 15 | 4716 | | G3 | 279 | 0.0336 | 0.1001 |
| 16 | 4681 | | G3 | 268 | 0.0348 | 0.0851 |
| 17 | 4644 | | G3 | 260 | 0.0278 | 0.0872 |
| 18 | 4693 | | G3 | 264 | 0.0476 | 0.0743 |
| 19 | 4732 | G4 | G4 | 216 | 0.0997 | 0.106 |
| 20 | 4721 | (sham) | G4 | 195 | 0.1417 | 0.1224 |
| 21 | 4717 | | G4 | 197 | 0.1287 | 0.1081 |
| 22 | 4699 | | G4 | 198 | 0.1128 | 0.1049 |
| 23 | 4666 | | G4 | 186 | 0.1255 | 0.1152 |
| 24 | 4706 | | G4 | 193 | 0.1011 | 0.0769 |
| 25 | 4660 | G5 | G5 | 286 | 0.0456 | 0.082 |
| 26 | 4658 | | G5 | 276 | 0.064 | 0.0674 |
| 27 | 4636 | | G5 | 277 | 0.0417 | 0.0672 |
| 28 | 4653 | | G5 | 263 | 0.0498 | 0.0715 |
| 29 | 4655 | | G5 | 255 | 0.0552 | 0.0364 |
| 30 | 4642 | | G5 | 266 | 0.052 | 0.0545 |
| 31 | 4726 | G6 | G6 | 271 | 0.0455 | 0.0856 |
| 32 | 4639 | | G6 | 270 | 0.0362 | 0.0536 |
| 33 | 4675 | | G6 | 265 | 0.0438 | 0.072 |
| 34 | 4643 | | G6 | 246 | 0.0496 | 0.0743 |
| 35 | 4663 | | G6 | 266 | 0.0433 | 0.0617 |
| 36 | 4687 | | G6 | 268 | 0.0527 | 0.0641 |
| 37 | 4662 | G7 | G7 | 277 | 0.0364 | 0.083 |
| 38 | 4710 | | G7 | 249 | 0.0431 | 0.0562 |
| 39 | 4665 | | G7 | 260 | 0.0587 | 0.0464 |
| 40 | 4637 | | G7 | 237 | 0.047 | 0.0571 |
| 41 | 4702 | | G7 | 254 | 0.031 | 0.0486 |
| 42 | 4645 | | G7 | 242 | 0.0333 | 0.0491 |
| 43 | 4656 | G8 | G8 | 274 | 0.0423 | 0.0736 |
| 44 | 4640 | | G8 | 277 | 0.0473 | 0.0425 |
| 45 | 4698 | | G8 | 257 | 0.0504 | 0.087 |
| 46 | 4700 | | G8 | 257 | 0.0652 | 0.0605 |
| 47 | 4676 | | G8 | 258 | 0.0423 | 0.0397 |
| 48 | 4694 | | G8 | 247 | 0.049 | 0.0727 |
| 49 | 4647 | G9 | G9 | 284 | 0.0498 | 0.0689 |
| 50 | 4723 | | G9 | 275 | 0.0414 | 0.0651 |
| 51 | 4638 | | G9 | 268 | 0.0438 | 0.0539 |
| 52 | 4711 | | G9 | 282 | 0.0339 | 0.065 |
| 53 | 4641 | | G9 | 258 | 0.052 | 0.0594 |
| 54 | 4679 | | G9 | 253 | 0.0427 | 0.0419 |
| 55 | 4661 | G10 | G10 | 280 | 0.048 | 0.061 |
| 56 | 4677 | | G10 | 277 | 0.0555 | 0.071 |
| 57 | 4678 | | G10 | 277 | 0.0586 | 0.0267 |
| 58 | 4720 | | G10 | 271 | 0.0484 | 0.0754 |
| 59 | 4730 | | G10 | 283 | 0.0438 | 0.1025 |
| 60 | 4649 | | G10 | 270 | 0.0538 | 0.0685 |
| 61 | 4635 | G11 | G11 | 297 | 0.0548 | 0.0365 |
| 62 | 4740 | | G11 | 273 | 0.0575 | 0.0606 |
| 63 | 4718 | | G11 | 265 | 0.0472 | 0.0446 |
| 64 | 4742 | | G11 | 255 | 0.044 | 0.0663 |
| 65 | 4739 | | G11 | 283 | 0.06 | 0.0574 |
| 66 | 4659 | | G11 | 279 | 0.046 | 0.046 |
| 67 | 4704 | G12 | G12 | 281 | 0.0568 | 0.0912 |
| 68 | 4719 | | G12 | 280 | 0.0445 | 0.0728 |
| 69 | 4648 | | G12 | 258 | 0.0414 | 0.0544 |
| 70 | 4715 | | G12 | 266 | 0.0495 | 0.0806 |
| 71 | 4695 | | G12 | 255 | 0.0363 | 0.0646 |
| 72 | 4664 | | G12 | 283 | 0.0501 | 0.0586 |
| 73 | 4696 | G13 | G13 | 295 | 0.0506 | 0.0611 |
| 74 | 4709 | | G13 | 284 | 0.0391 | 0.0794 |

TABLE 29-continued

Wet Weight

| Animal # | Animal ID | Group | Body Weight(g) | Wet Weight(g) uterine | Wet Weight(g) vagina |
|---|---|---|---|---|---|
| 75 | 4685 | | G13 | 257 | 0.054 | 0.0564 |
| 76 | 4684 | | G13 | 284 | 0.0393 | 0.0472 |
| 77 | 4701 | | G13 | 264 | 0.06 | 0.0602 |
| 78 | 4667 | | G13 | 275 | 0.0542 | 0.0819 |
| 79 | 4650 | G14 | G14 | 278 | 0.053 | 0.0793 |
| 80 | 4714 | | G14 | 296 | 0.0597 | 0.0642 |
| 81 | 4728 | | G14 | 258 | 0.0538 | 0.0658 |
| 82 | 4654 | | G14 | 278 | 0.0508 | 0.0518 |
| 83 | 4705 | | G14 | 268 | 0.0446 | 0.0809 |
| 84 | 4674 | | G14 | 251 | 0.0425 | 0.0531 |
| 85 | 4646 | G15 | G15 | 256 | 0.0485 | 0.0621 |
| 86 | 4708 | | G15 | 242 | 0.052 | 0.0427 |
| 87 | 4673 | | G15 | 238 | 0.044 | 0.0784 |
| 88 | 4672 | | G15 | 225 | 0.0536 | 0.0565 |
| 89 | 4690 | | G15 | 237 | 0.0498 | 0.0641 |
| 90 | 4727 | | G15 | 245 | 0.0402 | 0.05 |
| 91 | 4733 | G16 | G16 | 264 | 0.0485 | 0.0827 |
| 92 | 4712 | | G16 | 272 | 0.045 | 0.0715 |
| 93 | 4724 | | G16 | 252 | 0.0605 | 0.0852 |
| 94 | 4697 | | G16 | 249 | 0.06 | 0.0849 |
| 95 | 4691 | | G16 | 273 | 0.0551 | 0.0499 |
| 96 | 4669 | | G16 | 257 | 0.0544 | 0.081 |

TABLE 30

Blood Cholesterol Level

| Animal # | Animal ID | Group | | cholesterol level (mg/dl) |
|---|---|---|---|---|
| 1 | 4657 | G1 | G1 | 74.2 |
| 2 | 4741 | | G1 | 80.0 |
| 3 | 4652 | | G1 | 69.7 |
| 4 | 4683 | | G1 | 80.8 |
| 5 | 4731 | | G1 | 73.3 |
| 6 | 4703 | | G1 | 78.2 |
| 7 | 4682 | G2 | G2 | 69.9 |
| 8 | 4688 | | G2 | 72.8 |
| 9 | 4722 | | G2 | 78.0 |
| 10 | 4680 | | G2 | 91.0 |
| 11 | 4738 | | G2 | 88.9 |
| 12 | 4736 | | G2 | 81.6 |
| 13 | 4713 | G3 | G3 | 94.1 |
| 14 | 4725 | | G3 | 77.4 |
| 15 | 4716 | | G3 | 97.1 |
| 16 | 4681 | | G3 | 77.9 |
| 17 | 4644 | | G3 | 79.8 |
| 18 | 4693 | | G3 | 72.7 |
| 19 | 4732 | G4 (sham) | G4 | 69.7 |
| 20 | 4721 | | G4 | 58.9 |
| 21 | 4717 | | G4 | 53.9 |
| 22 | 4699 | | G4 | 68.9 |
| 23 | 4666 | | G4 | 58.3 |
| 24 | 4706 | | G4 | 47.0 |
| 25 | 4660 | G5 | G5 | 81.4 |
| 26 | 4658 | | G5 | 71.8 |
| 27 | 4636 | | G5 | 68.3 |
| 28 | 4653 | | G5 | 65.3 |
| 29 | 4655 | | G5 | 53.9 |
| 30 | 4642 | | G5 | 75.0 |
| 31 | 4726 | G6 | G6 | 57.6 |
| 32 | 4639 | | G6 | 57.0 |
| 33 | 4675 | | G6 | 86.1 |
| 34 | 4643 | | G6 | 61.0 |
| 35 | 4663 | | G6 | 75.5 |
| 36 | 4687 | | G6 | 75.8 |
| 37 | 4662 | G7 | G7 | 80.2 |
| 38 | 4710 | | G7 | 77.1 |
| 39 | 4665 | | G7 | 74.9 |
| 40 | 4637 | | G7 | 63.8 |
| 41 | 4702 | | G7 | 85.3 |

TABLE 30-continued

Blood Cholesterol Level

| Animal # | Animal ID | Group | | cholesterol level (mg/dl) |
|---|---|---|---|---|
| 42 | 4645 | | G7 | 75.5 |
| 43 | 4656 | G8 | G8 | 68.6 |
| 44 | 4640 | | G8 | 72.4 |
| 45 | 4698 | | G8 | 79.5 |
| 46 | 4700 | | G8 | 76.7 |
| 47 | 4676 | | G8 | 76.6 |
| 48 | 4694 | | G8 | 59.6 |
| 49 | 4647 | G9 | G9 | 86.9 |
| 50 | 4723 | | G9 | 68.8 |
| 51 | 4638 | | G9 | 71.1 |
| 52 | 4711 | | G9 | 81.6 |
| 53 | 4641 | | G9 | 71.1 |
| 54 | 4679 | | G9 | 88.2 |
| 55 | 4661 | G10 | G10 | 76.7 |
| 56 | 4677 | | G10 | 98.9 |
| 57 | 4678 | | G10 | 91.7 |
| 58 | 4720 | | G10 | 118.6 |
| 59 | 4730 | | G10 | 100.7 |
| 60 | 4649 | | G10 | 67.5 |
| 61 | 4635 | G11 | G11 | 97.8 |
| 62 | 4740 | | G11 | 78.8 |
| 63 | 4718 | | G11 | 98.5 |
| 64 | 4742 | | G11 | 76.1 |
| 65 | 4739 | | G11 | 55.8 |
| 66 | 4659 | | G11 | 52.5 |
| 67 | 4704 | G12 | G12 | 53.3 |
| 68 | 4719 | | G12 | 44.6 |
| 69 | 4648 | | G12 | 62.2 |
| 70 | 4715 | | G12 | 51.1 |
| 71 | 4695 | | G12 | 44.3 |
| 72 | 4664 | | G12 | 67.8 |
| 73 | 4696 | G13 | G13 | 44.6 |
| 74 | 4709 | | G13 | 128.6 |
| 75 | 4685 | | G13 | 46.9 |
| 76 | 4684 | | G13 | 48.3 |
| 77 | 4701 | | G13 | 29.6 |
| 78 | 4667 | | G13 | 50.8 |
| 79 | 4650 | G14 | G14 | 73.0 |
| 80 | 4714 | | G14 | 80.2 |
| 81 | 4728 | | G14 | 72.9 |
| 82 | 4654 | | G14 | 66.1 |
| 83 | 4705 | | G14 | 65.6 |
| 84 | 4674 | | G14 | 62.2 |
| 85 | 4646 | G15 | G15 | 66.9 |
| 86 | 4708 | | G15 | 59.6 |
| 87 | 4673 | | G15 | 32.1 |
| 88 | 4672 | | G15 | 65.7 |
| 89 | 4690 | | G15 | 85.1 |
| 90 | 4727 | | G15 | 53.2 |
| 91 | 4733 | G16 | G16 | 89.9 |
| 92 | 4712 | | G16 | 49.2 |
| 93 | 4724 | | G16 | 67.3 |
| 94 | 4697 | | G16 | 53.0 |
| 95 | 4691 | | G16 | 53.4 |
| 96 | 4669 | | G16 | 46.1 |

TABLE 31

Mucification of vaginal epithelium

| Animal # | Animal ID | Group | | Uterine | Vagina |
|---|---|---|---|---|---|
| 1 | 4657 | G1 | G1 | 0 | 0 |
| 2 | 4741 | | G1 | 0 | 0 |
| 3 | 4652 | | G1 | 0 | 1 |
| 4 | 4683 | | G1 | 0 | 1 |
| 5 | 4731 | | G1 | 0 | 1 |
| 6 | 4703 | | G1 | 0 | 0 |
| 7 | 4682 | G2 | G2 | 0 | 1 |
| 8 | 4688 | | G2 | 0 | 1 |
| 9 | 4722 | | G2 | 0 | 0 |

TABLE 31-continued

Mucification of vaginal epithelium

| Animal # | Animal ID | Group | | Uterine | Vagina |
|---|---|---|---|---|---|
| 10 | 4680 | | G2 | 0 | 1 |
| 11 | 4738 | | G2 | 0 | 1 |
| 12 | 4736 | | G2 | 0 | 1 |
| 13 | 4713 | G3 | G3 | 0 | 2 |
| 14 | 4725 | | G3 | 0 | 2 |
| 15 | 4716 | | G3 | 0 | 3 |
| 16 | 4681 | | G3 | 0 | 3 |
| 17 | 4644 | | G3 | 0 | 2 |
| 18 | 4693 | | G3 | 0 | 2 |
| 19 | 4732 | G4 (sham) | G4 | 0 | 0 |
| 20 | 4721 | | G4 | 0 | 0 |
| 21 | 4717 | | G4 | 0 | 1 |
| 22 | 4699 | | G4 | 0 | 4 |
| 23 | 4666 | | G4 | 0 | 4 |
| 24 | 4706 | | G4 | 0 | 0 |
| 25 | 4660 | G5 | G5 | 0 | 3 |
| 26 | 4658 | | G5 | 0 | 1 |
| 27 | 4636 | | G5 | 0 | 1 |
| 28 | 4653 | | G5 | 0 | 1 |
| 29 | 4655 | | G5 | 0 | 2 |
| 30 | 4642 | | G5 | 0 | 2 |
| 31 | 4726 | G6 | G6 | 0 | 2 |
| 32 | 4639 | | G6 | 0 | 2 |
| 33 | 4675 | | G6 | 0 | 1 |
| 34 | 4643 | | G6 | 0 | 1 |
| 35 | 4663 | | G6 | 0 | 1 |
| 36 | 4687 | | G6 | 0 | 1 |
| 37 | 4662 | G7 | G7 | 0 | 1 |
| 38 | 4710 | | G7 | 0 | 2 |
| 39 | 4665 | | G7 | 0 | 2 |
| 40 | 4637 | | G7 | 0 | 1 |
| 41 | 4702 | | G7 | 0 | 2 |
| 42 | 4645 | | G7 | 0 | 2 |
| 43 | 4656 | G8 | G8 | 0 | 2 |
| 44 | 4640 | | G8 | 0 | 1 |
| 45 | 4698 | | G8 | 0 | 1 |
| 46 | 4700 | | G8 | 0 | 3 |
| 47 | 4676 | | G8 | 0 | 1 |
| 48 | 4694 | | G8 | 0 | 2 |
| 49 | 4647 | G9 | G9 | 0 | 3 |
| 50 | 4723 | | G9 | 0 | 1 |
| 51 | 4638 | | G9 | 0 | 3 |
| 52 | 4711 | | G9 | 0 | 3 |
| 53 | 4641 | | G9 | 0 | 2 |
| 54 | 4679 | | G9 | 0 | 2 |
| 55 | 4661 | G10 | G10 | 0 | 3 |
| 56 | 4677 | | G10 | 0 | 2 |
| 57 | 4678 | | G10 | 0 | 2 |
| 58 | 4720 | | G10 | 0 | 3 |
| 59 | 4730 | | G10 | 0 | 2 |
| 60 | 4649 | | G10 | 0 | 3 |
| 61 | 4635 | G11 | G11 | 0 | 3 |
| 62 | 4740 | | G11 | 0 | 4 |
| 63 | 4718 | | G11 | 0 | 1 |
| 64 | 4742 | | G11 | 0 | 3 |
| 65 | 4739 | | G11 | 0 | 2 |
| 66 | 4659 | | G11 | 0 | 2 |
| 67 | 4704 | G12 | G12 | 0 | 3 |
| 68 | 4719 | | G12 | 0 | 3 |
| 69 | 4648 | | G12 | 0 | 3 |
| 70 | 4715 | | G12 | 0 | 3 |
| 71 | 4695 | | G12 | 0 | 2 |
| 72 | 4664 | | G12 | 0 | 4 |
| 73 | 4696 | G13 | G13 | 0 | 4 |
| 74 | 4709 | | G13 | 0 | 4 |
| 75 | 4685 | | G13 | 0 | 4 |
| 76 | 4684 | | G13 | 0 | 4 |
| 77 | 4701 | | G13 | 0 | 3 |
| 78 | 4667 | | G13 | 0 | 3 |
| 79 | 4650 | G14 | G14 | 0 | 4 |
| 80 | 4714 | | G14 | 0 | 3 |
| 81 | 4728 | | G14 | 0 | 3 |
| 82 | 4654 | | G14 | 0 | 4 |
| 83 | 4705 | | G14 | 0 | 4 |
| 84 | 4674 | | G14 | 0 | 3 |
| 85 | 4646 | G15 | G15 | 0 | 2 |
| 86 | 4708 | | G15 | 0 | 3 |
| 87 | 4673 | | G15 | 0 | 3 |
| 88 | 4672 | | G15 | 0 | 3 |
| 89 | 4690 | | G15 | 0 | 2 |
| 90 | 4727 | | G15 | 0 | 3 |
| 91 | 4733 | G16 | G16 | 0 | 2 |
| 92 | 4712 | | G16 | 0 | 3 |
| 93 | 4724 | | G16 | 0 | 3 |
| 94 | 4697 | | G16 | 0 | 3 |
| 95 | 4691 | | G16 | 0 | 4 |
| 96 | 4669 | | G16 | 0 | 3 |

TABLE 32

Thickness of the vaginal epithelium

| Animal # | Animal ID | Group | | Uterine | Vagina |
|---|---|---|---|---|---|
| 1 | 4657 | G1 | G1 | 9 | 14 |
| 2 | 4741 | | G1 | 9 | 13 |
| 3 | 4652 | | G1 | 9 | 16 |
| 4 | 4683 | | G1 | 6 | 18 |
| 5 | 4731 | | G1 | 13 | 21 |
| 6 | 4703 | | G1 | 10 | 19 |
| 7 | 4682 | G2 | G2 | 11 | 18 |
| 8 | 4688 | | G2 | 11 | 19 |
| 9 | 4722 | | G2 | 12 | 25 |
| 10 | 4680 | | G2 | 9 | 20 |
| 11 | 4738 | | G2 | 9 | 19 |
| 12 | 4736 | | G2 | 5 | 29 |
| 13 | 4713 | G3 | G3 | 6 | 23 |
| 14 | 4725 | | G3 | 7 | 23 |
| 15 | 4716 | | G3 | 7 | 22 |
| 16 | 4681 | | G3 | 7 | 21 |
| 17 | 4644 | | G3 | 8 | 15 |
| 18 | 4693 | | G3 | 8 | 18 |
| 19 | 4732 | G4 (sham) | G4 | 18 | 26 |
| 20 | 4721 | | G4 | 21 | 31 |
| 21 | 4717 | | G4 | 17 | 53 |
| 22 | 4699 | | G4 | 20 | 89 |
| 23 | 4666 | | G4 | 11 | 88 |
| 24 | 4706 | | G4 | 30 | 40 |
| 25 | 4660 | G5 | G5 | 9 | 26 |
| 26 | 4658 | | G5 | 9 | 30 |
| 27 | 4636 | | G5 | 8 | 32 |
| 28 | 4653 | | G5 | 8 | 27 |
| 29 | 4655 | | G5 | 9 | 32 |
| 30 | 4642 | | G5 | 9 | 16 |
| 31 | 4726 | G6 | G6 | 8 | 29 |
| 32 | 4639 | | G6 | 9 | 24 |
| 33 | 4675 | | G6 | 6 | 41 |
| 34 | 4643 | | G6 | 6 | 29 |
| 35 | 4663 | | G6 | 8 | 27 |
| 36 | 4687 | | G6 | 8 | 22 |
| 37 | 4662 | G7 | G7 | 8 | 27 |
| 38 | 4710 | | G7 | 7 | 18 |
| 39 | 4665 | | G7 | 8 | 21 |
| 40 | 4637 | | G7 | 7 | 20 |
| 41 | 4702 | | G7 | 8 | 17 |
| 42 | 4645 | | G7 | 9 | 20 |
| 43 | 4656 | G8 | G8 | 6 | 32 |
| 44 | 4640 | | G8 | 8 | 24 |
| 45 | 4698 | | G8 | 10 | 28 |
| 46 | 4700 | | G8 | 10 | 32 |
| 47 | 4676 | | G8 | 8 | 14 |
| 48 | 4694 | | G8 | 7 | 26 |
| 49 | 4647 | G9 | G9 | 7 | 21 |
| 50 | 4723 | | G9 | 9 | 15 |
| 51 | 4638 | | G9 | 6 | 25 |
| 52 | 4711 | | G9 | 6 | 15 |

TABLE 32-continued

Thickness of the vaginal epithelium

| Animal # | Animal ID | Group | Uterine | Vagina |
|---|---|---|---|---|
| 53 | 4641 |  | G9 | 7 | 17 |
| 54 | 4679 |  | G9 | 9 | 18 |
| 55 | 4661 | G10 | G10 | 9 | 27 |
| 56 | 4677 |  | G10 | 8 | 19 |
| 57 | 4678 |  | G10 | 8 | 17 |
| 58 | 4720 |  | G10 | 11 | 14 |
| 59 | 4730 |  | G10 | 9 | 22 |
| 60 | 4649 |  | G10 | 9 | 17 |
| 61 | 4635 | G11 | G11 | 5 | 17 |
| 62 | 4740 |  | G11 | 7 | 20 |
| 63 | 4718 |  | G11 | 7 | 15 |
| 64 | 4742 |  | G11 | 9 | 17 |
| 65 | 4739 |  | G11 | 7 | 25 |
| 66 | 4659 |  | G11 | 7 | 19 |
| 67 | 4704 | G12 | G12 | 9 | 16 |
| 68 | 4719 |  | G12 | 7 | 21 |
| 69 | 4648 |  | G12 | 6 | 17 |
| 70 | 4715 |  | G12 | 8 | 18 |
| 71 | 4695 |  | G12 | 7 | 20 |
| 72 | 4664 |  | G12 | 7 | 19 |
| 73 | 4696 | G13 | G13 | 6 | 20 |
| 74 | 4709 |  | G13 | 7 | 20 |
| 75 | 4685 |  | G13 | 8 | 18 |
| 76 | 4684 |  | G13 | 6 | 23 |
| 77 | 4701 |  | G13 | 8 | 19 |
| 78 | 4667 |  | G13 | 9 | 20 |
| 79 | 4650 | G14 | G14 | 8 | 15 |
| 80 | 4714 |  | G14 | 8 | 23 |
| 81 | 4728 |  | G14 | 6 | 13 |
| 82 | 4654 |  | G14 | 7 | 16 |
| 83 | 4705 |  | G14 | 9 | 18 |
| 84 | 4674 |  | G14 | 8 | 25 |
| 85 | 4646 | G15 | G15 | 9 | 21 |
| 86 | 4708 |  | G15 | 8 | 22 |
| 87 | 4673 |  | G15 | 8 | 23 |
| 88 | 4672 |  | G15 | 8 | 23 |
| 89 | 4690 |  | G15 | 8 | 23 |
| 90 | 4727 |  | G15 | 8 | 25 |
| 91 | 4733 | G16 | G16 | 7 | 20 |
| 92 | 4712 |  | G16 | 7 | 19 |
| 93 | 4724 |  | G16 | 6 | 16 |
| 94 | 4697 |  | G16 | 8 | 19 |
| 95 | 4691 |  | G16 | 6 | 22 |
| 96 | 4669 |  | G16 | 7 | 28 |

Example 10: Re-Formulations that Give 7 and 8

Due to the termination of the manufacturing of Capmul 907P, the availability of this surfactant may not be guaranteed in future. It was therefore the aim of this Example to develop SNEDDSs containing appropriate alternatives exhibiting equal droplet formation, droplet size, zeta potential as well as stability.

Within this study, Capmul 907P (HLB=7.5) was replaced by surfactants demonstrating nearly the same HLB value. The newly developed SNEDD formulations were prepared according to the original formulations (e.g., F-1) as well as in slightly modified ratios. In the following, SNEDDS were characterized regarding nanoemulsion formation, droplet size, zeta potential, and stability and the obtained results were compared with data of formulation F-1.

Thereby, Capmul PG-8 NF and Capryol 90 could be identified to be appropriate substitutes for Capmul 907P, as the corresponding SNEDDS demonstrated nearly the same droplet size of 92.4±10.2 nm and 81.3±1.7 nm after diluting with artificial vaginal fluid in a ratio of 1:2, respectively. The droplet size of the emulsion of the original formulation F-1 was in a range of 81.0±6.5 nm. All three nanoemulsions showed nearly no change in droplet size and zeta potential after three hours incubation period in an atmosphere of 37° C. By changing the ratio of surfactants and solvents no improvement in droplet size and distribution could be achieved. Regarding zeta potential, formulation F-1 containing Capmul 907P as well as the newly developed formulations 7 and 8 demonstrated a zeta potential of around zero. In formulation 7 and 8 the same concentration of 400 µg/ml Lasofoxifene as in formulation F-1 could be incorporated at once, demonstrating sufficient solubility and stability even after five performed freeze-thaw cycles.

Overall, vaginal SNEDD formulations with appropriate alternatives to Capmul 907P could be developed, as presented in Table 33. The use of Capmul PG-8 NF and Capryol 90 instead of Capmul 907P led to the formation of stable nanoemulsions. Therefore, formulation 7 (Capmul PG-8 NF) and formulation 8 (Capryol 90) might be promising SNEDDS for further in vivo studies.

TABLE 33

Composition (by weight) of the original formulation F-1 and the newly developed formulations 7 and 8.

|  | original formulation F-1 [%] | formulation 7 [%] | formulation 8 [%] |
|---|---|---|---|
| Polyethylene glycol 200 | 20 | 20 | 20 |
| Capmul 907P (Abitec) | 28 | — | — |
| Capmul PG-8 NF (Abitec) | — | 28 | — |
| Capryol 90 (Gattefosse) | — | — | 28 |
| Cremophor EL | 28 | 28 | 28 |
| Propylene glycol | 10 | 10 | 10 |
| Tetraglycol | 9 | 9 | 9 |
| Dimethyl sulfoxide | 5 | 5 | 5 |

Materials

Ammonium acetate (Lot: BCBK6717V, Sigma-Aldrich, Vienna, Austria)
Capmul 907 P (Lot: 120516-TMC, Abitec, Janesville, Wis.)
Capmul GMO-50 EP/NF (Lot: 140721-6, Abitec, Janesville, Wis.)
Capmul MCM (Lot: 080726-7, Abitec, Janesville, Wis.)
Capmul MCM C8 (Lot: 080707-8, Abitec, Janesville, Wis.)
Capmul PG12 EP/NF (Lot: 140903-P, Abitec, Janesville, Wis.)
Capmul PG-8 NF (Lot: 070322, Abitec, Janesville, Wis.)
Capmul PG-8-70 NF (Lot: 131210-8, Abitec, Janesville, Wis.)
Capryol 90 (Lot: 3254BM2, Gattefosse, Saint-Priest, France)
Capryol PGMC (Lot: 3241BM2, Gattefosse, Saint-Priest, France)
Cremophor EL (Lot: BCBP4773V, Sigma-Aldrich, Vienna, Austria)
Dimethyl sulfoxide (Lot: SZBE2800V, Sigma-Aldrich, Vienna, Austria)
Glucose (Lot: A20136101, Acros Organics, Vienna, Austria)
Labrofil M1944 CS (Lot: 156135, Gattefosse, Saint-Priest, France)
Labrofil M2125 CS (Lot: 156255, Gattefosse, Saint-Priest, France)

Labrofil M2130 CS (Lot: 154732, Gattefosse, Saint-Priest, France)

Lasofoxifen (Azure Biotech)

Lauroglycol 90 (Lot: 3244BM2, Gattefosse, Saint-Priest, France)

Lauroglycol FCC (Lot: 3219JV1, Gattefosse, Saint-Priest, France)

Magnesium sulfate (Lot: A019960201, Acros Organics, Vienna, Austria)

PEG 200 (Lot: BCBM0758V, Sigma-Aldrich, Vienna, Austria)

Plurol Oleique CC497 (Lot:156007, Gattefosse, Saint-Priest, France)

Potassium chloride (Lot: 351173748, Roth, Karlsruhe, Germany)

Propylene glycol (Lot: STBD3558V, Sigma-Aldrich, Vienna, Austria)

Sodium chloride (Lot: 295230559, Roth; Karlsruhe, Germany)

Tetragylcol (Lot: BCBR4816V, Sigma-Aldrich, Vienna, Austria)

Methods

Preparation of SNEDDS with Alternatives to Capmul 907P

As the manufacturing of Capmul 907P is discontinued, the availability of this excipient may not be guaranteed for the future. Therefore, vaginal SNEDDSs with alternatives to Capmul 907P were developed. The surfactant was replaced by excipients demonstrating nearly the same HLB value, as listed in Table 34. In order to guarantee availability of the most appropriate substitute, excipients offered by different suppliers were used.

TABLE 34

Alternatives to Capmul 907P for preparation of SNEDDS

| # | Chemical Name | Product Name | Supplier | HLB value |
|---|---|---|---|---|
| A1 | Glyceryl Monooleate | Capmul GMO-50 EP/NF | Abitec | 3-4 |
| A2 | Glyceryl Caprylate/Caprate | Capmul MCM | Abitec | 5-6 |
| A3 | Glyceryl Monocaprylate | Capmul MCM C8 | Abitec | 6-7 |
| 7 | Propylene glycol monocaprylate type II | Capmul PG-8 NF | Abitec | 6 |
| 8 | | Capryol 90 | Gattefosse | |
| A6 | Propylene glycol monocaprylate type I | Capmul PG-8-70 EP/NF | Abitec | 5 |
| A7 | | Capryol PGMC | Gattefosse | |
| A8 | Propylene glycol monolaurate type II | Capmul PG-12 EP/NF | Abitec | 5 |
| A9 | | Lauroglycol 90 | Gattefosse | |
| A10 | Propylene glycol monolaurate type I | Lauroglycol FCC | Gattefosse | 5 |
| A11 | Oleoyl macrogol-6 glycerides | Labrafil M1944CS | Gattefosse | 4 |
| A12 | Linoleoyl macrogol-6 glycerides | Labrafil M2125CS | Gattefosse | 4 |
| A13 | Lauroyl macrogol-6 glycerides | Labrafil M2130CS | Gattefosse | 4 |
| A14 | Polyglyceryl-3 dioleate | Plurol Oleique CC497 | Gattefosse | 6 |

Within the first modification process, SNEDDS were prepared according to the original formulation F-1 as provided in Table 35, however, Capmul 907P was replaced by different surfactants as listed above. The resulting lipophilic mixtures were examined visually concerning phase separation and tested regarding emulsion formation as described below.

TABLE 15

Composition (by weight) of the original formulation F-1 containing Capmul 907P

| | % |
|---|---|
| Polyethylene glycol 200 | 20 |
| Capmul 907P | 28 |
| Cremophor EL | 28 |
| Propylene glycol | 10 |
| Tetraglycol | 9 |
| Dimethyl sulfoxide | 5 |

For the second modification process, the two possible alternatives for Capmul 907P: Capmul PG-8 NF and Capryol 90, were used, and various SNEED formulations were prepared by assembling the solvents and surfactants in the ratios shown in Table 36. After the visual examination of the lipophilic mixture regarding phase separation the formulations were investigated concerning emulsion formation, droplet size, and zeta potential as described below.

TABLE 36

Composition (by weight) of modified formulations containing Capmul PG-8 NF or Capryol 90.

| formulation no. | PEG 200 % | Capmul PG-8 NF % | Cremophor EL % | PG % | TG % | DMSO % |
|---|---|---|---|---|---|---|
| 7a | 20 | 25 | 31 | 10 | 9 | 5 |
| 7b | 23 | 25 | 28 | 10 | 9 | 5 |
| 7c | 20 | 25 | 28 | 13 | 9 | 5 |
| 7d | 20 | 26 | 28 | 11 | 10 | 5 |
| 7e | 18 | 25 | 29 | 12 | 11 | 5 |
| 7f | 19 | 26 | 28 | 12 | 10 | 5 |
| 8a* | 22 | 23 | 31 | 10 | 9 | 5 |

TG refers to tetraglycol.
PG refers to propylene glycol.
*Capryol 90 was used instead of Capmul PG-8 NF.

Determination of Droplet Formation, Droplet Size, Zeta Potential, and Stability of these SNEDDSs in Artificial Vaginal Fluid The newly developed SNEDD formulations were characterized regarding droplet formation, droplet size, zeta potential, and stability. Therefore, the lipophilic mixtures were diluted 1:2 with artificial vaginal fluid containing 2.6 mM $MgSO_4$, 10.0 mM KCl, 40.0 mM glucose buffered with 50 mM acetate buffer pH 5.0 and incubated for three hours at 37° C. while shaking (300 rpm) from time to time. The resulting emulsions were examined visually regarding phase separation. Within emulsions resulting in one phase, Lasofoxifene was incorporated in the corresponding SNEDD formulations and visually investigated concerning dissolution.

In order to analyze droplet size distribution and zeta potential utilizing a particle analyzer (Nicomp 380 ZLS Particle Size and Zeta Potential Analyzer) the drug loaded SNEDD formulations were once more diluted 1:2 with artificial vaginal fluid previously equilibrated at 37° C. as described above. After three hours of incubation period at an atmosphere of 37° C., droplet size distribution and zeta potential were measured again to receive an indication concerning their stability. Results were compared with the characteristics of the Capmul 907P containing formulation F-1.

Stability Studies—Freeze-Thaw Cycles

In order to evaluate the stability and the solubility of the newly developed SNEDDS under stressed conditions, freeze-thaw cycles were performed with the two formulations containing Capmul PG-8 NF or Capryol 90, instead of Capmul 907P. Therefore, the SNEDDSs were prepared and Lasofoxifene was incorporated in a concentration of 300 µg/ml as well as 400 µg/ml. The freeze-thaw cycles were conducted five times by changing the temperature every 3 to 14 hours in the order as demonstrated in Table 37. After every freeze-thaw cycle, the formulations were centrifuged and visually examined regarding precipitation. Additionally, the lipophilic mixtures were diluted with artificial vaginal fluid previously equilibrated at 37° C. in a ratio of 1:2 to evaluate the formation of nanoemulsions. After an incubation period of 3 hours at 37° C., the formed nanoemulsions were examined again visually concerning stability.

TABLE 37

Order of freeze-thaw cycles. The temperature was changed every 3 to 14 hours.

| Storage place | Temperature [° C.] |
|---|---|
| Refrigerator | 5 |
| Incubator | 40 |
| Freezer | −20 |
| Climatic chamber | 25 |

Statistical Data Analysis

All studies and tests were carried out in quadruplicate at least unless otherwise noted.

Results

Preparation of SNEDDS with Alternatives to Capmul 907P

In order to generate alternative formulation without Capmul 907P, various SNEDDS were prepared by assembling surfactants, solvents, and appropriate substitutes according to the original formulation F-1 as well as in slightly varied ratios as shown in Tables 35 and 36. The resulting lipophilic mixtures were in the following investigated regarding phase separation (↓). Furthermore, formulations were diluted in a ratio of 1:2 with artificial vaginal fluid as described above and visually examined after three hours concerning phase separation (↓).

As listed in Table 38, a phase separation could be observed in the lipophilic mixture containing Labrafil M1944 CS, Labrafil M2125 CS, Labrafil M2130 CS as well as Plurol Oleique CC497 instead of Capmul 907P. In case of the four substitutes Capmul GMO-50 EP/NF, Capmul MCM, Capmul MCM C8, and Lauroglycol FCC, a phase separation was detected after diluting the corresponding SNEDD formulation 1:2 with artificial vaginal fluid. In Table 38 alternate surfactants of SNEDD formulations without any phase separation after dilution and incubation at 37° C. are highlighted (bolded and italicized).

TABLE 38

Examination of novel vaginal SNEDD formulations containing alternate surfactant with regard to phase separation (↓).

| formulation no. | product name | lipophilic mixture | 1:2 |
|---|---|---|---|
| A1 | Capmul GMO-50 EP/NF | — | ↓ |
| A2 | Capmul MCM | — | ↓ |
| A3 | Capmul MCM C8 | — | ↓ |
| 7 | *Capmul PG-8 NF* | — | — |
| 8 | *Capryol 90* | — | — |
| A6 | *Capmul PG-8-70 EP/NF* | — | — |
| A7 | *Capryol PGMC* | — | — |
| A8 | *Capmul PG-12 EP/NF* | — | — |

TABLE 38-continued

Examination of novel vaginal SNEDD formulations containing alternate surfactant with regard to phase separation (↓).

| formulation no. | product name | lipophilic mixture | 1:2 |
|---|---|---|---|
| *A9* | *Lauroglycol 90* | — | — |
| A10 | Lauroglycol FCC | — | ↓ |
| A11 | Labrafil M1944CS | ↓ | not examined |
| A12 | Labrafil M2125CS | ↓ | not examined |
| A13 | Labrafil M2130CS | ↓ | not examined |
| A14 | Plurol Oleique CC497 | ↓ | not examined |

Regarding SNEDD formulations prepared with Capmul PG-8 NF or Capryol 90 in slightly modified ratios, neither the lipophilic mixture nor the nanoemulsion showed phase separation.

Determination of Droplet Formation, Droplet Size, Zeta Potential, and Stability of these SNEDDSs in Artificial Vaginal Fluid Within emulsions resulting in one phase 400 µg/ml of Lasofoxifene were incorporated in the corresponding SNEDD formulations at once using the ultrasonic bath. After centrifugation for 10 minutes at 10000 rpm the lipophilic mixtures were investigated visually regarding dissolution. Each newly developed SNEDDS demonstrated sufficient solubility.

Additionally, all developed SNEDD formulations without phase separation were characterized regarding droplet size and zeta potential utilizing a particle analyzer. As described above, the lipophilic mixtures containing Lasofoxifene in a concentration of 400 µg/ml were diluted with artificial vaginal fluid previously equilibrated at 37° C. in a ratio of 1:2. The measurement was performed after a short incubation period at 37° C. Results are shown in Tables 39 and 40, whereas the polydispersity index is a measure of the distribution of the droplet size. Besides, depending on droplet size and distribution zeta potential was determined, however, zeta potential was not measured in case of insufficient results regarding droplet size as well as polydispersity index.

TABLE 39

Droplet size, polydispersity index and zeta potential of SNEDDS prepared according the original formulation and resulting in one phase after dilution 1:2 with artificial vaginal fluid. Indicated values are means of at least four experiments ± SD.

| formulation no. | droplet size [nm] | polydispersity index | zeta potential [mV] |
|---|---|---|---|
| original F-1 | 81.0 ± 6.5 | 0.547 | 0.4 ± 1.0 |
| 7 | 92.4 ± 10.2 | 0.606 | 0.2 ± 1.1 |
| 8 | 81.3 ± 1.7 | 0.576 | 0.2 ± 0.6 |
| A6 | 369.1 ± 206.8 | 0.812 | 0.2 ± 0.2 |
| A7 | 164.2 ± 89.7 | 0.767 | −0.2 ± 0.5 |
| A8 | 495.3 ± 27.8 | 0.718 | 0.0 ± 0.0 |
| A9 | 2047.9 ± 804.7 | 1.027 | not measured |

Compared to the original formulation F-1, formulation 7 containing Capmul PG-8 NF and formulation 8 containing Capryol 90, instead of Capmul 907P, demonstrated nearly the same droplet size range of 92.4±10.2 nm and 81.3±1.7 nm, respectively. Regarding zeta potential, all three formulations showed a zeta potential around zero. As Capmul PG-8 NF and Capryol 90 seemed to be an appropriate alternative to Capmul 907P, SNEDD formulations containing these surfactants in slightly modified ratios were prepared. However, as represented in Table 40, a change in concentration of the excipients did not lead to any improvement in droplet size and distribution.

TABLE 40

Droplet size, polydispersity index and zeta potential of SNEDDS prepared with Capmul PG-8 NF or Capryol 90 in slightly modified ratios and resulting in one phase after dilution 1:2 with artificial vaginal fluid. Indicated values are means of at least four experiments ± SD

| formulation no. | droplet size [nm] | polydispersity index | zeta potential [mV] |
| --- | --- | --- | --- |
| 7a | 860.7 ± 376.3 | 0.374 | not measured |
| 7b | 230.6 ± 36.6 | 0.647 | 0.2 ± 0.3 |
| 7c | 182.4 ± 6.3 | 0.649 | 0.0 ± 0.4 |
| 7d | 288.2 ± 50.8 | 0.628 | 0.1 ± 0.1 |
| 7e | 394.2 ± 17.7 | 0.625 | 0.2 ± 0.5 |
| 7f | 279.3 ± 88.0 | 0.669 | −0.2 ± 0.3 |
| 8a | 364.8 ± 60.3 | 1.072 | not measured |

Furthermore, in order to get an impression about the stability of the formed nanoemulsions, droplet size and zeta potential of the two SNEDD formulations, which are highlighted in Table 39, were measured again after an incubation period of three hours at 37° C. Both formulations 7 and 8 as well as the original formulation F-1 showed nearly no change in droplet size and zeta potential after three hours incubation period at 37° C., as shown in Table 41. Therefore, formulation 7 containing Capmul PG-8 NF and formulation 8 containing Capryol 90 instead of Capmul 907P prepared according the original formulation F-1 seem to be an appropriate alternative to the formulation F-1.

TABLE 41

Droplet size and zeta potential of SNEDDS F-1, 7, and 8 after dilution at time point 0 and after 3 hours at 37° C. Indicated values are means of at least four experiments ± SD.

| | 0 h | | 3 h | |
| --- | --- | --- | --- | --- |
| formulation no. | droplet size [nm] | zeta potential [mV] | droplet size [nm] | zeta potential [mV] |
| original F-1 | 81.0 ± 6.5 | 0.4 ± 1.0 | 80.5 ± 2.1 | 0.2 ± 1.1 |
| 7 | 92.4 ± 10.2 | 0.2 ± 1.1 | 87.8 ± 3.1 | 0.1 ± 0.7 |
| 8 | 81.3 ± 1.7 | 0.2 ± 0.6 | 80.2 ± 3.4 | −0.1 ± 0.3 |

Stability Studies—Freeze-Thaw Cycles

In order to investigate the stability of the newly developed SNEDDS under stressed conditions, five freeze-thaw cycles were performed with formulations 7 and 8 containing 300 µg/ml and 400 µg/ml Lasofoxifene by changing the temperature every 3 to 14 hours. After each cycle, the stability as well as the formation of nanoemulsions was tested. Thereby, all formulations demonstrated sufficient stability under stressed conditions as no precipitation could be seen after centrifugation and no alteration in the formation of nanoemulsions could be observed.

Example 11: Peroxide Value

Peroxide value measured at the opening of the container for the following excipients are given in Table 42. The unit of Peroxide value was measured as meq O2/kg (milliequivalent) as described in USP pharmacopeia (see, e.g., the iodine value test described in USP<401> of pharmacopeia).

TABLE 42

Peroxide values for select excipients.

| Excipient | Capsugel Reference | Capsugel Lot # | Peroxide value (O2/kg) |
| --- | --- | --- | --- |
| Cremophor EL | IF15230017 | QA131979 | <0.1 |
| Tetraglycol | IF16347027 | QA132090 | 1.55 |
| Polyethylene glycol | IF16347047 | QA132106 | <0.1 |

Example 12: Orientating Studies on the Storage Stability of Lasofoxifene in SNEDDS Orientating studies on the storage stability of Lasofoxifene in SNEEDS were performed at 60° C. and the samples were analyzed via HPLC. Samples had pre-incubation times of over 1 day or over 7 days. The SNEDD formulation 7 (see, e.g., Table 33) was freshly prepared. Then after oxygen elimination using argon, the antioxidants BHT and BHA (concentrations of 0.05% and 2%, respectively) were added to the SNEDD formulation. Afterwards, the oxygen elimination was carried out a second time and the SNEDD formulation containing BHT or BHA was stored at room temperature for one day. After one day, Lasofoxifene was added to the SNEDD formulation to achieve a concentration of 100 µg/ml. The final formulations were treated with argon and were closed using the crimped method. After a 5 and 12 day storage period at 60° C., the samples were analyzed with HPLC (high-performance liquid chromatography).

Figure 21:
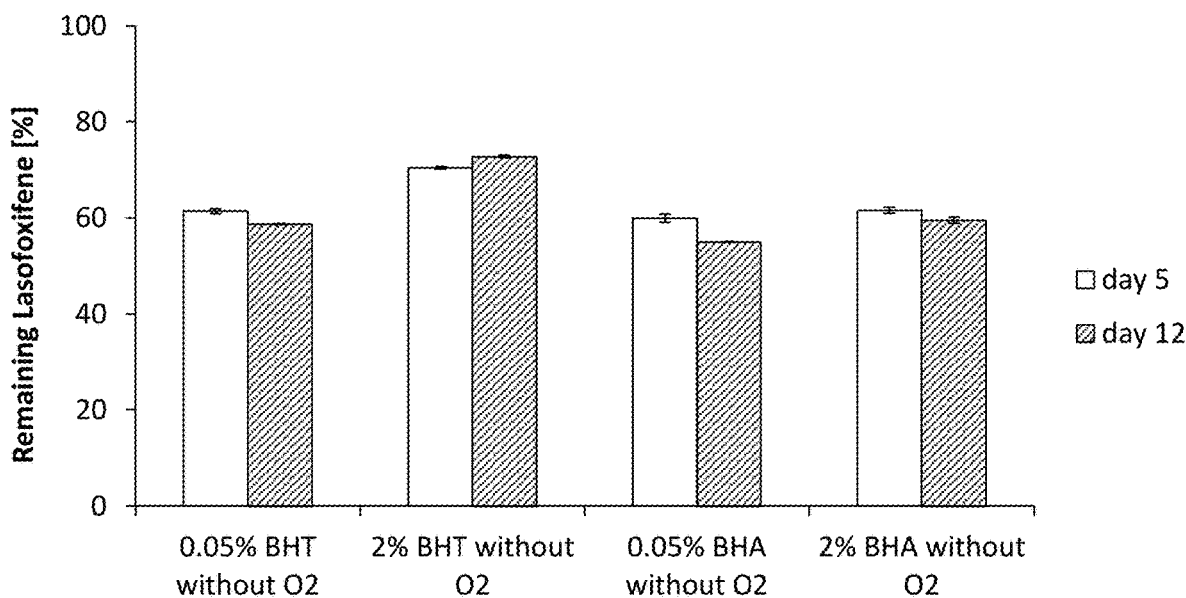
FIG. 21 shows the outcome of orientating stability studies over 12 days with one day pre-incubation at room temperature. Indicated values are means (n=4)±SD.
Figure 22:
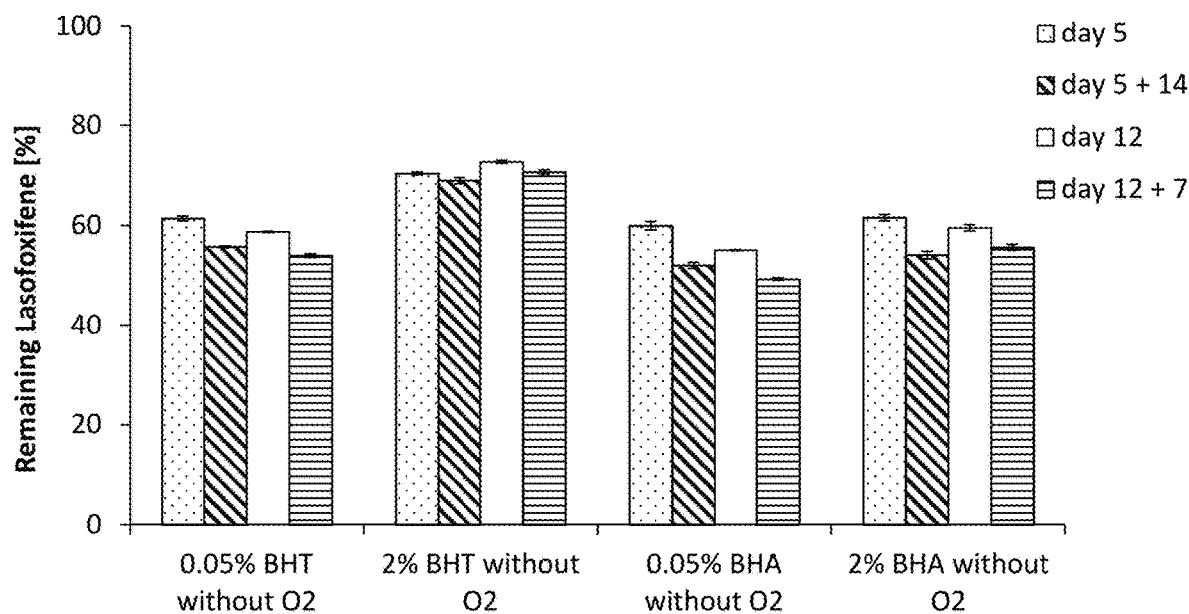
FIG. 22 shows the outcome of orientating stability studies over 19 days with one day pre-incubation. Indicated values are means (n=4)±SD.

The outcome of the orientating stability studies over 12 days with one day pre-incubation at room temperature for the SNEDD formulations containing BHT or BHA is shown in FIG. 21. The results indicate there is little degradation of the formulations over this time period. In order to investigate if the surrounding oxygen has an influence on degradation, the vials (unclosed) were stored overnight at room temperature. After closing the vials again (without the oxygen eliminating argon treatment), the vials were stored for an additional 7 and 14 days at 60° C. The outcome of orientating stability studies over 19 days with one day pre-incubation and no oxygen eliminating treatment for the formulations are shown in FIG. 22. Again, little degredagtion is observed even in the presence of oxygen.

Figure 23:
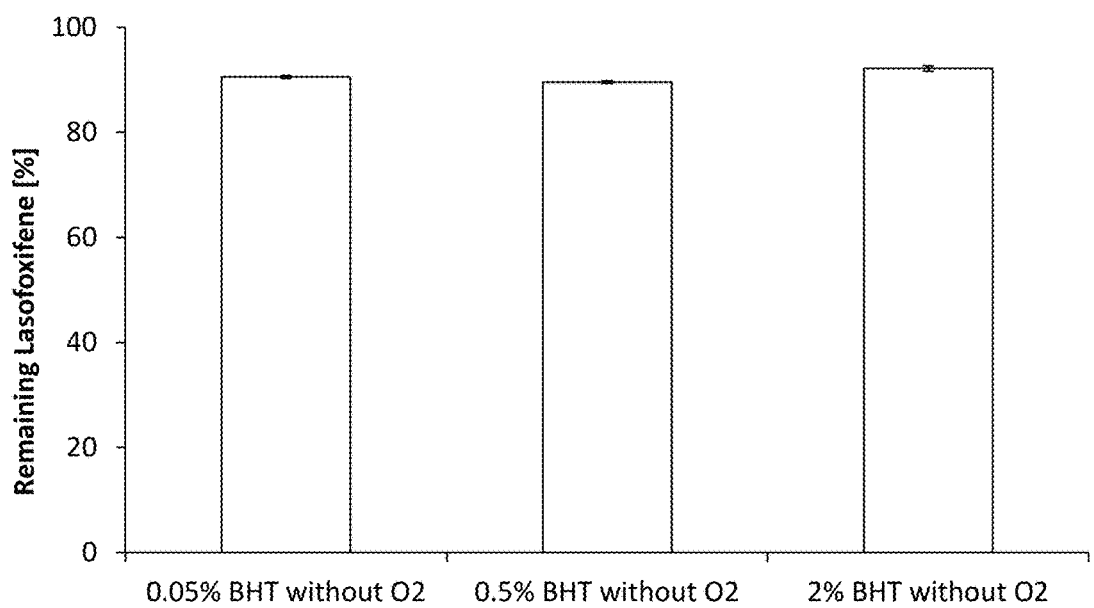
FIG. 23 shows the outcome of orientating stability studies over 5 days with seven days pre-incubation. Indicated values are means (n=3)±SD.

As the degradation process could not be completely inhibited, another orientating study including a longer pre-incubation time of the SNEDD formulation with antioxidant BHT was performed. After oxygen elimination using argon, the antioxidant BHT (three concentrations of 0.05%, 0.5% and 2%) were added to the SNEDD formulation. Afterwards, oxygen elimination was carried out a second time and the SNEDD formulations containing BHT were stored at 60° C. for 7 days. After the pre-incubation time, Lasofoxifene was added to the SNEDD formulation to achieve a concentration of 100 µg/ml. After a 5 day storage period at 60° C., the samples were analyzed with HPLC. The outcome of orientating stability studies over 5 days with seven days pre-incubation is shown in FIG. 23. There is very little degredation for all three concentrations of BHT.

Figure 25:
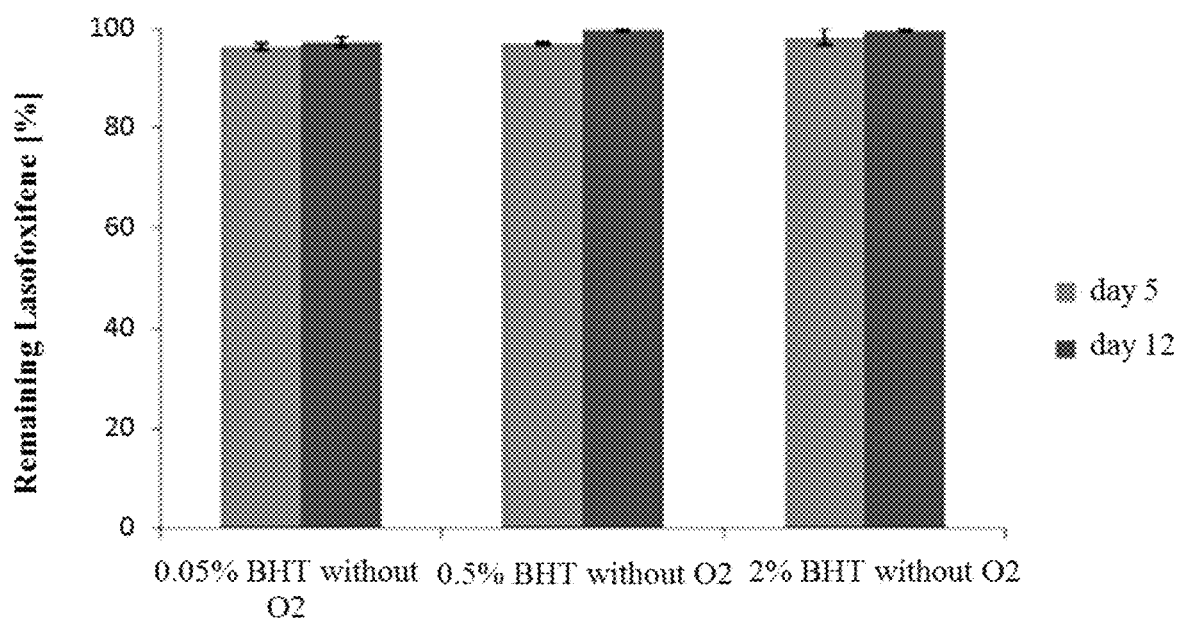
FIG. 25 shows the outcome of orientating storage stability studies at 60° C. after 5 and 12 days using SNEDD formulations pre-incubated with BHT for 14 days.

Formulation 7 was pre-incubated with BHT (0.05% or 2%) at room temperature without O2 for 14 days. The resulting formulations were subject to the orientating storage stability study at 60° C. for 5 and 12 days. The results are shown in FIG. 25.

Figure 24:
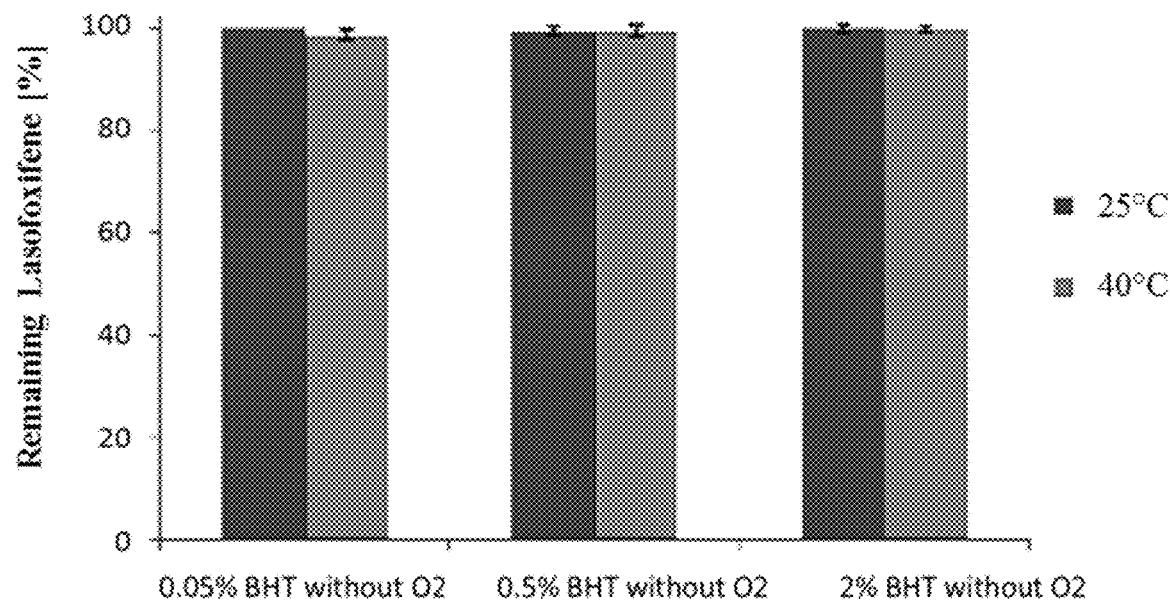
FIG. 24 shows the outcome of the long term stability studies after one month.

Formulation 7 was pre-incubated with BHT (0.05% or 2%) at room temperature without O2 for 14 days. The resulting formulations were subject to the orientating storage stability study at 25° C. or 40° C. for one month. The results are shown in FIG. 24.

In this Example, the tested formulations with BHT were more stable than the corresponding formulations without BHT. In this Example, the tested formulations with BHA were more stable than the corresponding formulations without BHA.

Example 13: Development of Tetraglycol Free SEDDS for Lasofoxifene

Introduction

Lasofoxifene, a third-generation selective estrogen receptor modulator (SERM) initially developed for the prevention and treatment of osteoporosis in postmenopausal woman [Gennari, L., *Lasofoxifene: a new type of selective estrogen receptor modulator for the treatment of osteoporosis*. Drugs Today (Barc), 2006. 42(6): p. 355-367], shows a positive impact on vaginal tissue [Ibe, C. and J. A. Simon, *Continuing Medical Education: Vulvovaginal Atrophy: Current and Future Therapies (CME)*. The Journal of Sexual Medicine, 2010. 7(3): p. 1042-1050].

Stability studies of Lasofoxifene in SEDDS formulations having been stored for 4 and 12 months, respectively, indicated a decrease in Lasofoxifene concentration over time. Thus, strategies in order to avoid the chemical degradation process were developed. As ethers are well known to form peroxides in the presence of oxygen and light, the generated SEDD formulation 7AA was pre-incubated with the antioxidant butylated hydroxytoluene (BHT) at 60° C. for at least two weeks. The resulting formulation with BHT showed increased stability of Lasofoxifene. Nevertheless, based on a high peroxide value of 1.55 μmol measured after opening the container of tetraglycol, a tetraglycol free formulation might further reduce the total peroxide value and thereby the relating degradation process of Lasofoxifene.

Prophetic Example

Study Design

In order to get as close as feasible to the already generated SEDDS formulation 7AA (Table 43), tetraglycol is replaced by other components such as PEG 200 in the formulation. Therefore, the amount of the other excipients of formulation 7AA is increased accordingly. Formulation 7AA demonstrated a droplet size of 92.4±10.2 nm. the alternative tetraglycol free formulations should exhibit similar droplet sizes. Therefore, droplet size distribution and zeta potential after dilution in artificial vaginal fluid over a time period of 4 hours are examined. Furthermore, solubility of Lasofoxifene in the novel SEDD formulations are reviewed via HPLC. After orientating stability studies at 60° C., long term stability studies of Lasofoxifene are performed at both 25° C. and 40° C.

TABLE 43

Composition of the current formulation 7AA.

| | formulation 7AA [% v/v] | formulation 16A [% by weight] |
|---|---|---|
| Polyethylene glycol 200 | 20 | 20.862 |
| Capmul PG-8 NF (Abitec) | 28 | 28.028 |
| Cremophor EL | 28 | 27.259 |
| Propylene glycol | 10 | 9.606 |
| Tetraglycol | 9 | 9.096 |

TABLE 43-continued

Composition of the current formulation 7AA.

| | formulation 7AA [% v/v] | formulation 16A [% by weight] |
|---|---|---|
| Dimethyl sulfoxide | 5 | 5.099 |
| BHT | — | 0.05 |

Materials

The following materials are used in the studies described herein: Acetonitrile (Lot: 1498316, Fisher, Vienna, Austria), Butylated hydroxytoluene (Lot: 012176575, Roth, Karlsruhe, Germany), Capmul PG-8 NF (Lot: 070322, Abitec, Janesville, Wis.), Cremophor EL (Lot: BCBK5166V, Sigma-Aldrich, Vienna, Austria), Dimethyl sulfoxide (Lot: SZBE2800V, Sigma-Aldrich, Vienna, Austria), Lasofoxifene (Azure Biotech), PEG 200 (Lot: BCBM0758V, Sigma-Aldrich, Vienna, Austria), Propylene glycol (Lot: STBD3558V, Sigma-Aldrich, Vienna, Austria), Tetraglycol (Lot: BCBN1446V, Sigma-Aldrich, Vienna, Austria), and Trifluoroacetic acid (Lot: STDB9271V, Sigma-Aldrich, Vienna, Austria).

HPLC Analyses of Lasofoxifene in SEDDS

This method is adopted by Thiomatrix based on the HPLC analysis described previously by Pfizer [Standard test procedure Pfizer: Assay and identification of Lasofoxifene in Lasofoxifene Tartrate drug substance by reversed phase liquid chromatography]. In order to maintain the pressure and to separate remaining formulation components, a pre-column is utilized. A HPLC System Merck, LaChrome Elite for Hitachi and HPLC Software Merck is used. A Waters Symmetry C18, 5 μm C18 4.6×250 mm column is used. The pre-column is a Symmetry C18 VanGuardCart 5μ 3.9×5 mm. The mobile phase A is water:TFA (Trifluoroacetic acid):ammonium hydroxide (2000:5:4 v/v/v/) pH=3.0, and the mobile phase B is water:ACN:TFA:ammonium hydroxide (200:1800:5:4 v/v/v/v/). The flow rate is 1.0 ml/min. The auto sampler is set to 4° C. and the column oven to 40° C. The detection is set at 230 nm, and the injection volume is 10 μl. The run time is 48 minutes, and the retention time is 12.5 minutes. The gradient of percent mobile phase A to the percent mobile phase B (A:B) is 55:45, 55:45, 30:70, 55:45, and 55:45 at 0, 5, 40, 41, and 48 minutes respectively.

Preparation and In Vitro Characterization of Five Different Tetraglycol Free Lasofoxifene SEDDS Formulations Containing 0.05% BHT Based on the high peroxide value of tetraglycol, alternative formulations are developed by increasing the amount of the other excipients within the formulation as shown in Table 44. Furthermore, 0.05% BHT is incorporated into the SEDDS formulations.

TABLE 44

Composition of the current formulation 7AA and a representative example of a tetraglycol-free formulation (14AA).

| | formulation 7AA [% v/v] | formulation 14AA [% v/v] |
|---|---|---|
| Polyethylene glycol 200 | 20 | 24 |
| Capmul PG-8 NF (Abitec) | 28 | 28 |
| Cremophor EL | 28 | 28 |
| Propylene glycol | 10 | 15 |
| Tetraglycol | 9 | — |
| Dimethyl sulfoxide | 5 | 5 |

Particle Size Distribution and Zeta Potential After Dilution in Artificial Vaginal Fluid Over a Time Period of 4 Hours The newly developed SEDDS formulations are characterized regarding droplet formation, droplet size, zeta potential and stability. Therefore, the lipophilic mixtures are diluted 1:2 with artificial vaginal fluid containing 2.6 mM MgSO4, 10.0 mM KCl, 40.0 mM glucose buffered with 50 mM acetate buffer pH 5.0 and incubated for four hours at 37° C. while shaking (300 rpm) from time to time. The resulting emulsions are examined visually regarding phase separation. Within emulsions resulting in one phase, Lasofoxifene is incorporated in the corresponding SEDD formulations and visually investigated concerning dissolution.

In order to analyze droplet size distribution and zeta potential utilizing a particle analyzer (Nicomp 380 ZLS Particle Size and Zeta Potential Analyzer) the drug loaded SEDDS formulations are once more diluted 1:2 with artificial vaginal fluid as described above. After four hours of incubation period at an atmosphere of 37° C., droplet size distribution and zeta potential are measured again to receive an indication concerning their stability. The results are compared with the characteristics of formulation 7AA.

Solubility Studies of Lasofoxifene in SEDDS (25 µg/ml Highest Concentration to be Tested) Via HPLC Analyses Lasofoxifene is dissolved in the newly designed SEDDS formulations described above in increasing concentrations up to 25 µg/ml. In addition to visual investigations, the solubility of Lasofoxifene is determined via HPLC. Therefore, the SEDDS formulations containing Lasofoxifene are diluted 1:3 with methanol. After centrifugation at 12000 rpm for 6 min, the samples are analyzed via HPLC as described above.

Stability of SEDDS During Freeze-Thaw Cycles

In order to evaluate the stability and the solubility of the newly developed SEDDS under stressed conditions, freeze-thaw cycles are performed with the tetraglycol free formulations. The freeze-thaw cycles are conducted five times by changing the temperature every 3 to 14 hours from 20° C. to −20° C. After every freeze-thaw cycle, the formulations are centrifuged and visually examined regarding precipitation, size distribution of in artificial vaginal fluid formed droplets, and drug solubility.

Orientating Storage Stability Studies at 60° C.

Orientating stability studies are performed at 60° C. After one week, Lasofoxifene is analyzed via HPLC. Based on the outcome of orientating stability studies, the most stable formulations are used for long term stability studies.

Storage Stability Studies of the Three Most Promising Formulations Under Long Term (25° C.) and Accelerated Storage Conditions (40° C.) for Three Months Storage stability studies of the most promising formulations are performed at 25° C. and 60% RH as well as at 40° C. and 75% RH over three months. After 1, 2 and 3 months, Lasofoxifene is analyzed via HPLC to determine the stability. In addition, the size distribution in artificial vaginal fluid of the formed droplets is determined.

Discussion

Capmul 907P demonstrates an HLB value of 7.5. Therefore, various surfactants with a similar HLB value were used in order to modify the original formulation F-1. Based on the outcome of nanoemulsion formation, droplet size, zeta potential measurement, and stability of SNEDD, formulation 7 containing Capmul PG-8 NF and formulation 8 containing Capryol 90 could be identified to be appropriate. Actually, Capmul PG-8 NF and Capryol 90 are both Propylene glycol monocaprylate type II with an HLB value of 5. The only difference between these two surfactants is their provider—Abitec in case of Capmul PG-8 NF and Gattefosse in case of Capryol 90. Nevertheless, Capryol 90 demonstrated the better results regarding droplet size and droplet size distribution seen in a PI of 0.576 instead of 0.606 in case of Capmul PG-8 NF. Therefore, formulation 8 containing Capyrol 90 might be a suitable alternate SNEDD formulation for vaginal use appropriate for in vivo studies.

REFERENCES

[1] L. Gennari, Lasofoxifene: a new type of selective estrogen receptor modulator for the treatment of osteoporosis, Drugs Today (Barc), 42 (2006) 355-367.
[2] C. Ibe, J. A. Simon, Continuing Medical Education: Vulvovaginal Atrophy: Current and Future Therapies (CME), The Journal of Sexual Medicine, 7 (2010) 1042-1050.

CONCLUSION

As Lasofoxifene has a positive impact on vaginal tissue in postmenopausal women the development of an appropriate drug delivery system for local application is highly in demand.

Within this study, different SNEDD formulations were successfully developed that spontaneously form nanoemulsions once contacting vaginal fluid. These lipophilic mixtures containing Lasofoxifene demonstrated an adequate formation of nanodroplets in a range of 30-130 nm, a sustained drug release, and a decrease in permeation across vaginal tissue. Furthermore, by encapsulating the API, mucus interactions could be avoided, resulting in a higher drug amount in the donor compartment.

During this project, two preparation methods were established, resulting in differences in stability and concentration. On the one hand, Lasofoxifene was incorporated in one step into the lipophilic mixture. On the other hand, the SNEDDSs was prepared in two steps by first dissolving the API in PEG 200 and DMSO. The two-step-preparation allowed a higher concentration of 750 µg/ml, however, the stability could not be guaranteed for more than 48 hours. A reason for insufficient stability might be the formation of a more unstable solvation shell. In the three most promising SNEDD formulations (1, 2, and 3), a concentration of 150 µg/ml was incorporated in one step. In order to increase the highest feasible drug amount, the already developed formulations could be improved by changing the interfering components and increasing the volume of DMSO.

In addition to SNEDD formulations, Lasofoxifene was incorporated into three different state-of-the-art o/w creams. As there is no state-of-the-art o/w cream for vaginal use available, the creams were selected due to their properties (nonionic and hydrophilic); however, it cannot be guaranteed that they are acceptable for vaginal tissues. Nevertheless, all excipients were screened in the "FDA Inactive Ingredients Guide" regarding vaginal use. Every excipient of the Nonionic Hydrophilic Cream SR DAC was found in the Guide. However, not all the excipients of the Excipial Hydrocreme and Nonionic Hydrophilic Cream DAB were listed in the Guide.

Overall, a promising drug delivery system for Lasofoxifene could be developed for vaginal use appropriate for in vivo study.

Overall, three promising SNEDD formulations were developed that demonstrate a sustained drug release profile and prevent the API from permeating across the vaginal mucosa.

REFERENCES

[1] L. Gennari, Lasofoxifene: a new type of selective estrogen receptor modulator for the treatment of osteoporosis, Drugs Today (Barc), 42 (2006) 355-367.
[2] C. Ibe, J. A. Simon, Continuing Medical Education: Vulvovaginal Atrophy: Current and Future Therapies (CME), The Journal of Sexual Medicine, 7 (2010) 1042-1050.
[3] J. V. Pinkerton, F. Z. Stanczyk, Clinical effects of selective estrogen receptor modulators on vulvar and vaginal atrophy, Menopause, 21 (2014).
[4] A. Bernkop-Schnürch, M. Hornof, Intravaginal drug delivery systems, American Journal of Drug Delivery, 1 (2003) 241-254.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A pharmaceutical composition comprising:
   (i) an estrogen receptor modulator (SERM), wherein the SERM is lasofoxifene, or a pharmaceutically acceptable salt thereof; and
   (ii) four or more pharmaceutically acceptable excipients comprising:
      (a) two or more (co)solvents, wherein:
         the first (co)solvent is a polyethylene glycol;
         the concentration of the first (co)solvent in the four or more pharmaceutically acceptable excipients is between 10% and 25% by weight, inclusive;
         the second (co)solvent is propylene glycol; and
         the concentration of the second (co)solvent in the four or more pharmaceutically acceptable excipients is between 10% and 15% by weight, inclusive;
      (b) one or more hydrophilic emulsifier(s), wherein:
         the first hydrophilic emulsifier is polyoxyl 35 hydrogenated castor oil; and
         the concentration of the first hydrophilic emulsifier in the four or more pharmaceutically acceptable excipients is between 15% and 35% by weight, inclusive; and
      (c) one or more lipophilic emulsifier(s), wherein:
         the first lipophilic emulsifier is propylene glycol monoheptanoate or propylene glycol monocaprylate; and
         the concentration of the first lipophilic emulsifier in the four or more pharmaceutically acceptable excipients is between 25% and 40% by weight, inclusive;
   provided that
      the combined concentrations of the four or more pharmaceutically acceptable excipients are 100%.

2. The pharmaceutical composition of claim 1, wherein the concentration of the SERM in the pharmaceutical composition is between 0.1 μg/ml and 3,000 μg/ml, inclusive.

3. The pharmaceutical composition of claim 1, wherein the two or more (co)solvents further comprise a third (co)solvent, wherein the concentration of the third (co)solvent in the four or more pharmaceutically acceptable excipients is not more than 10% by weight.

4. The pharmaceutical composition of claim 3, wherein the two or more (co)solvents further comprise a fourth (co)solvent, wherein the concentration of the fourth (co)solvent in the four or more pharmaceutically acceptable excipients is not more than 10% by weight.

5. The pharmaceutical composition of claim 4, wherein the fourth (co)solvent is a polyol.

6. The pharmaceutical composition of claim 1, wherein the one or more hydrophilic emulsifier(s) further comprise a second hydrophilic emulsifier, wherein the concentration of the second hydrophilic emulsifier in the four or more pharmaceutically acceptable excipients is not more than 10% by weight.

7. The pharmaceutical composition of claim 6, wherein the second hydrophilic emulsifier is a non-ionic emulsifier, and the HLB value of the second hydrophilic emulsifier is about 11 or between 13 and 15, inclusive, or is an ionic emulsifier that includes monovalent cation(s).

8. The pharmaceutical composition of claim 6, wherein the one or more hydrophilic emulsifier(s) further comprise a third hydrophilic emulsifier, wherein the concentration of the third hydrophilic emulsifier in the four or more pharmaceutically acceptable excipients is not more than 10% by weight.

9. The pharmaceutical composition of claim 1, wherein the four or more pharmaceutically acceptable excipients further comprise: (d) one or more organic solvent(s), wherein the concentration of the first organic solvent in the four or more pharmaceutically acceptable excipients is not more than 20% by weight.

10. The pharmaceutical composition of claim 9, wherein the organic solvents further comprise a second organic solvent, wherein the concentration of the second organic solvent in the four or more pharmaceutically acceptable excipients is not more than 20% by weight.

11. The pharmaceutical composition of claim 1, wherein the four or more pharmaceutically acceptable excipients further comprise: (e) one or more antioxidant(s), wherein the concentration of the first antioxidant in the four or more pharmaceutically acceptable excipients is not more than 5% by weight.

12. The pharmaceutical composition of claim 11, wherein the first antioxidant is butylated hydroxyanisole (BHA), butylated hydroxytoluene (BHT), tocopherol, or cysteine.

13. The pharmaceutical composition of claim 1, wherein the four or more pharmaceutically acceptable excipients further comprise: (f) one or more chelating agent(s), wherein the concentration of the first chelating agent in the four or more pharmaceutically acceptable excipients is not more than 5% by weight.

14. The pharmaceutical composition of claim 1, wherein the pharmaceutical composition is substantially free of dioxygen.

15. A method of delivering an estrogen receptor modulator (SERM) to a female subject in need thereof, the method comprising contacting the vagina of the female subject with a pharmaceutical composition of claim 1.

16. A method of preparing a pharmaceutical composition of claim 1, the method comprising:
mixing the four or more pharmaceutically acceptable excipients to form a mixture of pharmaceutically acceptable excipients; and
mixing the estrogen receptor modulator (SERM) with the mixture of pharmaceutically acceptable excipients.

17. A method of preparing a pharmaceutical composition of claim 1, the method comprising:
mixing the estrogen receptor modulator (SERM) with one or more of the (co)solvent(s) to form a mixture of the SERM and one or more of the (co)solvent(s); and
mixing the remaining pharmaceutically acceptable excipients with the mixture of the SERM and one or more of the (co)solvent(s).

18. A kit comprising:
a pharmaceutical composition of claim 1; and
instructions for using the pharmaceutical composition.

19. The pharmaceutical composition of claim 1, wherein the concentration of the SERM in the pharmaceutical composition is between 150 µg/ml and 750 µg/ml, inclusive.

20. The pharmaceutical composition of claim 1, wherein the first (co)solvent is polyethylene glycol 200.

21. The pharmaceutical composition of claim 3, wherein the third (co)solvent is dimethyl sulfoxide.

22. The pharmaceutical composition of claim 4, wherein the fourth (co)solvent is tetraglycol.

23. The pharmaceutical composition of claim 1, wherein the first lipophilic emulsifier is propylene glycol monocaprylate.

24. The pharmaceutical composition of claim 11, wherein the first antioxidant is butylated hydroxytoluene (BHT).

25. A pharmaceutical composition comprising:
(i) an estrogen receptor modulator (SERM), wherein the SERM is lasofoxifene, or a pharmaceutically acceptable salt thereof; and
(ii) four or more pharmaceutically acceptable excipients, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about $(19.99\pm20\%)\%$ by weight;
a second (co)solvent, wherein the second (co)solvent is propylene glycol, and the concentration of the second (co)solvent in the four or more pharmaceutically acceptable excipients is about $(9.995\pm20\%)\%$ by weight;
a third (co)solvent, wherein the third (co)solvent is dimethyl sulfoxide, and the concentration of the third (co)solvent in the four or more pharmaceutically acceptable excipients is about $(4.9975\pm20\%)\%$ by weight;
a fourth (co)solvent, wherein the fourth (co)solvent is tetraglycol, and the concentration of the fourth (co) solvent in the four or more pharmaceutically acceptable excipients is about $(8.9955\pm20\%)\%$ by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about $(27.986\pm20\%)\%$ by weight;
a lipophilic emulsifier, wherein the lipophilic emulsifier is propylene glycol monocaprylate, and the concentration of the lipophilic emulsifier in the four or more pharmaceutically acceptable excipients is about $(27.986\pm20\%)\%$ by weight; and
an antioxidant, wherein the antioxidant is butylated hydroxytoluene (BHT), and the concentration of the antioxidant in the four or more pharmaceutically acceptable excipients is about $(0.05\pm20\%)\%$ by weight;
provided that the combined concentrations of the four or more pharmaceutically acceptable excipients are 100%.

26. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 20% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 2% by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about 29% by weight;
a lipophilic emulsifier, wherein the lipophilic emulsifier is propylene glycol monoheptanoate, and the concentration of the lipophilic emulsifier in the four or more pharmaceutically acceptable excipients is about 29% by weight; and
an organic solvent, wherein the organic solvent is glyceryl tricaprylate, and the concentration of the organic solvent in the four or more pharmaceutically acceptable excipients is about 10% by weight.

27. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 20% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 2% by weight;
a first hydrophilic emulsifier, wherein the first hydrophilic emulsifier is polyoxyl 35 hydrogenated castor oil, and the concentration of the first hydrophilic emulsifier in the four or more pharmaceutically acceptable excipients is about 19% by weight;
a second hydrophilic emulsifier, wherein the second hydrophilic emulsifier is a mixture of monoesters, diesters, and triesters of glycerol, and monoesters and diesters of polyethylene glycols with a mean relative molecular weight between 200 and 400, inclusive, and the concentration of the second hydrophilic emulsifier in the four or more pharmaceutically acceptable excipients is about 10% by weight;
a lipophilic emulsifier, wherein the lipophilic emulsifier is propylene glycol monoheptanoate, and the concentration of the lipophilic emulsifier in the four or more pharmaceutically acceptable excipients is about 29% by weight; and
an organic solvent, wherein the organic solvent is glyceryl tricaprylate, and the concentration of the organic solvent in the four or more pharmaceutically acceptable excipients is about 10% by weight.

28. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 20% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 5% by weight;
a fourth (co)solvent, wherein the fourth (co)solvent is tetraglycol, and the concentration of the fourth (co)solvent in the four or more pharmaceutically acceptable excipients is about 9% by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about 28% by weight; and
a lipophilic emulsifier, wherein the lipophilic emulsifier is propylene glycol monoheptanoate, and the concentration of the lipophilic emulsifier in the four or more pharmaceutically acceptable excipients is about 28% by weight.

29. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 15% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 5% by weight;
a fourth (co)solvent, wherein the fourth (co)solvent is tetraglycol, and the concentration of the fourth (co)solvent in the four or more pharmaceutically acceptable excipients is about 10% by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about 25.5% by weight;
a lipophilic emulsifier, wherein the lipophilic emulsifier is propylene glycol monoheptanoate, and the concentration of the lipophilic emulsifier in the four or more pharmaceutically acceptable excipients is about 27% by weight; and
an organic solvent, wherein the organic solvent is glyceryl tricaprylate, and the concentration of the organic solvent in the four or more pharmaceutically acceptable excipients is about 7.5% by weight.

30. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 20% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 5% by weight;
a fourth (co)solvent, wherein the fourth (co)solvent is tetraglycol, and the concentration of the fourth (co)solvent in the four or more pharmaceutically acceptable excipients is about 10% by weight;
a first hydrophilic emulsifier, wherein the first hydrophilic emulsifier is polyoxyl 35 hydrogenated castor oil, and the concentration of the first hydrophilic emulsifier in the four or more pharmaceutically acceptable excipients is about 19% by weight;
a second hydrophilic emulsifier, wherein the second hydrophilic emulsifier is polyoxyethylenesorbitan trioleate, and the concentration of the second hydrophilic emulsifier in the four or more pharmaceutically acceptable excipients is about 7% by weight; and
a lipophilic emulsifier, wherein the lipophilic emulsifier is propylene glycol monoheptanoate, and the concentration of the lipophilic emulsifier in the four or more pharmaceutically acceptable excipients is about 29% by weight.

31. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 20% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 5% by weight;
a fourth (co)solvent, wherein the fourth (co)solvent is tetraglycol, and the concentration of the fourth (co)solvent in the four or more pharmaceutically acceptable excipients is about 9% by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about 28% by weight; and
a lipophilic emulsifier, wherein the lipophilic emulsifier is propylene glycol monocaprylate, and the concentration of the lipophilic emulsifier in the four or more pharmaceutically acceptable excipients is about 28% by weight.

32. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 20% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 5% by weight;
a fourth (co)solvent, wherein the fourth (co)solvent is tetraglycol, and the concentration of the fourth (co)solvent in the four or more pharmaceutically acceptable excipients is about 9% by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about 28% by weight; and
a lipophilic emulsifier, wherein the lipophilic emulsifier is propylene glycol monocaprylate type II, and the concentration of the lipophilic emulsifier in the four or more pharmaceutically acceptable excipients is about 28% by weight.

33. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 21% by weight;
a second (co)solvent, wherein the second (co)solvent is propylene glycol, and the concentration of the second (co)solvent in the four or more pharmaceutically acceptable excipients is about 10% by weight;
a third (co)solvent, wherein the third (co)solvent is dimethyl sulfoxide, and the concentration of the third (co)solvent in the four or more pharmaceutically acceptable excipients is about 5% by weight;
a fourth (co)solvent, wherein the fourth (co)solvent is tetraglycol, and the concentration of the fourth (co)solvent in the four or more pharmaceutically acceptable excipients is about 9% by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about 27% by weight;
a lipophilic emulsifier, wherein the lipophilic emulsifier is propylene glycol monocaprylate, and the concentration of the lipophilic emulsifier in the four or more pharmaceutically acceptable excipients is about 28% by weight; and
an antioxidant, wherein the antioxidant is butylated hydroxytoluene (BHT), and the concentration of the antioxidant in the four or more pharmaceutically acceptable excipients is about 0.05% by weight.

34. The pharmaceutical composition of claim 1, wherein the four or more pharmaceutically acceptable excipients consist of:
a first (co)solvent, wherein the first (co)solvent is polyethylene glycol 200, and the concentration of the first (co)solvent in the four or more pharmaceutically acceptable excipients is about 24% by weight;
a second (co)solvent, wherein the second (co)solvent is propylene glycol, and the concentration of the second (co)solvent in the four or more pharmaceutically acceptable excipients is about 15% by weight;
a third (co)solvent, wherein the third (co)solvent is dimethyl sulfoxide, and the concentration of the third (co)solvent in the four or more pharmaceutically acceptable excipients is about 5% by weight;
a hydrophilic emulsifier, wherein the hydrophilic emulsifier is polyoxyl 35 hydrogenated castor oil, and the concentration of the hydrophilic emulsifier in the four or more pharmaceutically acceptable excipients is about 28% by weight;

a lipophilic emulsifier, wherein the lipophilic emulsifier is propylene glycol monocaprylate, and the concentration of the lipophilic emulsifier in the four or more pharmaceutically acceptable excipients is about 28% by weight; and an antioxidant, wherein the antioxidant is butylated hydroxytoluene (BHT), and the concentration of the antioxidant in the four or more pharmaceutically acceptable excipients is about 0.05% by weight.

35. The pharmaceutical composition of claim 1, wherein the first lipophilic emulsifier is propylene glycol monoheptanoate.

36. The pharmaceutical composition of claim 25, wherein the four or more pharmaceutically acceptable excipients consist of:

a first (co)solvent, wherein the first (co)solvent is polyethylene glycol 200, and the concentration of the first (co)solvent in the four or more pharmaceutically acceptable excipients is about 19.99% by weight;

a second (co)solvent, wherein the second (co)solvent is propylene glycol, and the concentration of the second (co)solvent in the four or more pharmaceutically acceptable excipients is about 9.995% by weight;

a third (co)solvent, wherein the third (co)solvent is dimethyl sulfoxide, and the concentration of the third (co)solvent in the four or more pharmaceutically acceptable excipients is about 4.9975% by weight;

a fourth (co)solvent, wherein the fourth (co)solvent is tetraglycol, and the concentration of the fourth (co)solvent in the four or more pharmaceutically acceptable excipients is about 8.9955% by weight;

a hydrophilic emulsifier, wherein the hydrophilic emulsifier is polyoxyl 35 hydrogenated castor oil, and the concentration of the hydrophilic emulsifier in the four or more pharmaceutically acceptable excipients is about 27.986% by weight;

a lipophilic emulsifier, wherein the lipophilic emulsifier is propylene glycol monocaprylate, and the concentration of the lipophilic emulsifier in the four or more pharmaceutically acceptable excipients is about 27.986% by weight; and an antioxidant, wherein the antioxidant is butylated hydroxytoluene (BHT), and the concentration of the antioxidant in the four or more pharmaceutically acceptable excipients is about 0.05% by weight.

* * * * *